(12) United States Patent
Choi et al.

(10) Patent No.: US 12,060,339 B2
(45) Date of Patent: Aug. 13, 2024

(54) DUAL MODULATOR OF MGLUR5 AND 5-HT2A RECEPTOR, AND USE THEREOF

(71) Applicant: Vivozon Inc., Yongin-si (KR)

(72) Inventors: Dae Kyu Choi, Yongin-si (KR); Hyo Jin Kim, Yongin-si (KR); Mi Seon Bae, Yongin-si (KR); Jin Choi, Seoul (KR); Hyun Jin Heo, Yongin-si (KR); Yong Seok Lee, Yongin-si (KR); Geon Ho Lee, Yongin-si (KR); Mi Yon Shim, Yongin-si (KR); Jin Sun Park, Yongin-si (KR); Han Mi Lee, Yongin-si (KR)

(73) Assignee: Vivozon Inc., Yongin-si (KR)

( * ) Notice: Subject to any disclaimer, the term of this patent is extended or adjusted under 35 U.S.C. 154(b) by 101 days.

(21) Appl. No.: 17/631,212

(22) PCT Filed: Jul. 28, 2021

(86) PCT No.: PCT/KR2021/009826
§ 371 (c)(1),
(2) Date: Jan. 28, 2022

(87) PCT Pub. No.: WO2022/025636
PCT Pub. Date: Feb. 3, 2022

(65) Prior Publication Data
US 2022/0274939 A1    Sep. 1, 2022

(30) Foreign Application Priority Data
Jul. 29, 2020 (KR) .................. 10-2020-0094236

(51) Int. Cl.
| | | |
|---|---|---|
| *C07D 295/135* | (2006.01) | |
| *A61P 25/04* | (2006.01) | |
| *C07C 233/66* | (2006.01) | |
| *C07C 233/70* | (2006.01) | |
| *C07C 233/72* | (2006.01) | |
| *C07C 233/78* | (2006.01) | |
| *C07C 233/86* | (2006.01) | |
| *C07C 237/34* | (2006.01) | |
| *C07D 213/40* | (2006.01) | |
| *C07D 213/56* | (2006.01) | |
| *C07D 305/06* | (2006.01) | |
| *C07D 307/14* | (2006.01) | |
| *C07D 309/06* | (2006.01) | |
| *C07D 309/14* | (2006.01) | |
| *C07D 319/12* | (2006.01) | |

(52) U.S. Cl.
CPC .......... *C07D 295/135* (2013.01); *A61P 25/04* (2018.01); *C07C 233/66* (2013.01); *C07C 233/70* (2013.01); *C07C 233/72* (2013.01); *C07C 233/78* (2013.01); *C07C 233/86* (2013.01); *C07C 237/34* (2013.01); *C07D 213/40* (2013.01); *C07D 213/56* (2013.01); *C07D 305/06* (2013.01); *C07D 307/14* (2013.01); *C07D 309/06* (2013.01); *C07D 309/14* (2013.01); *C07D 319/12* (2013.01)

(58) Field of Classification Search
CPC ... C07C 233/66; C07C 233/70; C07C 233/72; C07C 233/78; C07C 233/86; C07C 237/34; C07D 213/40; C07D 213/56; C07D 295/135; C07D 305/06; C07D 307/14; C07D 309/06; C07D 309/14; C07D 319/12
See application file for complete search history.

(56) References Cited

FOREIGN PATENT DOCUMENTS

| | | |
|---|---|---|
| JP | 2010-155802 A | 7/2010 |
| KR | 10-2010-0033981 A | 3/2010 |
| KR | 10-2014-0002061 A | 1/2014 |
| KR | 10-1637337 B1 | 7/2016 |
| WO | 2008/151184 A1 | 12/2008 |
| WO | 2012/143340 A1 | 10/2012 |
| WO | 2013/049255 A1 | 4/2013 |

OTHER PUBLICATIONS

STN Registry database entry for CAS RN 1016053-72-7, Accessed Jul. 1, 2023, Entered STN Apr. 21, 2008.*
STN Registry database entry for CAS RN 2424410-97-7, Accessed Jul. 1, 2023, Entered STN Jun. 14, 2020.*
STN Registry database entry for CAS RN 2428552-21-8, Accessed Jul. 1, 2023, Entered STN Jun. 18, 2020.*
"Chemical Abstract Compound, STN express" 2 pages.
S.R. Chaplan, et al., "Quantitative assessment of tactile allodynia in the rat paw", Journal of Neuroscience Methods, 1994, pp. 55-63, vol. 53.
Sun Ho Kim, et al., "An experimental model for peripheral neuropathy produced by segmental spinal nerve ligation in the rat", Pain, 1992, 355-363, vol. 50.
International Search Report for PCT/KR2021/009826 dated Nov. 9, 2021 [PCT/ISA/210].

* cited by examiner

*Primary Examiner* — Alicia L Otton
(74) *Attorney, Agent, or Firm* — Sughrue Mion, PLLC

(57) ABSTRACT

Disclosed are a dual modulator of mGluR5 and 5-HT2AR (5-HT2A receptor), and use thereof. More specifically, disclosed are a compound which acts as modulator of mGluR5 and an antagonist of 5-HT2AR at the same time, and use thereof as therapeutic agent for pain.

11 Claims, 1 Drawing Sheet

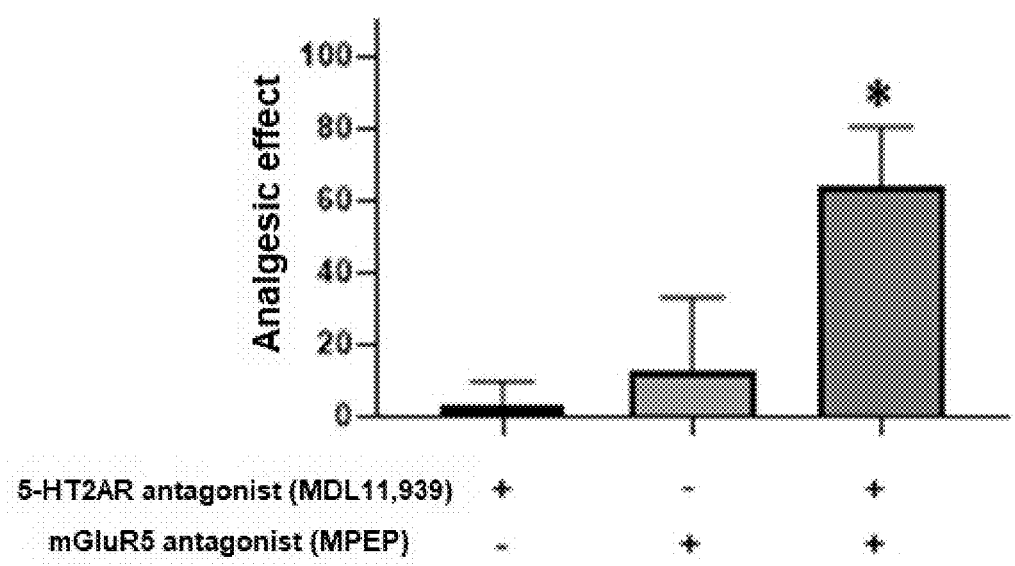

DUAL MODULATOR OF MGLUR5 AND 5-HT2A RECEPTOR, AND USE THEREOF

CROSS REFERENCE TO RELATED APPLICATIONS

This application is a National Stage of International Application No. PCT/KR2021/009826 filed Jul. 28, 2021, claiming priority based on Korean Patent Application No. 10-2020-0094236 filed Jul. 29, 2020.

TECHNICAL FIELD

Disclosed are a dual modulator of mGluR5 and 5-HT2AR (5-HT2A receptor), and use thereof. More specifically, disclosed are a compound which acts as a modulator of mGluR5 and an antagonist of 5-HT2AR at the same time, and use thereof as a therapeutic agent for pain.

BACKGROUND ART

According to the definition of the International Association for the Study of Pain (IASP), pain is an unpleasant sensory and emotional experience associated with, or resembling that associated with, actual or potential tissue damage. Pain may be broadly classified into physiological and pathological pain. Physiological pain is an adaptive response of the body to defend itself from external injury and disappears by removing the cause of the pain. Pathological pain is such a maladaptive state and it is continuously maintained even after the nociceptive stimulus disappears and the damaged tissues are recovered. Among pathological pains, neuropathic pain is a representative chronic pain caused by nerve damage or abnormal nerve function. It shows abnormal features such as allodynia to show the pain caused by non-harmful stimuli, hyperalgesia to present more severe pain in the presence of harmful stimuli, spontaneous pain, other paresthesia, dysesthesia, hyperpathia and so on.

In the process of pain transmission, when harmful stimuli such as hot thermal or strong mechanical stimulation are applied to the peripheral tissues such as skin or muscle, the peripheral nerve terminals are electrically excited and the action potentials are transmitted to the central nerve of the cerebrum through the spinal cord. Such process of transmitting the pain signals through the nerves involves the interaction of various kinds of neurotransmitters and receptors. Among these neurotransmitters, glutamate is a representative excitatory neurotransmitter in the central nervous system and induces signaling in neurons through glutamate receptors.

Glutamate receptors are largely divided into ionotropic glutamate receptors (iGluR) and metabotropic glutamate receptors (mGluR). The metabotropic glutamate receptor is a type of G protein-coupled receptor (GPCR) and classified into three groups—I, II, and III, according to the characteristics of the signal transduction process. Group I, which consists of mGluR1 and mGluR5, regulates neuronal excitability according to their location at the synapse and activates phospholipase C (PLC) through Gq protein. Group II (mGluR2 and mGluR3) and group III (mGluR4, mGluR6, mGluR7 and mGluR8) are known to inhibit the downstream signaling pathways of the adenylic cyclase (AC) activated through Gi protein as presynaptic receptors.

Serotonin (5-HT, 5-hydroxtryptamine) is also a typical neurotransmitter for central nervous system and is produced in the raphe nucleus of the brainstem. Serotonin plays a broad and important role on central and peripheral nervous systems through serotonin receptors, and is closely related to various nervous activities such as emotion, cognition, eating and sleep by greatly affecting the actions of other neurotransmitters such as dopamine and norepinephrine. For example, various pharmacological treatments for depression, obesity, smoking cessation, and irritable bowel syndrome have been developed by modulating the serotonin system. Serotonin receptors are classified into seven subtypes. Except for 5-HT3 receptors, which are ligand-gated ion channels, the others (5-HT1-2, 5-HT4-7) are all G protein-coupled receptors (GPCRs). These GPCR-type serotonin receptors modulate excitatory or inhibitory neurotransmission by triggering the intracellular second messenger cascade.

PRIOR ART DOCUMENTS

Patent Documents

International Publication No. WO 2013/049255
International Publication No. WO 2013/081400

DISCLOSURE OF INVENTION

Technical Problem

An object of the present invention is to provide a compound that acts on mGluR5 and 5-HT2AR at the same time.

Another object of the present invention is to provide the use of said compound for the treatment of pain.

Solution to Problem

To achieve the above object, there is provided a compound of the following Formula 1 or a pharmaceutically acceptable salt thereof:

[Formula 1]

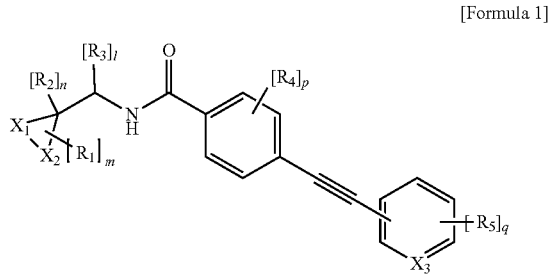

wherein
$X_1$ and $X_2$ together with carbon atom to which they are attached form 4- to 7-membered aliphatic ring or a 4- to 6-membered heteroaliphatic ring;
$X_3$ is CH or N;
$R_1$ is hydroxy, halo, alkyl, heterocycloalkyl or heterocycloalkyl-alkyl;
R2 is hydroxy, halo, alkyl, alkoxy, heterocycloalkyl, hydroxyalkyl, haloalkyl, amino, alkylamino, dialkylamino, cycloalkyl-alkyl, cycloalkylamino, haloalkylamino, aminocarbonyl, alkylaminocarbonyl, alkoxycarbonylalkyl, carboxyalkyl, aminocarbonylalkyl, hydroxyaminocarbonylalkyl, alkylaminocarbonylalkyl, dialkylaminocarbonylalkyl, or 5- or 6-membered heteroaryl;
$R_3$ is deuterium, halo or alkyl;
$R_4$ and $R_5$ are each independently halo or alkyl;

m is an integer of 0 to 3;
n is 0 or 1; and
l, p and q are each independently an integer of 0 to 2;
wherein the heteroaliphatic ring, heterocycloalkyl or heteroaryl has one or more heteroatoms selected from the group consisting of N, O and S;
provided that when $X_1$ and $X_2$ together with carbon atom to which they are attached form 6-membered aliphatic ring or 5-membered heteroaliphatic ring and $X_3$ is CH, n and q are not 0 at the same time.

In addition, there is provided a pharmaceutical composition for the prevention or treatment of pain comprising a therapeutically effective amount of the compound of Formula 1 or a pharmaceutically acceptable salt thereof as an active ingredient, together with a pharmaceutically acceptable carrier or excipient.

Furthermore, there is provided a method for treating pain comprising administering to a mammal the compound of Formula 1 or a pharmaceutically acceptable salt thereof.

Advantageous Effects of Invention

The compound of Formula 1 or a pharmaceutically acceptable salt thereof acts as a dual modulator for mGluR5 and 5-HT2AR. Dual modulatory action on mGluR5 and 5-HT2AR can show synergistic effects in the therapeutic effect of pain. Because of these properties, the compound of Formula 1 or a pharmaceutically acceptable salt thereof can exhibit analgesic effect without specific side effects even at low doses.

BRIEF DESCRIPTION OF DRAWINGS

FIG. 1 is a graph showing that mGluR5 modulator and 5-HT2AR antagonist exert a synergistic effect on analgesic action.

MODE FOR THE INVENTION

The present invention is described in detail hereinafter.

Among metabotropic glutamate receptors (mGluR), mGluR5—which belongs to group I—is highly expressed in the hippocampus, striatum, thalamus and cortex, and thus is closely related to various neurological diseases. In addition, mGluR5 is also distributed in the spinal cord dorsal horn and is known to play an important role in regulating the somatosensory pathway and nociceptive neurotransmission. Actually, in various animal models for inflammatory pain, neuropathic pain, visceral pain, post-operative pain, and orofacial pain, it was reported that the treatment with a negative allosteric modulator of mGluR5—i.e., an mGluR5 antagonist, showed a significant analgesic effect.

Serotonin also plays an important role in the development and regulation of pain, and it may induce pain or exhibit analgesic action depending on the site of action, cell and receptor types. In the trigeminal nerve system, when serotonin acts on 5-HT1B/D receptors, it reduces pain by inhibiting the release of neurotransmitter. However, when serotonin acts on 5-HT2A receptors in the periphery, it rather induces inflammatory and neuropathic hyperalgesia by sensitizing afferent nerve fibers. 5-HT2A receptors are expressed not only in the peripheral nerves but also at the dorsal region of the spinal cord, and may serve as an intermediate mediator that transmits serotonin-associated pain signals to the brain. It was reported that the expression of 5-HT2A receptors was increased at dorsal root ganglion (DRG) and spinal cord dorsal horn, which are the major locus in pain pathway in the animal models of neuropathic pain, and it has also been reported that ketanserin, which is a representative 5-HT2A receptor antagonist, suppressed pain induction.

Compounds that act as dual modulators of mGluR5 and 5-HT2AR are disclosed. If the compound exerts a synergistic effect by acting on the two receptors simultaneously, it is possible to maximize the therapeutic and preventive analgesic effects while minimize the adverse effects by using lower dose prescription.

According to one aspect of the present invention, there is provided a compound of the following Formula 1 or a pharmaceutically acceptable salt thereof:

[Formula 1]

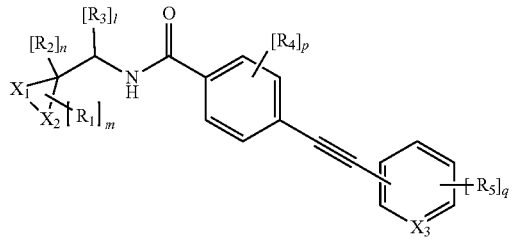

wherein
$X_1$ and $X_2$ together with carbon atom to which they are attached form 4- to 7-membered aliphatic ring or a 4- to 6-membered heteroaliphatic ring;
$X_3$ is CH or N;
$R_1$ is hydroxy, halo, alkyl, heterocycloalkyl or heterocycloalkyl-alkyl;
R2 is hydroxy, halo, alkyl, alkoxy, heterocycloalkyl, hydroxyalkyl, haloalkyl, amino, alkylamino, dialkylamino, cycloalkyl-alkyl, cycloalkylamino, haloalkylamino, aminocarbonyl, alkylaminocarbonyl, alkoxycarbonylalkyl, carboxyalkyl, aminocarbonylalkyl, hydroxyaminocarbonylalkyl, alkylaminocarbonylalkyl, dialkylaminocarbonylalkyl, or 5- or 6-membered heteroaryl;
$R_3$ is deuterium, halo or alkyl;
$R_4$ and $R_5$ are each independently halo or alkyl;
m is an integer of 0 to 3;
n is 0 or 1; and
l, p and q are each independently an integer of 0 to 2;
wherein the heteroaliphatic ring, heterocycloalkyl or heteroaryl has one or more heteroatoms selected from the group consisting of N, O and S;
provided that when $X_1$ and $X_2$ together with carbon atom to which they are attached form 6-membered aliphatic ring or 5-membered heteroaliphatic ring and $X_3$ is CH, n and q are not 0 at the same time.

Herein, the following concepts defined to the substituents are used to define the compound of Formula 1.

As used herein, the term "aliphatic cycle" refers to a non-aromatic hydrocarbon cycle, and the term "heteroaliphatic cycle" refers to a non-aromatic hydrocarbon cycle having one or more heteroatoms selected from the group consisting of N, O and S, more specifically N or O. Specific examples of the aliphatic cycle include, but are not limited to, rings having 4 to 7 carbon atoms such as cyclobutane, cyclopropane, cyclohexane and cycloheptane. Specific examples of the heteroaliphatic cycle include, but are not limited to, 4- to 6-membered heterocyclic rings such as oxetane, tetrahydrofuran, tetrahydropyran, dioxane and piperidine.

As used herein, the term "halo," either alone or in combination with additional terms (for example, haloalkyl), refers to a radical of fluorine (F), chlorine (Cl), bromine (Br) or iodine (I). More specifically, halo may be fluorine (F).

As used herein, the term "alkyl," either alone or in combination with additional terms (for example, haloalkyl), refers to a radical of a saturated or unsaturated aliphatic hydrocarbon group having 1 to 10 carbon atoms, preferably 1 to 5 carbon atoms of a linear or branched chain, and may include a single bond, a double bond or a triple bond. For example, the alkyl may include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl and the like, but is not limited thereto.

As used herein, the term "cycloalkyl" refers to a partially or fully saturated single or fused ring hydrocarbon, and may be $C_3$-$C_{12}$ cycloalkyl, preferably $C_3$-$C_7$ cycloalkyl, and more specifically $C_3$-$C_6$ cycloalkyl. For example, the cycloalkyl may include cyclopropyl, cyclobutyl, cyclopentyl, cyclohexyl, cyclohexynyl, cycloheptyl and the like, but is not limited thereto.

Unless indicated otherwise, the term "alkoxy" used herein refers to alkyloxy having 1 to 10 carbon atoms, preferably 1 to 5 carbon atoms.

As used herein, the term "heterocycloalkyl" refers to a fully saturated hydrocarbon which forms a ring including one or more heteroatoms selected from N, O and S, preferably 1 to 3 heteroatoms selected from N and O, and is preferably 4- to 6-membered heterocycloalkyl. Examples of heterocycloalkyl include, but are not limited to, oxetanyl, tetrahydrofuranyl, tetrahydropyranyl, dioxanyl, piperidinyl, morpholinyl and the like.

According to one embodiment of the present invention, in the above Formula 1, $X_1$ and $X_2$ together with carbon atom to which they are attached form $C_4$-$C_7$ cycloalkyl or 4- to 6-membered heterocycloalkyl;

$X_3$ is CH or N;

$R_1$ is hydroxy, halo or $C_1$-$C_5$ alkyl;

$R_2$ is hydroxy, halo, $C_1$-$C_5$ alkyl, $C_1$-$C_5$ alkoxy, 4- to 6-membered heterocycloalkyl, hydroxy-$C_1$-$C_5$ alkyl, halo-$C_1$-$C_8$ alkyl, $C_1$-$C_5$ alkylamino, $C_3$-$C_6$ cycloalkyl-$C_1$-$C_8$ alkyl, $C_3$-$C_6$ cycloalkylamino, halo-$C_1$-$C_8$ alkylamino, $C_1$-$C_5$ alkylaminocarbonyl, $C_1$-$C_5$ alkoxycarbonyl-$C_1$-$C_5$ alkyl, carboxy-$C_1$-$C_5$ alkyl, aminocarbonyl-$C_1$-$C_5$ alkyl, hydroxyaminocarbonyl-$C_1$-$C_5$ alkyl, $C_1$-$C_5$ alkylaminocarbonyl-$C_1$-$C_5$ alkyl, di($C_1$-$C_5$ alkyl)aminocarbonyl-$C_1$-$C_5$ alkyl or pyridyl;

$R_3$ is deuterium, fluoro or $C_1$-$C_5$ alkyl;

$R_4$ and $R_5$ are each independently halo or $C_1$-$C_5$ alkyl;

m is an integer of 0 to 2;

n is 0 or 1; and l, p and q are each independently an integer of 0 to 2;

wherein the heterocycloalkyl has 1 to 3 heteroatoms selected from the group consisting of N and O.

According to another embodiment of the present invention, examples of $R_1$ include, but are not limited to, hydroxy, fluoro, methyl, oxetanylmethyl, oxetanyl and the like.

According to another embodiment of the present invention, examples of $R_2$ include, but are not limited to, hydroxy; methoxy; fluoro; methyl, ethyl, cyclopropylmethyl, fluoromethyl, hydroxymethyl, hydroxypropyl, carboxymethyl, carboxyethyl, methoxycarbonylmethyl, methoxycarbonylethyl, aminocarbonylmethyl, hydroxyaminocarbonylmethyl, methylaminocarbonylmethyl, dimethylaminocarbamoylmethyl; isopropylamino, 2,2-dimethylpropylamino, cyclopropylamino, 2,2,2-trifluoroamino, morpholinyl, methylaminocarbonyl, pyridyl and the like.

According to another embodiment of the present invention, the 4- to 7-membered aliphatic ring is cyclobutane, cyclopentane, cyclohexane or cycloheptane According to another embodiment of the present invention, the 4- to 6-membered heteroaliphatic ring is oxetane, tetrahydrofuran, tetrahydropyran, dioxane or piperidine According to another embodiment of the present invention, in the above Formula 1, $X_1$ and $X_2$ together with carbon atom to which they are attached form oxetane, tetrahydrofuran, tetrahydropyran, cyclobutane, cyclopentane or cyclohexane.

According to another embodiment of the present invention, in the above Formula 1, p is 0.

According to another embodiment of the present invention, in the above Formula 1, $X_3$ is CH.

According to another embodiment of the present invention, in the above Formula 1, at least one of n and q is not 0.

According to another embodiment of the present invention, in the above Formula 1, $R_5$ is fluoro, and q is 1 or 2.

According to another embodiment of the present invention, in the above Formula 1, $R_5$ is substituted at ortho and/or para position of phenyl.

In another embodiment according to the present invention, representative examples of the compound of Formula 1 may include the following compounds, but are not limited thereto:

N-((1-(cyclopropylamino)cycloheptyl)methyl)-4-(pyridin-2-ylethynyl)benzamide;

N-((1-(cyclopropylamino)cyclopentyl)methyl)-4-(pyridin-4-ylethynyl)benzamide;

N-((1-(cyclopropylamino)cyclopentyl)methyl)-4-((5-fluoropyridin-2-yl)ethynyl)benzamide;

N-((1-(cyclopropylamino)cyclobutyl)methyl)-4-((5-fluoropyridin-2-yl)ethynyl)benzamide;

N-((1-(cyclopropylamino)cyclobutyl)methyl)-4-(pyridin-4-ylethynyl)benzamide;

N-((1-(cyclopropylamino)cyclobutyl)methyl)-4-((4-fluorophenyl)ethynyl)benzamide;

N-((1-(cyclopropylamino)cyclobutyl)methyl)-3-fluoro-4-(pyridin-4-ylethynyl)benzamide;

N-((1-(cyclopropylamino)cyclobutyl)methyl)-4-(pyridin-2-ylethynyl)benzamide;

N-((1-(cyclopropylamino)cyclobutyl)methyl)-4-((2-fluorophenyl)ethynyl)benzamide;

N-((1-(cyclopropylamino)cyclobutyl)methyl)-2-fluoro-4-(pyridin-4-ylethynyl)benzamide;

N-((1-(cyclopropylamino)cyclopentyl)methyl)-4-((2-fluorophenyl)ethynyl)benzamide;

N-((1-(cyclopropylamino)cycloheptyl)methyl)-4-((2-fluorophenyl)ethynyl)benzamide;

N-((1-(cyclopropylamino)cyclopentyl)methyl)-4-((4-fluorophenyl)ethynyl)benzamide;

N-((1-(cyclopropylamino)cycloheptyl)methyl)-4-((4-fluorophenyl)ethynyl)benzamide;

N-((1-(cyclopropylamino)cycloheptyl)methyl)-4-((5-fluoropyridin-2-yl)ethynyl)benzamide;

N-((1-(cyclopropylamino)cycloheptyl)methyl)-4-((3-fluoropyridin-4-yl)ethynyl)benzamide;

N-((1-(cyclopropylamino)cyclopentyl)methyl)-4-((3,4-difluorophenyl)ethynyl)benzamide;

N-((1-(cyclopropylamino)cycloheptyl)methyl)-4-((3,4-difluorophenyl)ethynyl)benzamide;
N-((1-(cyclopropylamino)cyclohexyl)methyl)-4-((4-fluorophenyl)ethynyl)benzamide;
N-((1-(cyclopropylamino)cyclohexyl)methyl)-4-((2-fluorophenyl)ethynyl)benzamide;
N-((1-(cyclopropylamino)cyclopentyl)methyl)-4-((2-methylpyridin-4-yl)ethynyl)benzamide;
N-((4-(cyclopropylamino)tetrahydro-2H-pyran-4-yl)methyl)-4-((2-fluorophenyl)ethynyl)benzamide;
4-((2-fluorophenyl)ethynyl)-N-((1-morpholinocyclopentyl)methyl)benzamide;
4-((2-fluorophenyl)ethynyl)-N-((4-(isopropylamino)tetrahydro-2H-pyran-4-yl)methyl)benzamide;
4-((2-fluorophenyl)ethynyl)-N-((1-(isopropylamino)cyclohexyl)methyl)benzamide;
N-((1-cyclopropylamino)-4-methylcyclohexyl)methyl)-4-((2-fluorophenyl)ethynyl)benzamide;
4-((2-fluorophenyl)ethynyl)-N-((tetrahydro-2H-pyran-4-yl)methyl)benzamide;
4-((2-fluorophenyl)ethynyl)-N-((1-(neopentylamino)cyclohexyl)methyl)benzamide;
N-((4-(cyclopropylmethyl)tetrahydro-2H-pyran-4-yl)methyl)-4-((2-fluorophenyl)ethynyl)benzamide;
4-((2-fluorophenyl)ethynyl)-N-((1-(isopropylamino)cyclopentyl)methyl)benzamide;
4-(pyridin-4-ylethynyl)-N-((1-((2,2,2-trifluoroethyl)amino)cyclohexyl)methyl)benzamide;
4-((2-fluorophenyl)ethynyl)-N-((1-hydroxycyclohexyl)methyl)benzamide;
4-((4-fluorophenyl)ethynyl)-N-((tetrahydro-2H-pyran-4-yl)methyl)benzamide;
4-((2-fluorophenyl)ethynyl)-N-((1-(pyridin-3-yl)cyclopentyl)methyl)benzamide;
2-fluoro-4-((2-fluorophenyl)ethynyl)-N-((tetrahydro-2H-pyran-4-yl)methyl)benzamide;
4-((2-fluorophenyl)ethynyl)-N-((4-methyltetrahydro-2H-pyran-4-yl)methyl)benzamide;
4-((2-fluorophenyl)ethynyl)-N-((1-(hydroxymethyl)cyclohexyl)methyl)benzamide;
4-((2-fluorophenyl)ethynyl)-N-((4-(hydroxymethyl)tetrahydro-2H-pyran-4-yl)methyl)benzamide;
N-((4,4-difluorocyclohexyl)methyl)-4-((2-fluorophenyl)ethynyl)benzamide;
4-((2-fluorophenyl)ethynyl)-N-((tetrahydro-2H-pyran-3-yl)methyl)benzamide;
4-((2-fluorophenyl)ethynyl)-N-((4-hydroxytetrahydro-2H-pyran-4-yl)methyl)benzamide
4-((2-fluorophenyl)ethynyl)-N-(1-(tetrahydro-2H-pyran-4-yl)ethyl)benzamide;
4-((2-fluorophenyl)ethynyl)-N-((tetrahydrofuran-3-yl)methyl)benzamide;
4-((2,4-difluorophenyl)ethynyl)-N-((tetrahydro-2H-pyran-4-yl)methyl)benzamide;
(R)-4-(2-fluorophenyl)ethynyl)-N-((tetrahydrofuran-2-yl)methyl)benzamide;
(S)-4-((2-fluorophenyl)ethynyl)-N-((tetrahydrofuran-2-yl)methyl)benzamide;
(R)-4-((2-fluorophenyl)ethynyl)-N-(1-(tetrahydro-2H-pyran-4-yl)ethyl)benzamide;
4-((2-fluorophenyl)ethynyl)-N-((4-fluorotetrahydro-2H-pyran-4-yl)methyl)benzamide;
4-(phenylethynyl)-N-((tetrahydro-2H-pyran-4-yl)methyl)benzamide;
N-((4-(fluoromethyl)tetrahydro-2H-pyran-4-yl)methyl)-4-((2-fluorophenyl)ethynyl)benzamide;
N-((1,4-dioxan-2-yl)methyl)-4-((2-fluorophenyl)ethynyl)benzamide;
4-((2-fluorophenyl)ethynyl)-N-((3-methyloxetan-3-yl)methyl)benzamide;
4-((4-(2-fluorophenyl)ethynyl)benzamido)methyl)-N-methyltetrahydro-2H-pyran-4-carboxamide;
4-((2-fluorophenyl)ethynyl)-N-((tetrahydro-2H-pyran-2-yl)methyl)benzamide;
N-((1-(isopropylamino)cyclohexyl)methyl)-4-(phenylethynyl)benzamide;
N-((3,3-difluorocyclobutyl)methyl)-4-(2-fluorophenyl)ethynyl)benzamide;
4-((2-fluorophenyl)ethynyl)-N-((1-hydroxycyclobutyl)methyl)benzamide;
4-((2-fluorophenyl)ethynyl)-N-(oxetan-2-ylmethyl)benzamide;
methyl 3-(1-((4-((2-fluorophenyl)ethynyl)benzamido)methyl)cyclohexyl)propanoate;
3-(4-((4-((2-fluorophenyl)ethynyl)benzamido)methyl)tetrahydro-2H-pyran-4-yl)propanoic acid;
3-(1-((4-((2-fluorophenyl)ethynyl)benzamido)methyl)cyclohexyl)propanoic acid;
4-((2-fluorophenyl)ethynyl)-N-((1-(3-hydroxypropyl)cyclohexyl)methyl)benzamide;
4-((2-fluorophenyl)ethynyl)-N-((2-hydroxycyclohexyl)methyl)benzamide;
4-((2-fluorophenyl)ethynyl)-N-(3-hydroxycyclohexyl)methyl)benzamide;
4-((2-fluorophenyl)ethynyl)-N-((1-methoxycyclohexyl)methyl)benzamide;
4-((2-fluorophenyl)ethynyl)-N-((4-methoxytetrahydro-2H-pyran-4-yl)methyl)benzamide
N-((2,2-dimethyltetrahydro-2H-pyran-4-yl)methyl)-4-((2-fluorophenyl)ethynyl)benzamide;
4-((2-fluorophenyl)ethynyl)-N-((tetrahydro-2H-pyran-4-yl)methyl-$d_2$)benzamide;
(R)-4-(2-fluorophenyl)ethynyl)-N-((tetrahydrofuran-3-yl)methyl)benzamide;
N-((5,5-dimethyltetrahydrofuran-3-yl)methyl)-4-((2-fluorophenyl)ethynyl)benzamide;
4-((2-fluorophenyl)ethynyl)-N-((tetrahydrofuran-2-yl)methyl)benzamide;
N-((3-ethyloxetan-3-yl)methyl)-4-((2-fluorophenyl)ethynyl)benzamide;
4-((2,4-difluorophenyl)ethynyl)-N-((1-fluorocyclohexyl)methyl)benzamide;
methyl 2-(1-((4-((2-fluorophenyl)ethynyl)benzamido)methyl)cyclohexyl)acetate;
methyl 2-(4-((4-((2-fluorophenyl)ethynyl)benzamido)methyl)tetrahydro-2H-pyran-4-yl)acetate;
2-(1-((4-((2-fluorophenyl)ethynyl)benzamido)methyl)cyclohexyl)acetic acid;
N-((1-(2-amino-2-oxoethyl)cyclohexyl)methyl)-4-((2-fluorophenyl)ethynyl)benzamide;
N-((4-(2-amino-2-oxoethyl)tetrahydro-2H-pyran-4-yl)methyl)-4-((2-fluorophenyl)ethynyl)benzamide;
4-((2-fluorophenyl)ethynyl)-N-((1-(2-(hydroxyamino)-2-oxoethyl)cyclohexyl)methyl)benzamide;
4-((2-fluorophenyl)ethynyl)-N-((1-(2-(methylamino)-2-oxoethyl)cyclohexyl)methyl)benzamide;
N-((1-(2-(dimethylamino)-2-oxoethyl)cyclohexyl)methyl)-4-((2-fluorophenyl)ethynyl)benzamide;
4-((2-fluorophenyl)ethynyl)-N-(3-hydroxyoxetan-3-yl)methyl)benzamide;
4-((4-fluorophenyl)ethynyl)-N-(3-methyloxetan-3-yl)methyl)benzamide;

3-fluoro-4-((2-fluorophenyl)ethynyl)-N-(3-methyloxetan-3-yl)methyl)benzamide;
4-((2-fluorophenyl)ethynyl)-N-(((1s,3s)-3-hydroxycyclobutyl)methyl)benzamide;
4-((2-fluorophenyl)ethynyl)-N-(((1r,3r)-3-hydroxycyclobutyl)methyl)benzamide;
4-((2-fluorophenyl)ethynyl)-N-(((1s,3s)-3-hydroxy-3-methylcyclobutyl)methyl)benzamide;
N-((4,4-difluorocyclohexyl)methyl)-4-(pyridin-4-ylethynyl)benzamide;
N-((3,3-difluorocyclobutyl)methyl)-4-(pyridin-4-ylethynyl)benzamide;
N-((3,3-difluorocyclobutyl)methyl)-4-(phenylethynyl)benzamide;
(S)-4-((2-fluorophenyl)ethynyl)-N-((tetrahydro-2H-pyran-3-yl)methyl)benzamide;
(R)-4-(2-fluorophenyl)ethynyl)-N-((tetrahydro-2H-pyran-3-yl)methyl)benzamide;
(S)-4-((2-fluorophenyl)ethynyl)-N-((tetrahydrofuran-3-yl)methyl)benzamide;
4-((4-fluorophenyl)ethynyl)-N-((tetrahydrofuran-3-yl)methyl)benzamide;
4-((2-fluorophenyl)ethynyl)-N-(3-methyloxetan-3-yl)methyl-d)benzamide;
4-((2-fluorophenyl)ethynyl)-N-((1-morpholinocyclobutyl)methyl)benzamide;
N-((3,3-difluoro-1-methylcyclobutyl)methyl)-4-((2-fluorophenyl)ethynyl)benzamide;
4-((2-fluorophenyl)ethynyl)-N-((2-methyltetrahydrofuran-2-yl)methyl)benzamide;
(R)-4-((4-fluorophenyl)ethynyl)-N-((tetrahydro-2H-pyran-3-yl)methyl)benzamide;
(S)-4-((4-fluorophenyl)ethynyl)-N-((tetrahydro-2H-pyran-3-yl)methyl)benzamide;
(R)-4-(4-fluorophenyl)ethynyl)-N-((tetrahydrofuran-3-yl)methyl)benzamide;
(S)-4-((4-fluorophenyl)ethynyl)-N-((tetrahydrofuran-3-yl)methyl)benzamide;
N-((3-fluorooxetan-3-yl)methyl)-4-((2-fluorophenyl)ethynyl)benzamide;
4-((4-fluorophenyl)ethynyl)-N-((1-methylcyclohexyl)methyl)benzamide;
4-((2-fluorophenyl)ethynyl)-N-((1-methylcyclobutyl)methyl)benzamide;
4-((4-fluorophenyl)ethynyl)-N-((1-methylcyclobutyl)methyl)benzamide;
4-((2,4-difluorophenyl)ethynyl)-N-((1-methylcyclobutyl)methyl)benzamide;
4-((2,4-difluorophenyl)ethynyl)-N-((1-methylcyclopentyl)methyl)benzamide;
(R)-4-((2,4-difluorophenyl)ethynyl)-N-((tetrahydrofuran-3-yl)methyl)benzamide;
(R)-4-(4-fluorophenyl)ethynyl)-N-((tetrahydrofuran-2-yl)methyl)benzamide;
(S)-4-((4-fluorophenyl)ethynyl)-N-((tetrahydrofuran-2-yl)methyl)benzamide;
N-((3-ethyloxetan-3-yl)methyl)-4-((4-fluorophenyl)ethynyl)benzamide;
(S)-4-((2,4-difluorophenyl)ethynyl)-N-((tetrahydrofuran-3-yl)methyl)benzamide;
(R)-4-((2,4-difluorophenyl)ethynyl)-N-((tetrahydrofuran-2-yl)methyl)benzamide;
4-((2,4-difluorophenyl)ethynyl)-N-((tetrahydro-2H-pyran-2-yl)methyl)benzamide;
4-((4-fluorophenyl)ethynyl)-N-((2-methyltetrahydrofuran-2-yl)methyl)benzamide;
(S)-4-((2,4-difluorophenyl)ethynyl)-N-((tetrahydrofuran-2-yl)methyl)benzamide;
4-((2,4-difluorophenyl)ethynyl)-N-(oxetan-2-ylmethyl)benzamide;
4-((2,4-difluorophenyl)ethynyl)-N-((2-methyltetrahydrofuran-2-yl)methyl)benzamide;
N-((3,3-difluorocyclobutyl)methyl)-4-(2,4-difluorophenyl)ethynyl)benzamide;
N-((4,4-difluorocyclohexyl)methyl)-4-((2,4-difluorophenyl)ethynyl)benzamide;
4-((2,4-difluorophenyl)ethynyl)-N-((3-ethyloxetan-3-yl)methyl)benzamide;
4-((2,4-difluorophenyl)ethynyl)-N-((3-fluorooxetan-3-yl)methyl)benzamide;
(S)-4-((2,4-difluorophenyl)ethynyl)-N-((tetrahydro-2H-pyran-3-yl)methyl)benzamide; and
4-((2,4-difluorophenyl)ethynyl)-N-((4-methyltetrahydro-2H-pyran-4-yl)methyl)benzamide.

The compound of Formula 1 acts as a dual modulator of mGluR5 and 5-HT2AR.

All of the compounds of Formula 1 have $IC_{50}$ of 2 μM or less for mGluR5 and 5-HT2AR. In another embodiment according to the present invention, the compound of Formula 1 has $IC_{50}$ of 1.5 μM or less for mGluR5 and 5-HT2AR at the same time. In another embodiment according to the present invention, the compound of Formula 1 has $IC_{50}$ of 1.0 μM or less for mGluR5 and 5-HT2AR at the same time.

In another embodiment according to the present invention, more specific examples of the compound of Formula 1 may include the following compounds:
N-((1-(cyclopropylamino)cyclobutyl)methyl)-4-((2-fluorophenyl)ethynyl)benzamide;
N-((1-(cyclopropylamino)cyclopentyl)methyl)-4-((2-fluorophenyl)ethynyl)benzamide;
4-((2-fluorophenyl)ethynyl)-N-((1-(isopropylamino)cyclohexyl)methyl)benzamide;
4-((2-fluorophenyl)ethynyl)-N-((tetrahydro-2H-pyran-4-yl)methyl)benzamide;
4-((2-fluorophenyl)ethynyl)-N-((tetrahydro-2H-pyran-3-yl)methyl)benzamide;
4-((2-fluorophenyl)ethynyl)-N-((tetrahydrofuran-3-yl)methyl)benzamide;
4-(phenylethynyl)-N-((tetrahydro-2H-pyran-4-yl)methyl)benzamide;
4-((2-fluorophenyl)ethynyl)-N-(3-methyloxetan-3-yl)methyl)benzamide;
(R)-4-((2-fluorophenyl)ethynyl)-N-((tetrahydrofuran-3-yl)methyl)benzamide;
4-((2-fluorophenyl)ethynyl)-N-(3-hydroxyoxetan-3-yl)methyl)benzamide;
4-((4-fluorophenyl)ethynyl)-N-(3-methyloxetan-3-yl)methyl)benzamide;
4-((2-fluorophenyl)ethynyl)-N-(((1s,3s)-3-hydroxy-3-methylcyclobutyl)methyl)benzamide;
4-((4-fluorophenyl)ethynyl)-N-((tetrahydrofuran-3-yl)methyl)benzamide;
(S)-4-((4-fluorophenyl)ethynyl)-N-((tetrahydrofuran-3-yl)methyl)benzamide;
(R)-4-(2,4-difluorophenyl)ethynyl)-N-((tetrahydrofuran-3-yl)methyl)benzamide;
4-((4-fluorophenyl)ethynyl)-N-((2-methyltetrahydrofuran-2-yl)methyl)benzamide;
4-((2,4-difluorophenyl)ethynyl)-N-((2-methyltetrahydrofuran-2-yl)methyl)benzamide; and
(S)-4-((2,4-difluorophenyl)ethynyl)-N-((tetrahydro-2H-pyran-3-yl)methyl)benzamide.

The above compounds have IC$_{50}$ of 1.0 μM or less for mGluR5 and 5-HT2AR at the same time. In addition, the compounds exhibit an excellent analgesic effect in a spinal nerve ligation model.

The medicinal effect of the compound according to one embodiment of the present invention may be maintained even in the form of a pharmaceutically acceptable salt. The pharmaceutically acceptable salts include acid or base addition salts and their stereochemical isomers form. The salt may include any salt that maintains the activity of a parent compound in a subject to be administered and does not cause any undesirable effect, but is not limited thereto. The term "additional salt" may be taken to include solvates obtainable from any of the compound of Formula 1 and a pharmaceutically acceptable salt thereof. Examples of these solvates are hydrates or alcoholates.

In addition, since the compound of Formula 1 according to the present invention can have an asymmetric carbon center, they can exist as R- or S-isomer, racemic mixtures or diastereoisomer mixtures and each diastereoisomer, all of which are within the scope of the present invention.

Pharmaceutical Composition

According to another aspect of the present invention, there is provided a pharmaceutical composition for the prevention or treatment of pain comprising a therapeutically effective amount of the compound of Formula 1 or a pharmaceutically acceptable salt thereof as an active ingredient, together with a pharmaceutically acceptable carrier or excipient.

The pharmaceutical composition may be formulated in various oral or parenteral dosage forms. For example, the pharmaceutical composition may be formulated into any dosage form for oral administration, such as tablets, pills, hard/soft capsules, solutions, suspensions, emulsifiers, syrups, granules or elixirs.

When the pharmaceutical composition is formulated into a parenteral dosage form, the pharmaceutical composition may be administered by a parenteral administration method such as subcutaneous injection, intravenous injection, intramuscular injection or intrathoracic injection. The pharmaceutical composition may be prepared as a solution or a suspension by mixing an active ingredient—i.e., a compound of Formula 1 or a pharmaceutically acceptable salt thereof, with a stabilizer or a buffer in water, and the solution or the suspension may be prepared as a unit dosage form of an ampoule or a vial.

Medical Usefulness

According to still another aspect of the present invention, there is provided a method for suppressing or treating pain in an aminal, comprising administering to the animal a therapeutically effective amount of one or more of the compound of Formula 1 and a pharmaceutically acceptable salt thereof.

The compound of Formula 1 acts as a dual modulator for mGluR5 and 5-HT2AR. Specifically, the compound of Formula 1 acts as an antagonist for the 5-HT2A receptor, and may function as a negative modulator (inhibitory functional modulator) in the receptor sub-signaling system for mGluR5. The compound of Formula 1 having these characteristics may be administered to a patient in a small dose due to a synergistic effect between targets to minimize side effects and maximize analgesic efficacy.

The compound of Formula 1 may be used for the treatment and prevention of pain, specifically neuropathic pain. The neuropathic pain may include diabetic neuropathic pain, spinal stenosis, pain after spine surgery, allodynia, causalgia, hyperalgesia, hyperpathia, neuralgia, postherpetic neuralgia, post-thoracotomic pain, trigeminal neuralgia, multiple sclerosis-related pain, thalamic pain, phantom limb pain, anesthesia dolorosa, HIV-associated neuropathic pain, spinal cord disorder-induced paraplegic pain or complex regional pain syndrome, post-seizure pain, neuropathy-related pain such as idiopathic or post-traumatic neuropathy and mononeuritis, cancer-associated neuropathic pain, carpal tunnel-related neuropathic pain, spinal cord injury-related pain, fibromyalgia-related neuropathic pain, back and neck pain, reflex sympathetic dystrophy, phantom limb syndrome and spontaneous pain, trauma-induced neuropathic pain, demyelination-induced pain, chemotherapy-induced neuropathy, back pain, bone pain, chronic alcoholism, hypothyroidism, neuropathic pain due to uremia or vitamin deficiency, and central post-stroke pain.

In one embodiment, a method for suppressing or treating pain comprises administering to an animal a pharmaceutical composition comprising an effective amount of one or more of the compound of Formula 1 and a pharmaceutically acceptable carrier. The method is particularly suitable for use in humans, but may also be used in other animals, particularly mammals.

The specific administration method and therapeutically effective amount of the compound of Formula 1 or a pharmaceutically acceptable salt thereof may be determined by a person skilled in the art in consideration of the type of target mammal, the type of disease, and the type of the compound of Formula 1, and not specifically limited.

For example, the compound of Formula 1 or a pharmaceutically acceptable salt thereof may be included in the pharmaceutical composition in an effective dose of 0.1 to 1,000 mg/kg (body weight), preferably 0.5 to 500 mg/kg (body weight) per day for mammals including humans. The pharmaceutical composition may be administered once or divided two or more times a day and administered through an oral or parenteral route.

Hereinafter, a method of preparing the compound of Formula 1 will be described. The following description is merely illustrative, and the methods may be properly changed according to the selection of a person skilled in the art.

As shown in Reaction Scheme 1 below, the compound of Formula 1 may be obtained through an amide bond reaction between the amine compound of Intermediate 4 and the carboxylic acid compound of Intermediate 5.

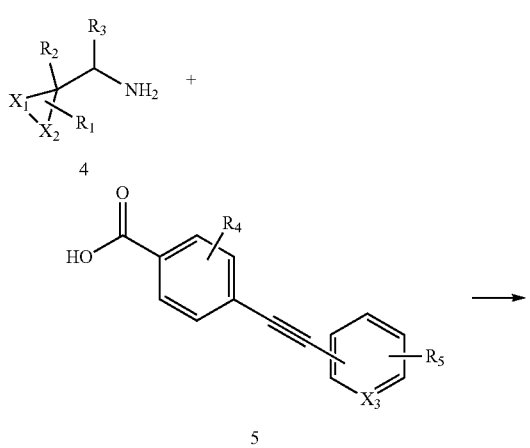

-continued

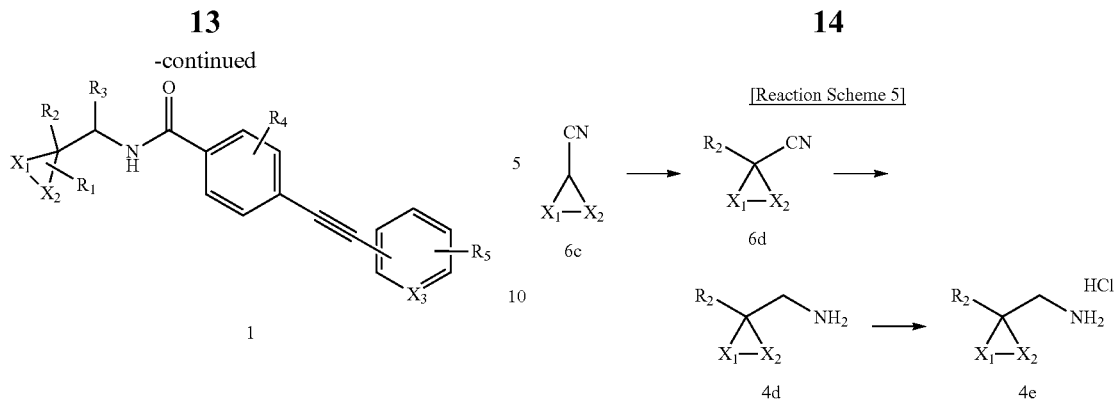

The amine compound of Intermediate 4 may be prepared by various methods including, but is not limited to, methods of Reaction Schemes 2 to 8, depending on substituents.

[Reaction Scheme 2]

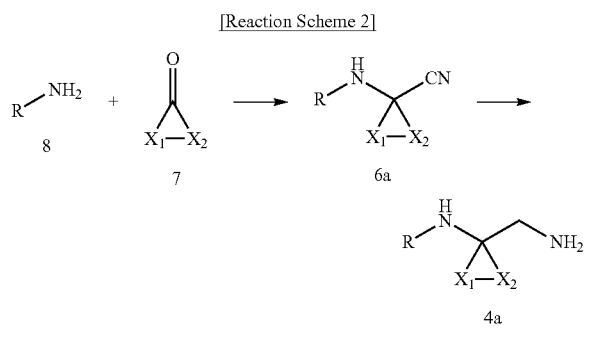

After forming an imine compound from amine compound 8 and ketone compound 7 as starting materials, intermediate 6a can be obtained through a nucleophilic addition reaction using potassium nitrile (KCN), and the amine compound of intermediate 4a can be obtained by reduction.

[Reaction Scheme 3]

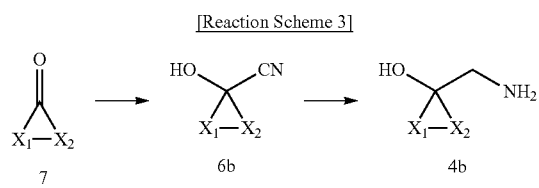

Cyanohydrin compound 6b can be obtained from the ketone compound 7 by a nucleophilic addition reaction using potassium nitrile, and the amine compound of intermediate 4b can be obtained by carrying out a reduction reaction from this compound.

[Reaction Scheme 4]

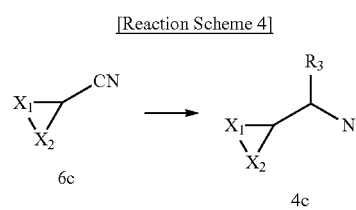

The amine compound of intermediate 4c can be obtained through a reduction reaction from the cyano compound 6c.

[Reaction Scheme 5]

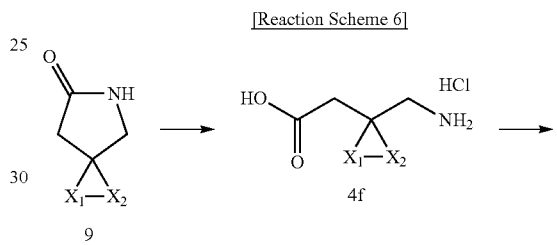

Compound 6d can be obtained through a substitution reaction from cyano compound 6c, and the amine compound of intermediate 4d can be obtained by reduction. Intermediate 4e in the form of the amine hydrochloride may be obtained under hydrochloric acid conditions.

[Reaction Scheme 6]

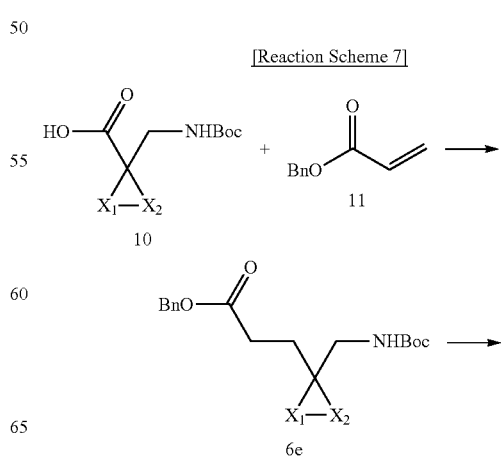

The amine compound of intermediate 4f containing carboxylic acid can be obtained from lactam compound 9 through decyclization under strong acid conditions. In addition, intermediate 4g containing esters can be obtained under acid conditions.

[Reaction Scheme 7]

-continued

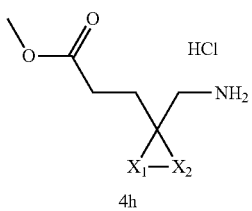
4h

The carboxylic acid compound 10 can be coupled with the acrylate compound 11 to obtain the compound 6e, and the amine compound of the deprotected intermediate 4 h can be obtained by using a strong acid.

[Reaction Scheme 8]

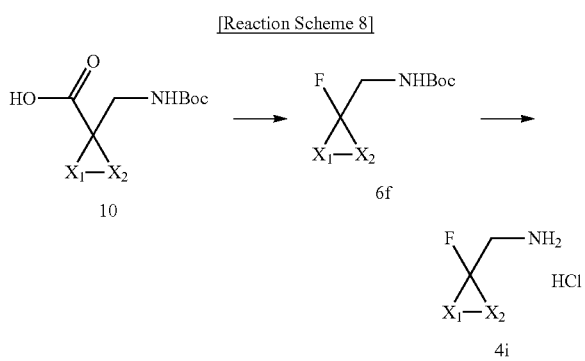

From the carboxylic acid compound 10, the compound 6f substituted with fluorine can be obtained by a coupling reaction using ditetrafluoroborate under visible light, and the amine compound of the intermediate 4i can be obtained through a deprotection reaction.

[Reaction Scheme 9]

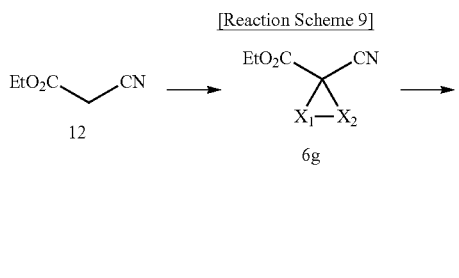

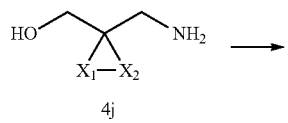
4j

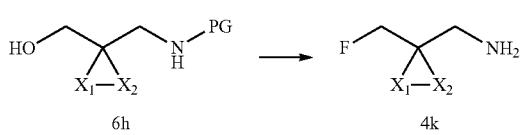

The compound 6g containing a ring can be obtained from compound 12 through a substitution reaction under basic condition, and the ester and nitrile are reduced to obtain the amine compound of intermediate 4j. It is selectively protected to obtain 6 h of alcohol, and from substitution of hydroxy by fluoro, the compound of intermediate 4k can be obtained.

The carboxylic acid compound of intermediate 5 may be prepared by various methods including, but are not limited to, the method of the following Reaction Scheme 10.

[Reaction Scheme 10]

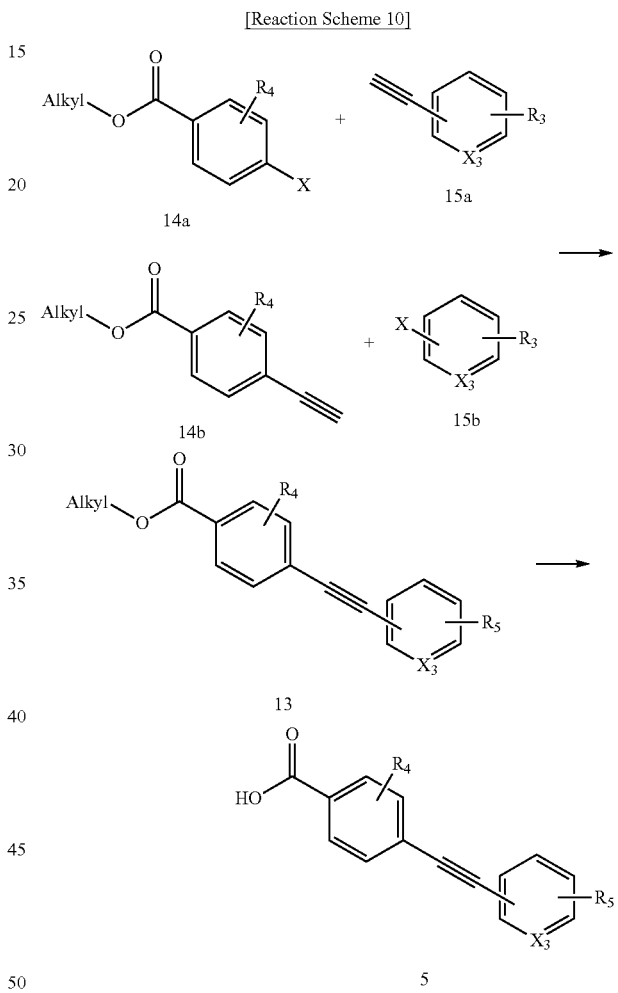

Compound 13 can be obtained from the halogen-containing compound (14a or 15b) and the acetylene-containing compound (15a, 14b) through a Sonogashira coupling reaction, and the carboxylic acid compound of intermediate 5 can be obtained through hydrolysis.

EXAMPLES

Hereinafter, the present invention is explained in more detail with the following examples. However, it must be understood that the protection scope of the present disclosure is not limited to the examples.

Example 1: Synthesis of N-((1-(cyclopropylamino)cycloheptyl)methyl)-4-(pyridin-2-ylethynyl)benzamide

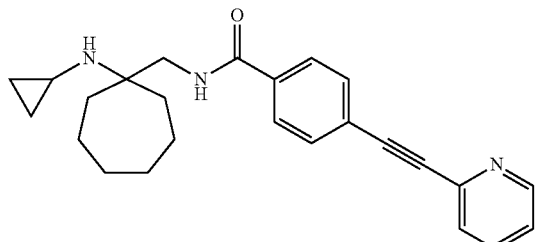

Step 1: Synthesis of 4-(pyridin-2-ylethynyl)benzoic acid

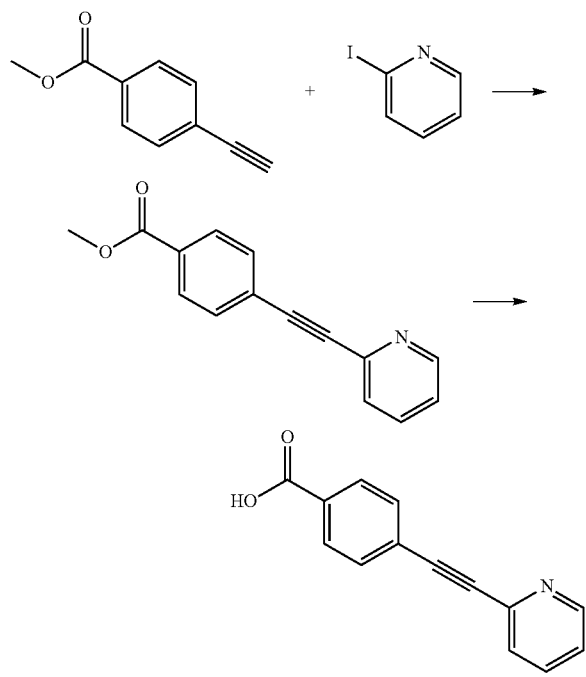

Methyl 4-ethynylbenzoate (1.500 g, 9.365 mmol), 2-iodopyridine (2.112 g, 10.302 mmol), tetrakis(triphenylphosphine)palladium (0.216 g, 0.187 mmol), copper iodide (0.036 g, 0.187 mmol) and piperidine (9.251 mL, 93.650 mmol) were dissolved in toluene (15 mL) at room temperature and the resulting solution was stirred at 90° C. for 18 hours, and then the temperature was lowered to room temperature to terminate the reaction. A saturated aqueous ammonium chloride solution was poured into the reaction mixture, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain methyl 4-(pyridin-2-ylethynyl)benzoate (1.705 g, 76.7%) as a white solid. 1.705 g (7.186 mmol) of the obtained compound and lithium hydroxide monohydrate (0.603 g, 14.372 mmol) were dissolved in methanol (5 mL)/water (5 mL)/tetrahydrofuran (5 mL) at room temperature and the resulting mixture was stirred at the same temperature for 3 hours. After removing the solvent from the reaction mixture under reduced pressure, 1N hydrochloric acid aqueous solution was added to the concentrate and stirred. The precipitated solid was filtered, washed with water and dried to obtain 4-(pyridin-2-ylethynyl)benzoic acid (0.695 g, 43.3) %) as yellow solid: LRMS (ES) m/z 224.00 [M+H]$^+$, calculated MW 223.23.

Step 2: Synthesis of 1-(aminomethyl)-N-cyclopropylcycloheptan-1-amine

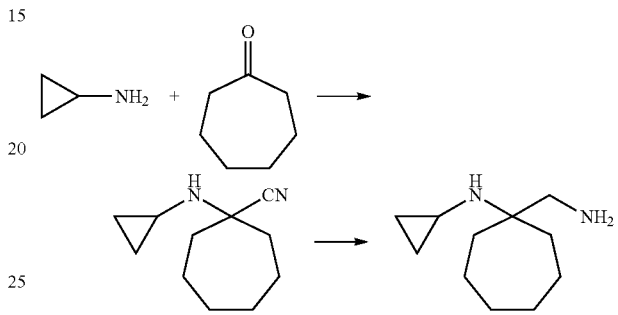

Cyclopropanamine (5.700 g, 99.825 mmol) and cycloheptanone (11.197 g, 99.825 mmol) were dissolved in water (200 mL) at room temperature. To the resulting solution, sodium hydrogen sulfite (NaHSO$_3$, 40.00% solution in water, 12.984 mL, 49.912 mmol) was added and stirred at the same temperature for 2 hours. Potassium cyanide (9.750 g, 149.737 mmol) was added to the reaction mixture, and the reaction mixture was further stirred at the same temperature for 24 hours. Water was added to the reaction mixture and extracted with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain 1-(cyclopropylamino)cycloheptane-1-carbonitrile (12.670 g, 71.2%) as colorless oil. To the solution in which the obtained product was dissolved in diethyl ether (200 mL) at 0° C., lithium aluminum hydride (2.40 M solution, 88.835 mL, 213.204 mmol) was added and stirred at room temperature for 16 hours. Then, water (7.684 mL, 426.408 mmol) and sodium hydroxide (1.00 M solution, 35.534 mL, 35.534 mmol) were added to the reaction mixture at 0° C., followed by stirring for 30 minutes to terminate the reaction. The reaction mixture was filtered through a Celite pad to remove solids, and the solvent was removed from the filtrate under reduced pressure. The obtained product was used without further purification (1-(aminomethyl)-N-cyclopropylcycloheptan-1-amine, 12.000 g, 92.6%, colorless oil): LRMS (ES) m/z 183.16 [M+H]$^+$, calculated MW 182.31.

Step 3: Synthesis of N-((1-(cyclopropylamino)cycloheptyl)methyl)-4-(pyridin-2-ylethynyl)benzamide

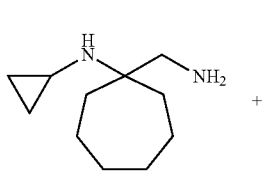

-continued

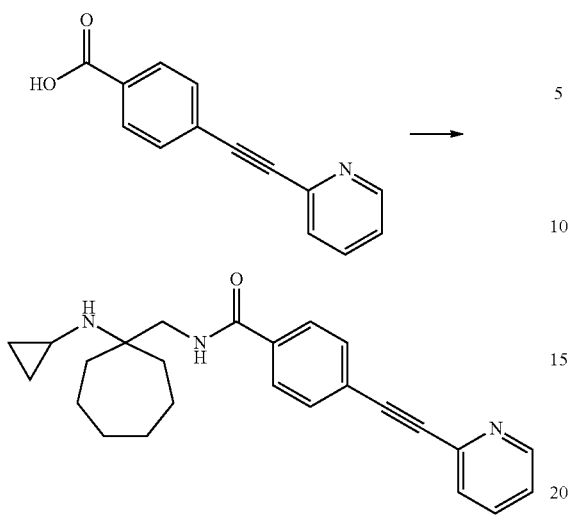

4-(Pyridin-2-ylethynyl)benzoic acid (0.031 g, 0.139 mmol), 1-(aminomethyl)-N-cyclopropylcycloheptan-1-amine (0.025 g, 0.139 mmol), 1-ethyl-3-(3-dimethylaminopropyl)carbodiimide hydrochloride (EDC-HCl, 0.040 g, 0.208 mmol), 1H-benzo[d][1,2,3]triazol-1-ol (HOBt, 0.028 g, 0.208 mmol) and N,N-diisopropylethylamine (0.121 mL, 0.694 mmol) were dissolved in N,N-dimethylformamide (2 mL) at room temperature, and the resulting solution was stirred at the same temperature for 18 hours. A saturated aqueous sodium hydrogen carbonate solution was poured into the reaction mixture, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain N-((1-(cyclopropylamino)cycloheptyl)methyl)-4-(pyridin-2-ylethynyl)benzamide (0.008 g, 14.9%) as yellow solid: LRMS (ES) m/z 388.41 [M+H]$^+$, calculated MW 387.53; $^1$H-NMR (400 MHz, CDCl$_3$) d 9.24 (s, 1H), 8.63 (d, J=4.0 Hz, 1H), 8.41 (t, J=5.6 Hz, 1H), 8.14 (d, J=8.4 Hz, 2H), 7.71 (t, J=7.8 Hz, 1H), 7.64 (d, J=8.4 Hz, 2H), 7.54 (d, J=8.0 Hz, 1H), 7.28 (m, 1H), 3.93 (d, J=5.6 Hz, 2H), 2.54 (s, 1H), 2.12 (m, 2H), 1.98 (m, 2H), 1.68 (m, 12H).

Example 2: Synthesis of N-((1-(cyclopropylamino)cyclopentyl)methyl)-4-(pyridin-4-ylethynyl)benzamide

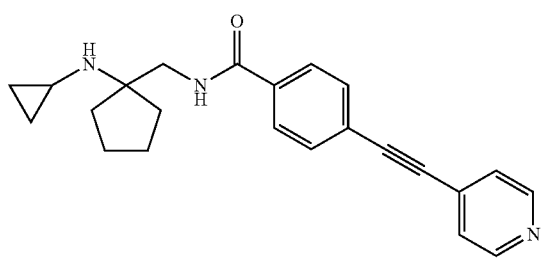 [SMILES: O=C(NCC1(NC2CC2)CCCC1)c1ccc(C#Cc2ccncc2)cc1]

Step 1: Synthesis of methyl 4-(pyridin-4-ylethynyl)benzoic acid

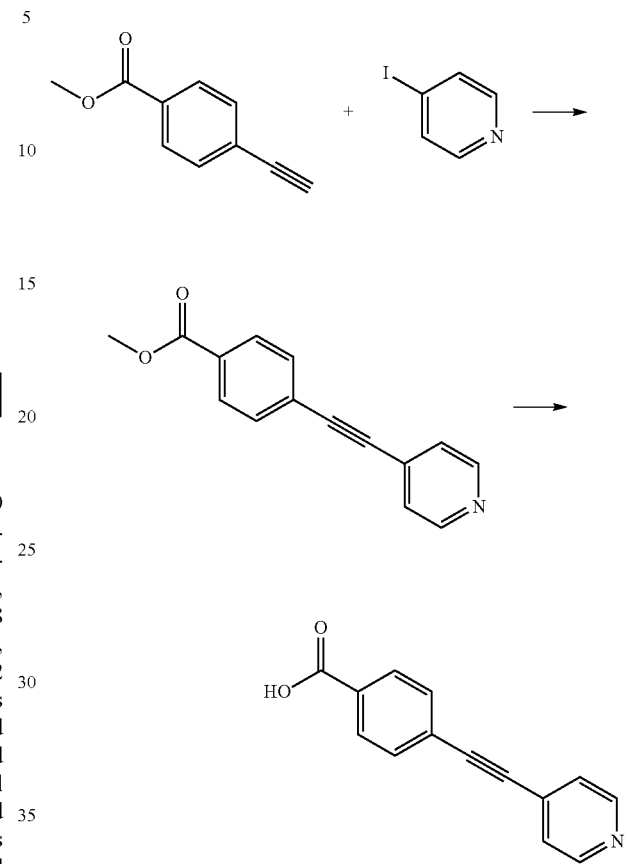

4-Iodopyridine (2.816 g, 13.735 mmol) instead of 2-iodopyridine was used in a similar manner to Step 1 of Example 1 to obtain methyl 4-(pyridin-4-ylethynyl)benzoate (2.500 g, 84.4%) as a white solid, followed by obtaining 4-(pyridin-4-ylethynyl)benzoic acid (2.484 g, 97.6%) as white solid.

Step 2: Synthesis of 1-(aminomethyl)-N-cyclopropylcyclopentan-1-amine

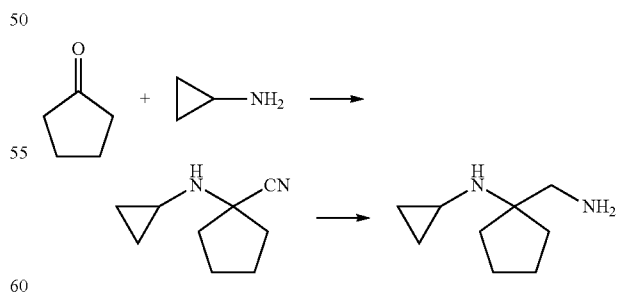

Cyclopentanone (10.000 mL, 112.934 mmol) instead of cycloheptanone was used in a similar manner to Step 2 of Example 1 to obtain 1-(cyclopropylamino)cyclopentane-1-carbonitrile (13.659 g, 80.5%) as yellow liquid, followed by obtaining 1-(aminomethyl)-N-cyclopropylcyclopentan-1-amine as yellow liquid (11.510 g, 82.1%, yellow liquid).

Step 3: Synthesis of N-((1-(cyclopropylamino)cyclopentyl)methyl)-4-(pyridin-4-ylethynyl)benzamide

Step 1: Synthesis of 4-((5-fluoropyridin-2-yl)ethynyl)benzoic acid

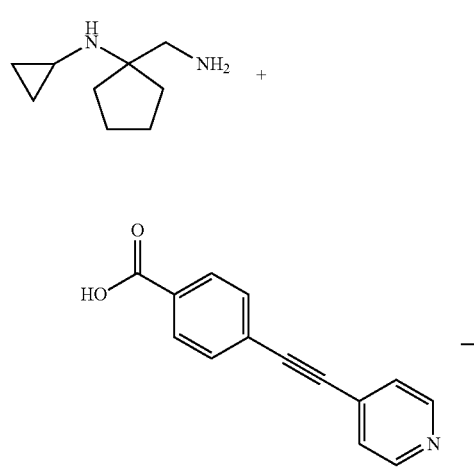

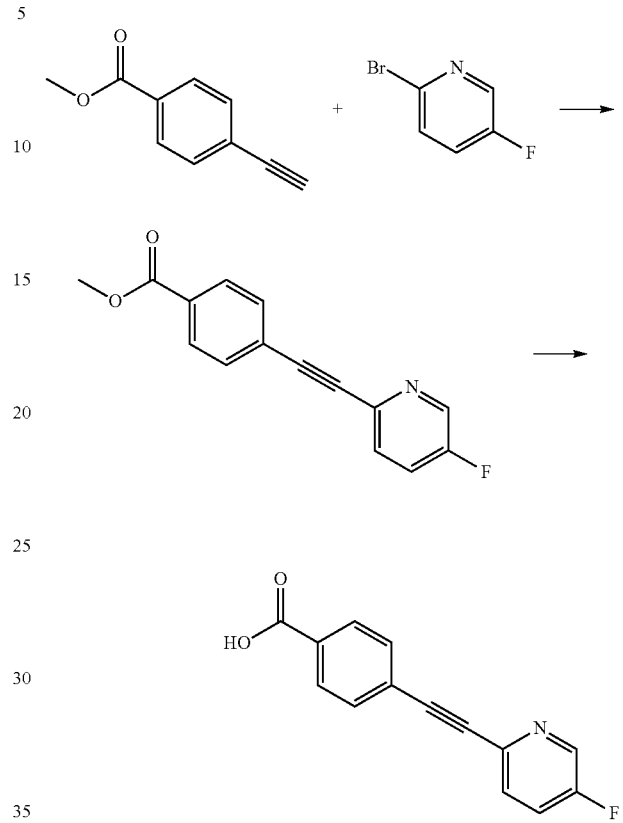

4-(Pyridin-4-ylethynyl)benzoic acid (0.100 g, 0.448 mmol) and 1-(aminomethyl)-N-cyclopropylcyclopentan-1-amine (0.083 g, 0.538 mmol) as starting materials were used in a similar manner to Step 3 of Example 1 to obtain N-((1-(cyclopropylamino)cyclopentyl)methyl)-4-(pyridin-4-ylethynyl)benzamide (0.097 g, 60.2%) as a yellow solid: LRMS (ES) m/z 360.19 [M+H]$^+$, calculated MW 359.47; $^1$H-NMR (400 MHz, CDCl$_3$) d 8.60 (d, J=9.6 Hz, 2H), 7.83 (d, J=22.8 Hz, 2H), 7.59~7.55 (m, 2H), 7.37 (d, J=6.0 Hz, 2H), 3.57 (s, 2H), 2.27~2.20 (m, 1H), 1.88~1.71 (m, 8H), 0.59~0.58 (m, 4H).

Example 3: Synthesis of N-((1-(cyclopropylamino)cyclopentyl)methyl)-4-((5-fluoropyridin-2-yl)ethynyl)benzamide

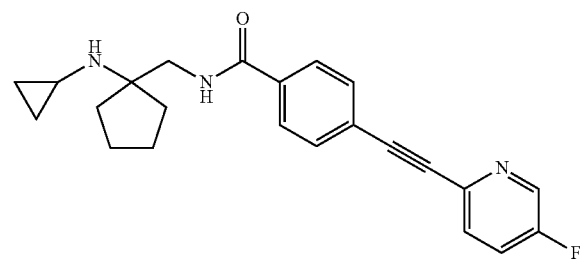 [SMILES: O=C(NCC1(NC2CC2)CCCC1)c1ccc(C#Cc2ccc(F)cn2)cc1]

Methyl 4-ethynylbenzoate (1.000 g, 6.243 mmol), 2-bromo-5-fluoropyridine (1.099 g, 6.243 mmol), copper iodide (0.119 g, 0.624 mmol), tetrakis(triphenylphosphine)palladium (0.433 g, 0.375 mmol) and triethylamine (8.702 mL, 62.434 mmol) were dissolved in toluene (25 mL) at room temperature. The resulting solution was stirred at 100° C. for 16 hours, and then the temperature was lowered to room temperature to terminate the reaction. The reaction mixture was filtered through a Celite pad to remove solids, and water was added to the filtrate, followed by extraction with dichloromethane. The organic layer was washed with a saturated aqueous sodium chloride solution, dried over anhydrous magnesium sulfate, filtered and concentrated under reduced pressure. The concentrate was purified by column chromatography and concentrated to obtain methyl 4-((5-fluoropyridin-2-yl)ethynyl)benzoate (0.980 g, 61.5%) as brown solid.

Then, the solution in which the obtained product and lithium hydroxide monohydrate (0.322 g, 7.679 mmol) were dissolved in tetrahydrofuran (5 mL)/methanol (5 mL)/water (5 mL) at room temperature was stirred at 50° C. for 6 hours, and then the temperature was lowered to room temperature to terminate the reaction. After removing the solvent from the reaction mixture under reduced pressure, 1N hydrochloric acid aqueous solution was added to the concentrate and stirred. The precipitated solid was filtered, washed with water and dried to obtain 4-((5-fluoropyridin-2-yl)ethynyl)benzoic acid (0.860 g, 92.9%) as brown solid: LRMS (ES) m/z 241.72 [M+H]$^+$, calculated MW 241.22.

Step 2: Synthesis of N-((1-(cyclopropylamino)cyclopentyl)methyl)-4-((5-fluoropyridin-2-yl)ethynyl)benzamide

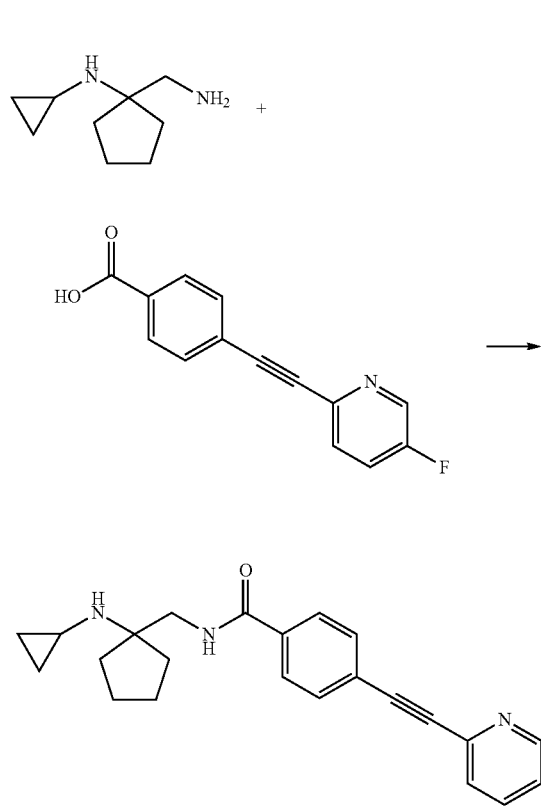

4-((5-Fluoropyridin-2-yl)ethynyl)benzoic acid (0.156 g, 0.648 mmol) and 1-(aminomethyl)-N-cyclopropylcyclopentan-1-amine (0.100 g, 0.648 mmol) as starting materials were used in a similar manner to Step 3 of Example 1 to obtain N-((1-(cyclopropylamino)cyclopentyl)methyl)-4-((5-fluoropyridin-2-yl)ethynyl)benzamide (0.085 g, 34.7%) as white solid: LRMS (ES) m/z 378.18 [M+H]$^+$, calculated MW 377.46; $^1$H-NMR (400 MHz, CD$_3$OD) d 8.48 (m, 1H), 7.86 (d, J=8.4 Hz, 2H), 7.72~7.63 (m, 4H), 3.56 (s, 2H), 2.21~2.17 (m, 1H), 1.79~1.62 (m, 8H), 0.52~0.48 (m, 2H), 0.37~0.35 (m, 2H).

Example 4: Synthesis of N-((1-(cyclopropylamino)cyclobutyl)methyl)-4-((5-fluoropyridin-2-yl)ethynyl)benzamide

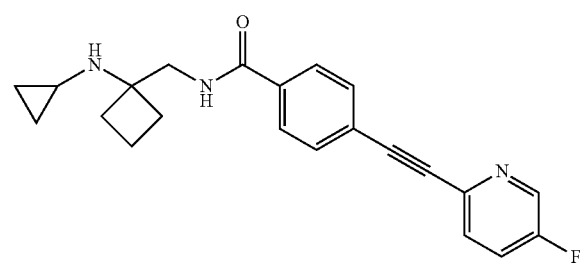 [SMILES: O=C(NCC1(NC2CC2)CCC1)c1ccc(C#Cc2ccc(F)cn2)cc1]

Step 1: Synthesis of 1-(aminomethyl)-N-cyclopropylcyclobutan-1-amine

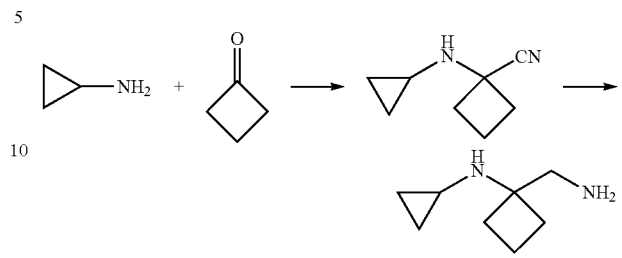

In a similar manner to Step 2 of Example 1 except that cyclobutanone (1.706 mL, 22.828 mmol) was used instead of cycloheptanone, 1-(cyclopropylamino)cyclobutane-1-carbonitrile (0.823 g, 26.5%) as yellow liquid was obtained, followed by obtaining 1-(aminomethyl)-N-cyclopropylcyclobutan-1-amine as yellow solid (0.760 g, 92.3%): LRMS (ES) m/z 140.96 [M+H]$^+$, calculated MW 140.23

Step 2: Synthesis of N-((1-(cyclopropylamino)cyclobutyl)methyl)-4-((5-fluoropyridin-2-yl)ethynyl)benzamide

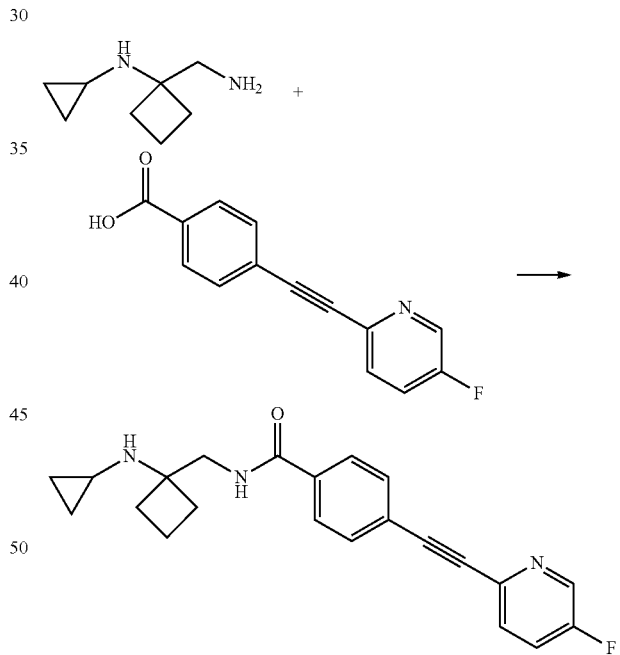

4-((5-Fluoropyridin-2-yl)ethynyl)benzoic acid (0.070 g, 0.290 mmol) and 1-(aminomethyl)-N-cyclopropylcyclobutan-1-amine (0.061 g, 0.435 mmol) were used in a similar manner to Step 3 of Example 1 to obtain N-((1-(cyclopropylamino)cyclobutyl)methyl)-4-((5-fluoropyridin-2-yl)ethynyl)benzamide (0.044 g, 41.7%) as yellow liquid: LRMS (ES) m/z 364.10 [M+H]$^+$, calculated MW 363.44; $^1$H-NMR (400 MHz, CD$_3$OD) d 8.48 (d, J=2.4 Hz, 1H), 7.87 (d, J=6.8 Hz, 2H), 7.75~7.59 (m, 4H), 3.61 (s, 2H), 2.12~2.06 (m, 3H), 2.01~1.98 (m, 2H), 1.83~1.79 (m, 2H), 0.52~0.48 (m, 2H), 0.36~0.33 (m, 2H).

Example 5: Synthesis of N-((1-(cyclopropylamino)cyclobutyl)methyl)-4-(pyridin-4-ylethynyl)benzamide

Example 6: Synthesis of N-((1-(cyclopropylamino)cyclobutyl)methyl)-4-((4-fluorophenyl)ethynyl)benzamide

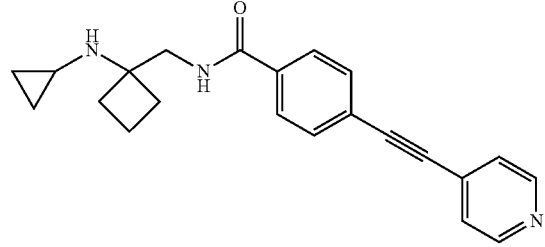 [SMILES: O=C(NCC1(NC2CC2)CCC1)c1ccc(C#Cc2ccncc2)cc1]

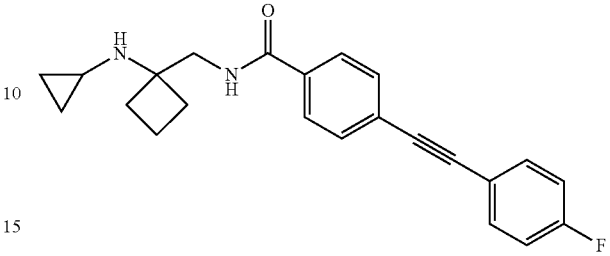

Step 1: Synthesis of N-((1-(cyclopropylamino)cyclobutyl)methyl)-4-(pyridin-4-ylethynyl)benzamide

Step 1: Synthesis of 4-((4-fluorophenyl)ethynyl)benzoic acid

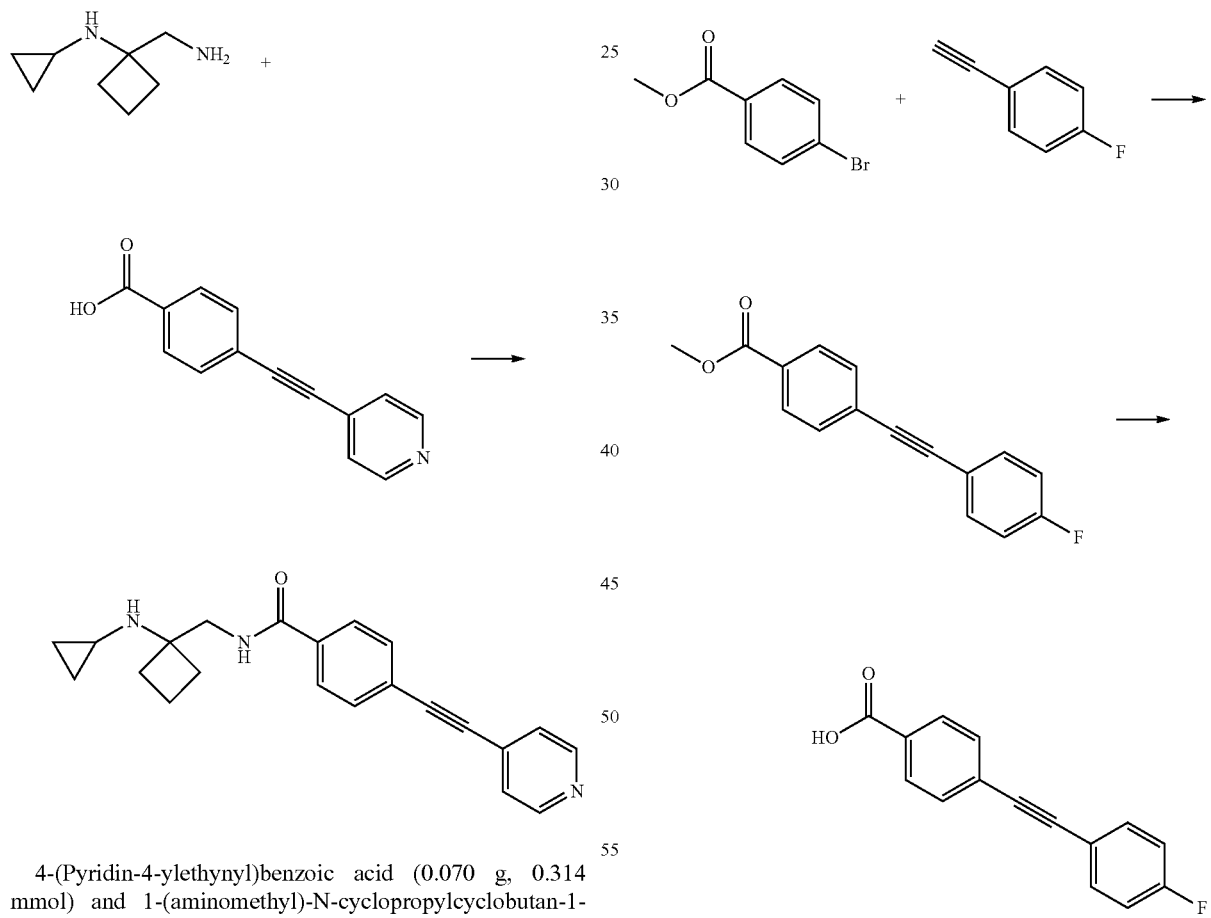

4-(Pyridin-4-ylethynyl)benzoic acid (0.070 g, 0.314 mmol) and 1-(aminomethyl)-N-cyclopropylcyclobutan-1-amine (0.066 g, 0.470 mmol) as starting materials were used in a similar manner to Step 3 of Example 1 to obtain N-((1-(cyclopropylamino)cyclobutyl)methyl)-4-(pyridin-4-ylethynyl)benzamide (0.078 g, 72.0%) as yellow liquid: LRMS (ES) m/z 346.18 [M+H]$^+$, calculated MW 345.45; $^1$H-NMR (400 MHz, CD$_3$OD) d 8.55 (d, J=6.0 Hz, 2H), 7.88 (d, J=8.4 Hz, 2H), 7.66 (d, J=12.0 Hz, 2H), 7.53 (d, J=6.0 Hz, 2H), 3.70 (s, 2H), 2.14~2.09 (m, 3H), 2.07~1.97 (m, 2H), 1.84~1.81 (m, 2H), 0.51~0.49 (m, 2H), 0.37~0.35 (m, 2H).

Methyl 4-bromobenzoate (0.985 g, 4.578 mmol) and 1-ethynyl-4-fluorobenzene (0.500 g, 4.162 mmol) as starting materials were used in a similar manner to Step 1 of Example 3 to obtain methyl 4-((4-fluorophenyl)ethynyl)benzoate (0.779 g, 73.6%) as white solid, followed by obtaining 4-((4-fluorophenyl)ethynyl)benzoic acid (0.672 g, 91.3%) as pale yellow solid: LRMS (ES) m/z 239.05 [M−H]$^+$, calculated MW 240.23.

Step 2: Synthesis of N-((1-(cyclopropylamino)cyclobutyl)methyl)-4-((4-fluorophenyl)ethynyl)benzamide

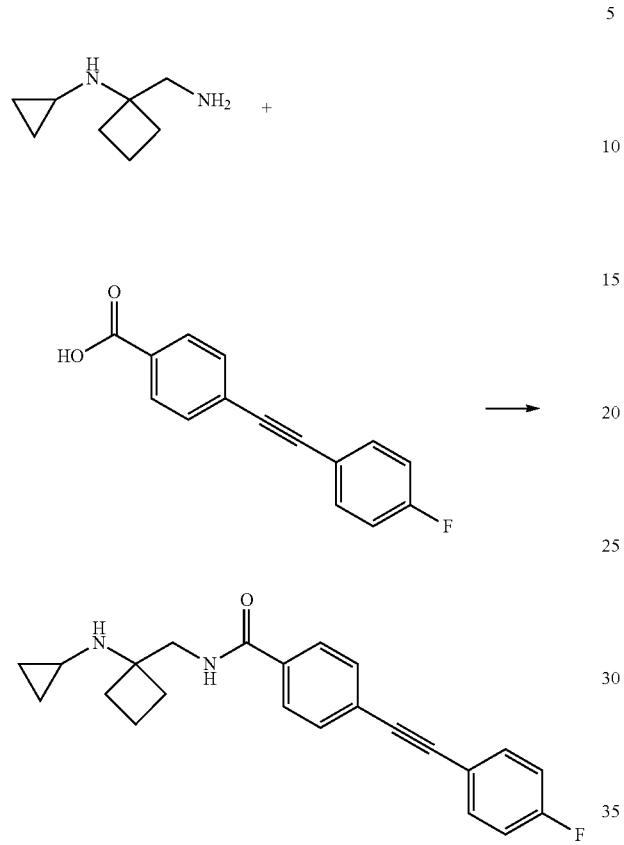

4-((4-Fluorophenyl)ethynyl)benzoic acid (0.070 g, 0.291 mmol) and 1-(aminomethyl)-N-cyclopropylcyclobutan-1-amine (0.061 g, 0.437 mmol) as starting materials were used in a similar manner to Step 3 of Example 1 to obtain N-((1-(cyclopropylamino)cyclobutyl)methyl)-4-((4-fluorophenyl)ethynyl)benzamide (0.078 g, 73.9%) as yellow liquid: LRMS (ES) m/z 363.12 [M+H]$^+$, calculated MW 362.45; $^1$H-NMR (400 MHz, CD$_3$OD) d 7.84 (dt, J=8.4, 1.9 Hz, 2H), 7.60~7.53 (m, 4H), 7.12 (t, J=8.6 Hz, 2H), 3.89 (s, 2H), 2.13~2.06 (m, 3H), 2.03~1.98 (m, 2H), 1.85~1.79 (m, 2H), 0.51~0.48 (m, 2H), 0.36~0.34 (m, 2H).

Example 7: Synthesis of N-((1-(cyclopropylamino)cyclobutyl)methyl)-3-fluoro-4-(pyridin-4-ylethynyl)benzamide

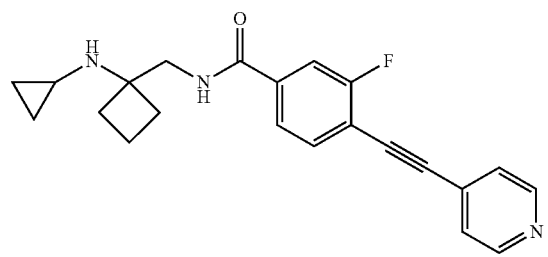 [SMILES: O=C(NCC1(NC2CC2)CCC1)c1ccc(C#Cc2ccncc2)c(F)c1]

Step 1: Synthesis of 3-fluoro-4-(pyridin-4-ylethynyl)benzoic acid

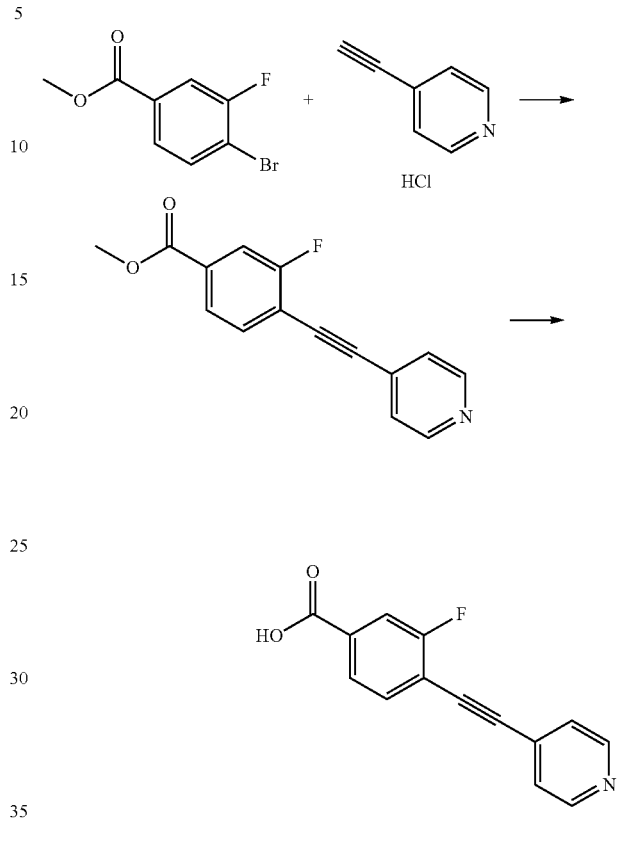

Methyl 4-bromo-3-fluorobenzoate (1.000 g, 4.291 mmol) and 4-ethynylpyridine hydrochloride (0.493 g, 4.506 mmol) as starting materials were used in a similar manner to Step 1 of Example 3 to obtain methyl 3-fluoro-4-(pyridin-4-ylethynyl) benzoate (0.868 g, 79.2%) as brown solid, followed by obtaining 3-fluoro-4-(pyridin-4-ylethynyl)benzoic acid (0.813 g, 100.0%) as pale yellow solid: LRMS (ES) m/z 242.09 [M+H]$^+$, calculated MW 241.22.

Step 2: Synthesis of N-((1-(cyclopropylamino)cyclobutyl)methyl)-3-fluoro-4-(pyridin-4-ylethynyl)benzamide

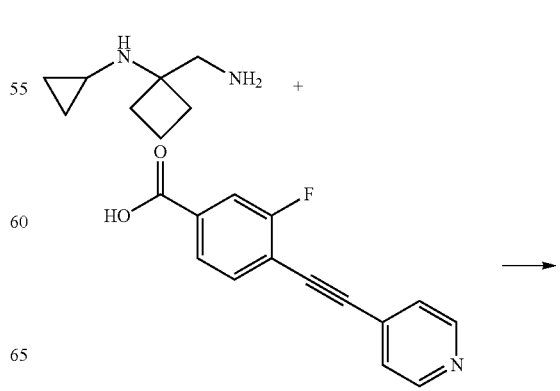

-continued

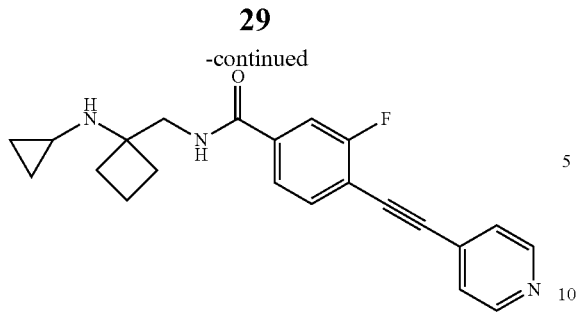

3-Fluoro-4-(pyridin-4-ylethynyl)benzoic acid (0.070 g, 0.290 mmol) and 1-(aminomethyl)-N-cyclopropylcyclobutan-1-amine (0.061 g, 0.435 mmol) as starting materials were used in a similar manner to Step 3 of Example 1 to obtain N-((1-(cyclopropylamino)cyclobutyl)methyl)-3-fluoro-4-(pyri din-4-ylethynyl)benzamide (0.071 g, 67.3%) as yellow liquid: LRMS (ES) m/z 364.10 $[M+H]^+$, calculated MW 363.44; $^1$H-NMR (400 MHz, $CD_3OD$) d 8.57 (dd, J=4.6, 1.8 Hz, 2H), 7.73~7.68 (m, 3H), 7.55 (dd, J=4.2, 1.8 Hz, 2H), 3.70 (s, 2H), 2.15~2.07 (m, 3H), 2.03~1.97 (m, 2H), 1.85~1.77 (m, 2H), 0.50 (dt, J=8.8, 3.4 Hz, 2H), 0.37~0.33 (m, 2H).

Example 8: Synthesis of N-((1-(cyclopropylamino)cyclobutyl)methyl)-4-(pyridin-2-ylethynyl)benzamide

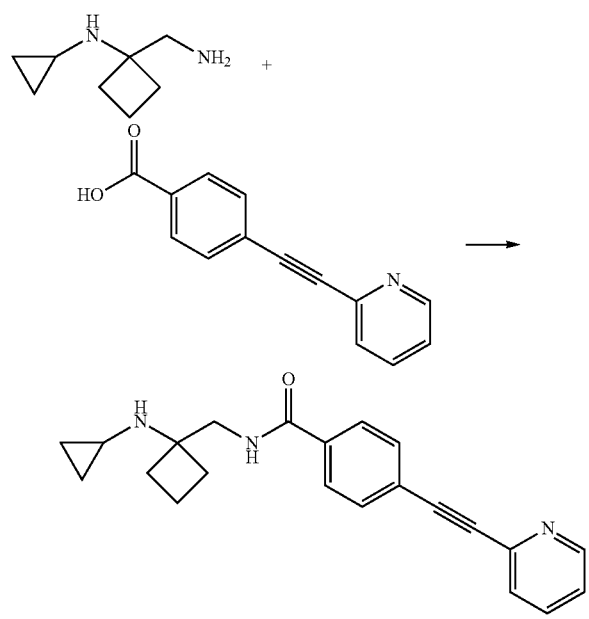

1-(Aminomethyl)-N-cyclopropylcyclobutan-1-amine (0.066 g, 0.470 mmol) as a starting material instead of 1-(aminomethyl)-N-cyclopropylcycloheptan-1-amine was used in a similar manner to Step 3 of Example 1 to obtain N-((1-(cyclopropylamino)cyclobutyl)methyl)-4-(pyridin-2-ylethynyl)benzamide (0.071 g, 65.5%) as yellow liquid: LRMS (ES) m/z 346.18 $[M+H]^+$, calculated MW 345.45; $^1$H-NMR (400 MHz, $CD_3OD$) d 8.54 (d, J=4.4 Hz, 1H), 7.89~7.85 (m, 3H), 7.69~7.65 (m, 3H), 7.44~7.40 (m, 2H), 3.70 (s, 2H), 2.13~2.07 (m, 3H), 2.03~1.97 (m, 2H), 1.88~1.77 (m, 2H), 0.53~0.49 (m, 2H), 0.37~0.33 (m, 2H).

Example 9: Synthesis of N-((1-(cyclopropylamino)cyclobutyl)methyl)-4-((2-fluorophenyl)ethynyl)benzamide

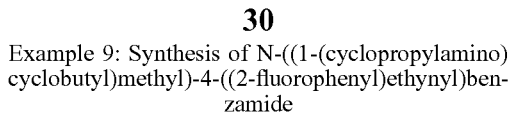

Step 1: Synthesis of 4-((2-fluorophenyl)ethynyl)benzoic acid

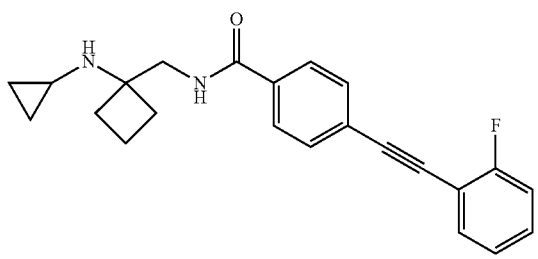 [SMILES: O=C(NCC1(NC2CC2)CCC1)c1ccc(C#Cc2ccccc2F)cc1]

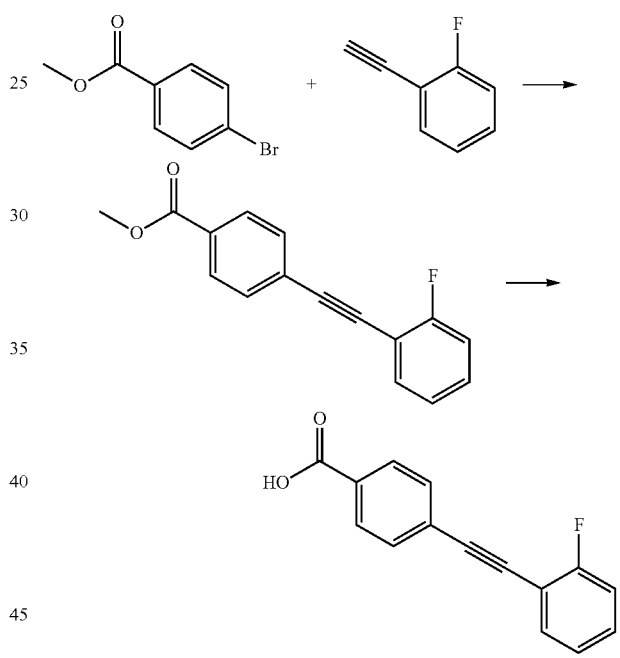

1-Ethynyl-2-fluorobenzene (0.500 g, 4.162 mmol) and methyl 4-bromobenzoate (0.940 g, 4.370 mmol) as starting materials were used in a similar manner to Step 1 of Example 3 to obtain methyl 4-((2-fluorophenyl)ethynyl) benzoate (0.775 g, 73.2%) as white solid, followed by obtaining 4-((2-fluorophenyl)ethynyl)benzoic acid (0.703 g), 96.0%) as pale yellow solid: LRMS (ES) m/z 239.12 $[M-H]^+$, calculated MW 240.23.

Step 2: Synthesis of N-((1-(cyclopropylamino)cyclobutyl)methyl)-4-((2-fluorophenyl)ethynyl)benzamide

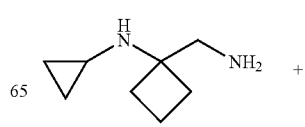

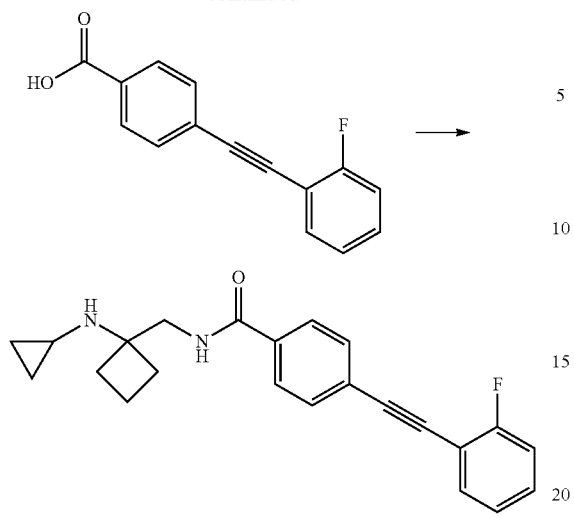

4-((2-Fluorophenyl)ethynyl)benzoic acid (0.070 g, 0.291 mmol) and 1-(aminomethyl)-N-cyclopropylcyclobutan-1-amine (0.061 g, 0.437 mmol) as starting materials were used in a similar manner to Step 3 of Example 1 to obtain N-((1-(cyclopropylamino)cyclobutyl)methyl)-4-((2-fluorophenyl)ethynyl)benzamide (0.087 g, 82.4%) was obtained as pale yellow liquid: LRMS (ES) m/z 363.12 [M+H]$^+$, calculated MW 362.45; $^1$H-NMR (400 MHz, CD$_3$OD) d 7.83 (d, J=11.2 Hz, 2H), 7.61 (d, J=10.0 Hz, 2H), 7.55 (td, J=7.6, 1.7 Hz, 1H), 7.42~7.37 (m, 1H), 7.21~7.15 (m, 2H), 3.69 (s, 2H), 2.14~2.06 (m, 3H), 2.03~1.98 (m, 2H), 1.85~1.79 (m, 2H), 0.52~0.48 (m, 2H), 0.36~0.32 (m, 2H).

Example 10: Synthesis of N-((1-(cyclopropylamino)cyclobutyl)methyl)-2-fluoro-4-(pyridin-4-ylethynyl)benzamide

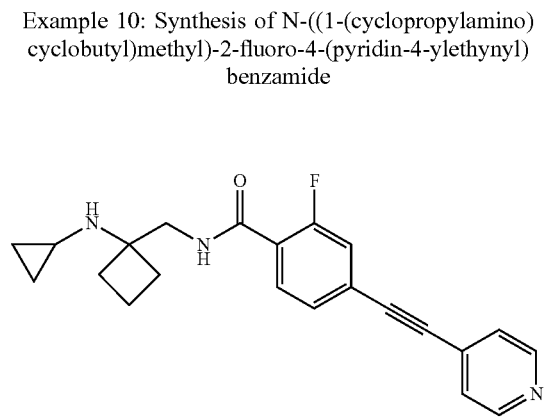

Step 1: Synthesis of 2-fluoro-4-(pyridin-4-ylethynyl)benzoic acid

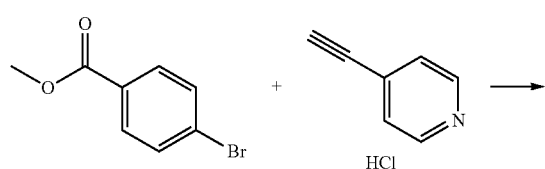

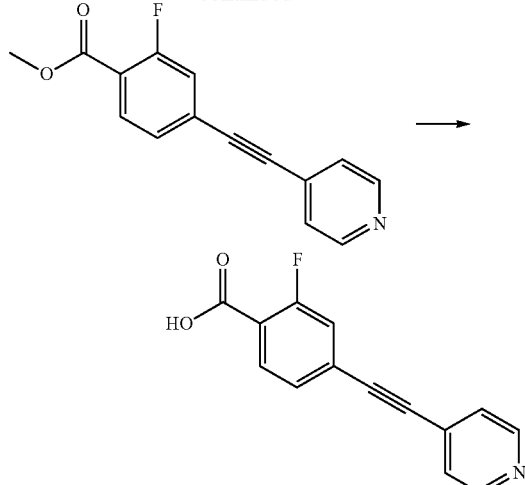

Methyl 4-bromo-2-fluorobenzoate (1.000 g, 4.291 mmol) and 4-ethynylpyridine hydrochloride (0.629 g, 4.506 mmol) as starting materials were used in a similar manner to Step 1 of Example 3 to obtain methyl 2-fluoro-4-(pyridin-4-ylethynyl)benzoate (0.786 g, 71.8%) as pale yellow solid, followed by obtaining 2-fluoro-4-(pyridin-4-ylethynyl)benzoic acid (0.568 g, 77.1%) as yellow solid: LRMS (ES) m/z 242.16 [M+H]$^+$, calculated MW 241.22.

Step 2: Synthesis of N-((1-(cyclopropylamino)cyclobutyl)methyl)-2-fluoro-4-(pyridin-4-ylethynyl)benzamide 2-Fluoro-4-(pyridin-4-ylethynyl)benzoic acid (0.070 g, 0.290 mmol) and 1-(aminomethyl)-N-cyclopropylcyclobutan-1-amine (0.061 g, 0.435 mmol) as starting materials were used in a similar manner to Step 3 of Example 1 to obtain N-((1-(cyclopropylamino)cyclobutyl)methyl)-2-fluoro-4-(pyridin-4-ylethynyl)benzamide (0.082 g, 77.7%)

as pale yellow liquid: LRMS (ES) m/z 364.17 [M+H]+, calculated MW 363.44; $^1$H-NMR (400 MHz, CD$_3$OD) d 8.56 (dd, J=4.6, 1.8 Hz, 2H), 7.81 (t, J=7.8 Hz, 1H), 7.54 (dd, J=4.6, 1.4 Hz, 2H), 7.49~7.43 (m, 2H), 3.68 (s, 2H), 2.12~2.04 (m, 3H), 2.01~1.94 (m, 2H), 1.85~1.77 (m, 2H), 0.45~0.46 (m, 2H), 0.33~0.30 (m, 2H).

Example 11: Synthesis of N-((1-(cyclopropylamino)cyclopentyl)methyl)-4-((2-fluorophenyl)ethynyl)benzamide

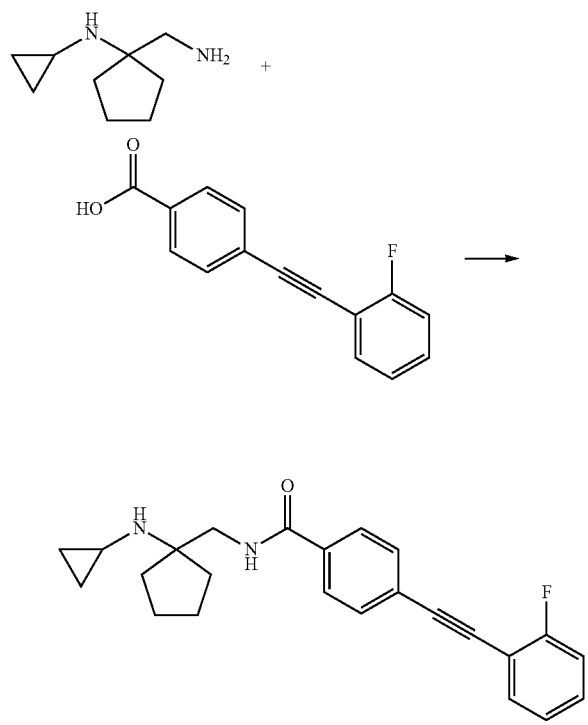

4-((2-Fluorophenyl)ethynyl)benzoic acid (0.300 g, 1.249 mmol), 1-(aminomethyl)-N-cyclopropylcyclopentan-1-amine (0.231 g, 1.499 mmol), 1-[bis(dimethylamino)methylene]-1H-1,2,3-triazolo[4,5-b]pyridinium 3-oxide hexafluorophosphate (HATU, 0.712 g, 1.873 mmol) and N,N-diisopropylethylamine (1.088 mL, 6.244 mmol) were dissolved in N,N-dimethylformamide (10 mL) at room temperature, and the resulting solution was stirred at the same temperature for 18 hours. A saturated aqueous sodium hydrogen carbonate solution was poured into the reaction mixture, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain N-((1-(cyclopropylamino)cyclopentyl)methyl)-4-((2-fluorophenyl)ethynyl)benzamide (0.230 g, 48.9%) as yellow solid: LRMS (ES) m/z 377.32 [M+H]+, calculated MW 376.48; $^1$H-NMR (400 MHz, CD$_3$OD) d 7.85 (dt, J=8.0, 1.8 Hz, 2H), 7.62 (d, J=6.4 Hz, 2H), 7.57~7.53 (m, 1H), 7.43~7.38 (m, 1H), 7.21~7.15 (m, 2H), 3.57 (s, 2H), 2.24 (m, 1H), 1.74~1.67 (m, 8H), 0.59~0.51 (m, 2H), 0.41~0.37 (m, 2H).

Example 12: Synthesis of N-((1-(cyclopropylamino)cycloheptyl)methyl)-4-((2-fluorophenyl)ethynyl)benzamide

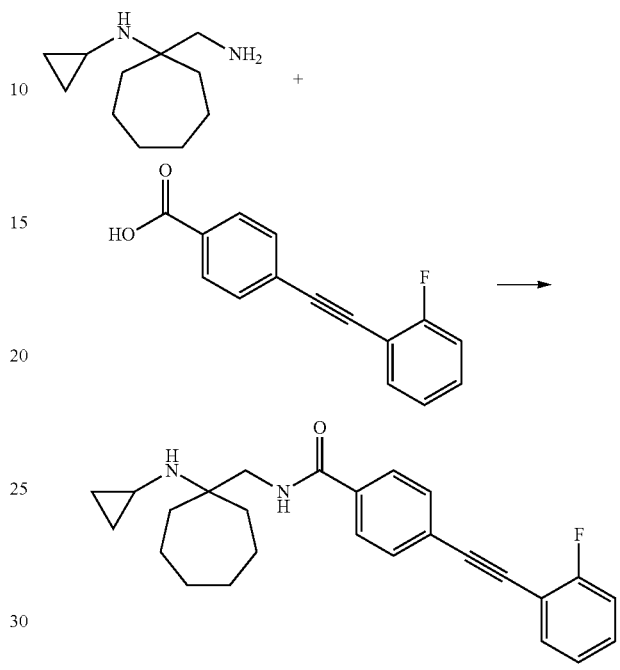

4-((2-Fluorophenyl)ethynyl)benzoic acid (0.066 g, 0.274 mmol) and 1-(aminomethyl)-N-cyclopropylcycloheptan-1-amine (0.050 g, 0.274 mmol) as starting materials were used in a similar manner to Example 11 to obtain N-((1-(cyclopropylamino)cycloheptyl)methyl)-4-((2-fluorophenyl)ethynyl)benzamide (0.040 g, 36.1%) as white solid: LRMS (ES) m/z 405.20 [M+H]+, calculated MW 404.53; $^1$H-NMR (400 MHz, CD$_3$OD) d 7.84 (d, J=8.4 Hz, 2H), 7.61 (d, J=8.0 Hz, 3H), 7.40 (m, 1H), 7.21~7.15 (m, 2H), 3.47 (s, 2H), 2.17 (m, 1H), 1.77~1.49 (m, 12H), 0.49 (m, 2H), 0.34 (m, 2H).

Example 13: Synthesis of N-((1-(cyclopropylamino)cyclopentyl)methyl)-4-((4-fluorophenyl)ethynyl)benzamide

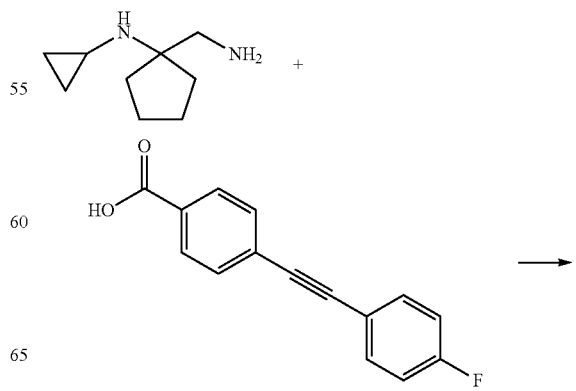

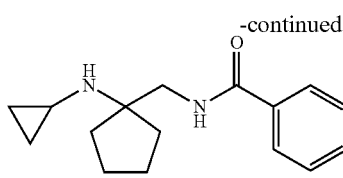

4-((4-Fluorophenyl)ethynyl)benzoic acid (0.078 g, 0.324 mmol) as a starting material instead of 4-((2-fluorophenyl)ethynyl)benzoic acid was used in a similar manner to Example 11 to obtain N-((1-(cyclopropylamino)cyclopentyl)methyl)-4-((4-fluorophenyl)ethynyl)benzamide (0.045 g, 36.9%) as white solid: LRMS (ES) m/z 377.13 [M+H]$^+$, calculated MW 376.48; $^1$H-NMR (400 MHz, CD$_3$OD) d 7.84~7.82 (m, 2H), 7.60~7.52 (m, 4H), 7.15~7.10 (m, 2H), 3.56 (s, 2H), 2.20~2.17 (m, 1H), 1.75~1.62 (m, 8H), 0.52~0.49 (m, 2H), 0.37~0.33 (m, 2H).

Example 14: Synthesis of N-((1-(cyclopropylamino)cycloheptyl)methyl)-4-((4-fluorophenyl)ethynyl)benzamide

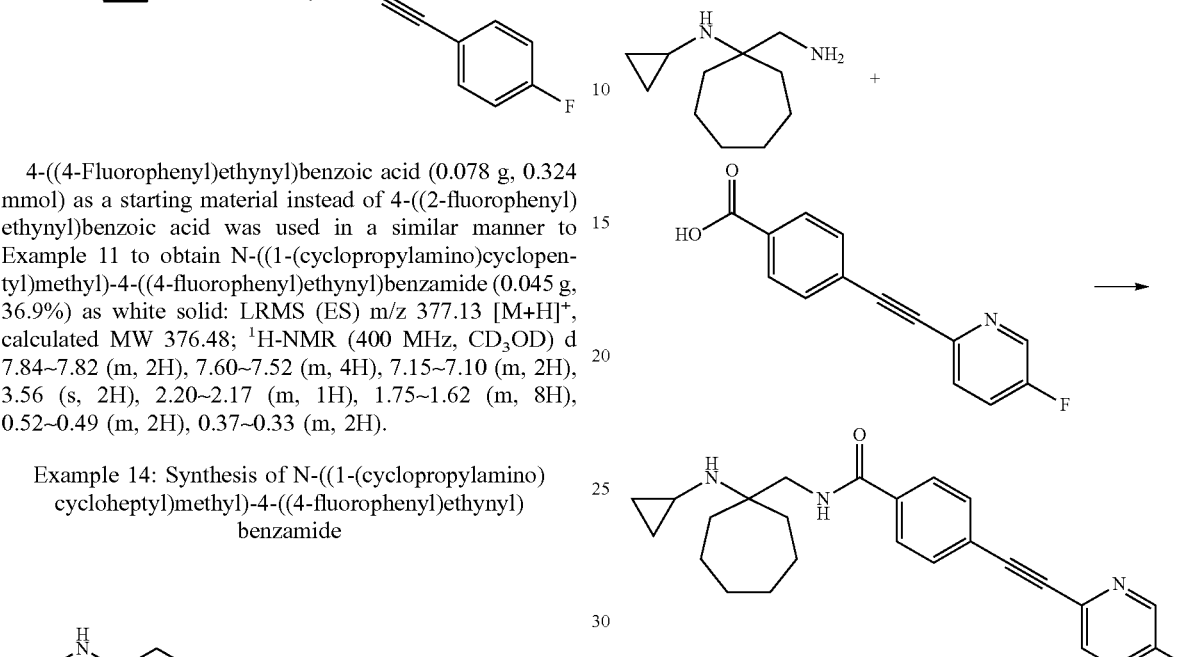

4-((4-Fluorophenyl)ethynyl)benzoic acid (0.066 g, 0.274 mmol) and 1-(aminomethyl)-N-cyclopropylcycloheptan-1-amine (0.050 g, 0.274 mmol) as starting materials were used in a similar manner to Example 11 to obtain N-((1-(cyclopropylamino)cycloheptyl)methyl)-4-((4-fluorophenyl)ethynyl)benzamide (0.035 g, 31.5%) as yellow solid: LRMS (ES) m/z 405.20 [M+H]$^+$, calculated MW 404.53; $^1$H-NMR (400 MHz, CD$_3$OD) d 7.82 (dd, J=6.8, 2.0 Hz, 2H), 7.60~7.53 (m, 4H), 7.15~7.10 (m, 2H), 3.46 (s, 2H), 2.16 (m, 1H), 1.78~1.45 (m, 12H), 0.50~0.46 (m, 2H), 0.35~0.33 (m, 2H).

Example 15: Synthesis of N-((1-(cyclopropylamino)cycloheptyl)methyl)-4-((5-fluoropyridin-2-yl)ethynyl)benzamide

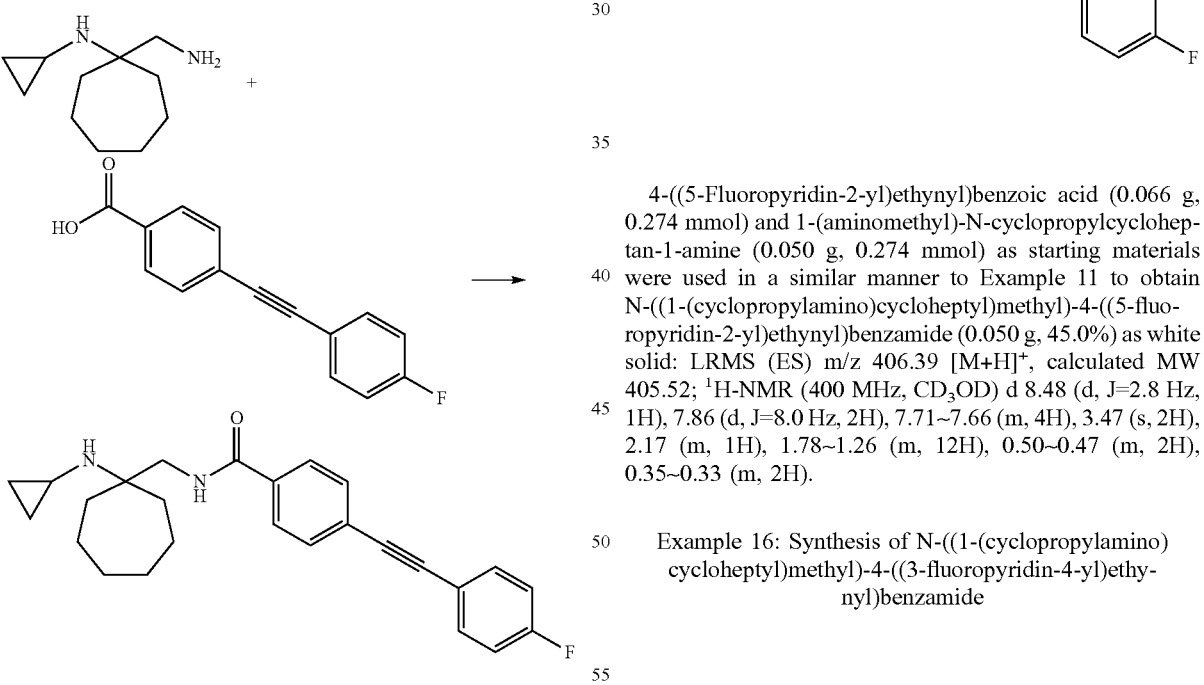

4-((5-Fluoropyridin-2-yl)ethynyl)benzoic acid (0.066 g, 0.274 mmol) and 1-(aminomethyl)-N-cyclopropylcycloheptan-1-amine (0.050 g, 0.274 mmol) as starting materials were used in a similar manner to Example 11 to obtain N-((1-(cyclopropylamino)cycloheptyl)methyl)-4-((5-fluoropyridin-2-yl)ethynyl)benzamide (0.050 g, 45.0%) as white solid: LRMS (ES) m/z 406.39 [M+H]$^+$, calculated MW 405.52; $^1$H-NMR (400 MHz, CD$_3$OD) d 8.48 (d, J=2.8 Hz, 1H), 7.86 (d, J=8.0 Hz, 2H), 7.71~7.66 (m, 4H), 3.47 (s, 2H), 2.17 (m, 1H), 1.78~1.26 (m, 12H), 0.50~0.47 (m, 2H), 0.35~0.33 (m, 2H).

Example 16: Synthesis of N-((1-(cyclopropylamino)cycloheptyl)methyl)-4-((3-fluoropyridin-4-yl)ethynyl)benzamide

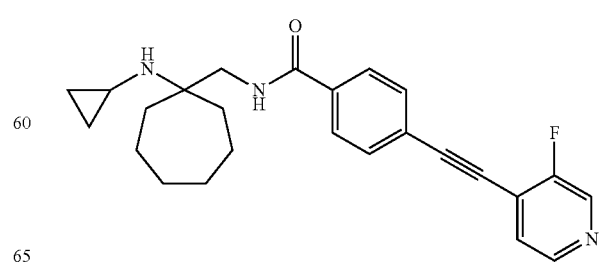

Step 1: Synthesis of 4-((3-fluoropyridin-4-yl)ethynyl)benzoic acid

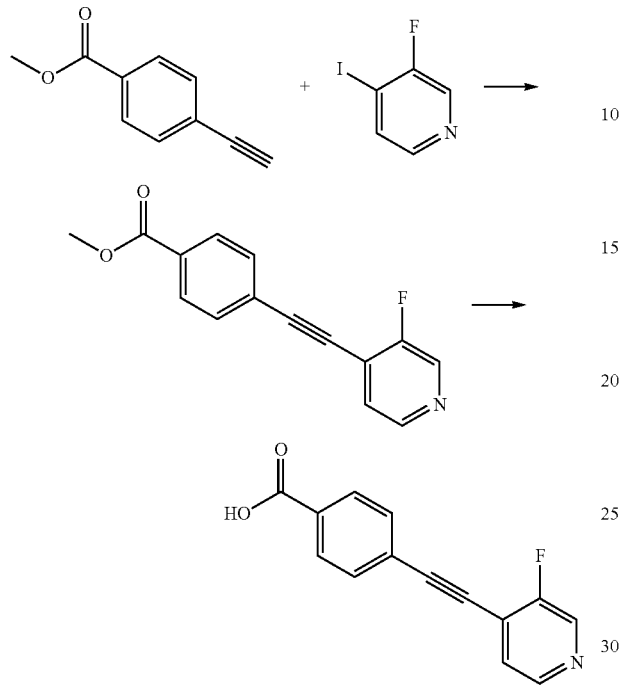

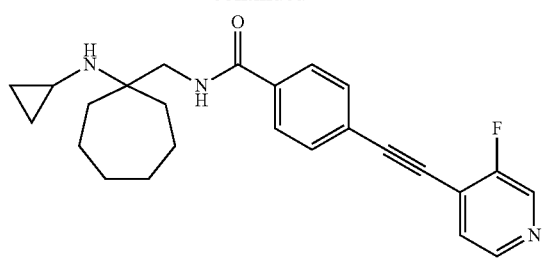 [SMILES: O=C(NCC1(NC2CC2)CCCCCC1)c1ccc(C#Cc2ccncc2F)cc1]

Methyl 4-ethynylbenzoate (2.000 g, 12.487 mmol) and 3-fluoro-4-iodopyridine (2.784 g, 12.487 mmol) were used in a similar manner to Step 1 of Example 3 to obtain methyl 4-((3-fluoropyridin-4-yl)ethynyl)benzoate (2.300 g, 72.2%) as yellow solid, followed by obtaining 4-((3-fluoropyridin-4-yl)ethynyl)benzoic acid (2.150 g, 98.9%) as beige solid: LRMS (ES) m/z 242.09 [M+H]$^+$, calculated MW 241.22.

Step 2: Synthesis of N-((1-(cyclopropylamino)cycloheptyl)methyl)-4-((3-fluoropyridin-4-yl)ethynyl)benzamide

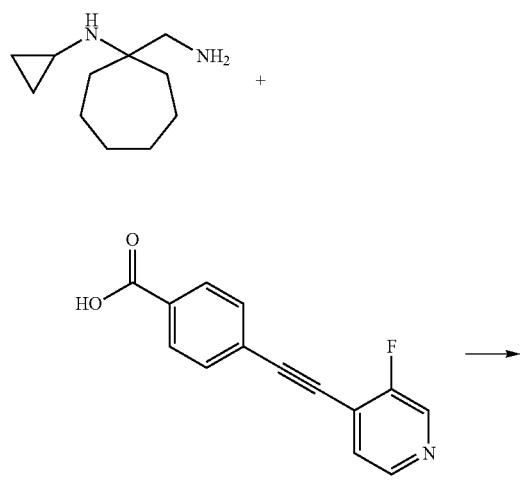

4-((3-Fluoropyridin-4-yl)ethynyl)benzoic acid (0.066 g, 0.274 mmol) and 1-(aminomethyl)-N-cyclopropylcycloheptan-1-amine (0.050 g, 0.274 mmol)) as starting materials were used in a similar manner to Example 11 to obtain N-((1-(cyclopropylamino)cycloheptyl)methyl)-4-((3-fluoropyridin-4-yl)ethynyl)benzamide (0.040 g, 36.0%) as light yellow solid: LRMS (ES) m/z 406.18 [M+H]$^+$, calculated MW 405.52; $^1$H-NMR (400 MHz, CD$_3$OD) d 8.55 (d, J=1.6 Hz, 1H), 8.41 (d, J=5.2 Hz, 1H), 7.88 (d, J=8.4 Hz, 2H), 7.69 (d, J=8.4 Hz, 2H), 7.63 (m, 1H), 3.48 (s, 2H), 2.19 (m, 1H), 1.75~1.43 (m, 12H), 0.52~0.48 (m, 2H), 0.37~0.33 (m, 2H).

Example 17: Synthesis of N-((1-(cyclopropylamino)cyclopentyl)methyl)-4-((3,4-difluorophenyl)ethynyl)benzamide

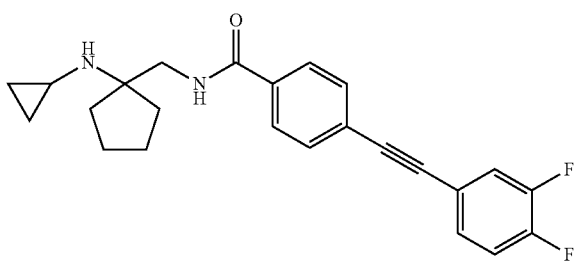 [SMILES: O=C(NCC1(NC2CC2)CCCC1)c1ccc(C#Cc2ccc(F)c(F)c2)cc1]

Step 1: Synthesis of 4-((3,4-difluorophenyl)ethynyl)benzoic acid

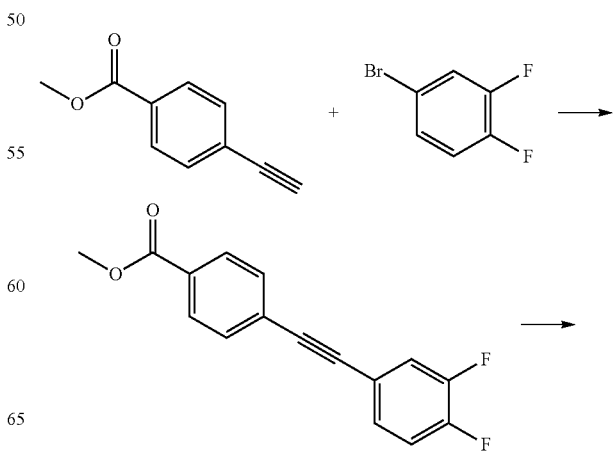

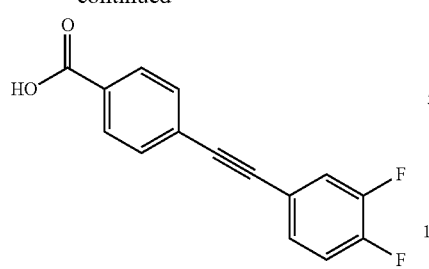

4-Bromo-1,2-difluorobenzene (1.325 g, 6.868 mmol) instead of 2-bromo-5-fluoropyridine was used in a similar manner to Step 1 of Example 3 to obtain methyl 4-((3,4-difluorophenyl)ethynyl)benzoate (0.300 g, 17.6%) as white solid, followed by obtaining 4-((3,4-difluorophenyl)ethynyl)benzoic acid (0.280 g, 98.4%) as white solid: LRMS (ES) m/z 257.05 [M−H]+, calculated MW 258.22.

Step 2: Synthesis of N-((1-(cyclopropylamino)cyclopentyl)methyl)-4-((3,4-difluorophenyl)ethynyl)benzamide

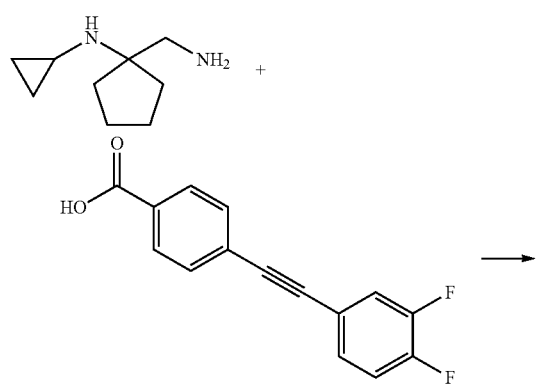

4-((3,4-Difluorophenyl)ethynyl)benzoic acid (0.084 g, 0.324 mmol) and 1-(aminomethyl)-N-cyclopropylcyclopentan-1-amine (0.050 g, 0.324 mmol) as starting materials were used in a similar manner to Example 11 to obtain N-((1-(cyclopropylamino)cyclopentyl)methyl)-4-((3,4-difluorophenyl)ethynyl)benzamide (0.030 g, 23.5%) as light yellow solid: LRMS (ES) m/z 395.19 [M+H]+, calculated MW 394.47; 1H-NMR (400 MHz, CD3OD) d 7.85~7.82 (m, 2H), 7.61~7.59 (m, 2H), 7.47 (m, 1H), 7.38~7.28 (m, 2H), 3.56 (s, 2H), 2.19~2.17 (m, 1H), 1.88~1.62 (m, 8H), 0.51~0.49 (m, 2H), 0.37~0.34 (m, 2H).

Example 18: Synthesis of N-((1-(cyclopropylamino)cycloheptyl)methyl)-4-((3,4-difluorophenyl)ethynyl)benzamide

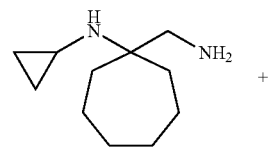

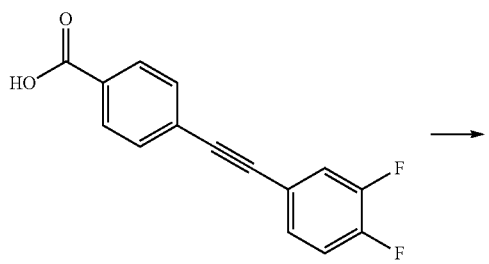

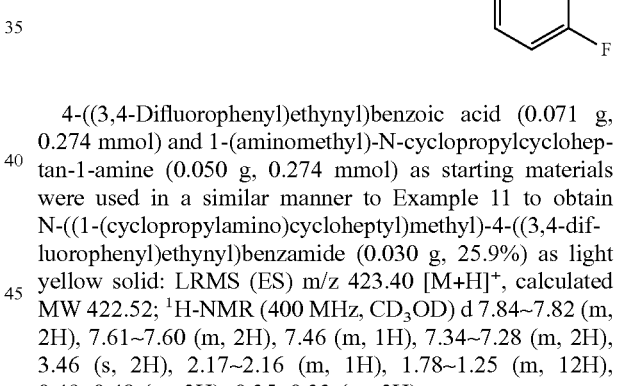

4-((3,4-Difluorophenyl)ethynyl)benzoic acid (0.071 g, 0.274 mmol) and 1-(aminomethyl)-N-cyclopropylcycloheptan-1-amine (0.050 g, 0.274 mmol) as starting materials were used in a similar manner to Example 11 to obtain N-((1-(cyclopropylamino)cycloheptyl)methyl)-4-((3,4-difluorophenyl)ethynyl)benzamide (0.030 g, 25.9%) as light yellow solid: LRMS (ES) m/z 423.40 [M+H]+, calculated MW 422.52; 1H-NMR (400 MHz, CD3OD) d 7.84~7.82 (m, 2H), 7.61~7.60 (m, 2H), 7.46 (m, 1H), 7.34~7.28 (m, 2H), 3.46 (s, 2H), 2.17~2.16 (m, 1H), 1.78~1.25 (m, 12H), 0.49~0.48 (m, 2H), 0.35~0.33 (m, 2H).

Example 19: Synthesis of N-((1-(cyclopropylamino)cyclohexyl)methyl)-4-((4-fluorophenyl)ethynyl)benzamide

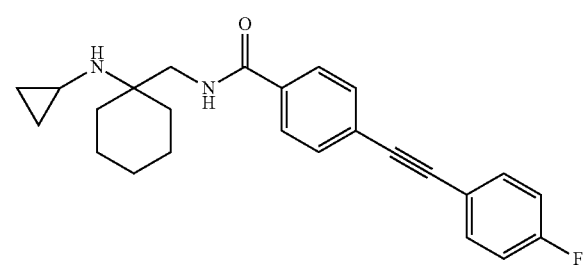 [SMILES: O=C(NCC1(NC2CC2)CCCCC1)c1ccc(C#Cc2ccc(F)cc2)cc1]

Step 1: Synthesis of 1-(aminomethyl)-N-cyclopropylcyclohexan-1-amine

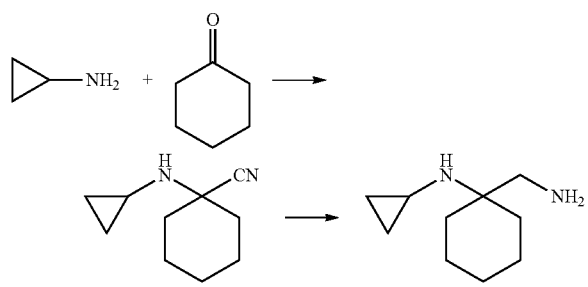

Cyclohexanone (2.112 mL, 20.377 mmol) instead of cycloheptanone was used in a similar manner to Step 2 of Example 1 to obtain 1-(aminomethyl)-N-cyclopropylcyclohexan-1-amine (2.921 g, 96.0%, white oil): LRMS (ES) m/z 169.11 [M+H]$^+$, calculated MW 168.28.

Step 2: Synthesis of N-((1-(cyclopropylamino)cyclohexyl)methyl)-4-((4-fluorophenyl)ethynyl)benzamide

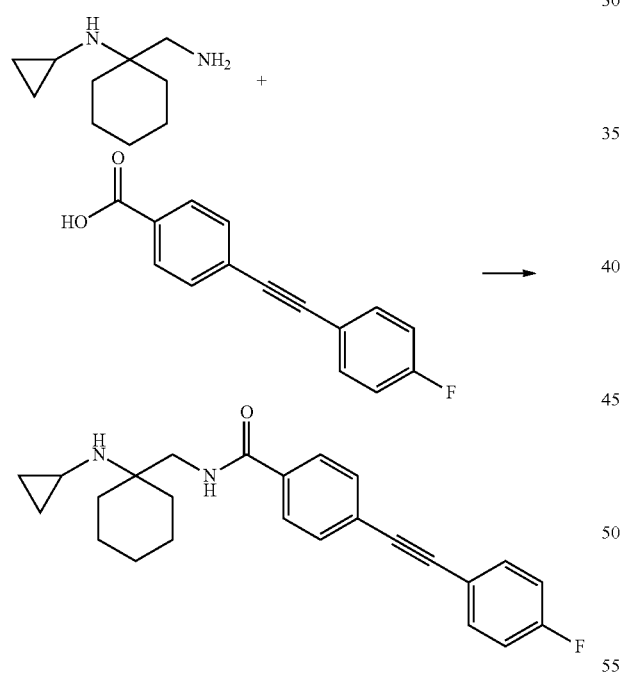

4-((4-Fluorophenyl)ethynyl)benzoic acid (0.070 g, 0.291 mmol) and 1-(aminomethyl)-N-cyclopropylcyclohexan-1-amine (0.074 g, 0.437 mmol) as starting materials were used in a similar manner to Step 3 of Example 1 to obtain N-((1-(cyclopropylamino)cyclohexyl)methyl)-4-((4-fluorophenyl)ethynyl)benzamide (0.078 g, 68.5%) as white solid: LRMS (ES) m/z 391.31 [M+H]$^+$, calculated MW 390.5; $^1$H-NMR (400 MHz, CD$_3$OD) d 7.87~7.76 (m, 2H), 7.63~7.49 (m, 4H), 7.18~7.07 (m, 2H), 3.55 (t, J=14.8 Hz, 2H), 2.22~2.12 (m, 1H), 1.58~1.37 (m, 10H), 0.54~0.42 (m, 2H), 0.37~0.28 (m, 2H).

Example 20: Synthesis of N-((1-(cyclopropylamino)cyclohexyl)methyl)-4-((2-fluorophenyl)ethynyl)benzamide

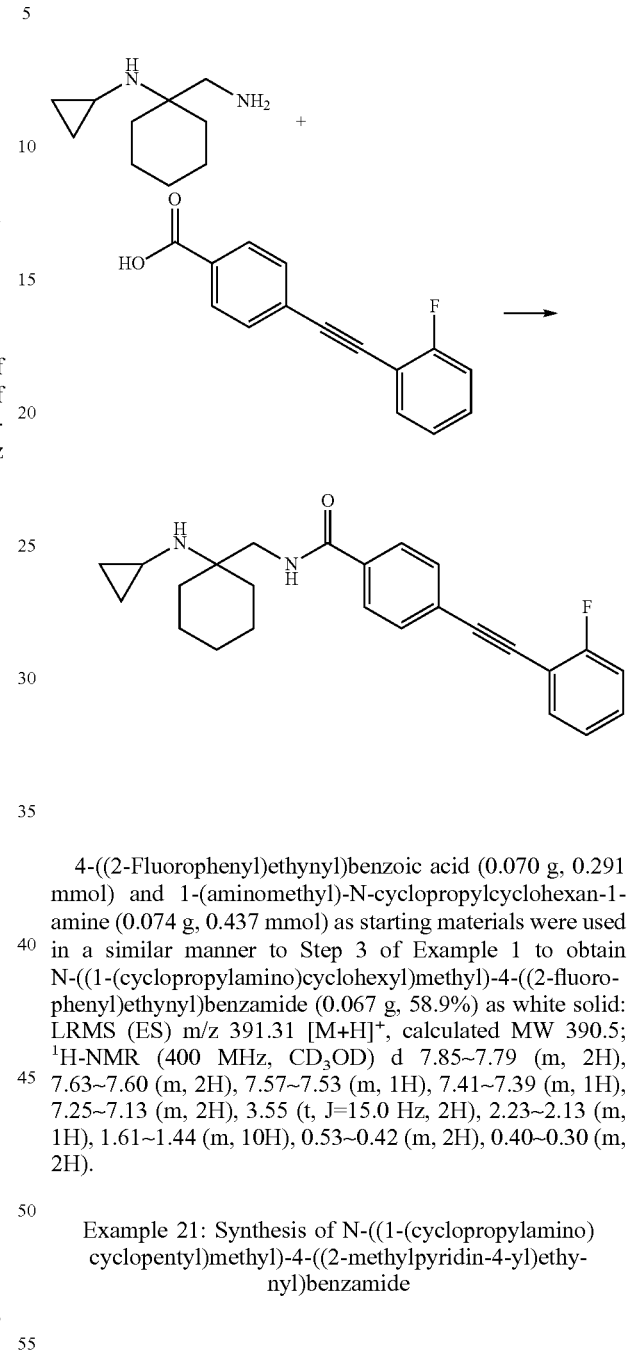

4-((2-Fluorophenyl)ethynyl)benzoic acid (0.070 g, 0.291 mmol) and 1-(aminomethyl)-N-cyclopropylcyclohexan-1-amine (0.074 g, 0.437 mmol) as starting materials were used in a similar manner to Step 3 of Example 1 to obtain N-((1-(cyclopropylamino)cyclohexyl)methyl)-4-((2-fluorophenyl)ethynyl)benzamide (0.067 g, 58.9%) as white solid: LRMS (ES) m/z 391.31 [M+H]$^+$, calculated MW 390.5; $^1$H-NMR (400 MHz, CD$_3$OD) d 7.85~7.79 (m, 2H), 7.63~7.60 (m, 2H), 7.57~7.53 (m, 1H), 7.41~7.39 (m, 1H), 7.25~7.13 (m, 2H), 3.55 (t, J=15.0 Hz, 2H), 2.23~2.13 (m, 1H), 1.61~1.44 (m, 10H), 0.53~0.42 (m, 2H), 0.40~0.30 (m, 2H).

Example 21: Synthesis of N-((1-(cyclopropylamino)cyclopentyl)methyl)-4-((2-methylpyridin-4-yl)ethynyl)benzamide

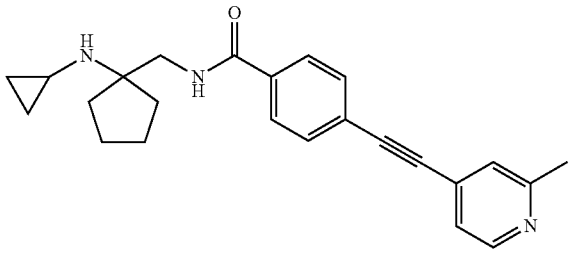 [SMILES: Cc1cc(C#Cc2ccc(C(=O)NCC3(NC4CC4)CCCC3)cc2)ccn1]

Step 1: Synthesis of 4-((2-methylpyridin-4-yl)ethynyl)benzoic acid

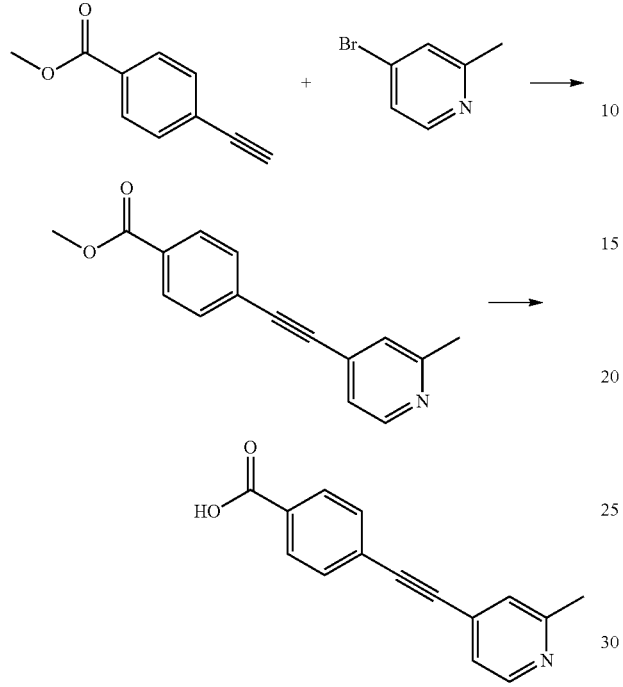

Methyl 4-ethynylbenzoate (0.400 g, 2.497 mmol) and 4-bromo-2-methylpyridine (0.473 g, 2.747 mmol) as starting materials were used in a similar manner to Step 1 of Example 3 to obtain methyl 4-((2-methylpyridin-4-yl)ethynyl)benzoate (0.531 g, 84.6%) as pale yellow solid, followed by obtaining 4-((2-methylpyridin-4-yl)ethane yl)benzoic acid (0.337 g, 89.2%) as ivory solid: LRMS (ES) m/z 238.06 [M+H]$^+$, calculated MW 237.26.

Step 2: Synthesis of N-((1-(cyclopropylamino)cyclopentyl)methyl)-4-((2-methylpyridin-4-yl)ethynyl)benzamide

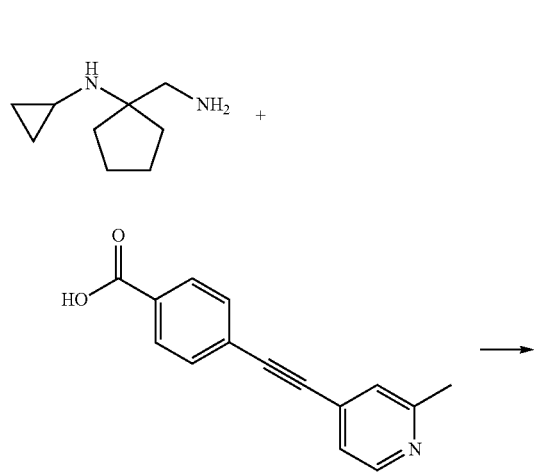

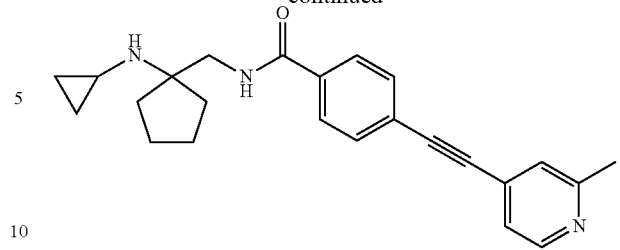

4-((2-Methylpyridin-4-yl)ethanyl)benzoic acid (0.046 g, 0.194 mmol) instead of 4-((2-fluorophenyl)ethynyl)benzoic acid was used in a similar manner to Example 11 to obtain N-((1-(cyclopropylamino)cyclopentyl)methyl)-4-((2-methylpyridin-4-yl)ethynyl)benzamide (0.020 g, 27.5%) as yellow oil: LRMS (ES) m/z 374.21 [M+H]$^+$, calculated MW 373.5; $^1$H-NMR (400 MHz, CD$_3$OD) d 8.41 (d, J=4.8 Hz, 1H), 7.88~7.85 (m, 2H), 7.66 (m, 2H), 7.42 (s, 1H), 7.34~7.33 (m, 1H), 3.57 (s, 2H), 2.53 (s, 3H), 2.21~2.20 (m, 1H), 1.78~1.66 (m, 8H), 0.52~0.49 (m, 2H), 0.38~0.36 (m, 2H).

Example 22: Synthesis of N-((4-(cyclopropylamino)tetrahydro-2H-pyran-4-yl)methyl)-4-((2-fluorophenyl)ethynyl)benzamide

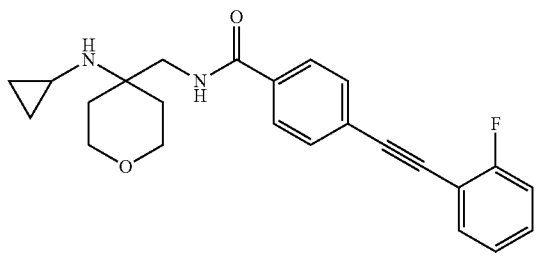 [SMILES: O=C(NCC1(NC2CC2)CCOCC1)c1ccc(C#Cc2ccccc2F)cc1]

Step 1: Synthesis of 4-(aminomethyl)-N-cyclopropyltetrahydro-2H-pyran-4-amine

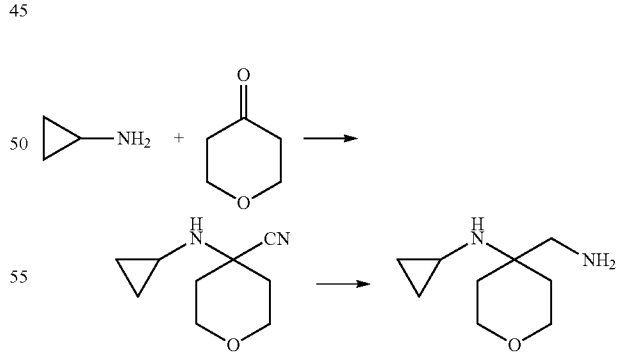

Tetrahydro-4H-pyran-4-one (8.767 g, 87.566 mmol) instead of cycloheptanone was used in a similar manner to Step 2 of Example 1 to obtain 4-(cyclopropylamino)tetrahydro-2H-pyran-4-carbonitrile (12.000 g, 82.4%, colorless oil), and then the obtained product was used without purification to obtain 4-(aminomethyl)-N-cyclopropyltetrahydro-2H-pyran-4-amine (5.100 g), 91.2%) as colorless oil: LRMS (ES) m/z 171.09 [M+H]$^+$, calculated MW 170.26.

Step 2: Synthesis of N-((4-(cyclopropylamino)tetra-hydro-2H-pyran-4-yl)methyl)-4-((2-fluorophenyl)ethynyl)benzamide Step 1: Synthesis of (1-morpholinocyclopentyl)methanamine

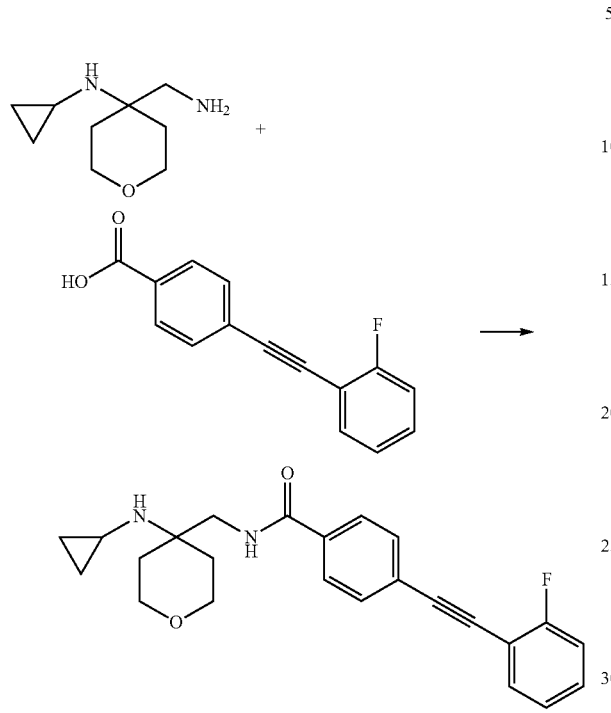

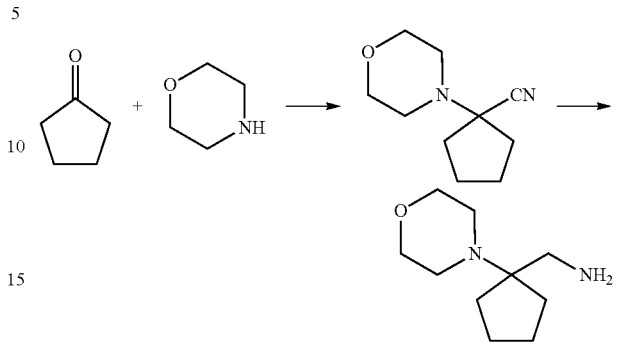

Cyclopentanone (3.000 mL, 33.880 mmol) and morpholine (3.810 mL, 44.044 mmol) as starting materials were used in a similar manner to Step 2 of Example 1 to obtain 1-morpholinocyclopentane-1-carbonitrile (5.510 g, 90.2%) as white solid, followed by obtaining (1-morpholinocyclopentyl)methanamine (5.500 g, 97.6%, light yellow liquid): LRMS (ES) m/z 185.09 [M+H]$^+$, calculated MW 184.28.

Step 2: Synthesis of 4-((2-fluorophenyl)ethynyl)-N-((1-morpholinocyclopentyl)methyl)benzamide

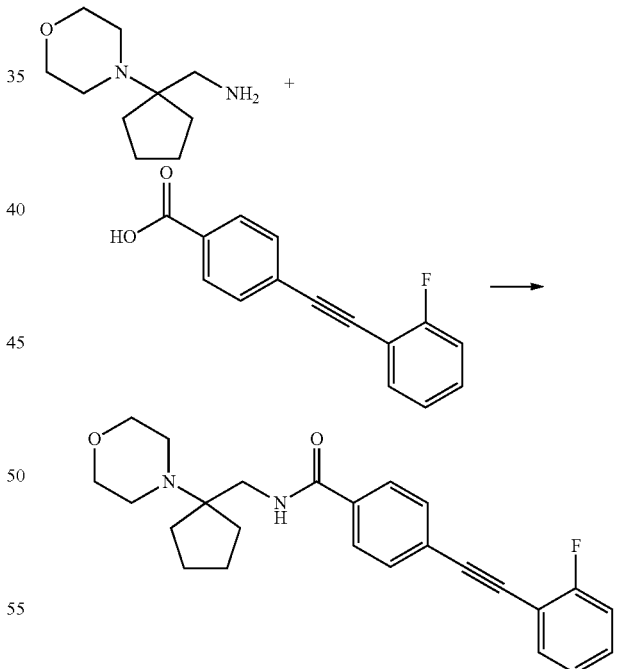

4-((2-Fluorophenyl)ethynyl)benzoic acid (0.282 g, 1.175 mmol) and 4-(aminomethyl)-N-cyclopropyltetrahydro-2H-pyran-4-amine (0.200 g, 1.175 mmol) were used in a similar manner to Example 11 to obtain N-((4-(cyclopropylamino)tetrahydro-2H-pyran-4-yl)methyl)-4-((2-fluorophenyl)ethynyl) benzamide (0.230 g, 49.9%) as white solid: LRMS (ES) m/z 393.09 [M+H]$^+$, calculated MW 392.47; $^1$H-NMR (400 MHz, CD$_3$OD) d 7.84 (d, J=8.4 Hz, 2H), 7.61 (d, J=8.4 Hz, 2H), 7.55 (m, 1H), 7.39 (m, 1H), 7.21~7.15 (m, 2H), 3.77~3.75 (m, 2H), 3.68~3.62 (m, 2H), 3.61 (s, 2H), 2.23~2.20 (m, 1H), 1.70~1.63 (m, 4H), 0.51~0.46 (m, 2H), 0.35~0.32 (m, 2H).

Example 23: Synthesis of 4-((2-fluorophenyl)ethynyl)-N-((1-morpholinocyclopentyl)methyl)benzamide

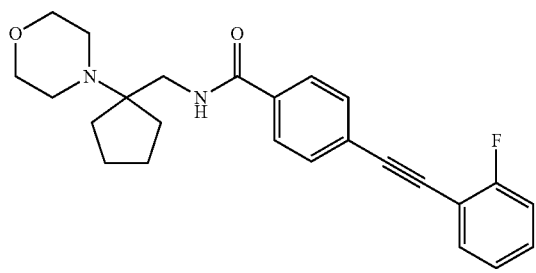 [SMILES: O=C(NCC1(N2CCOCC2)CCCC1)c1ccc(C#Cc2ccccc2F)cc1]

4-((2-Fluorophenyl)ethynyl)benzoic acid (0.091 g, 0.380 mmol) and (1-morpholinocyclopentyl)methanamine (0.070 g, 0.380 mmol) as starting materials were used in a similar manner to Example 11 to obtain 4-((2-fluorophenyl)ethynyl)-N-((1-morpholinocyclopentyl)methyl)benzamide (0.020 g, 13.0%) as colorless oil: LRMS (ES) m/z 407.10 [M+H]$^+$, calculated MW 406.5; $^1$H-NMR (400 MHz, DMSO-d$_6$) d 8.21 (t, J=6.2 Hz, 1H), 7.84 (d, J=8.4 Hz, 2H), 7.65~7.63 (m, 3H), 7.48 (m, 1H), 7.33 (m, 1H), 7.25 (m, 1H), 3.50~3.48 (m, 4H), 3.37 (m, 2H), 2.58 (m, 4H), 1.60 (m, 8H).

Example 24: Synthesis of 4-((2-fluorophenyl)ethynyl)-N-((4-(isopropylamino)tetrahydro-2H-pyran-4-yl)methyl)benzamide

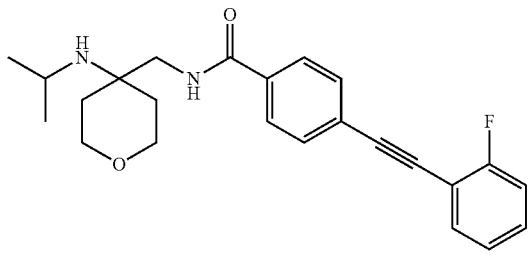 [SMILES: CC(C)NC1(CNC(=O)c2ccc(C#Cc3ccccc3F)cc2)CCOCC1]

Step 1: Synthesis of 4-(aminomethyl)-N-isopropyltetrahydro-2H-pyran-4-amine

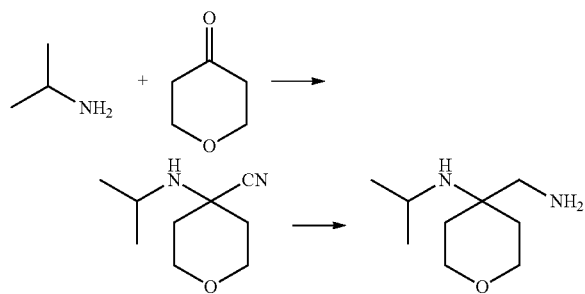

Propan-2-amine (2.060 mL, 23.971 mmol) and tetrahydro-4H-pyran-4-one (1.845 mL, 19.976 mmol) were used in a similar manner to Step 2 of Example 1 to obtain 4-(isopropylamino)tetrahydro-2H-pyran-4-carbonitrile (2.108 g, 62.7%), followed by obtaining 4-(aminomethyl)-N-isopropyltetrahydro-2H-pyran-4-amine (2.100 g, 97.6%, ivory solid): LRMS (ES) m/z 173.07 [M+H]$^+$, calculated MW 172.27.

Step 2: Synthesis of 4-((2-fluorophenyl)ethynyl)-N-((4-(isopropylamino)tetrahydro-2H-pyran-4-yl)methyl)benzamide

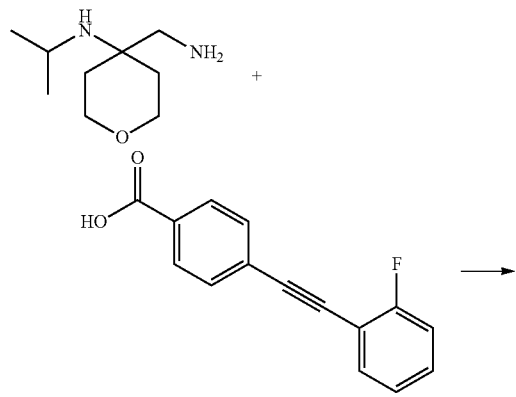

-continued

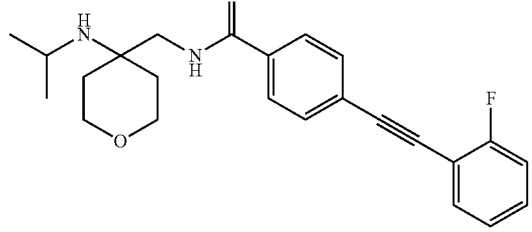

4-((2-Fluorophenyl)ethynyl)benzoic acid (0.100 g, 0.416 mmol) and 4-(aminomethyl)-N-isopropyltetrahydro-2H-pyran-4-amine (0.086 g, 0.500 mmol)) as a starting material were used in a similar manner to Example 11 to obtain 4-((2-fluorophenyl)ethynyl)-N-((4-(isopropylamino)tetrahydro-2H-pyran-4-yl)methyl)benzamide (0.018 g, 11.0%) as yellow liquid: $^1$H-NMR (400 MHz, CD$_3$OD) d 7.87~7.83 (m, 2H), 7.63~7.60 (m, 2H), 7.57~7.53 (m, 1H), 7.43~7.38 (m, 1H), 7.21~7.15 (m, 2H), 3.83~3.79 (m, 2H), 3.74~3.71 (m, 1H), 3.69~3.63 (m, 2H), 3.55 (s, 2H), 1.65 (t, J=5.4 Hz, 4H), 1.11 (d, J=6.4 Hz, 6H).

Example 25: Synthesis of 4-((2-fluorophenyl)ethynyl)-N-((1-(isopropylamino)cyclohexyl)methyl)benzamide

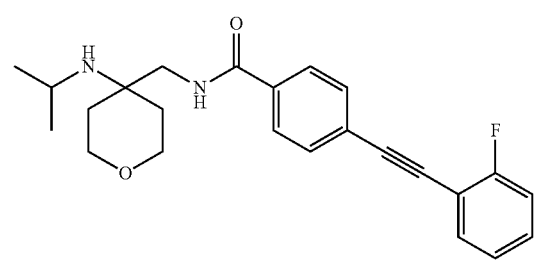 [SMILES: CC(C)NC1(CNC(=O)c2ccc(C#Cc3ccccc3F)cc2)CCOCC1]

Step 1: Synthesis of 1-(aminomethyl)-N-isopropylcyclohexan-1-amine

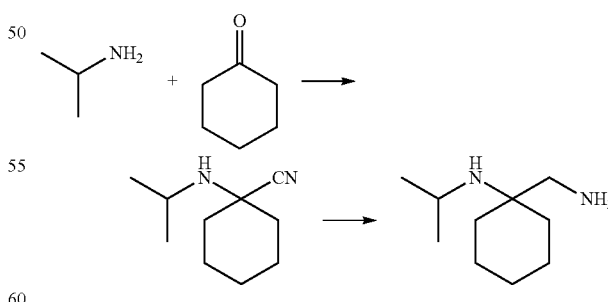

Propan-2-amine (2.000 g, 33.835 mmol) and cyclohexanone (3.321 g, 33.835 mmol) as starting materials were used in a similar manner to Step 2 of Example 1 to obtain 1-(aminomethyl)-N-isopropylcyclohexan-1-amine (3.000 g, 93.6%, colorless oil): LRMS (ES) m/z 171.09 [M+H]$^+$, calculated MW 170.3.

Step 2: Synthesis of 4-((2-fluorophenyl)ethynyl)-N-((1-(isopropylamino)cyclohexyl)methyl)benzamide Step 1: Synthesis of 1-(aminomethyl)-N-cyclopropyl-4-methylcyclohexan-1-amine

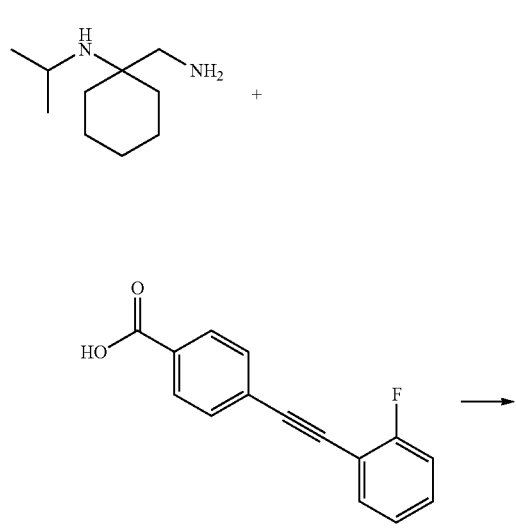

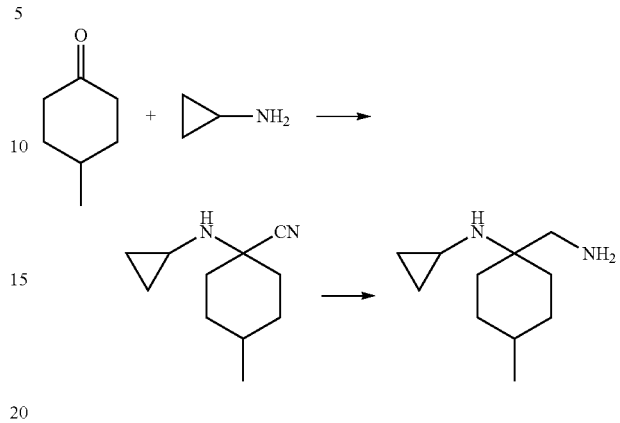

4-Methylcyclohexan-1-one (1.000 mL, 6.865 mmol) instead of cycloheptanone was used in a similar manner to Step 2 of Example 1 to obtain 1-(cyclopropylamino)-4-methylcyclohexane-1-carbonitrile (1.098 g, 89.7%) as pale yellow liquid, followed by obtaining 1-(aminomethyl)-N-cyclopropyl-4-methylcyclohexan-1-amine (0.936 g, 83.4%, pale yellow liquid): LRMS (ES) m/z 183.12 [M+H]$^+$, calculated MW 182.31.

Step 2: Synthesis of N-((1-(cyclopropylamino)-4-methylcyclohexyl)methyl)-4-((2-fluorophenyl)ethynyl)benzamide

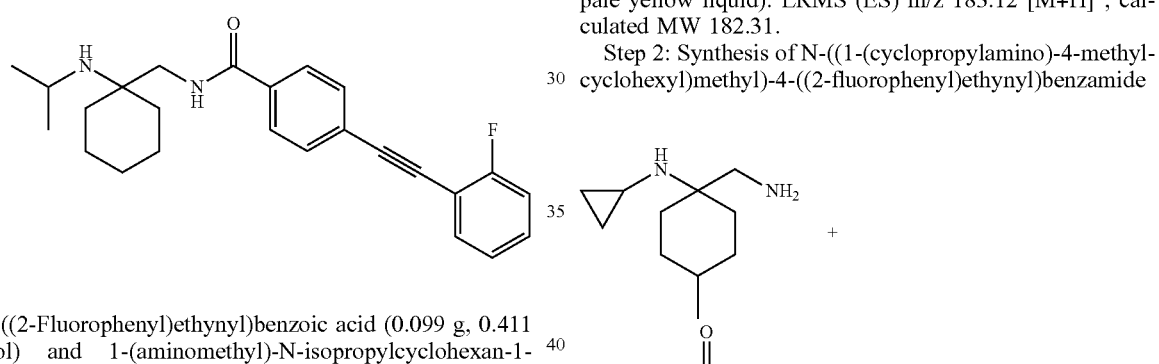

4-((2-Fluorophenyl)ethynyl)benzoic acid (0.099 g, 0.411 mmol) and 1-(aminomethyl)-N-isopropylcyclohexan-1-amine (0.070 g, 0.411 mmol) as starting materials were used in a similar manner to Example 11 to obtain 4-((2-fluorophenyl)ethynyl)-N-((1-(isopropylamino)cyclohexyl)methyl)benzamide (0.085 g, 52.7%) as colorless oil: LRMS (ES) m/z 393.23 [M+H]$^+$, calculated MW 392.52; $^1$H-NMR (400 MHz, CD$_3$OD) d 7.85 (d, J=8.4 Hz, 2H), 7.64~7.61 (m, 2H), 7.65 (m, 1H), 7.38~7.43 (m, 1H), 7.21~7.15 (m, 2H), 3.46 (s, 2H), 1.65~1.35 (m, 11H), 1.14 (s, 3H), 1.13 (s, 3H).

Example 26: Synthesis of N-((1-(cyclopropylamino)-4-methylcyclohexyl)methyl)-4-((2-fluorophenyl)ethynyl)benzamide

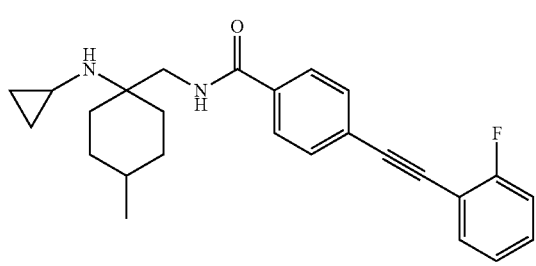 [SMILES: CC1CCC(CNC(=O)c2ccc(C#Cc3ccccc3F)cc2)(NC2CC2)CC1]

4-((2-Fluorophenyl)ethynyl)benzoic acid (0.100 g, 0.416 mmol) and 1-(aminomethyl)-N-cyclopropyl-4-methylcyclohexan-1-amine (0.114 g, 0.624 mmol) as starting materials were used in a similar manner to Step 3 of Example 1 to obtain N-((1-(cyclopropylamino)-4-methylcyclohexyl)methyl)-4-((2-fluorophenyl)ethynyl)benzamide (0.065 g, 38.6%) as yellow solid: LRMS (ES) m/z 405.26 [M+H]$^+$, calculated MW 404.53; $^1$H-NMR (400 MHz, CD$_3$OD) d 7.84 (dt, J=8.8, 2.3 Hz, 2H), 7.61 (dt, J=8.0, 1.8 Hz, 2H), 7.55 (td, J=7.4, 1.5 Hz, 1H), 7.53~7.38 (m, 1H), 7.21~7.15 (m, 2H), 3.64 (s, 2H), 2.26~2.18 (m, 1H), 1.78 (d, J=13.2 Hz, 2H), 1.60 (dd, J=13.6, 3.2 Hz, 2H), 1.51~1.37 (m, 3H), 1.25~1.18 (m, 2H), 0.93 (d, J=6.4 Hz, 3H), 0.52~0.47 (m, 2H), 0.35~0.31 (m, 2H).

Example 27: Synthesis of 4-((2-fluorophenyl)ethynyl)-N-((tetrahydro-2H-pyran-4-yl)methyl)benzamide

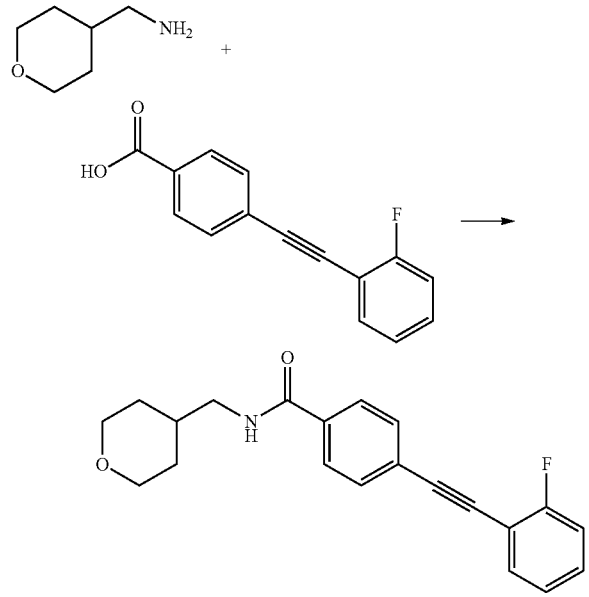

4-((2-Fluorophenyl)ethynyl)benzoic acid (0.070 g, 0.291 mmol) and (tetrahydro-2H-pyran-4-yl)methanamine (0.050 g, 0.437 mmol) as starting materials were used in a similar manner to Step 3 of Example 1 to obtain 4-((2-fluorophenyl)ethynyl)-N-((tetrahydro-2H-pyran-4-yl)methyl)benzamide (0.075 g, 76.3%) as white solid: LRMS (ES) m/z 338.21 [M+H]+, calculated MW 337.39; 1H-NMR (400 MHz, CD3OD) d 7.82 (d, J=8.8 Hz, 2H), 7.60 (d, J=8.8 Hz, 2H), 7.55 (t, J=7.6 Hz, 1H), 7.45~7.37 (m, 1H), 7.21~7.14 (m, 2H), 3.93 (dd, J=11.2, 4.0 Hz, 2H), 3.39 (t, J=11.8 Hz, 2H), 3.28~3.26 (m, 2H), 1.90~1.86 (m, 1H), 1.69 (s, 2H), 1.37~1.27 (m, 2H).

Example 28: Synthesis of 4-((2-fluorophenyl)ethynyl)-N-((1-(neopentylamino)cyclohexyl)methyl)benzamide

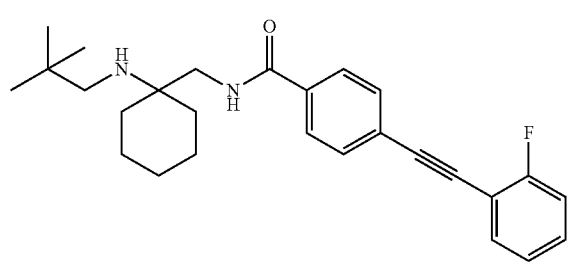 [SMILES: CC(C)(C)CNC1(CNC(=O)c2ccc(C#Cc3ccccc3F)cc2)CCCCC1]

Step 1: Synthesis of 1-(aminomethyl)-N-neopentylcyclohexan-1-amine

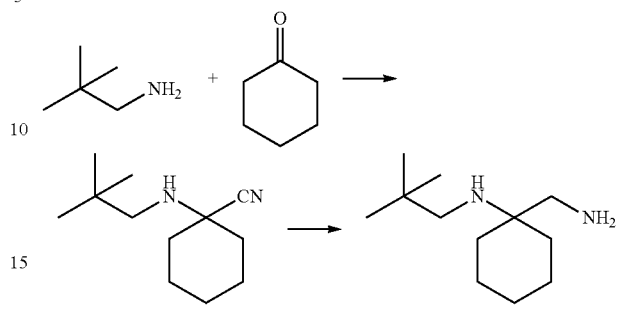

2,2-Dimethylpropan-1-amine (2.861 mL, 24.452 mmol) and cyclohexanone (2.105 mL, 20.377 mmol) as starting materials were used in a similar manner to Step 2 of Example 1 to obtain 1-(neopentylamino)cyclohexane-1-carbonitrile (3.600 g, 90.9%) as clear liquid, followed by obtaining 1-(aminomethyl)-N-neopentylcyclohexan-1-amine (3.200 g, 87.1%, white solid): LRMS (ES) m/z 199.23 [M+H]+, calculated MW 198.35.

Step 2: Synthesis of 4-((2-fluorophenyl)ethynyl)-N-((1-(neopentylamino)cyclohexyl)methyl)benzamide

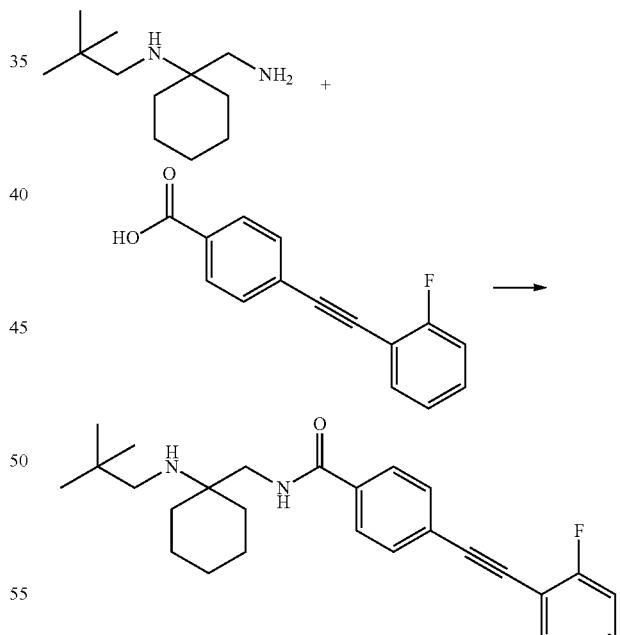

4-((2-Fluorophenyl)ethynyl)benzoic acid (0.070 g, 0.291 mmol) and 1-(aminomethyl)-N-neopentylcyclohexan-1-amine (0.087 g, 0.437 mmol) were used in a similar manner to Step 3 of Example 1 to obtain 4-((2-fluorophenyl)ethynyl)-N-((1-(neopentylamino)cyclohexyl)methyl)benzamide (0.119 g, 97.1%) as pale yellow solid: LRMS (ES) m/z 421.30 [M+H]+, calculated MW 420.57; 1H-NMR (400 MHz, CD3OD) d 7.80~7.78 (m, 2H), 7.62~7.60 (m, 2H), 7.56~7.53 (m, 1H), 7.42~7.38 (m, 1H), 7.21~7.14 (m, 2H), 3.33 (s, 2H), 2.30 (s, 2H), 1.60~1.37 (m, 10H), 0.91 (s, 9H).

Example 29: Synthesis of N-((4-(cyclopropylmethyl)tetrahydro-2H-pyran-4-yl)methyl)-4-((2-fluorophenyl)ethynyl)benzamide

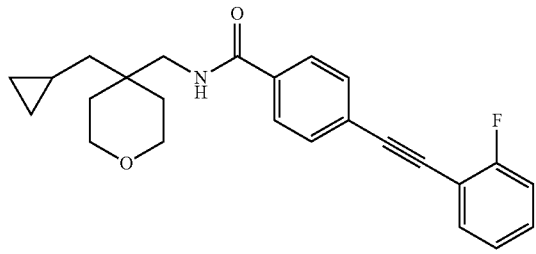 [SMILES: O=C(NCC1(CC2CC2)CCOCC1)c1ccc(C#Cc2ccccc2F)cc1]

Step 1-1: Synthesis of 4-(cyclopropylmethyl)tetrahydro-2H-pyran-4-carbonitrile

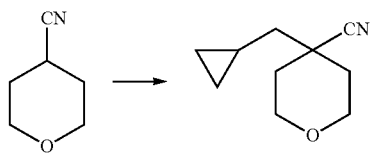 [SMILES: N#CC1CCOCC1 ; N#CC1(CC2CC2)CCOCC1]

To the solution in which tetrahydro-2H-pyran-4-carbonitrile (3.333 g, 29.989 mmol) was dissolved in tetrahydrofuran (65 mL) at −78° C., lithium bis(trimethylsilyl)amide (1.30 M solution in THF, 25.375 mL, 32.988 mmol) was added, and the reaction mixture was stirred at the same temperature for 1 hour. (Bromomethyl)cyclopropane (3.490 mL, 35.987 mmol) was added to the reaction mixture and further stirred at room temperature for 12 hours. A saturated aqueous ammonium chloride solution was poured into the reaction mixture, followed by extraction with hexane. The organic layer was washed with a saturated aqueous sodium chloride solution, dried over anhydrous magnesium sulfate, filtered and concentrated under reduced pressure. The concentrate was purified by column chromatography and concentrated to obtain 4-(cyclopropylmethyl)tetrahydro-2H-pyran-4-carbonitrile (4.600 g, 92.8%) as pale yellow liquid: $^1$H-NMR (400 MHz, CDCl$_3$) d 7.55 (d, J=3.6 Hz, 2H), 7.33 (bs, 1H), 7.46 (s, 2H), 5.52 (d, J=5.2 Hz, 1H), 2.08 (s, 3H), 1.41 (s, 9H), 1.35~1.34 (m, 1H), 1.34 (d, J=1.6 Hz, 1H), 0.88 (m, 1H), 0.76 (m, 1H), 0.65 (m, 1H).

Step 1-2: Synthesis of (4-(cyclopropylmethyl)tetrahydro-2H-pyran-4-yl)methanamine hydrochloride

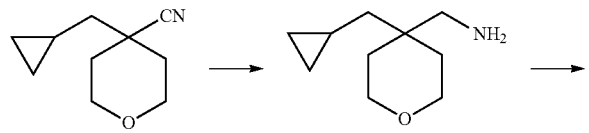

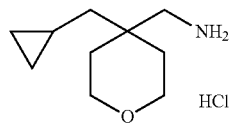

To the solution in which 4-(cyclopropylmethyl)tetrahydro-2H-pyran-4-carbonitrile (4.600 g, 27.838 mmol) was dissolved in tetrahydrofuran (200 mL) at 0° C., lithium aluminum hydride (2.40 M solution in THF, 25.518 mL, 61.244 mmol) was added, and the reaction mixture was stirred at room temperature for 3 hours. Then, water (3.010 mL, 167.030 mmol) was poured into the reaction mixture at room temperature and stirred for 30 minutes to terminate the reaction: $^1$H-NMR (400 MHz, CDCl$_3$) d 4.24~4.23 (m, 1H), 3.12, 3.12 (ABq, J=0.7, 0.4 Hz, 2H), 3.12 (q, J=0.4 Hz, 2H), 1.83 (t, J=0.4 Hz, 1H).

To the solution in which the obtained (4-(cyclopropylmethyl)tetrahydro-2H-pyran-4-yl)methanamine (4.000 g, 23.631 mmol) was dissolved in methanol (200 mL) at 0° C., hydrogen chloride (1.00 M solution in ethyl acetate, 47.262 mL, 47.262 mmol) was added, and the reaction mixture was stirred at the same temperature for 10 minutes. After removing the solvent from the reaction mixture under reduced pressure, ethyl acetate (200 mL) was added to the concentrate and stirred. The precipitated solid was filtered and washed with hexane to obtain (4-(cyclopropylmethyl)tetrahydro-2H-pyran-4-yl)methanamine hydrochloride (2.490 g, 51.2%) as white solid.

Step 2: Synthesis of N-((4-(cyclopropylmethyl)tetrahydro-2H-pyran-4-yl)methyl)-4-((2-fluorophenyl)ethynyl)benzamide

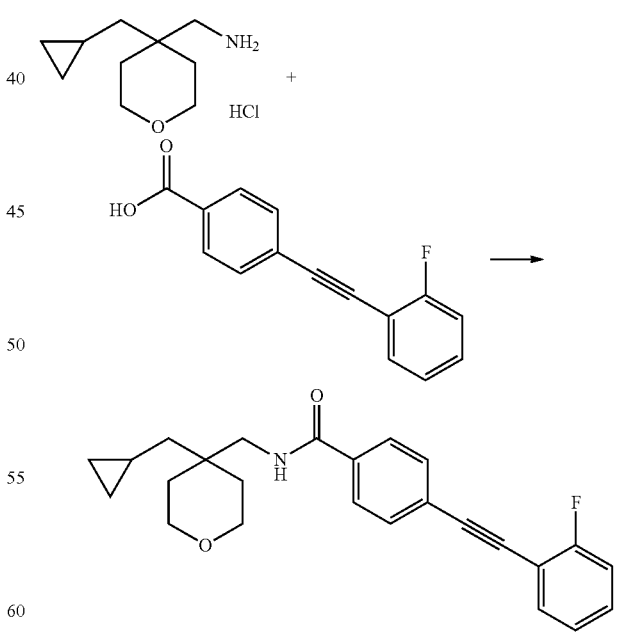

4-((2-Fluorophenyl)ethynyl)benzoic acid (0.100 g, 0.416 mmol) and (4-(cyclopropylmethyl)tetrahydro-2H-pyran-4-yl)methanamine hydrochloride (0.127 g, 0.624 mmol) as starting materials were used in a similar manner to Step 3 of Example 1 to obtain N-((4-(cyclopropylmethyl)tetrahydro- 2H-pyran-4-yl)methyl)-4-((2-fluorophenyl)ethynyl)benzamide (0.010 g, 6.1%) as white solid: LRMS (ES) m/z 392.24 [M+H]⁺, calculated MW 391.49; ¹H-NMR (400 MHz, CD₃OD) d 7.82 (d, J=0.4 Hz, 2H), 7.61 (d, J=8.4 Hz, 2H), 7.55 (td, J=7.5, 1.5 Hz, 1H), 7.43~7.37 (m, 1H), 7.21~7.15 (m, 2H), 3.77~3.75 (m, 2H), 3.68~3.64 (m, 2H), 1.64~1.55 (m, 5H), 1.41~1.39 (m, 3H), 0.82~0.76 (m, 1H), 0.50~0.48 (m, 2H), 0.09~0.05 (m, 2H).

Example 30: Synthesis of 4-((2-fluorophenyl)ethynyl)-N-((1-(isopropylamino)cyclopentyl)methyl)benzamide

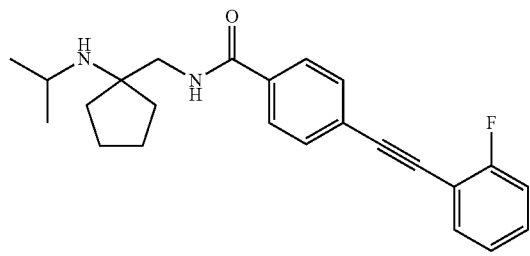 [SMILES: CC(C)NC1(CNC(=O)c2ccc(C#Cc3ccccc3F)cc2)CCCC1]

Step 1: Synthesis of 1-(aminomethyl)-N-isopropylcyclopentan-1-amine

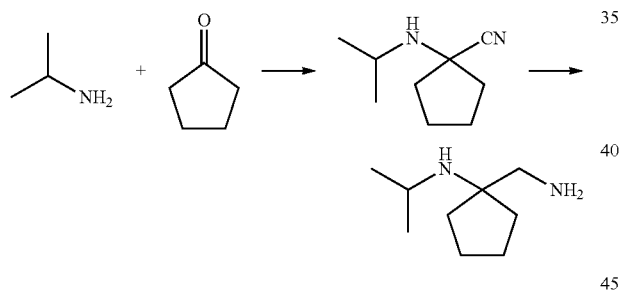

Propan-2-amine (3.504 mL, 42.796 mmol) and cyclopentanone (3.155 mL, 35.663 mmol) as starting materials were used in a similar manner to Step 2 of Example 1 to obtain 1-(isopropylamino)cyclopentane-1-carbonitrile (2.618 g, 48.2%) as white solid, followed by obtaining 1-(aminomethyl)-N-isopropylcyclopentan-1-amine (2.600 g, 96.8%, white solid): LRMS (ES) m/z 157.07 [M+H]⁺, calculated MW 156.27.

Step 2: Synthesis of 4-((2-fluorophenyl)ethynyl)-N-((1-(isopropylamino)cyclopentyl)methyl)benzamide

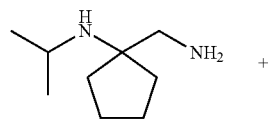 +

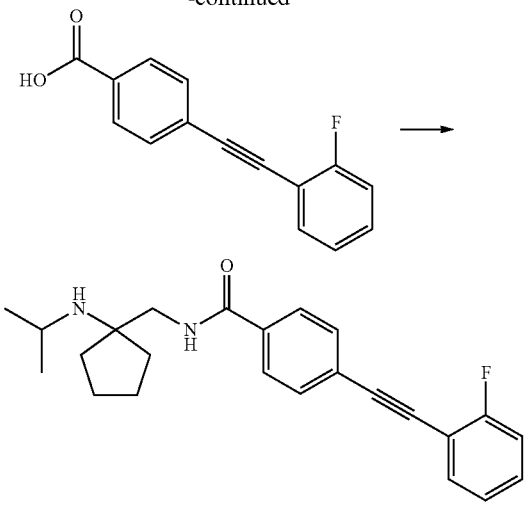

4-((2-Fluorophenyl)ethynyl)benzoic acid (0.070 g, 0.291 mmol) and 1-(aminomethyl)-N-isopropylcyclopentan-1-amine (0.068 g, 0.437 mmol) as starting materials were used in a similar manner to Step 3 of Example 1 to obtain 4-((2-fluorophenyl)ethynyl)-N-((1-(isopropylamino)cyclopentyl)methyl)benzamide (0.018 g, 16.3%) as white solid: LRMS (ES) m/z 379.30 [M+H]⁺, calculated MW 378.49; ¹H-NMR (400 MHz, CD₃OD) d 7.85 (dd, J=8.2, 1.8 Hz, 2H), 7.62 (dd, J=8.2, 1.4 Hz, 2H), 7.55~7.53 (m, 1H), 7.43~7.38 (m, 1H), 7.21~7.15 (m, 2H), 3.47 (s, 2H), 3.08 (m, 1H), 1.74~1.65 (m, 8H), 1.12~1.10 (m, 6H).

Example 31: Synthesis of 4-(pyridin-4-ylethynyl)-N-((1-((2,2,2-trifluoroethyl)amino)cyclohexyl)methyl)benzamide

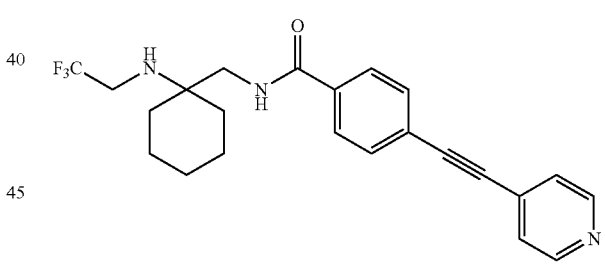

Step 1: Synthesis of 1-(aminomethyl)-N-(2,2,2-trifluoroethyl)cyclohexan-1-amine

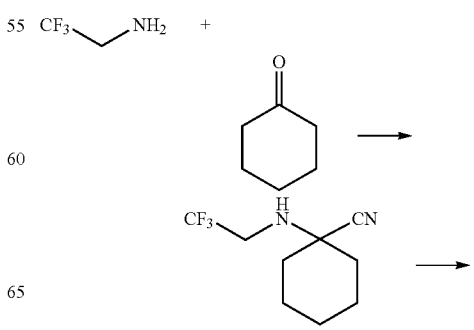

-continued

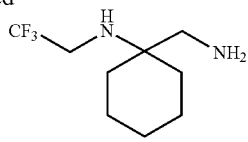

Cyclohexanone (3.000 g, 30.565 mmol) and 2,2,2-trifluoroethan-1-amine (3.633 g, 36.679 mmol) as starting materials were used in a similar manner to Step 2 of Example 1 to obtain 1-(aminomethyl)-N-(2,2,2-trifluoroethyl)cyclohexan-1-amine (3.230 g, 94.3%, white solid): LRMS (ES) m/z 211.12 [M+H]+, calculated MW 210.24.

Step 2: Synthesis of 4-(pyridin-4-ylethynyl)-N-((1-((2,2,2-trifluoroethyl)amino)cyclohexyl)methyl)benzamide

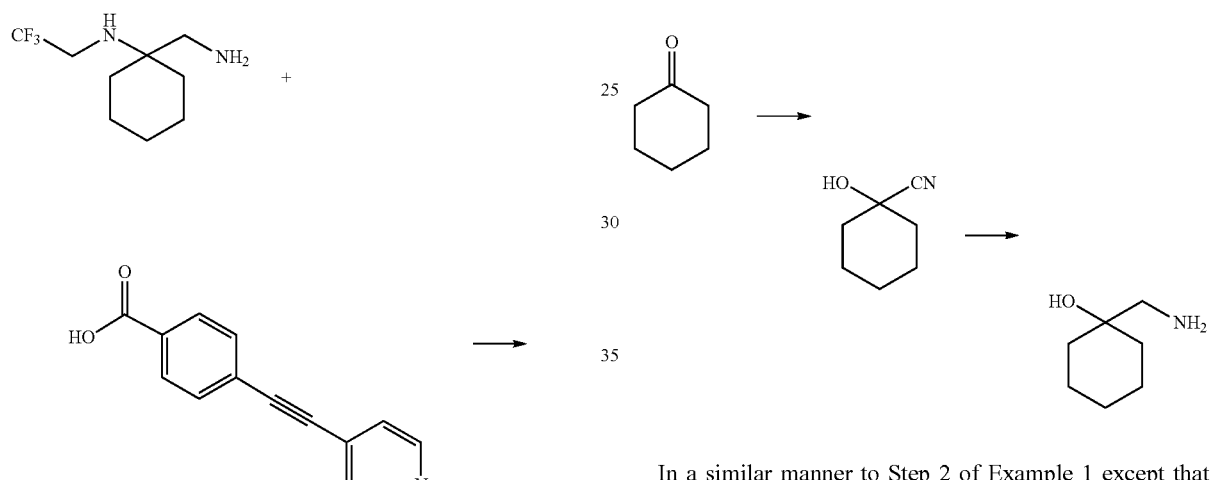

4-(Pyridin-4-ylethynyl)benzoic acid (0.070 g, 0.314 mmol) and 1-(aminomethyl)-N-(2,2,2-trifluoroethyl)cyclohexan-1-amine (0.099 g, 0.470 mmol) as starting materials were used in a similar manner to Step 3 of Example 1 to obtain 4-(pyridin-4-ylethynyl)-N-((1-((2,2,2-trifluoroethyl)amino)cyclohexyl)methyl)benzamide (0.060 g, 46.1%) as white solid: LRMS (ES) m/z 416.29 [M+H]+, calculated MW 415.46; $^1$H-NMR (400 MHz, CD$_3$OD) d 8.56~8.54 (m, 2H), 7.83 (d, J=8.4 Hz, 2H), 7.66 (d, J=8.4 Hz, 2H), 7.54~7.53 (m, 2H), 3.36 (s, 2H), 3.27~3.20 (m, 2H), 1.66~1.31 (m, 10H).

Example 32: Synthesis of 4-((2-fluorophenyl)ethynyl)-N-((1-hydroxycyclohexyl)methyl)benzamide

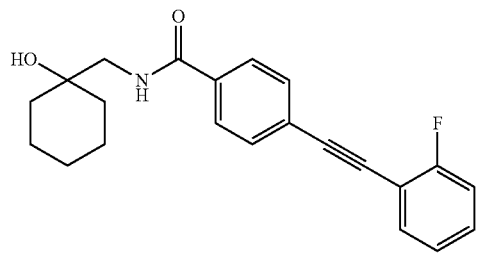 [SMILES: O=C(NCC1(O)CCCCC1)c1ccc(C#Cc2ccccc2F)cc1]

Step 1: Synthesis of 1-(aminomethyl)cyclohexan-1-ol

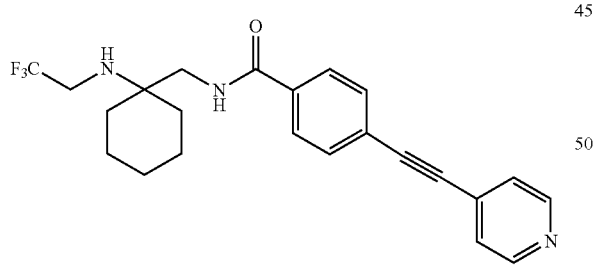

In a similar manner to Step 2 of Example 1 except that only cyclohexanone (3.000 g, 30.565 mmol) was used instead of cyclopropanamine and cycloheptanone, 1-hydroxycyclohexane-1-carbonitrile (3.400 g, 88.9%, colorless oil) was obtained and subsequently 1-(aminomethyl)cyclohexan-1-ol (2.750 g, 98.7%, colorless oil) was obtained: LRMS (ES) m/z 129.99 [M+H]+, calculated MW 129.2.

Step 2: Synthesis of 4-((2-fluorophenyl)ethynyl)-N-((1-hydroxycyclohexyl)methyl)benzamide

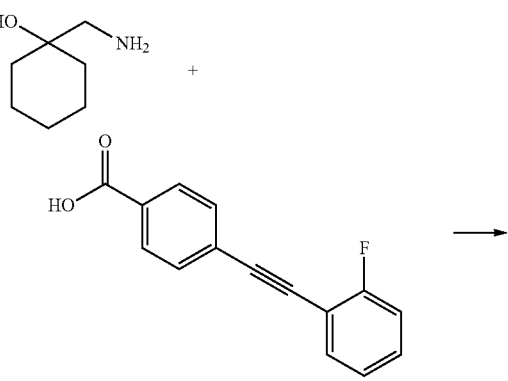

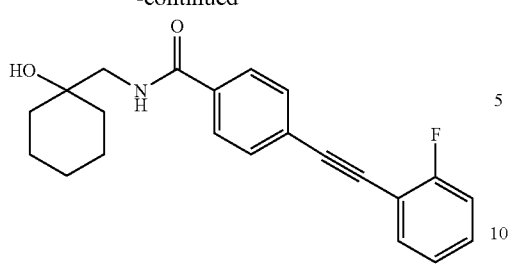

1-(Aminomethyl)cyclohexan-1-ol (0.200 g, 1.548 mmol) instead of 1-(aminomethyl)-N-cyclopropylcyclopentan-1-amine was used in a similar manner to Example 11 to obtain 4-((2-fluorophenyl)ethynyl)-N-((1-hydroxycyclohexyl)methyl)benzamide (0.350 g, 64.3%) as yellow solid: LRMS (ES) m/z 352.15 [M+H]$^+$, calculated MW 351.42; $^1$H-NMR (400 MHz, DMSO-$d_6$) d 8.27 (t, J=5.6 Hz, 1H), 7.88 (m, 2H), 7.65~7.61 (m, 3H), 7.47 (m, 1H), 7.43 (t, J=23.4 Hz, 1H), 7.28 (t, J=14.8 Hz, 1H), 4.33 (s, 1H), 3.24 (d, J=6.0 Hz, 2H), 1.53~1.15 (m, 10H).

Example 33: Synthesis of 4-((4-fluorophenyl)ethynyl)-N-((tetrahydro-2H-pyran-4-yl)methyl)benzamide

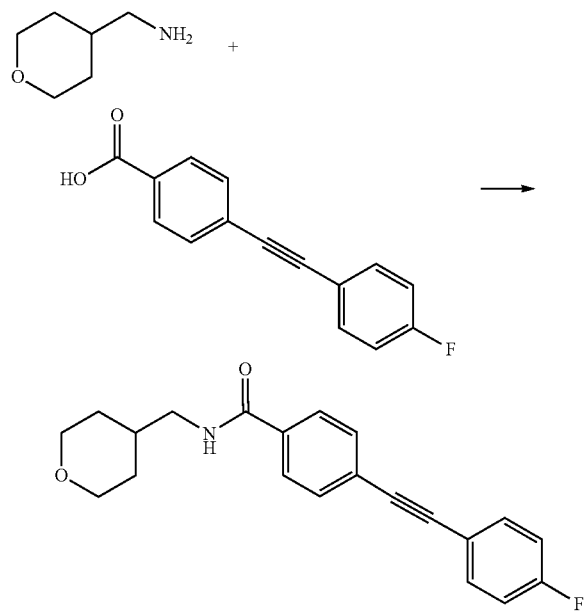

4-((4-Fluorophenyl)ethynyl)benzoic acid (0.070 g, 0.291 mmol) and (tetrahydro-2H-pyran-4-yl)methanamine (0.050 g, 0.437 mmol) as starting materials were used in a similar manner to Step 3 of Example 1 to obtain 4-((4-fluorophenyl)ethynyl)-N-((tetrahydro-2H-pyran-4-yl)methyl)benzamide (0.073 g, 74.3%) as white solid: LRMS (ES) m/z 338.15 [M+H]$^+$, calculated MW 337.39; $^1$H-NMR (400 MHz, CD$_3$OD) d 7.80 (d, J=8.4 Hz, 2H), 7.58~7.53 (m, 4H), 7.12 (t, J=9.0 Hz, 2H), 3.93 (dd, J=11.6, 2.8 Hz, 2H), 3.39 (td, J=11.7, 2.0 Hz, 2H), 3.31~3.25 (m, 2H), 1.94~1.83 (m, 1H), 1.66 (dd, J=13.4, 1.8 Hz, 2H), 1.37~1.27 (m, 2H).

Example 34: Synthesis of 4-((2-fluorophenyl)ethynyl)-N-((1-(pyridin-3-yl)cyclopentyl)methyl)benzamide

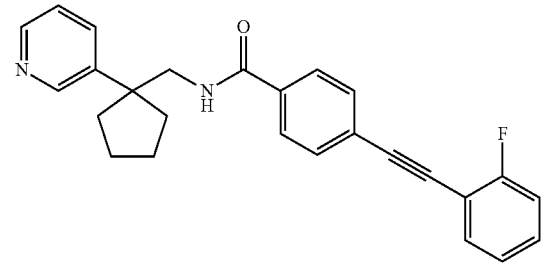 [SMILES: O=C(NCC1(c2cccnc2)CCCC1)c1ccc(C#Cc2ccccc2F)cc1]

Step 1-1: Synthesis of 1-(pyridin-3-yl)cyclopentane-1-carbonitrile

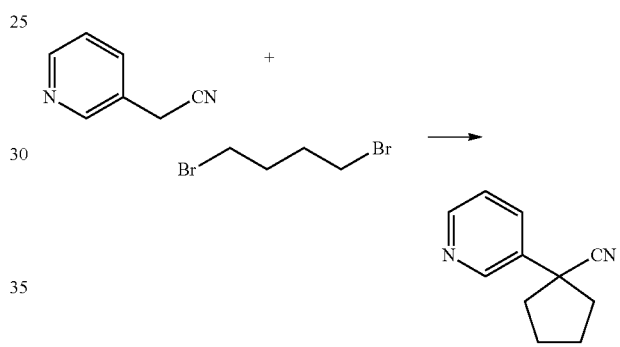

To a stirred solution of sodium hydride (NaH, 60.00%, 0.745 g, 18.622 mmol) in dimethylsulfoxide (15 mL)/diethylether (5 mL), 2-(pyridin-3-yl)acetonitrile (1.000 g, 8.465 mmol) was added at 0° C. The reaction mixture was stirred at the same temperature for 0.5 hr, treated at the room temperature with 1,4-dibromobutane (1.828 g, 8.465 mmol), stirred for additional 1 hr, and partitioned between dichloromethane and water. The organic layer was washed with aqueous saturated sodium chloride solution, separated, dried over anhydrous Na$_2$SO$_4$, filtered and concentrated in vacuo. The residue was chromatographed and concentrated to obtain 1-(pyridin-3-yl)cyclopentane-1-carbonitrile as pink oil (0.387 g, 26.5%): LRMS (ES) m/z 173.00 [M+H]$^+$, calculated MW 172.23.

Step 1-2: Synthesis of (1-(pyridin-3-yl)cyclopentyl)methanamine

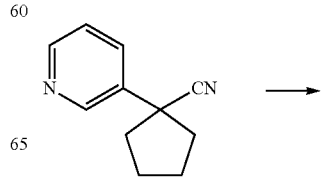

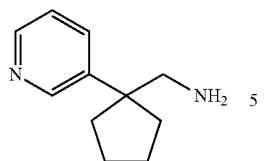

1-(Pyridin-3-yl)cyclopentane-1-carbonitrile (0.378 g, 2.195 mmol) and lithium aluminum hydride (2.40 M solution, 1.829 mL, 4.389 mmol) were dissolved in diethyl ether (50 mL), and the resulting solution was stirred at 0° C. for 0.5 hour and further stirred at room temperature for 18 hours. Then, sodium hydroxide (NaOH) (1.00 M solution in water, 1.097 mL, 1.097 mmol) and water (0.237 mL, 13.168 mmol) were added to the reaction mixture at room temperature and stirred for 30 minutes to terminate the reaction. Water was poured into the reaction mixture, followed by extraction with dichloromethane. The organic layer was washed with a saturated aqueous sodium chloride solution, dried over anhydrous sodium sulfate, filtered and concentrated under reduced pressure. The obtained product was used without further purification ((1-(pyridin-3-yl)cyclopentyl)methanamine, 0.222 g, 57.4%, yellow liquid): LRMS (ES) m/z 177.02 [M+H]$^+$, calculated MW 176.26.

Step 2: Synthesis of 4-((2-fluorophenyl)ethynyl)-N-((1-(pyridin-3-yl)cyclopentyl)methyl)benzamide

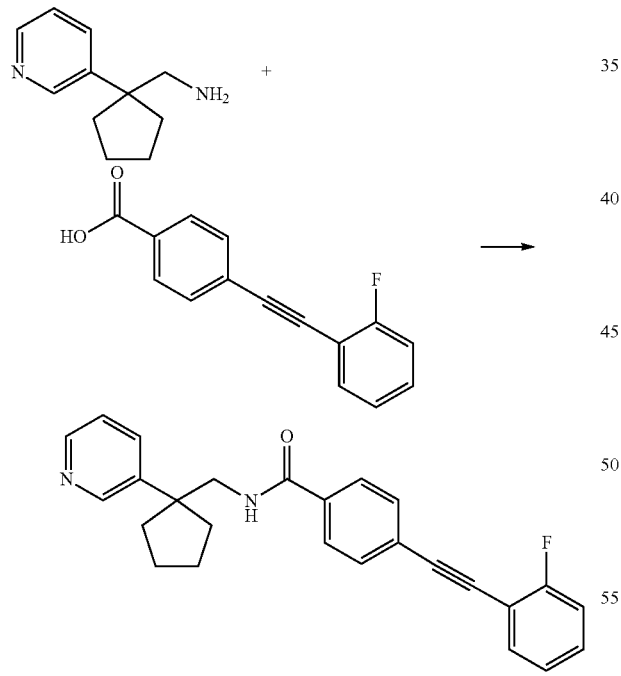

(1-(Pyridin-3-yl)cyclopentyl)methanamine (0.050 g, 0.284 mmol) and 4-((2-fluorophenyl)ethynyl)benzoic acid (0.068 g, 0.284 mmol) as starting materials were used in a similar manner to Example 11 to obtain 4-((2-fluorophenyl)ethynyl)-N-((1-(pyridin-3-yl)cyclopentyl)methyl)benzamide (0.055 g, 48.7%) as beige solid: LRMS (ES) m/z 399.24 [M+H]$^+$, calculated MW 398.48; $^1$H-NMR (400 MHz, DMSO-d$_6$) d 8.48 (d, J=2.4 Hz, 1H), 8.32 (m, 2H), 7.70 (d, J=8.8 Hz, 2H), 7.68~7.57 (m, 4H), 7.48 (m, 1H), 7.38~7.25 (m, 3H), 3.42 (d, J=6.4 Hz, 2H), 2.08 (m, 2H), 2.08~1.74 (m, 4H), 1.61 (m, 2H).

Example 35: Synthesis of 2-fluoro-4-((2-fluorophenyl)ethynyl)-N-((tetrahydro-2H-pyran-4-yl)methyl)benzamide Step 1: Synthesis of 2-fluoro-4-((2-fluorophenyl)ethynyl)benzoic acid

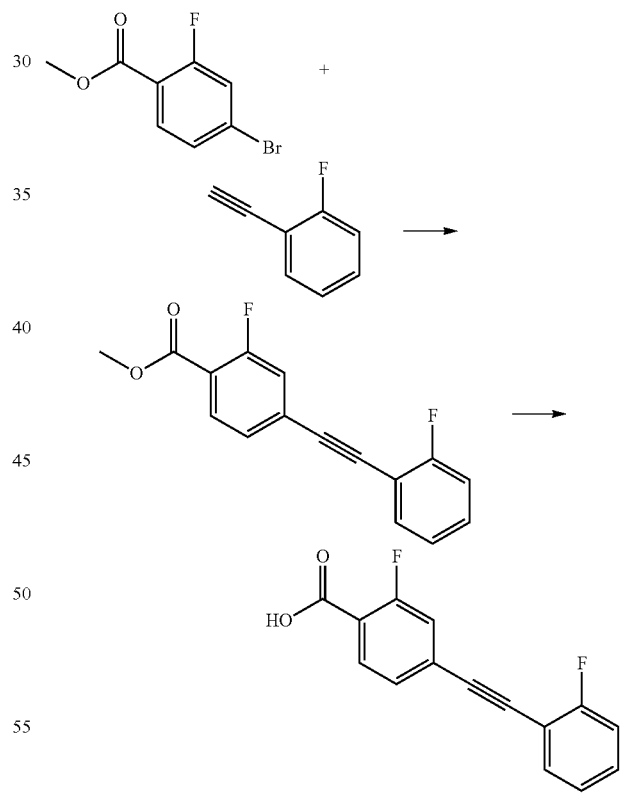

Methyl 4-bromo-2-fluorobenzoate (2.000 g, 8.582 mmol) and 1-ethynyl-2-fluorobenzene (1.031 g, 8.582 mmol) as starting materials were used in a similar manner to Step 1 of Example 3 to obtain methyl 2-fluoro-4-((2-fluorophenyl)ethynyl)benzoate (2.000 g, 85.6%) as white solid, followed by obtaining 2-fluoro-4-((2-fluorophenyl)ethynyl)benzoic acid (1.850 g, 97.5%) as white solid: LRMS (ES) m/z 258.94 [M+H]$^+$, calculated MW 258.22.

Step 2: Synthesis of 2-fluoro-4-((2-fluorophenyl)ethynyl)-N-((tetrahydro-2H-pyran-4-yl)methyl)benzamide

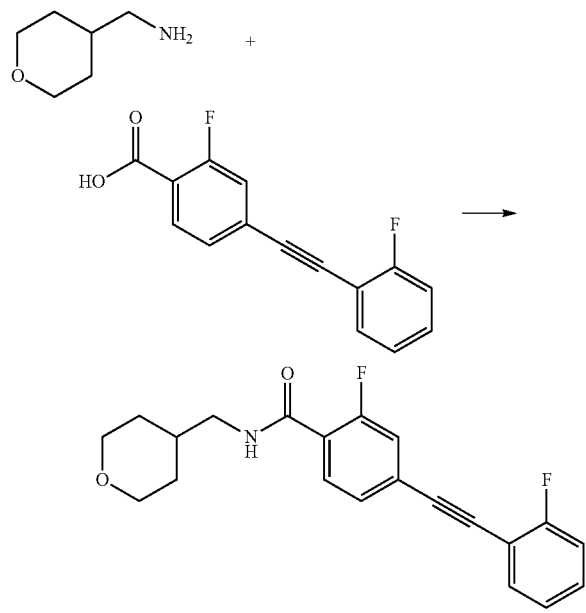

2-Fluoro-4-((2-fluorophenyl)ethynyl)benzoic acid (0.070 g, 0.271 mmol) and (tetrahydro-2H-pyran-4-yl)methanamine (0.046 mL, 0.407 mmol) as starting materials were used in a similar manner to Step 3 of Example 1 to obtain 2-fluoro-4-((2-fluorophenyl)ethynyl)-N-((tetrahydro-2H-pyran-4-yl)methyl)benzamide (0.077 g, 79.9%) as white solid: LRMS (ES) m/z 356.11 [M+H]$^+$, calculated MW 355.38; $^1$H-NMR (400 MHz, CD$_3$OD) d 7.68 (t, J=7.6 Hz, 1H), 7.56 (td, J=7.6, 1.6 Hz, 1H), 7.43~7.40 (m, 2H), 7.36 (dd, J=11.0, 1.4 Hz, 1H), 7.22~7.13 (m, 2H), 3.94 (dd, J=11.6, 2.8 Hz, 2H), 3.40 (td, J=11.8, 1.9 Hz, 2H), 3.32~3.26 (m, 2H), 1.93~1.82 (m, 1H), 1.68 (dd, J=12.8, 2.0 Hz, 2H), 1.38~1.28 (m, 2H).

Example 36: Synthesis of 4-((2-fluorophenyl)ethynyl)-N-((4-methyltetrahydro-2H-pyran-4-yl)methyl)benzamide

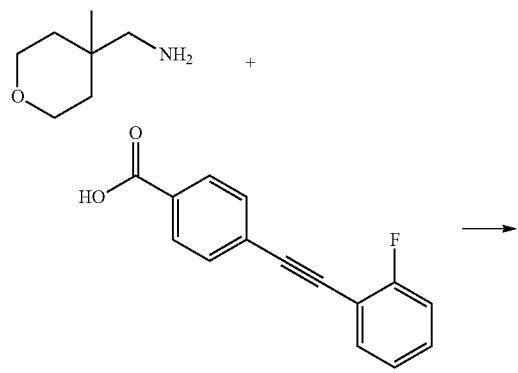

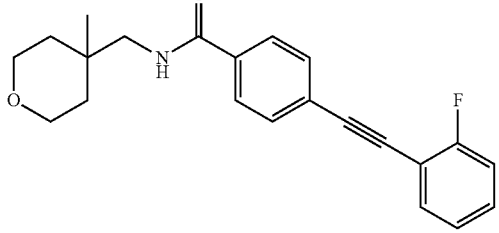

4-((2-Fluorophenyl)ethynyl)benzoic acid (0.070 g, 0.291 mmol) and (4-methyltetrahydro-2H-pyran-4-yl)methanamine (0.056 g, 0.437 mmol) as starting materials were used in a similar manner to Step 3 of Example 1 to obtain 4-((2-fluorophenyl)ethynyl)-N-((4-methyltetrahydro-2H-pyran-4-yl)methyl)benzamide (0.045 g, 43.9%) as white solid: LRMS (ES) m/z 352.22 [M+H]$^+$, calculated MW 351.42; $^1$H-NMR (400 MHz, CD$_3$OD) d 7.82 (dt, J=8.8, 1.9 Hz, 2H), 7.61 (d, J=8.8 Hz, 2H), 7.55 (td, J=7.5, 1.5 Hz, 1H), 7.43~7.37 (m, 1H), 7.21~7.15 (m, 2H), 3.72~3.74 (m, 2H), 3.67~3.61 (m, 2H), 3.32 (s, 2H), 1.61~1.54 (m, 2H), 1.37~1.33 (m, 2H), 1.05 (s, 3H).

Example 37: Synthesis of 4-((2-fluorophenyl)ethynyl)-N-((1-(hydroxymethyl)cyclohexyl)methyl)benzamide

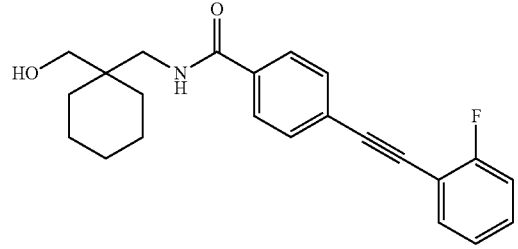 [SMILES: O=C(NCC1(CO)CCCCC1)c1ccc(C#Cc2ccccc2F)cc1]

Step 1: Synthesis of (1-(aminomethyl)cyclohexyl)methanol

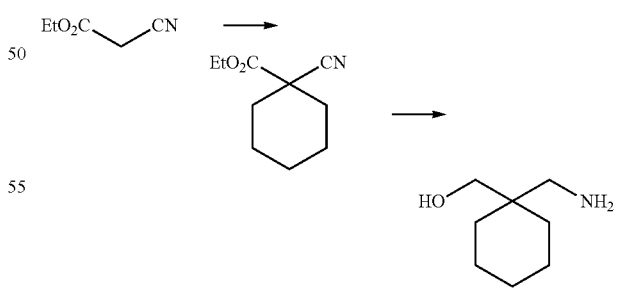

Ethyl 2-cyanoacetate (5.377 mL, 50.389 mmol) was dissolved in N,N-dimethylformamide (200 mL), and cesium carbonate (Cs$_2$CO$_3$, 41.044 g, 125.972 mmol) and 1,5-dibromopentane (6.816 mL, 50.389 mmol) was added thereto at 0° C., followed by stirring at the same temperature for 30 minutes and further stirring at room temperature for 12 hours. Water was poured into the reaction mixture, followed by extraction with ethyl acetate. The organic layer was washed with a saturated aqueous sodium chloride solution, dried over anhydrous sodium sulfate, filtered and concentrated under reduced pressure to obtain ethyl 1-cyanocyclohexane-1-carboxylate (7.050 g, 77.2%, colorless liquid). To the solution in which the obtained product was dissolved in tetrahydrofuran (200 mL) at 0° C., lithium aluminum hydride (2.40 M solution in THF, 43.681 mL, 104.833 mmol) was added, and the reaction mixture was stirred at room temperature for 3 hours. Then, water (4.534 mL, 251.600 mmol) was poured into the reaction mixture and stirred for 30 minutes to terminate the reaction. The reaction mixture was filtered through a Celite pad to remove solids, and the solvent was removed from the filtrate under reduced pressure. The obtained product was used without further purification ((1-(aminomethyl)cyclohexyl)methanol, 5.260 g, 87.6%, colorless liquid).

Step 2: Synthesis of 4-((2-fluorophenyl)ethynyl)-N-((1-(hydroxymethyl)cyclohexyl)methyl)benzamide

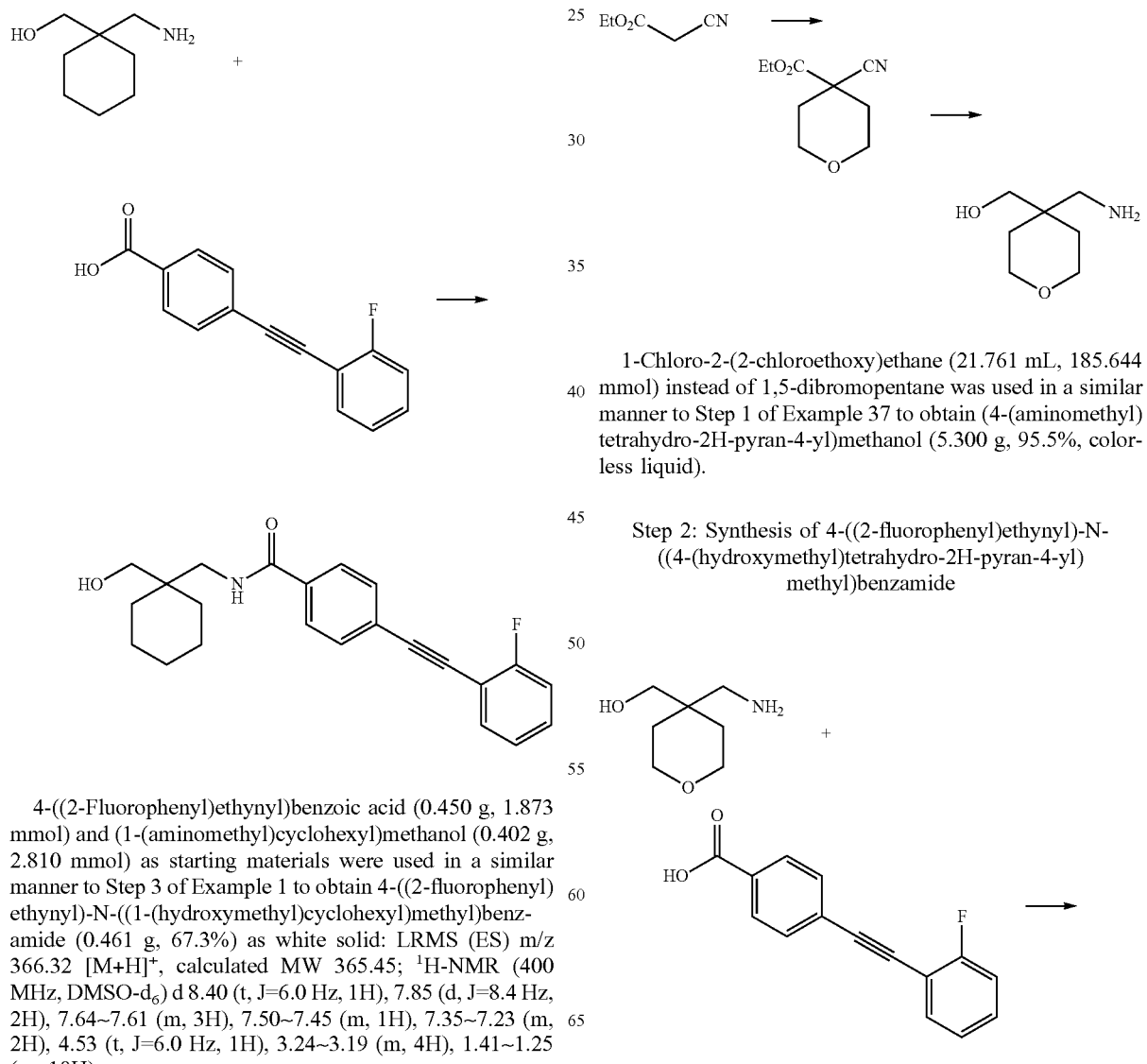

4-((2-Fluorophenyl)ethynyl)benzoic acid (0.450 g, 1.873 mmol) and (1-(aminomethyl)cyclohexyl)methanol (0.402 g, 2.810 mmol) as starting materials were used in a similar manner to Step 3 of Example 1 to obtain 4-((2-fluorophenyl)ethynyl)-N-((1-(hydroxymethyl)cyclohexyl)methyl)benzamide (0.461 g, 67.3%) as white solid: LRMS (ES) m/z 366.32 [M+H]$^+$, calculated MW 365.45; $^1$H-NMR (400 MHz, DMSO-d$_6$) d 8.40 (t, J=6.0 Hz, 1H), 7.85 (d, J=8.4 Hz, 2H), 7.64~7.61 (m, 3H), 7.50~7.45 (m, 1H), 7.35~7.23 (m, 2H), 4.53 (t, J=6.0 Hz, 1H), 3.24~3.19 (m, 4H), 1.41~1.25 (m, 10H).

Example 38: Synthesis of 4-((2-fluorophenyl)ethynyl)-N-((4-(hydroxymethyl)tetrahydro-2H-pyran-4-yl)methyl)benzamide Step 1: Synthesis of (4-(aminomethyl)tetrahydro-2H-pyran-4-yl)methanol

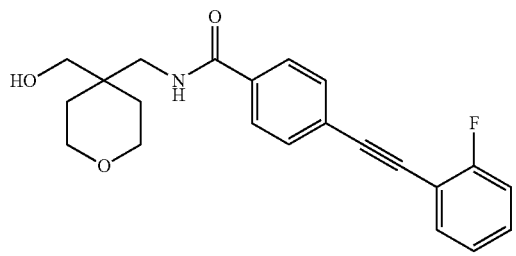 [SMILES: O=C(NCC1(CO)CCOCC1)c1ccc(C#Cc2ccccc2F)cc1]

1-Chloro-2-(2-chloroethoxy)ethane (21.761 mL, 185.644 mmol) instead of 1,5-dibromopentane was used in a similar manner to Step 1 of Example 37 to obtain (4-(aminomethyl)tetrahydro-2H-pyran-4-yl)methanol (5.300 g, 95.5%, colorless liquid).

Step 2: Synthesis of 4-((2-fluorophenyl)ethynyl)-N-((4-(hydroxymethyl)tetrahydro-2H-pyran-4-yl)methyl)benzamide -continued

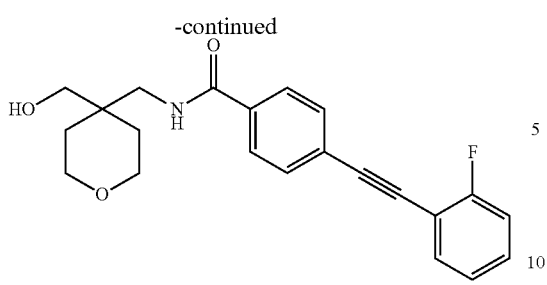

(4-(Aminomethyl)tetrahydro-2H-pyran-4-yl)methanol (0.300 g, 2.066 mmol) and 4-((2-fluorophenyl)ethynyl)benzoic acid (0.496 g, 2.066 mmol) as starting materials were used in a similar manner to Example 11 to obtain 4-((2-fluorophenyl)ethynyl)-N-((4-(hydroxymethyl)tetrahydro-2H-pyran-4-yl)methyl)benzamide (0.450 g, 59.3%) as white solid: LRMS (ES) m/z 368.27 [M+H]$^+$, calculated MW 367.42; $^1$H-NMR (400 MHz, DMSO-$d_6$) d 8.48 (t, J=6.2 Hz, 1H), 7.86 (d, J=8.0 Hz, 2H), 7.65~7.63 (m, 3H), 7.48 (m, 1H), 7.33 (m, 1H), 7.27~7.25 (m, 1H), 4.61 (t, J=6.0 Hz, 1H), 3.58~3.48 (m, 4H), 3.32~3.25 (m, 4H), 1.36~1.28 (m, 4H).

Example 39: Synthesis of N-((4,4-difluorocyclohexyl)methyl)-4-((2-fluorophenyl)ethynyl)benzamide

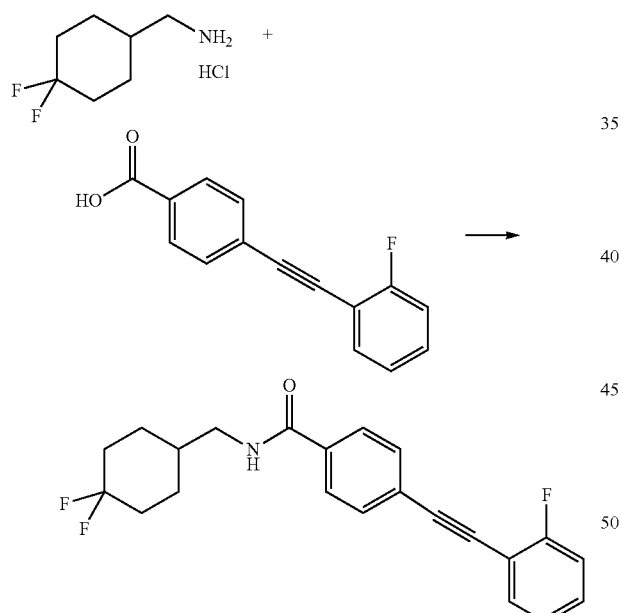

4-((2-Fluorophenyl)ethynyl)benzoic acid (0.200 g, 0.833 mmol) and (4,4-difluorocyclohexyl)methanamine hydrochloride (0.232 g, 1.249 mmol) as starting materials were used in a similar manner to Step 3 of Example 1 to obtain N-((4,4-difluorocyclohexyl)methyl)-4-((2-fluorophenyl)ethynyl)benzamide (0.175 g, 56.6%) as white solid: LRMS (ES) m/z 372.23 [M+H]$^+$, calculated MW 371.4; $^1$H-NMR (400 MHz, DMSO-$d_6$) d 8.63 (t, J=6.0 Hz, 1H), 7.87 (d, J=8.8 Hz, 2H), 7.65~7.61 (m, 3H), 7.49~7.45 (m, 1H), 7.33 (t, J=9.2 Hz, 1H), 7.25 (td, J=7.6, 1.2 Hz, 1H), 3.14 (t, J=6.4 Hz, 2H), 2.01~1.96 (m, 2H), 1.81~1.66 (m, 5H), 1.22~1.13 (m, 2H).

Example 40: Synthesis of 4-((2-fluorophenyl)ethynyl)-N-((tetrahydro-2H-pyran-3-yl)methyl)benzamide

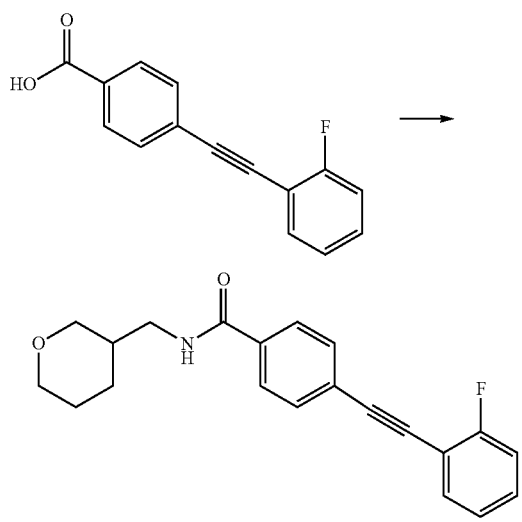

4-((2-Fluorophenyl)ethynyl)benzoic acid (0.200 g, 0.833 mmol) and (tetrahydro-2H-pyran-3-yl)methanamine (0.144 g, 1.249 mmol) as starting materials were used in a similar manner to Step 3 of Example 1 to obtain 4-((2-fluorophenyl)ethynyl)-N-((tetrahydro-2H-pyran-3-yl)methyl)benzamide (0.157 g, 55.9%) as white solid: LRMS (ES) m/z 338.21 [M+H]$^+$, calculated MW 337.39; $^1$H-NMR (400 MHz, DMSO-$d_6$) d 8.56 (t, J=5.8 Hz, 1H), 7.86 (d, J=8.8 Hz, 2H), 7.65~7.61 (m, 3H), 7.48~7.45 (m, 1H), 7.33 (t, J=9.2 Hz, 1H), 7.24 (td, J=14.9, 10.1 Hz, 1H), 3.75~3.65 (m, 2H), 3.28~3.23 (m, 1H), 3.13~3.06 (m, 3H), 1.82~1.72 (m, 2H), 1.57~1.52 (m, 1H), 1.47~1.37 (m, 1H), 1.25~1.16 (m, 1H).

Example 41: Synthesis of 4-((2-fluorophenyl)ethynyl)-N-((4-hydroxytetrahydro-2H-pyran-4-yl)methyl)benzamide

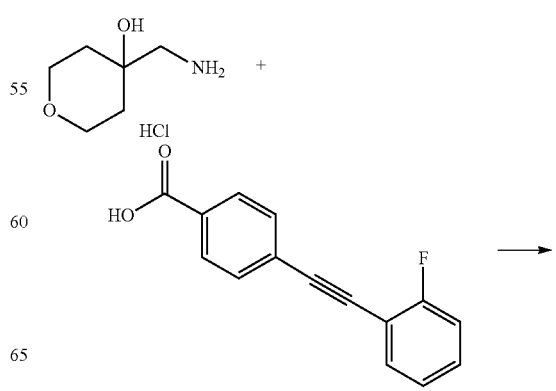

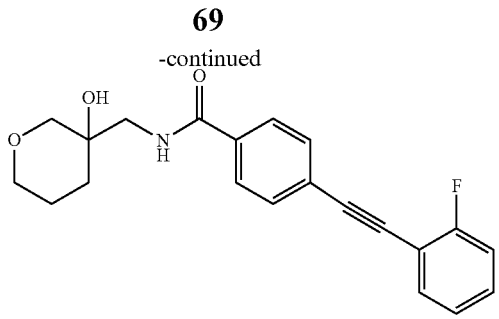

4-((2-Fluorophenyl)ethynyl)benzoic acid (0.070 g, 0.291 mmol) and 4-(aminomethyl)tetrahydro-2H-pyran-4-ol hydrochloride (0.073 g, 0.437 mmol) as starting materials were used in a similar manner to Step 3 of Example 1 to obtain 4-((2-fluorophenyl)ethynyl)-N-((4-hydroxytetrahydro-2H-pyran-4-yl)methyl)benzamide (0.075 g, 72.8%) as white solid: LRMS (ES) m/z 354.20 [M+H]$^+$, calculated MW 353.39; $^1$H-NMR (400 MHz, CD$_3$OD) d 7.86 (d, J=8.8 Hz, 2H), 7.61 (d, J=8.4 Hz, 2H), 7.57~7.53 (m, 1H), 7.43~7.38 (m, 1H), 7.21~7.15 (m, 2H), 3.78~3.73 (m, 4H), 3.43 (s, 2H), 1.75~1.67 (m, 2H), 1.53 (d, J=14.0 Hz, 2H).

Example 42: Synthesis of 4-((2-fluorophenyl)ethynyl)-N-(1-(tetrahydro-2H-pyran-4-yl)ethyl)benzamide

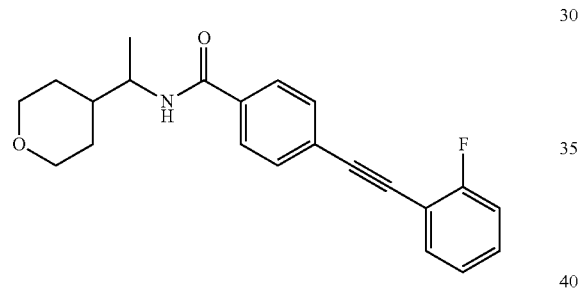

Step 1: Synthesis of (Z)-2-methyl-N-((tetrahydro-2H-pyran-4-yl)methylene)propane-2-sulfinamide

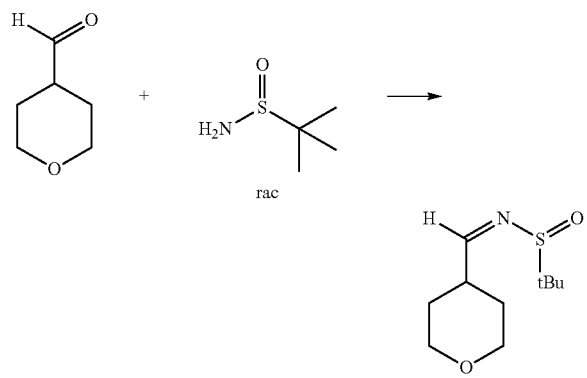

2-Methylpropane-2-sulfinamide (1.000 g, 8.251 mmol), tetrahydro-2H-pyran-4-carbaldehyde (2.072 g, 18.152 mmol), magnesium sulfate (MgSO$_4$, 5.462 g, 45.380 mmol) and pyridinium p-toluenesulfonate (0.107 g, 0.495 mmol) were dissolved in 1,2-dichloroethane (14 mL) at room temperature, and the resulting solution was stirred at the same temperature under visible light (Blue LED, 40 W) for 24 hours. Water was poured into the reaction mixture, followed by extraction with dichloromethane. The organic layer was washed with a saturated aqueous sodium chloride solution, dried over anhydrous sodium sulfate, filtered and concentrated under reduced pressure. The concentrate was purified by column chromatography and concentrated to obtain (Z)-2-methyl-N-((tetrahydro-2H-pyran-4-yl)methylene)propane-2-sulfinamide (0.800 g, 44.6%) as white solid.

Step 2: Synthesis of 1-(tetrahydro-2H-pyran-4-yl)ethan-1-amine hydrochloride

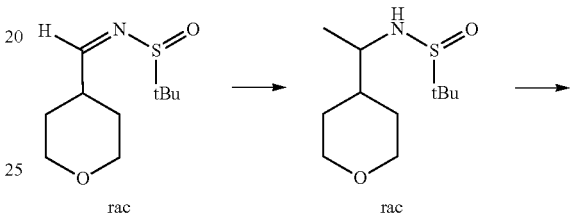

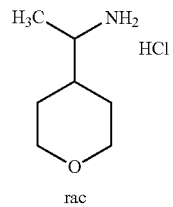

(Z)-2-methyl-N-((tetrahydro-2H-pyran-4-yl)methylene)propane-2-sulfinamide (0.800 g, 3.681 mmol) and methylmagnesium bromide (1.40 M solution in THF/toluene, 5.259 mL, 7.362 mmol) were dissolved in dichloromethane (15 mL), and the resulting solution was stirred at room temperature for 1 hour and further stirred at the same temperature for 18 hours. Water was poured into the reaction mixture, followed by extraction with dichloromethane. The organic layer was washed with a saturated aqueous sodium chloride solution, dried over anhydrous sodium sulfate, filtered and concentrated under reduced pressure. The concentrate was purified by column chromatography and concentrated to obtain 2-methyl-N-(1-(tetrahydro-2H-pyran-4-yl)ethyl)propane-2-sulfinamide (0.475 g, 55.3%) as colorless liquid. 0.400 g (1.714 mmol) of obtained product and hydrogen chloride (4.00 M solution in 1,4-dioxane, 1.286 mL, 5.142 mmol) were dissolved in methanol (2 mL) at room temperature, and the resulting solution was stirred at the same temperature for 30 minutes. After removing the solvent from the reaction mixture under reduced pressure, ethyl acetate (1 mL) and hexane (10 mL) were added to the concentrate and stirred. The precipitated solid was filtered, washed with hexane and dried to obtain 1-(tetrahydro-2H-pyran-4-yl)ethan-1-amine hydrochloride (0.143 g, 50.4%) as pink solid.

Step 3: Synthesis of 4-((2-fluorophenyl)ethynyl)-N-(1-(tetrahydro-2H-pyran-4-yl)ethyl)benzamide

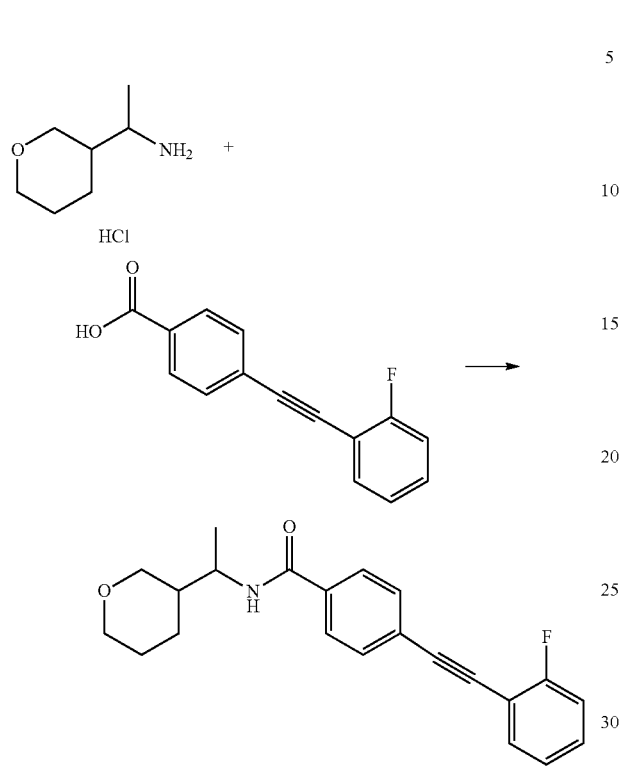

4-((2-Fluorophenyl)ethanyl)benzoic acid (0.051 g, 0.211 mmol) and 1-(tetrahydro-2H-pyran-4-yl)ethan-1-amine hydrochloride (0.035 g, 0.211 mmol) as starting materials were used in a similar manner to Example 11 to obtain 4-((2-fluorophenyl)ethynyl)-N-(1-(tetrahydro-2H-pyran-4-yl)ethyl)benzamide (0.045 g, 60.6%) was obtained as white solid: LRMS (ES) m/z 352.13 [M+H]$^+$, calculated MW 351.42; $^1$H-NMR (400 MHz, DMSO-$d_6$) d 8.27 (d, J=8.4 Hz, 1H), 7.87 (d, J=8.4 Hz, 2H), 7.63~7.61 (m, 3H), 7.46 (m, 1H), 7.32 (t, J=15.4 Hz, 1H), 7.26 (t, J=4.0 Hz, 1H), 3.88~3.77 (m, 3H), 3.24 (q, J=14.0 Hz, 2H), 1.62~1.56 (m, 3H), 1.22~1.15 (m, 2H), 1.09 (d, J=6.8 Hz, 3H).

Example 43: Synthesis of 4-((2-fluorophenyl)ethynyl)-N-((tetrahydrofuran-3-yl)methyl)benzamide

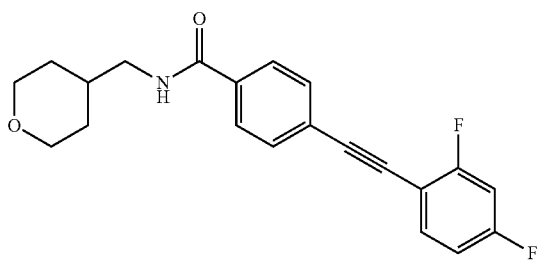 [SMILES: O=C(NCC1CCOCC1)c1ccc(C#Cc2ccc(F)cc2F)cc1]

-continued

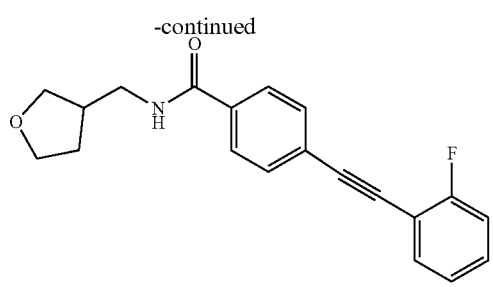

4-((2-Fluorophenyl)ethynyl)benzoic acid (0.150 g, 0.624 mmol) and (tetrahydrofuran-3-yl)methanamine (0.098 mL, 0.937 mmol) as starting materials were used in a similar manner to Step 3 of Example 1 to obtain 4-((2-fluorophenyl)ethynyl)-N-((tetrahydrofuran-3-yl)methyl)benzamide (0.143 g, 70.8%) as white solid: LRMS (ES) m/z 324.21 [M+H]$^+$, calculated MW 323.37; $^1$H-NMR (400 MHz, DMSO-$d_6$) d 8.68 (t, J=5.6 Hz, 1H), 7.86 (dd, J=6.8, 2.0 Hz, 2H), 7.64~7.59 (m, 3H), 7.50~7.44 (m, 1H), 7.33 (t, J=8.6 Hz, 1H), 7.25 (td, J=7.6, 0.9 Hz, 1H), 3.71~3.54 (m, 3H), 3.45~3.36 (m, 2H), 3.30~3.13 (m, 2H), 1.93~1.87 (m, 1H), 1.62~1.50 (m, 1H).

Example 44: Synthesis of 4-((2,4-difluorophenyl)ethynyl)-N-((tetrahydro-2H-pyran-4-yl)methyl)benzamide Step 1: Synthesis of 4-((2,4-difluorophenyl)ethynyl)benzoic acid

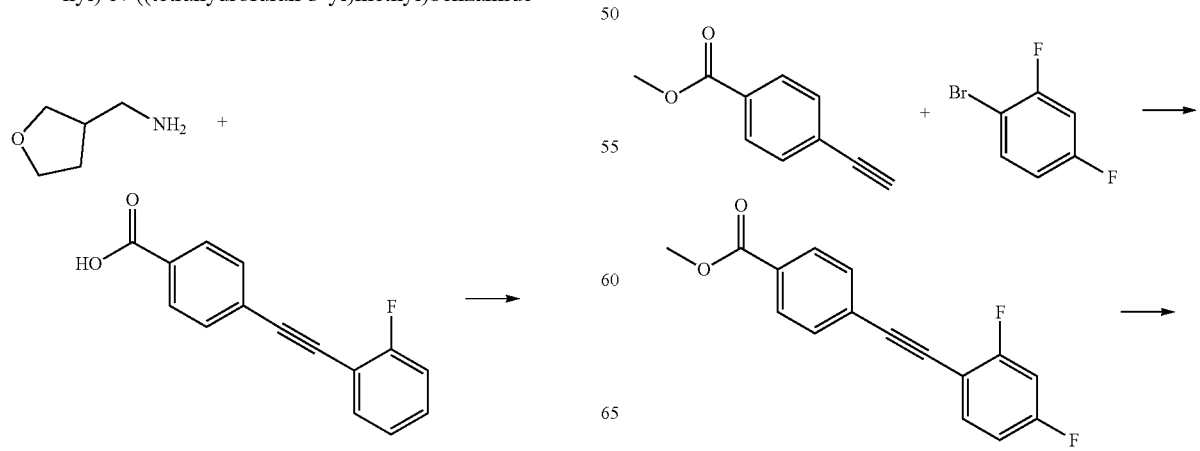

73

-continued

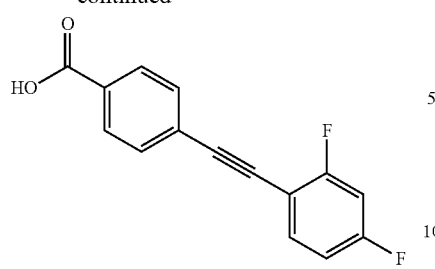

Methyl 4-ethynylbenzoate (2.000 g, 12.487 mmol) and 1-bromo-2,4-difluorobenzene (2.410 g, 12.487 mmol) were used in a similar manner to Step 1 of Example 1 to obtain methyl 4-((2,4-difluorophenyl)ethynyl)benzoate (0.780 g, 22.9%) as white solid, followed by obtaining 4-((2,4-difluorophenyl)ethynyl)benzoic acid (0.730 g, 98.7%) as white solid: LRMS (ES) m/z 256.98 (M−1) [M+H]$^+$, calculated MW 258.22.

Step 2: Synthesis of 4-((2,4-difluorophenyl)ethynyl)-N-((tetrahydro-2H-pyran-4-yl)methyl)benzamide

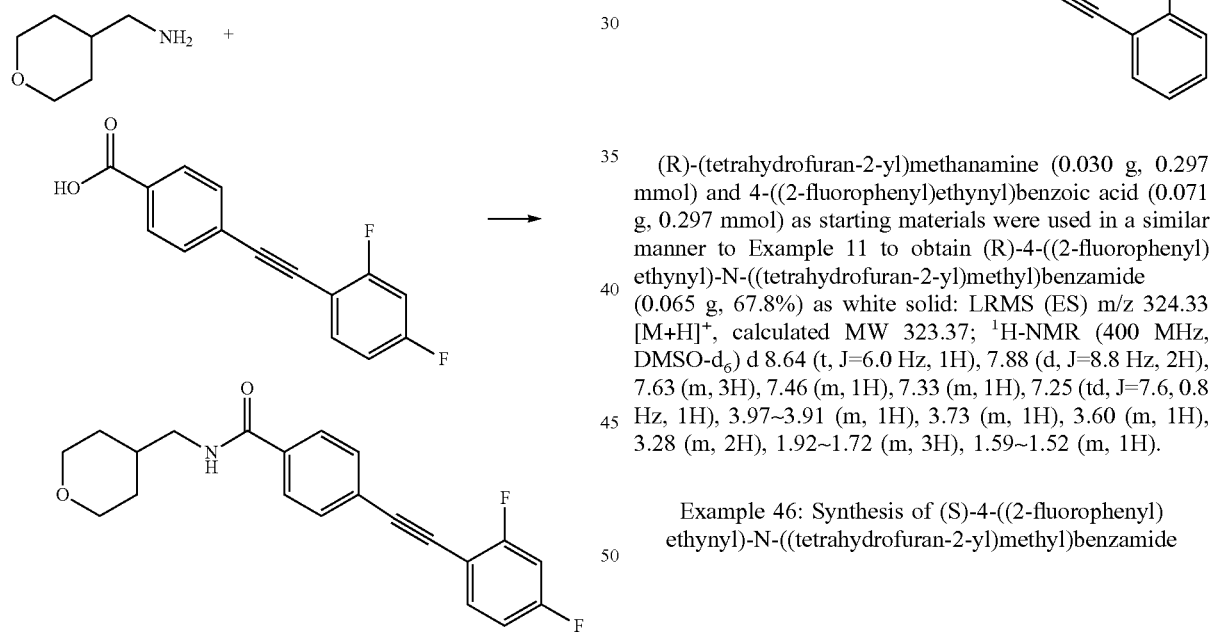

4-((2,4-Difluorophenyl)ethynyl)benzoic acid (0.150 g, 0.581 mmol) and (tetrahydro-2H-pyran-4-yl)methanamine (0.074 g, 0.639 mmol) were used in a similar manner to Example 11 to obtain 4-((2,4-difluorophenyl)ethynyl)-N-((tetrahydro-2H-pyran-4-yl)methyl)benzamide (0.156 g, 75.6%) as white solid: LRMS (ES) m/z 356.42 [M+H]$^+$, calculated MW 355.38; $^1$H-NMR (400 MHz, DMSO-d$_6$) d 8.58 (t, J=5.6 Hz, 1H), 7.86 (d, J=8.4 Hz, 2H), 7.70 (q, J=7.9 Hz, 1H), 7.61 (d, J=8.0 Hz, 2H), 7.42 (td, J=9.6, 2.8 Hz, 1H), 7.17 (td, J=7.8, 2.5 Hz, 1H), 3.80 (dd, J=11.2, 2.4 Hz, 2H), 3.22 (t, J=11.8 Hz, 2H), 3.12 (t, J=6.2 Hz, 2H), 1.78~1.73 (m, 1H), 1.55 (d, J=12.8 Hz, 2H), 1.20~1.10 (m, 2H).

74

Example 45: Synthesis of (R)-4-((2-fluorophenyl)ethynyl)-N-((tetrahydrofuran-2-yl)methyl)benzamide

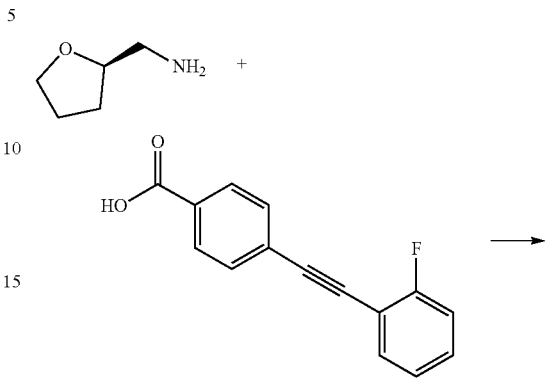

(R)-(tetrahydrofuran-2-yl)methanamine (0.030 g, 0.297 mmol) and 4-((2-fluorophenyl)ethynyl)benzoic acid (0.071 g, 0.297 mmol) as starting materials were used in a similar manner to Example 11 to obtain (R)-4-((2-fluorophenyl)ethynyl)-N-((tetrahydrofuran-2-yl)methyl)benzamide (0.065 g, 67.8%) as white solid: LRMS (ES) m/z 324.33 [M+H]$^+$, calculated MW 323.37; $^1$H-NMR (400 MHz, DMSO-d$_6$) d 8.64 (t, J=6.0 Hz, 1H), 7.88 (d, J=8.8 Hz, 2H), 7.63 (m, 3H), 7.46 (m, 1H), 7.33 (m, 1H), 7.25 (td, J=7.6, 0.8 Hz, 1H), 3.97~3.91 (m, 1H), 3.73 (m, 1H), 3.60 (m, 1H), 3.28 (m, 2H), 1.92~1.72 (m, 3H), 1.59~1.52 (m, 1H).

Example 46: Synthesis of (S)-4-((2-fluorophenyl)ethynyl)-N-((tetrahydrofuran-2-yl)methyl)benzamide

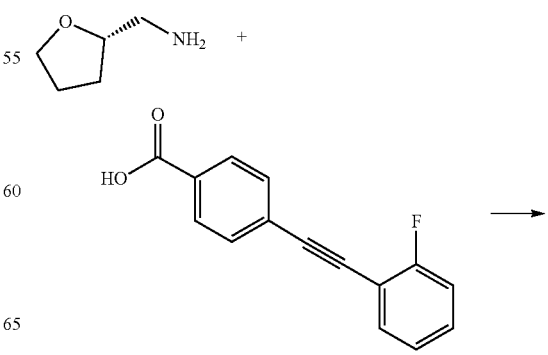

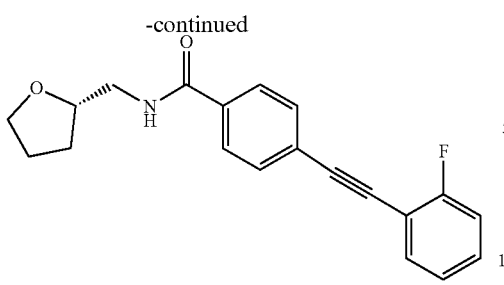

4-((2-Fluorophenyl)ethynyl)benzoic acid (0.150 g, 0.624 mmol) and (S)-(tetrahydrofuran-2-yl)methanamine (0.095 g, 0.937 mmol) as starting materials were used in a similar manner to Example 11 to obtain (S)-4-((2-fluorophenyl)ethynyl)-N-((tetrahydrofuran-2-yl)methyl)benzamide (0.162 g, 80.2%) as white solid: LRMS (ES) m/z 324.54 [M+H]+, calculated MW 323.37; ¹H-NMR (400 MHz, DMSO-d₆) d 8.65 (t, J=5.8 Hz, 1H), 7.87 (dd, J=6.4, 1.6 Hz, 2H), 7.65~7.61 (m, 3H), 7.50~7.44 (m, 1H), 7.33 (t, J=9.6 Hz, 1H), 7.25 (td, J=7.6, 1.2 Hz, 1H), 3.94~3.91 (m, 1H), 3.76~3.71 (m, 1H), 3.63~3.56 (m, 1H), 3.28~3.24 (m, 2H), 1.90~1.85 (m, 1H), 1.83~1.68 (m, 2H), 1.60~1.50 (m, 1H).

Example 47: Synthesis of (R)-4-((2-fluorophenyl)ethynyl)-N-(1-(tetrahydro-2H-pyran-4-yl)ethyl)benzamide

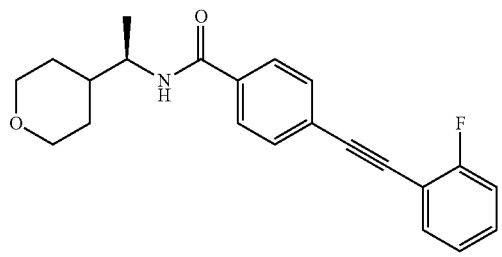 [SMILES: C[C@@H](NC(=O)c1ccc(C#Cc2ccccc2F)cc1)C1CCOCC1]

Step 1: Synthesis of (S,E)-2-methyl-N-((tetrahydro-2H-pyran-4-yl)methylene)propane-2-sulfinamide

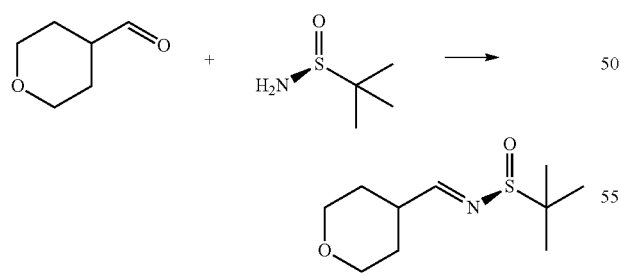

Tetrahydro-2H-pyran-4-carbaldehyde (1.000 g, 8.761 mmol), pyridinium p-toluenesulfonate (0.047 g, 0.219 mmol) and magnesium sulfate (MgSO₄, 2.636 g, 21.903 mmol) were dissolved in 1,2-dichloroethane (16 mL), and the resulting solution was stirred at room temperature for 0.5 hour, and (S)-2-methylpropane-2-sulfinamide (0.531 g, 4.381 mmol) was added thereto and further stirred at the same temperature for 18 hours. A saturated aqueous sodium hydrogen carbonate solution was poured into the reaction mixture, followed by extraction with dichloromethane. The organic layer was washed with a saturated aqueous sodium chloride solution, dried over anhydrous magnesium sulfate, filtered and concentrated under reduced pressure. The concentrate was purified by column chromatography and concentrated to obtain (S,E)-2-methyl-N-((tetrahydro-2H-pyran-4-yl)methylene)propane-2-sulfinamide (0.470 g, 24.7%) as white solid: LRMS (ES) m/z 218.05 [M+H]+, calculated MW 217.33.

Step 2: Synthesis of (R)-1-(tetrahydro-2H-pyran-4-yl)ethan-1-amine hydrochloride

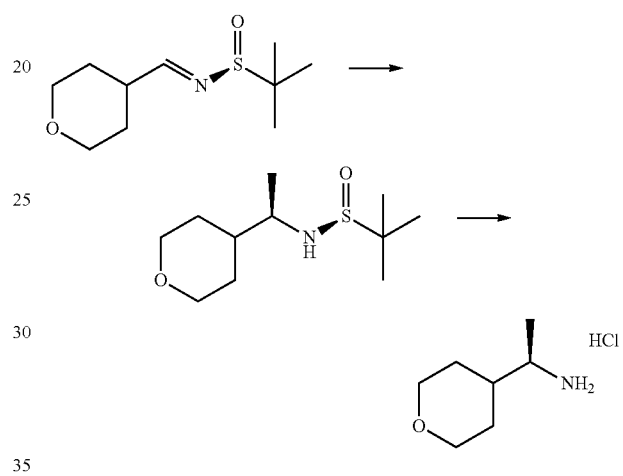

(S,E)-2-methyl-N-((tetrahydro-2H-pyran-4-yl)methylene)propane-2-sulfinamide (0.470 g, 2.163 mmol) was used in a similar manner to Step 2 of Example 42 to obtain (R)-1-(tetrahydro-2H-pyran-4-yl)ethan-1-amine hydrochloride (0.310 g, 99.3%) as yellow solid: LRMS (ES) m/z 129.97 [M+H]+, calculated MW 165.66.

Step 3: Synthesis of (R)-4-((2-fluorophenyl)ethynyl)-N-(1-(tetrahydro-2H-pyran-4-yl)ethyl)benzamide

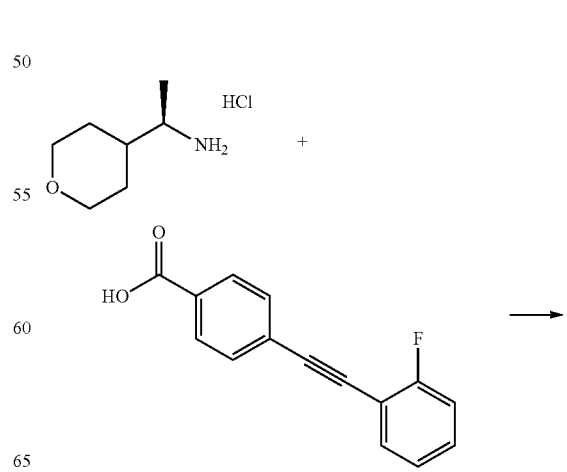

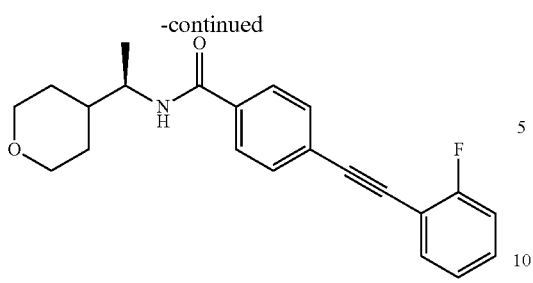

(R)-1-(tetrahydro-2H-pyran-4-yl)ethan-1-amine hydrochloride (0.050 g, 0.302 mmol) and 4-((2-fluorophenyl)ethanyl)benzoic acid (0.073 g, 0.302 mmol) as starting materials were used in a similar manner to Example 11 to obtain (R)-4-((2-fluorophenyl)ethynyl)-N-(1-(tetrahydro-2H-pyran-4-yl)ethyl)benzamide (0.075 g, 70.7%) as white solid: LRMS (ES) m/z 352.20 [M+H]$^+$, calculated MW 351.42; $^1$H-NMR (400 MHz, DMSO-d$_6$) d 8.27 (d, J=8.8 Hz, 1H), 7.87 (d, J=8.4 Hz, 2H), 7.65~7.61 (m, 3H), 7.48~7.46 (m, 1H), 7.33 (m, 1H), 7.25 (t, J=7.6 Hz, 1H), 3.85~3.79 (m, 3H), 3.20 (q, J=11.9 Hz, 2H), 1.68~1.52 (m, 3H), 1.25~1.13 (m, 2H), 1.09 (d, J=6.4 Hz, 3H).

Example 48: Synthesis of 4-((2-fluorophenyl)ethynyl)-N-((4-fluorotetrahydro-2H-pyran-4-yl)methyl)benzamide

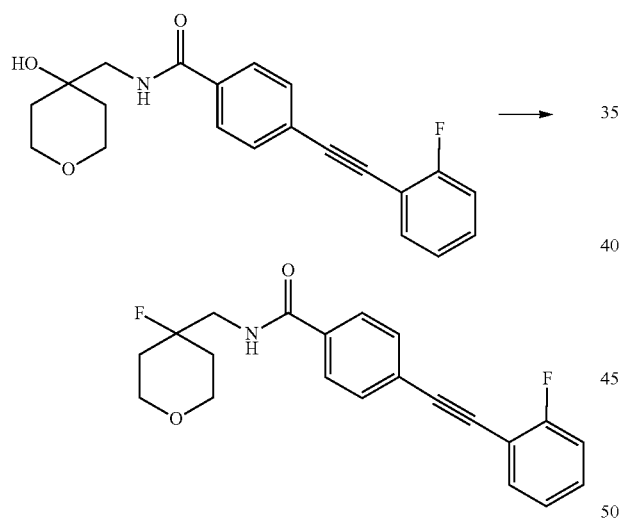

To the solution in which 4-((2-fluorophenyl)ethynyl)-N-((4-hydroxytetrahydro-2H-pyran-4-yl)methyl)benzamide (0.165 g, 0.467 mmol) obtained in Example 41 was dissolved in dichloromethane (10 mL) at 0° C., diethylaminosulfur trifluoride (DAST, 0.068 mL, 0.514 mmol) was added, and the reaction mixture was stirred at room temperature for 0.5 hour. A saturated aqueous sodium hydrogen carbonate solution was poured into the reaction mixture, followed by extraction with dichloromethane. The organic layer was washed with a saturated aqueous sodium chloride solution, dried over anhydrous magnesium sulfate, filtered and concentrated under reduced pressure. The concentrate was purified twice by column chromatography and concentrated to obtain 4-((2-fluorophenyl)ethynyl)-N-((4-fluorotetrahydro-2H-pyran-4-yl)methyl)benzamide (0.025 g, 15.1%) as white solid: LRMS (ES) m/z 356.12 [M+H]$^+$, calculated MW 355.38; $^1$H-NMR (400 MHz, DMSO-d$_6$) d 8.74 (t, J=6.2 Hz, 1H), 7.90 (d, J=8.4 Hz, 2H), 7.64~7.62 (m, 3H), 7.45 (m, 1H), 7.33 (m, 1H), 7.26 (t, J=4.4 Hz, 1H), 3.71~3.67 (m, 2H), 3.54~3.48 (m, 4H), 1.80~1.60 (m, 4H).

Example 49: Synthesis of 4-(phenylethynyl)-N-((tetrahydro-2H-pyran-4-yl)methyl)benzamide

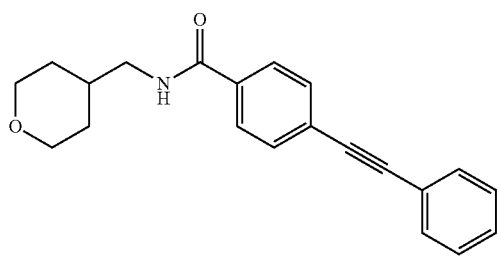 [SMILES: O=C(NCC1CCOCC1)c1ccc(C#Cc2ccccc2)cc1]

Step 1: Synthesis of 4-(phenylethynyl)benzoic acid

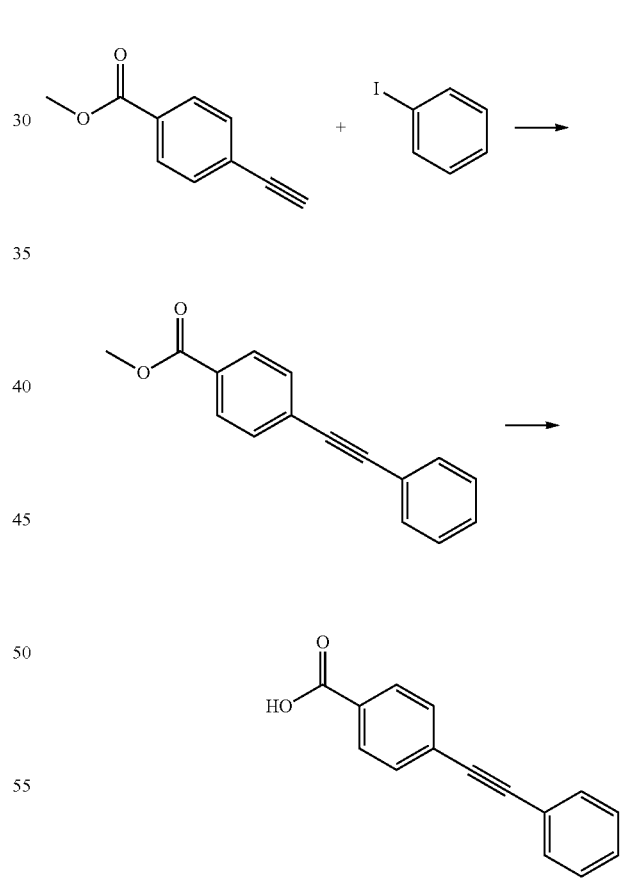

Methyl 4-ethynylbenzoate (0.500 g, 3.122 mmol) and iodobenzene (0.764 g, 3.746 mmol) as starting materials were used in a similar manner to Step 1 of Example 3 to obtain methyl 4-(phenylethynyl)benzoate (0.544 g, 73.8%) as clear liquid, followed by obtaining 4-(phenylethynyl)benzoic acid (0.477 g, 93.2%) as white solid: LRMS (ES) m/z 221.25 [M–H]$^+$, calculated MW 222.24.

Step 2: Synthesis of 4-(phenylethynyl)-N-((tetrahydro-2H-pyran-4-yl)methyl)benzamide Step 1: Synthesis of tert-butyl ((4-(hydroxymethyl)tetrahydro-2H-pyran-4-yl)methyl)carbamate

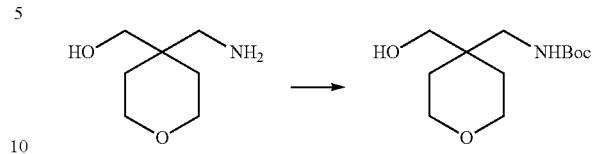

2.520 g (17.355 mmol) of (4-(aminomethyl)tetrahydro-2H-pyran-4-yl)methanol obtained in Step 1 of Example 38 and di-tert-butyl dicarbonate (3.987 mL, 17.355 mmol) were dissolved in dichloromethane (150 mL) at room temperature, and the resulting solution was stirred at the same temperature for 24 hours. Water was poured into the reaction mixture, followed by extraction with dichloromethane. The organic layer was washed with a saturated aqueous sodium chloride solution, dried over anhydrous sodium sulfate, filtered and concentrated under reduced pressure. The concentrate was purified by column chromatography and concentrated to obtain tert-butyl ((4-(hydroxymethyl)tetrahydro-2H-pyran-4-yl)methyl)carbamate (2.606 g, 61.2%) as white solid.

Step 2: Synthesis of (4-(fluoromethyl)tetrahydro-2H-pyran-4-yl)methanamine hydrochloride

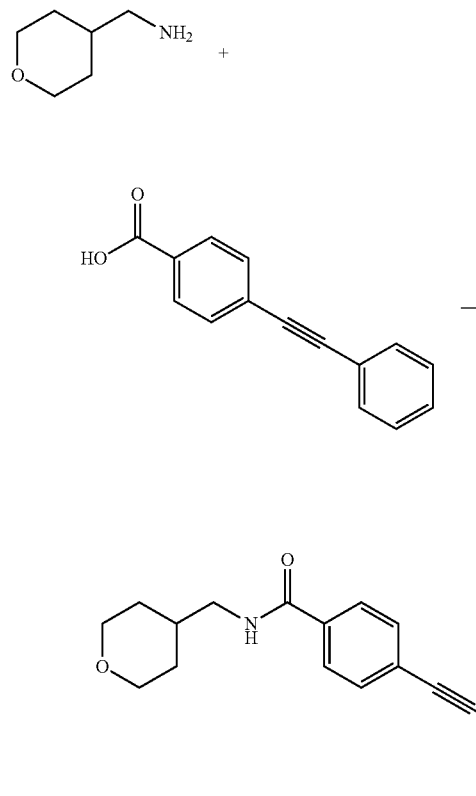

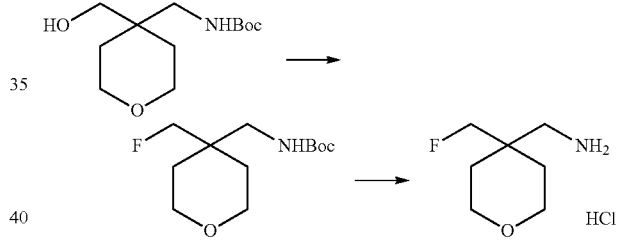

4-(Phenylethynyl)benzoic acid (0.070 g, 0.315 mmol) and (tetrahydro-2H-pyran-4-yl)methanamine (0.054 g, 0.472 mmol) as starting materials were used in a similar manner to Step 3 of Example 1 to obtain 4-(phenylethynyl)-N-((tetrahydro-2H-pyran-4-yl)methyl)benzamide (0.065 g, 64.6%) as white solid: LRMS (ES) m/z 320.27 [M+H]$^+$, calculated MW 319.4; $^1$H-NMR (400 MHz, CD$_3$OD) d 7.81 (dd, J=6.8, 2.0 Hz, 2H), 7.59~7.56 (m, 2H), 7.56~7.50 (m, 2H), 7.38~7.35 (m, 3H), 3.93 (dd, J=11.6, 3.2 Hz, 2H), 3.39 (td, J=11.7, 2.1 Hz, 2H), 3.25 (s, 2H), 1.92~1.84 (m, 1H), 1.67 (dd, J=13.2, 1.6 Hz, 2H), 1.37~1.27 (m, 2H).

Tert-butyl ((4-(hydroxymethyl)tetrahydro-2H-pyran-4-yl)methyl)carbamate (0.300 g, 1.223 mmol), PyFluor (0.217 g, 1.345 mmol) and 2,3,4,6,7,8,9,10-octahydropyrimido[1,2-c]azepine (DBU, 0.366 mL, 2.446 mmol) were dissolved in toluene (3 mL) at 60° C. The resulting solution was stirred at the same temperature as 48 hours, and the temperature was lowered to room temperature to terminate the reaction. Water was poured into the reaction mixture, followed by extraction with ethyl acetate. The organic layer was washed with a saturated aqueous sodium chloride solution, dried over anhydrous sodium sulfate, filtered and concentrated under reduced pressure. The concentrate was purified by column chromatography and concentrated to obtain tert-butyl ((4-(fluoromethyl)tetrahydro-2H-pyran-4-yl)methyl)carbamate (0.140 g, 46.3%) as white solid: $^1$H-NMR (400 MHz, CDCl$_3$) d 4.24~4.23 (m, 1H), 3.12, 3.12 (ABq, J=0.7, 0.4 Hz, 2H), 3.12 (q, J=0.4 Hz, 2H), 1.83 (t, J=0.4 Hz, 1H).

Example 50: Synthesis of N-((4-(fluoromethyl)tetrahydro-2H-pyran-4-yl)methyl)-4-((2-fluorophenyl)ethynyl)benzamide

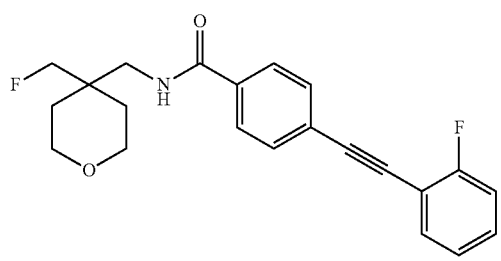 [SMILES: O=C(NCC1(CF)CCOCC1)c1ccc(C#Cc2ccccc2F)cc1]

0.070 g (0.283 mmol) of the obtained product and hydrogen chloride (4.00 M solution in 1,4-dioxane, 0.212 mL, 0.849 mmol) were dissolved in dichloromethane (2 mL) at room temperature, and the resulting solution was stirred at the same temperature for 18 hours. After the solvent was removed from the reaction mixture under reduced pressure, the obtained product was used without further purification ((4-(fluoromethyl)tetrahydro-2H-pyran-4-yl)methanamine hydrochloride, 0.051 g, 98.1%, white solid): LRMS (ES) m/z 148.18 [M+H]⁺, calculated MW 147.19.

Step 3: Synthesis of N-((4-(fluoromethyl)tetrahydro-2H-pyran-4-yl)methyl)-4-((2-fluorophenyl)ethynyl)benzamide

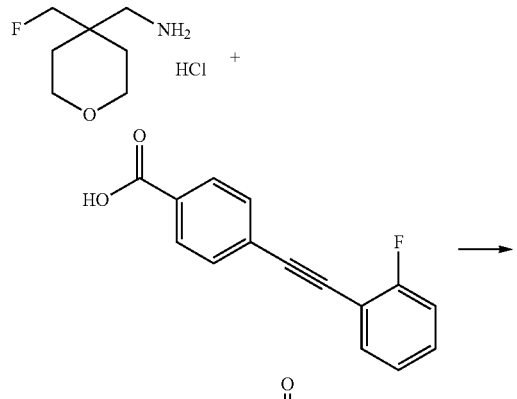

4-((2-Fluorophenyl)ethynyl)benzoic acid (0.050 g, 0.208 mmol) and (4-(fluoromethyl)tetrahydro-2H-pyran-4-yl)methanamine hydrochloride (0.057 g, 0.312 mmol) as starting materials were used in a similar manner to Step 3 of Example 1 to obtain N-((4-(fluoromethyl)tetrahydro-2H-pyran-4-yl)methyl)-4-((2-fluorophenyl)ethynyl)benzamide (0.032 g, 41.6%) as white solid: LRMS (ES) m/z 370.12 [M+H]⁺, calculated MW 369.41; ¹H-NMR (400 MHz, CD₃OD) d 7.82 (dt, J=8.4, 1.8 Hz, 2H), 7.60 (dt, J=6.8, 2.1 Hz, 2H), 7.55 (td, J=7.6, 1.6 Hz, 1H), 7.43~7.37 (m, 1H), 7.21~7.15 (m, 2H), 4.45~4.31 (m, 2H), 3.81~3.76 (m, 2H), 3.72~3.67 (m, 2H), 3.55 (s, 2H), 1.61~1.48 (m, 4H).

Example 51: Synthesis of N-((1,4-dioxan-2-yl)methyl)-4-((2-fluorophenyl)ethynyl)benzamide

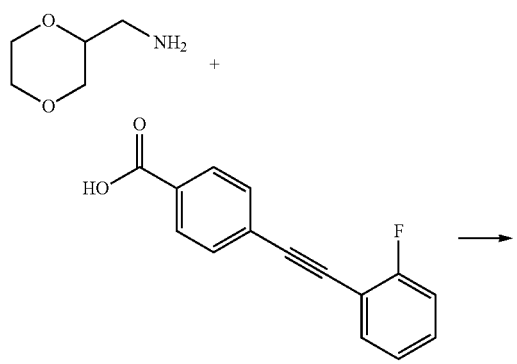

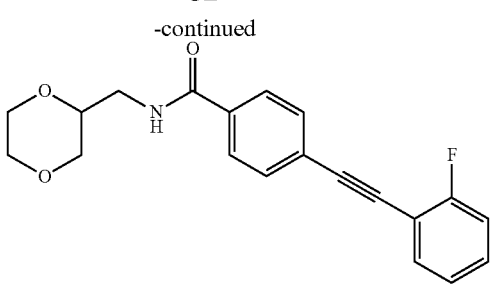

4-((2-Fluorophenyl)ethynyl)benzoic acid (0.100 g, 0.416 mmol) and (1,4-dioxan-2-yl)methanamine (0.054 g, 0.458 mmol) as starting materials were used in a similar manner to Example 11 to obtain N-((1,4-dioxan-2-yl)methyl)-4-((2-fluorophenyl)ethynyl)benzamide (0.120 g, 84.9%) as white solid: LRMS (ES) m/z 340.33 [M+H]⁺, calculated MW 339.37; ¹H-NMR (400 MHz, DMSO-d₆) d 8.66~8.64 (m, 1H), 7.87 (d, J=8.4 Hz, 2H), 7.64~7.61 (m, 3H), 7.50~7.45 (m, 1H), 7.33 (t, J=9.0 Hz, 1H), 7.25 (t, J=7.6 Hz, 1H), 3.72~3.39 (m, 6H), 3.29~3.17 (m, 3H).

Example 52: Synthesis of 4-((2-fluorophenyl)ethynyl)-N-((3-methyloxetan-3-yl)methyl)benzamide

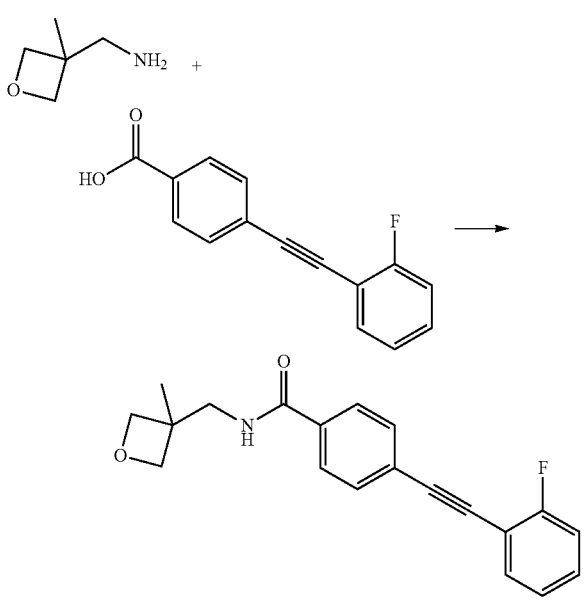

4-((2-Fluorophenyl)ethynyl)benzoic acid (0.070 g, 0.291 mmol) and (3-methyloxetan-3-yl)methanamine (0.044 g, 0.437 mmol) as starting materials were used in a similar manner to Step 3 of Example 1 to obtain 4-((2-fluorophenyl)ethynyl)-N-(3-methyloxetan-3-yl)methyl)benzamide (0.052 g, 55.2%) as white solid: LRMS (ES) m/z 324.33 [M+H]⁺, calculated MW 323.37; ¹H-NMR (400 MHz, DMSO-d₆) d 8.71 (t, J=6.0 Hz, 1H), 7.88 (dd, J=6.4, 2.0 Hz, 2H), 7.66~7.61 (m, 3H), 7.50~7.45 (m, 1H), 7.33 (td, J=9.1, 1.1 Hz, 1H), 7.25 (td, J=7.6, 1.1 Hz, 1H), 4.44 (d, J=5.2 Hz, 2H), 4.17 (d, J=5.2 Hz, 2H), 3.44 (d, J=6.0 Hz, 2H), 1.22 (s, 3H).

Example 53: Synthesis of 4-((4-((2-fluorophenyl)ethynyl)benzamido)methyl)-N-methyltetrahydro-2H-pyran-4-carboxamide

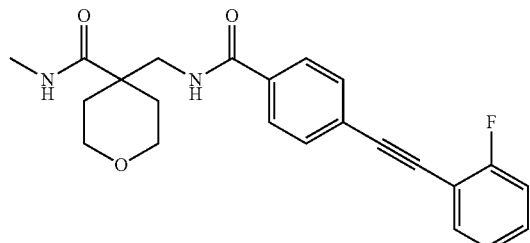

Step 1: Synthesis of ethyl 4-(aminomethyl)tetrahydro-2H-pyran-4-carboxylate

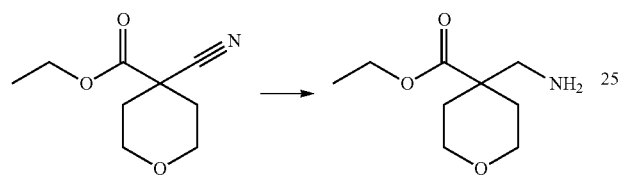

Ethyl 4-cyanotetrahydro-2H-pyran-4-carboxylate (2.000 g, 10.916 mmol) and cobalt chloride (CoCl$_2$, 2.835 g, 21.833 mmol) were dissolved in ethanol (10 mL). The resulting solution was stirred at room temperature for 1 hour, and sodium borohydride (4.130 g, 109.164 mmol) was added thereto and further stirred at the same temperature for 18 hours. Then, water (0.197 mL, 10.916 mmol) was poured into the reaction mixture at room temperature, and the reaction was terminated by stirring for 30 minutes. The reaction mixture was filtered through a Celite pad to remove solids, and the solvent was removed from the filtrate under reduced pressure. The obtained product was used without further purification (ethyl 4-(aminomethyl)tetrahydro-2H-pyran-4-carboxylate, 1.500 g, 73.4%, colorless oil): LRMS (ES) m/z 188.09 [M+H]$^+$, calculated MW 187.24.

Step 2: Synthesis of ethyl 4-((4-((2-fluorophenyl)ethynyl)benzamido)methyl)tetrahydro-2H-pyran-4-carboxylate

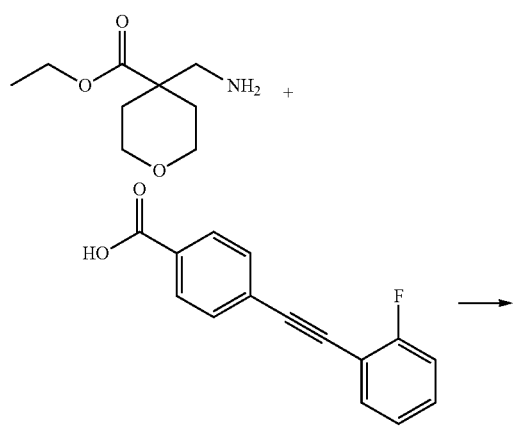

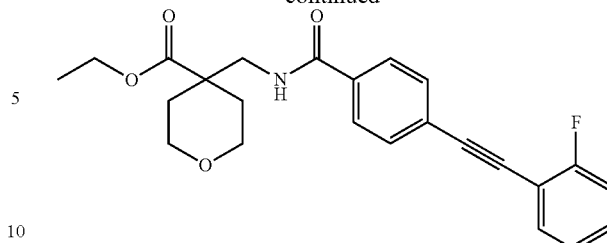

Ethyl 4-(aminomethyl)tetrahydro-2H-pyran-4-carboxylate (0.450 g, 2.403 mmol) and 4-((2-fluorophenyl)ethynyl)benzoic acid (0.577 g, 2.403 mmol) as starting materials were used in a similar manner to Example 11 to obtain ethyl 4-((4-((2-fluorophenyl)ethynyl)benzamido)methyl)tetrahydro-2H-pyran-4-carboxylate (0.680 g, 69.1%) as white solid: LRMS (ES) m/z 410.38 [M+H]$^+$, calculated MW 409.46.

Step 3: Synthesis of 4-((4-((2-fluorophenyl)ethynyl)benzamido)methyl)-N-methyltetrahydro-2H-pyran-4-carboxamide

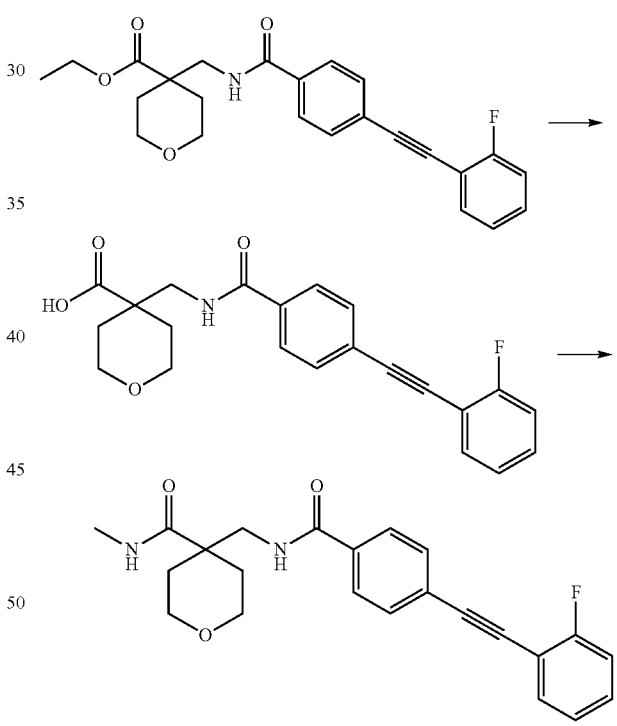

Ethyl 4-((4-((2-fluorophenyl)ethynyl)benzamido)methyl)tetrahydro-2H-pyran-4-carboxylate (0.400 g, 0.977 mmol) and lithium hydroxide monohydrate (0.082 g, 1.954 mmol) were dissolved in methanol (5 mL)/tetrahydrofuran (5 mL)/water (5 mL) at room temperature, and the resulting solution was stirred at the same temperature for 16 hours. After removing the solvent from the reaction mixture under reduced pressure, 2N hydrochloric acid aqueous solution was added to the concentrate and stirred. The precipitated solid was filtered, washed with water and dried to obtain 4-((4-((2-fluorophenyl)ethynyl)benzamido)methyl)tetrahydro-2H-pyran-4-carboxylic acid as white solid: (0.360 g, 96.6%, LRMS (ES) m/z 382.31 [M+H]+, calculated MW 381.4).

0.040 g (0.105 mmol) of the obtained product, methanamine hydrochloride (0.007 g, 0.105 mmol), 1-[bis(dimethylamino)methylene]-1H-1,2,3-triazolo[4,5-b]pyridinium 3-oxide hexafluorophosphate (HATU, 0.052 g, 0.136 mmol) and N,N-diisopropylethylamine (0.091 mL, 0.524 mmol) were dissolved in N,N-dimethylformamide (2 mL) at room temperature, and the resulting solution was stirred at the same temperature for 16 hours. The solvent was removed from the reaction mixture under reduced pressure, and a saturated aqueous sodium hydrogen carbonate solution was poured into the obtained concentrate, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain 4-((4-((2-fluorophenyl)ethynyl)benzamido)methyl)-N-methyltetrahydro-2H-pyran-4-carboxamide (0.035 g, 84.6%) as white solid: LRMS (ES) m/z 395.40 [M+H]+, calculated MW 394.45; 1H-NMR (400 MHz, DMSO-d6) d 8.37 (t, J=6.2 Hz, 1H), 7.82 (d, J=8.4 Hz, 2H), 7.77~7.61 (m, 4H), 7.48 (m, 1H), 7.35 (m, 1H), 7.28 (t, J=10.2 Hz, 1H), 3.66 (d, J=11.2 Hz, 2H), 3.35 (m, 4H), 2.58 (m, 3H), 1.95~1.92 (m, 2H), 1.49~1.45 (m, 2H).

Example 54: Synthesis of 4-((2-fluorophenyl)ethynyl)-N-((tetrahydro-2H-pyran-2-yl)methyl)benzamide

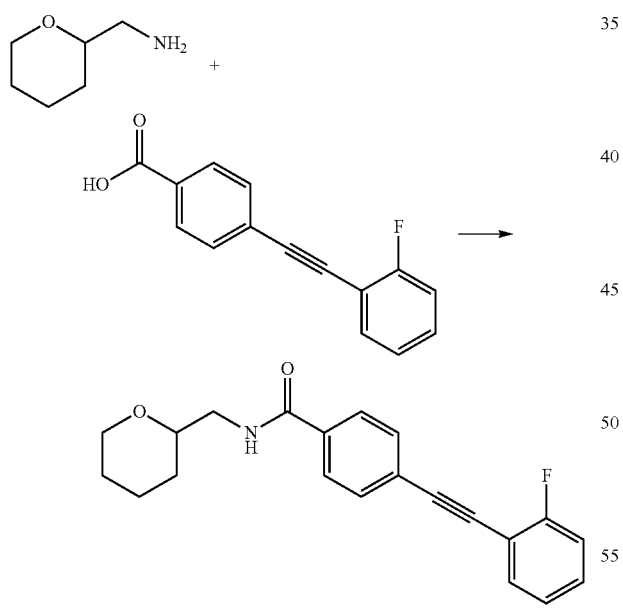

4-((2-Fluorophenyl)ethynyl)benzoic acid (0.100 g, 0.416 mmol) and (tetrahydro-2H-pyran-2-yl)methanamine (0.058 g, 0.500 mmol) as starting materials were used in a similar manner to Example 11 to obtain 4-((2-fluorophenyl)ethynyl)-N-((tetrahydro-2H-pyran-2-yl)methyl)benzamide (0.120 g, 85.4%) as ivory solid: MOTS (ES) m/z 338.13 [M+H]+, calculated MW 337.39; 1H-NMR (400 MHz, DMSO-d6) d 8.62 (t, J=5.8 Hz, 1H), 7.89~7.87 (m, 2H), 7.65~7.61 (m, 3H), 7.48~7.64 (m, 1H), 7.35~7.31 (m, 1H), 7.27~7.23 (m, 1H), 3.83 (dd, J=10.4, 2.4 Hz, 1H), 3.37~3.32 (m, 1H), 3.25~3.24 (m, 1H), 3.23~3.21 (m, 2H), 1.73 (d, J=3.2 Hz, 1H), 1.57 (d, J=13.2 Hz, 1H), 1.45~1.34 (m, 3H), 1.17~1.06 (m, 1H).

Example 55: Synthesis of N-((1-(isopropylamino) cyclohexyl)methyl)-4-(phenylethynyl)benzamide

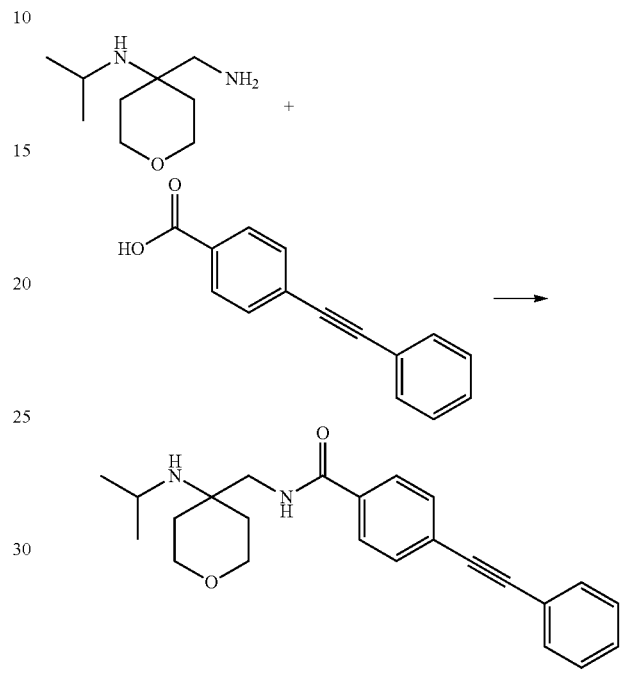

4-(Phenylethynyl)benzoic acid (0.100 g, 0.450 mmol) and 1-(aminomethyl)-N-isopropylcyclohexan-1-amine (0.084 g, 0.495 mmol) as starting materials were used in a similar manner to Example 11 to obtain N-((1-(isopropylamino) cyclohexyl)methyl)-4-(phenylethynyl)benzamide (0.102 g, 60.5%) as ivory solid: LRMS (ES) m/z 375.17 [M+H]+, calculated MW 374.53; 1H-NMR (400 MHz, CD3OD) d 7.84 (d, J=7.6 Hz, 2H), 7.62 (d, J=8.4 Hz, 2H), 7.59~7.51 (m, 2H), 7.42 (s, 3H), 3.40 (s, 2H), 3.11~3.03 (m, 1H), 1.58~1.36 (m, 10H), 1.08~1.05 (m, 6H).

Example 56: Synthesis of N-((3,3-difluorocyclobutyl)methyl)-4-((2-fluorophenyl)ethynyl)benzamide

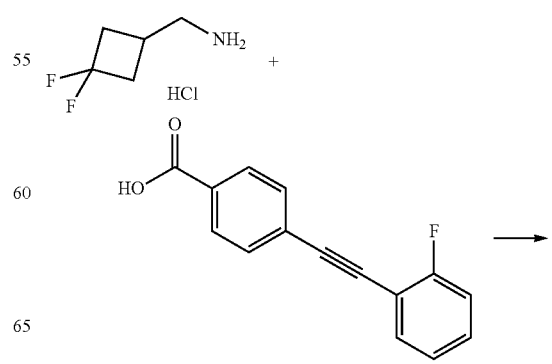

-continued

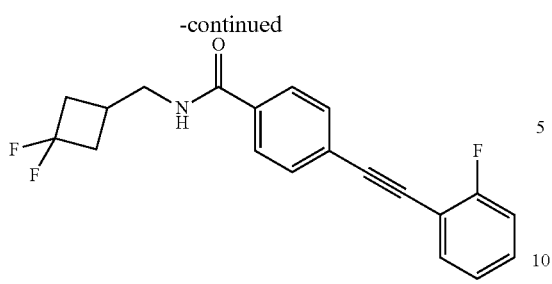

4-((2-Fluorophenyl)ethynyl)benzoic acid (0.070 g, 0.291 mmol) and (3,3-difluorocyclobutyl)methanamine hydrochloride (0.069 g, 0.437 mmol) as starting materials were used in a similar manner to Example 11 to obtain N-((3,3-difluorocyclobutyl)methyl)-4-((2-fluorophenyl)ethynyl)benzamide (0.075 g, 75.0%) as white solid: LRMS (ES) m/z 344.22 [M+H]$^+$, calculated MW 343.35; $^1$H-NMR (400 MHz, DMSO-d$_6$) d 8.72 (t, J=5.6 Hz, 1H), 7.86 (d, J=7.6 Hz, 2H), 7.64~7.61 (m, 3H), 7.47 (q, J=6.4 Hz, 1H), 7.33 (t, J=9.2 Hz, 1H), 7.25 (t, J=7.6 Hz, 1H), 2.63~2.55 (m, 3H), 2.38~2.29 (m, 4H).

Example 57: Synthesis of 4-((2-fluorophenyl)ethynyl)-N-((1-hydroxycyclobutyl)methyl)benzamide

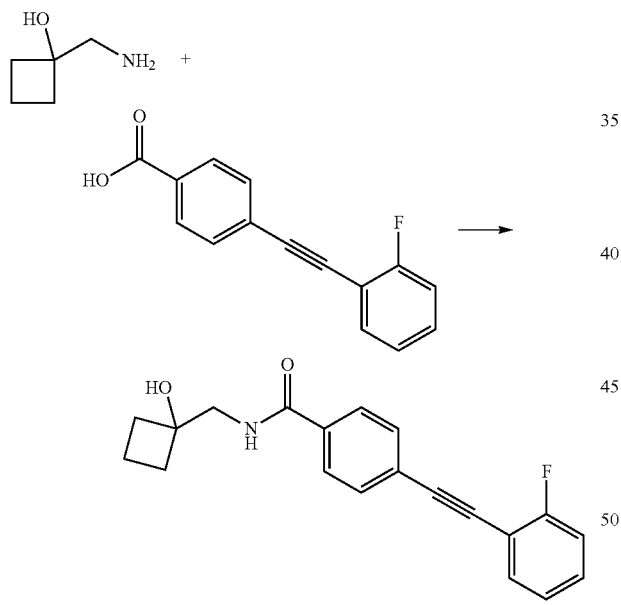

4-((2-Fluorophenyl)ethynyl)benzoic acid (0.070 g, 0.291 mmol) and 1-(aminomethyl)cyclobutan-1-ol (0.044 g, 0.437 mmol) as starting materials were used in a similar manner to Example 11 to obtain 4-((2-fluorophenyl)ethynyl)-N-((1-hydroxycyclobutyl)methyl)benzamide (0.063 g, 66.9%) as white solid: LRMS (ES) m/z 324.21 [M+H]$^+$, calculated MW 323.37; $^1$H-NMR (400 MHz, DMSO-d$_6$) d 8.42 (t, J=6.8 Hz, 1H), 7.90 (d, J=8.4 Hz, 2H), 7.64~7.62 (m, 3H), 7.47 (q, J=6.4 Hz, 1H), 7.33 (t, J=9.2 Hz, 1H), 7.25 (t, J=7.6 Hz, 1H), 5.15 (s, 1H), 3.39 (d, J=5.6 Hz, 2H), 2.03~1.98 (m, 2H), 1.91~1.84 (m, 2H), 1.63~1.58 (m, 1H), 1.49~1.38 (m, 1H).

Example 58: Synthesis of 4-((2-fluorophenyl)ethynyl)-N-(oxetan-2-ylmethyl)benzamide

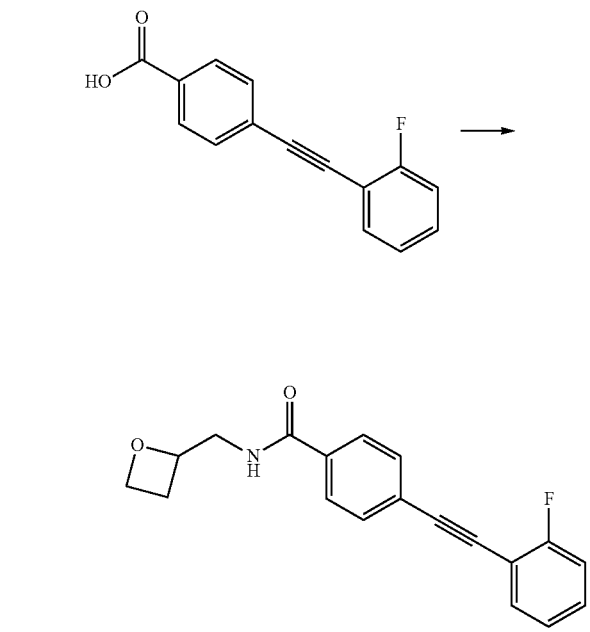

4-((2-Fluorophenyl)ethynyl)benzoic acid (0.070 g, 0.291 mmol) and oxetan-2-ylmethanamine (0.038 g, 0.437 mmol) as starting materials were used in a similar manner to Example 11 to obtain 4-((2-fluorophenyl)ethynyl)-N-(oxetan-2-ylmethyl)benzamide (0.065 g, 72.1%) as white solid: LRMS (ES) m/z 310.19 [M+H]$^+$, calculated MW 309.34; $^1$H-NMR (400 MHz, DMSO-d$_6$) d 8.74 (t, J=5.4 Hz, 1H), 7.89 (d, J=8.0 Hz, 2H), 7.64~7.62 (m, 3H), 7.47 (q, J=6.4 Hz, 1H), 7.33 (t, J=9.2 Hz, 1H), 7.25 (t, J=7.6 Hz, 1H), 4.78 (q, J=6.3 Hz, 1H), 4.49~4.36 (m, 2H), 3.57~3.38 (m, 2H), 2.65~2.55 (m, 2H).

Example 59: Synthesis of methyl 3-(1-((4-((2-fluorophenyl)ethynyl)benzamido)methyl)cyclohexyl)propanoate

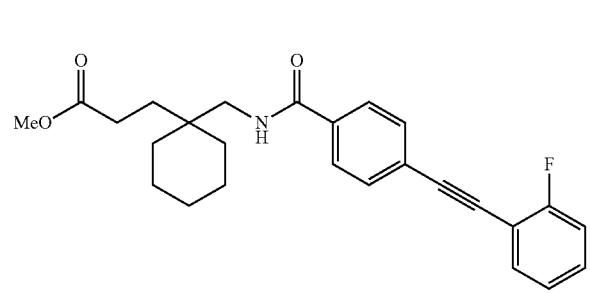 [SMILES: COC(=O)CCC1(CNC(=O)c2ccc(C#Cc3ccccc3F)cc2)CCCCC1]

Step 1: Synthesis of methyl 3-(1-(aminomethyl)cyclohexyl)propanoate hydrochloride

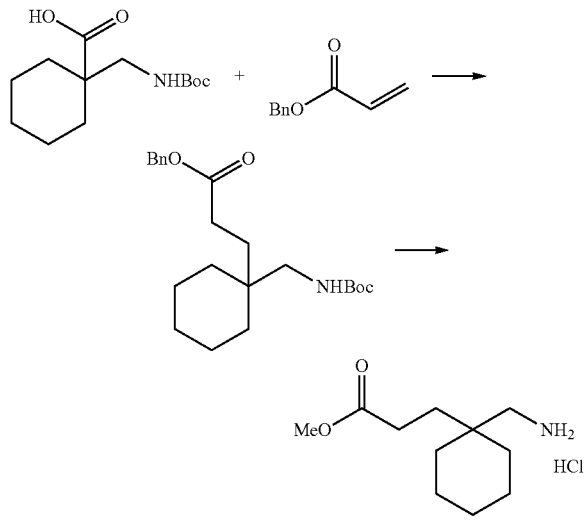

1-(((Tert-butoxycarbonyl)amino)methyl)cyclohexane-1-carboxylic acid (0.250 g, 0.972 mmol), benzyl acrylate (0.149 mL, 0.972 mmol), [Ir{dF(CF$_3$)ppy}$_2$(dtbpy)]PF$_6$ (0.011 g, 0.010 mmol) and potassium hydrogen phosphate (K$_2$HPO$_4$, 0.203 g, 1.166 mmol) were dissolved in N,N-dimethylacetamide (4 mL) at room temperature, and the resulting solution was stirred at the same temperature under visible light (Blue LED, 40 W) for 24 hours. Water was poured into the reaction mixture, followed by extraction with ethyl acetate. The organic layer was washed with a saturated aqueous sodium chloride solution, dried over anhydrous sodium sulfate, filtered and concentrated under reduced pressure. The concentrate was purified by column chromatography and concentrated to obtain benzyl 3-(1-(((tert-butoxycarbonyl)amino)methyl)cyclohexyl)propanoate as colorless liquid. (0.268 g, 73.5%, LRMS (ES) m/z No detection [M+H]$^+$, calculated MW 375.51)

The solution in which the obtained product and hydrochloric acid (0.129 g, 3.529 mmol) were dissolved in methanol (10 mL) at room temperature was stirred at the same temperature for 1 hour. After removing the solvent from the reaction mixture under reduced pressure, ethyl acetate (20 mL) and hexane (10 mL) were added to the concentrate and stirred. The precipitated solid was filtered, washed with hexane and dried to obtain methyl 3-(1-(aminomethyl)cyclohexyl)propanoate hydrochloride (0.145 g, 87.2%) in the form of a colorless liquid.

Step 2: Synthesis of methyl 3-(1-((4-((2-fluorophenyl)ethynyl)benzamido)methyl)cyclohexyl)propanoate

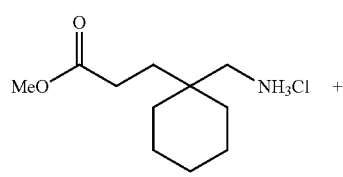

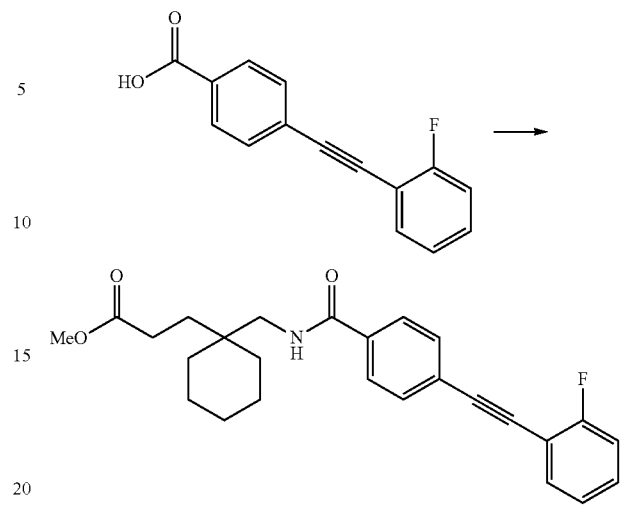

Methyl 3-(1-(aminomethyl)cyclohexyl)propanoate hydrochloride (0.150 g, 0.636 mmol) and 4-((2-fluorophenyl)ethynyl)benzoic acid (0.153 g, 0.636 mmol) as starting materials were used in a similar manner to Example 11 to obtain methyl 3-(1-((4-((2-fluorophenyl)ethynyl)benzamido)methyl)cyclohexyl)propanoate (0.211 g, 78.7%) as white solid: LRMS (ES) m/z 422.36 [M+H]$^+$, calculated MW 421.51; $^1$H-NMR (400 MHz, CD$_3$OD) d 7.80 (d, J=8.4 Hz, 2H), 7.61~7.53 (m, 3H), 7.41 (m, 1H), 7.20~7.15 (m, 2H), 3.64 (s, 3H), 2.40 (t, J=5.2 Hz, 2H), 1.65 (t, J=7.4 Hz, 2H), 1.55~1.47 (m, 2H), 1.44~1.26 (m, 10H).

Example 60: Synthesis of 3-(4-((4-((2-fluorophenyl)ethynyl)benzamido)methyl)tetrahydro-2H-pyran-4-yl)propanoic acid

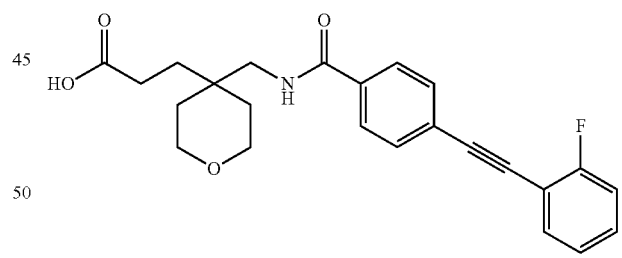

Step 1: Synthesis of methyl 3-(4-(aminomethyl)tetrahydro-2H-pyran-4-yl)propanoate hydrochloride

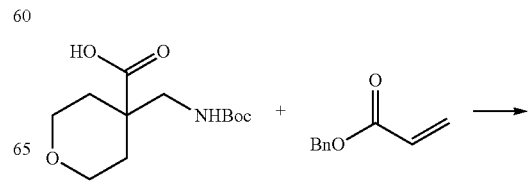

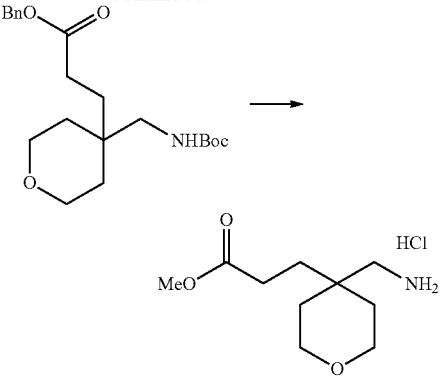

4-(((Tert-butoxycarbonyl)amino)methyl)tetrahydro-2H-pyran-4-carboxylic acid (0.130 g, 0.501 mmol) as a starting material was used in a similar manner to Step 1 of Example 59 to obtain benzyl 3-(4-(((tert-butoxycarbonyl)amino)methyl)tetrahydro-2H-pyran-4-yl)propanoate (0.165 g, 87.2%) as pale yellow liquid, followed by obtaining methyl 3-(4-(aminomethyl)tetrahydro-2H-pyran-4-yl)propanoate hydrochloride (0.094 g, 90.5%) as colorless liquid.

Step 2: Synthesis of methyl 3-(4-((4-((2-fluorophenyl)ethynyl)benzamido)methyl)tetrahydro-2H-pyran-4-yl)propanoate

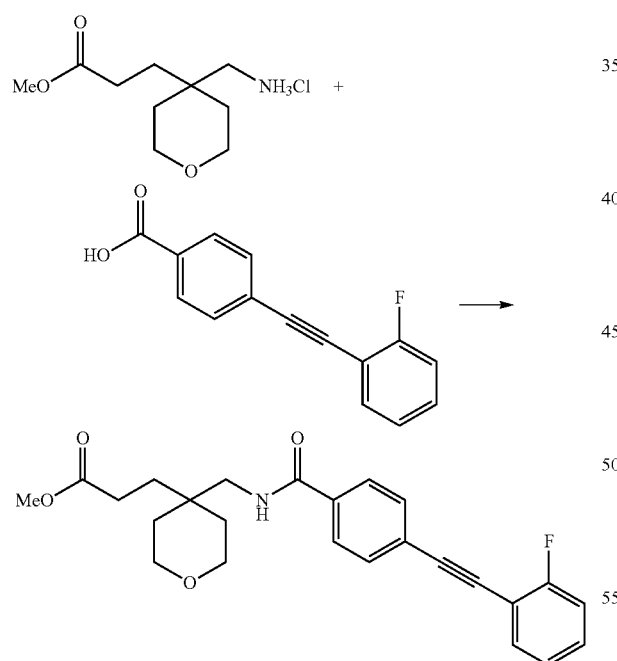

Methyl 3-(4-(aminomethyl)tetrahydro-2H-pyran-4-yl)propanoate hydrochloride (0.100 g, 0.421 mmol) and 4-((2-fluorophenyl)ethynyl)benzoic acid (0.101 g, 0.421 mmol) as starting materials were used in a similar manner to Example 11 to obtain methyl 3-(4-((4-(((2-fluorophenyl)ethynyl)benzamido)methyl)tetrahydro-2H-pyran-4-yl)propanoate (0.084 g, 47.2%) as white solid: LRMS (ES) m/z 424.34 [M+H]$^+$, calculated MW 423.48.

Step 3: Synthesis of 3-(4-((4-((2-fluorophenyl)ethynyl)benzamido)methyl)tetrahydro-2H-pyran-4-yl)propanoic acid

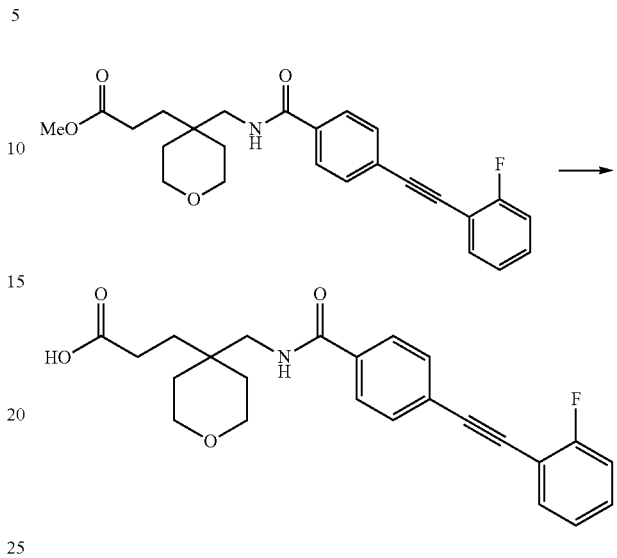

The solution in which methyl 3-(4-((4-((2-fluorophenyl)ethynyl)benzamido)methyl)tetrahydro-2H-pyran-4-yl)propanoate (0.080 g, 0.189 mmol) and sodium hydroxide (NaOH, 5.00 M solution, 0.189 mL, 0.945 mmol) were dissolved in methanol (1 mL)/tetrahydrofuran (1 mL) at room temperature was stirred at the same temperature for 3 hours. Then, hydrochloric acid (0.069 g, 1.889 mmol) was added to the reaction mixture at room temperature and stirred for 3 minutes to terminate the reaction. Water was poured into the reaction mixture, followed by extraction with ethyl acetate. The organic layer was washed with a saturated aqueous sodium chloride solution, dried over anhydrous sodium sulfate, filtered and concentrated under reduced pressure to obtain 3-(4-((4-((2-fluorophenyl)ethynyl)benzamido)methyl)tetrahydro-2H-pyran-4-yl)propanoic acid (0.074 g, 95.7%, white solid): LRMS (ES) m/z 408.16 [M−H]$^+$, calculated MW 409.46; $^1$H-NMR (400 MHz, CD$_3$OD) d 7.84~7.81 (m, 2H), 7.61 (dd, J=8.6, 1.8 Hz, 2H), 7.57~7.53 (m, 1H), 7.43~7.38 (m, 1H), 7.21~7.15 (m, 2H), 3.77~3.75 (m, 2H), 3.70~3.68 (m, 2H), 3.47~3.68 (m, 2H), 2.42 (t, J=7.8 Hz, 2H), 1.74 (t, J=7.8 Hz, 2H), 1.51~1.50 (m, 2H), 1.47~1.45 (m, 2H).

Example 61: Synthesis of 3-(1-((4-((2-fluorophenyl)ethynyl)benzamido)methyl)cyclohexyl)propanoic acid

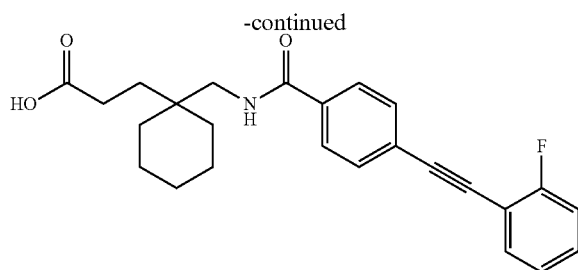

Methyl 3-(1-((4-((2-fluorophenyl)ethynyl)benzamido)methyl)cyclohexyl)propanoate (Example 59, 0.120 g, 0.285 mmol) as a starting material was used in a similar manner to Step 3 of Example 60 to obtain 3-(1-((4-((2-fluorophenyl)ethynyl)benzamido)methyl)cyclohexyl)propanoic acid (0.094 g, 81.0%, white solid): LRMS (ES) m/z 406.18 [M−H]+, calculated MW 407.49; $^1$H-NMR (400 MHz, CD$_3$OD) d 7.81 (dt, J=8.4, 1.9 Hz, 2H), 7.61~7.59 (m, 2H), 7.56~7.55 (m, 1H), 7.41~7.39 (m, 1H), 7.21~7.15 (m, 2H), 3.30~3.29 (m, 2H), 2.39~2.35 (m, 2H), 1.66 (t, J=8.0 Hz, 2H), 1.56~1.31 (m, 10H).

Example 62: Synthesis of 4-((2-fluorophenyl)ethynyl)-N-((1-(3-hydroxypropyl)cyclohexyl)methyl)benzamide

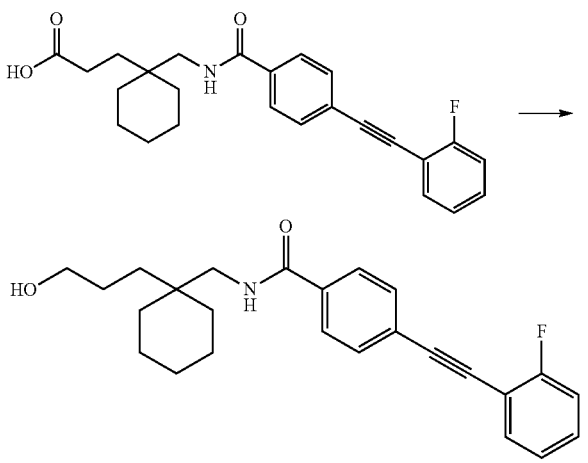

To the solution in which 3-(1-((4-((2-fluorophenyl)ethynyl)benzamido)methyl)cyclohexyl)propanoic acid (0.050 g, 0.123 mmol) obtained in Example 61 and 4-methylmorpholine (0.015 mL, 0.135 mmol) were dissolved in tetrahydrofuran (2 mL) at 0° C., isopropyl carbonochloridate (0.016 mL, 0.135 mmol) was added and stirred for 1 hour. Sodium borohydride (0.009 g, 0.245 mmol) was added to the reaction mixture and stirred at the same temperature for 1 hour. Water was poured into the reaction mixture, followed by extraction with dichloromethane. The organic layer was washed with a saturated aqueous sodium chloride solution, dried over anhydrous sodium sulfate, filtered, and concentrated under reduced pressure. The concentrate was purified by column chromatography and concentrated to obtain 4-((2-fluorophenyl)ethynyl)-N-((1-(3-hydroxypropyl)cyclohexyl)methyl)benzamide (0.037 g, 76.6%) as white solid: LRMS (ES) m/z 394.35 [M+H]+, calculated MW 393.5; $^1$H-NMR (400 MHz, CD$_3$OD) d 7.80 (dd, J=6.8, 2.0 Hz, 2H), 7.60 (dd, J=6.8, 2.0 Hz, 2H), 7.56~7.55 (m, 1H), 7.41~7.39 (m, 1H), 7.21~7.15 (m, 2H), 3.54 (t, J=6.2 Hz, 2H), 1.56~1.47 (m, 8H), 1.47~1.34 (m, 8H).

Example 63: Synthesis of 4-((2-fluorophenyl)ethynyl)-N-((2-hydroxycyclohexyl)methyl)benzamide

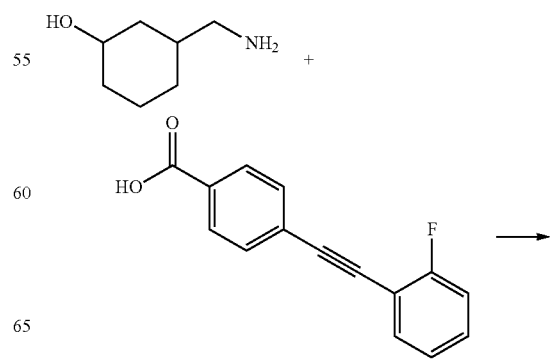

4-((2-Fluorophenyl)ethynyl)benzoic acid (0.070 g, 0.291 mmol) and 2-(aminomethyl)cyclohexan-1-ol (0.056 g, 0.437 mmol) as starting materials were used in a similar manner to Example 11 to obtain 4-((2-fluorophenyl)ethynyl)-N-((2-hydroxycyclohexyl)methyl)benzamide (0.060 g, 58.6%) as white solid: LRMS (ES) m/z 352.28 [M+H]+, calculated MW 351.42; $^1$H-NMR (400 MHz, DMSO-d$_6$) d 8.50~8.46 (m, 1H), 7.86 (d, J=8.0 Hz, 2H), 7.62 (d, J=8.0 Hz, 3H), 7.47 (q, J=6.4 Hz, 1H), 7.33 (t, J=9.2 Hz, 1H), 7.25 (t, J=7.6 Hz, 1H), 4.52 (m, 1H), 3.47~3.44 (m, 1H), 3.26~3.08 (m, 2H), 1.80~1.53 (m, 4H), 1.39~1.31 (m, 2H), 1.14~0.86 (m, 3H).

Example 64: Synthesis of 4-((2-fluorophenyl)ethynyl)-N-((3-hydroxycyclohexyl)methyl)benzamide

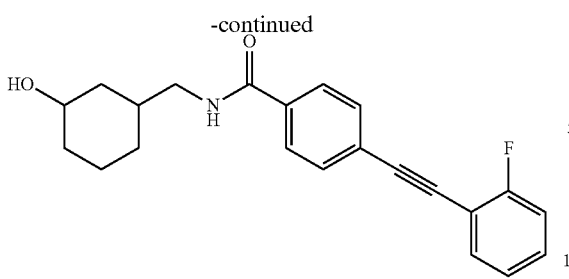

4-((2-Fluorophenyl)ethynyl)benzoic acid (0.070 g, 0.291 mmol) and 3-(aminomethyl)cyclohexan-1-ol (0.056 g, 0.437 mmol) as starting materials were used in a similar manner to Example 11 to obtain 4-((2-fluorophenyl)ethynyl)-N-(3-hydroxycyclohexyl)methyl)benzamide (0.085 g, 83.0%) was obtained as white solid: LRMS (ES) m/z 352.22 [M+H]$^+$, calculated MW 351.42; $^1$H-NMR (400 MHz, DMSO-d$_6$) d 8.55~8.54 (m, 1H), 7.86 (d, J=8.4 Hz, 2H), 7.62 (d, J=7.6 Hz, 3H), 7.47 (q, J=6.3 Hz, 1H), 7.33 (t, J=9.0 Hz, 1H), 7.25 (t, J=7.6 Hz, 1H), 4.48 (s, 1H), 3.12~3.06 (m, 2H), 2.65~2.65 (m, 4H), 1.86~1.75 (m, 1H), 1.66~1.57 (m, 2H), 1.19~1.10 (m, 1H), 1.03~0.94 (m, 1H), 0.81~0.72 (m, 1H).

Example 65: Synthesis of 4-((2-fluorophenyl)ethynyl)-N-((1-methoxycyclohexyl)methyl)benzamide

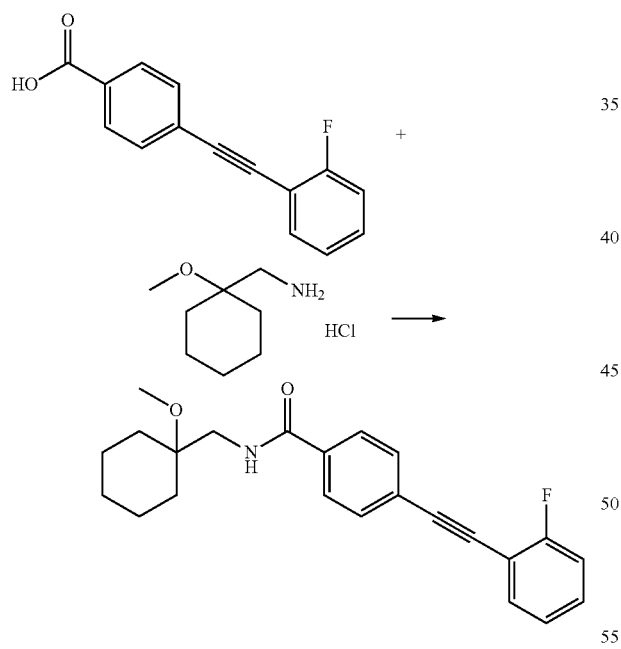

4-((2-Fluorophenyl)ethynyl)benzoic acid (0.070 g, 0.291 mmol) and (1-methoxycyclohexyl)methanamine hydrochloride (0.052 g, 0.291 mmol) as starting materials were used in a similar manner to Example 11 to obtain 4-((2-fluorophenyl)ethynyl)-N-((1-methoxycyclohexyl)methyl)benzamide (0.085 g, 79.8%, light yellow oil): LRMS (ES) m/z 366.29 [M+H]$^+$, calculated MW 365.45; $^1$H-NMR (400 MHz, CDCl$_3$) d 7.77 (m, 2H), 7.61 (m, 2H), 7.58~7.50 (m, 1H), 7.34 (m, 1H), 7.15~7.11 (m, 2H), 6.34 (s, 1H), 3.50 (d, J=4.8 Hz, 2H), 3.26 (s, 3H), 1.77 (m, 2H), 1.63~1.26 (m, 8H).

Example 66: Synthesis of 4-((2-fluorophenyl)ethynyl)-N-((4-methoxytetrahydro-2H-pyran-4-yl)methyl)benzamide

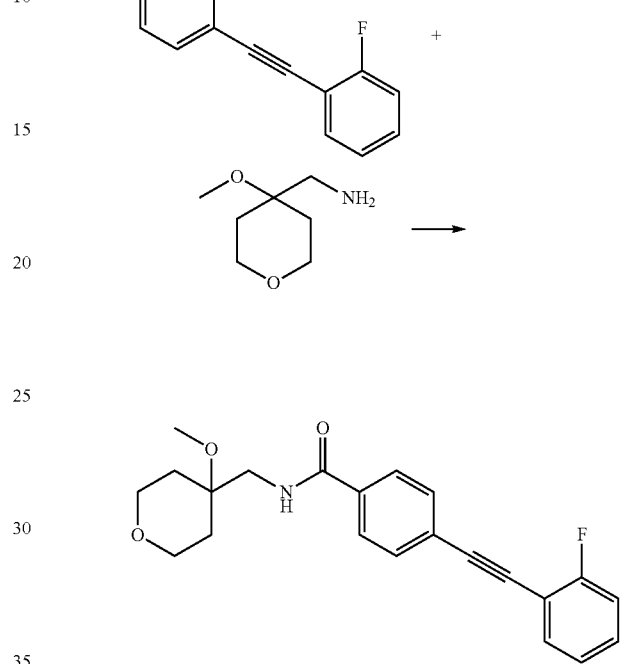

4-((2-Fluorophenyl)ethynyl)benzoic acid (0.070 g, 0.291 mmol) and (4-methoxytetrahydro-2H-pyran-4-yl)methanamine (0.042 g, 0.291 mmol) as starting materials were used in a similar manner to Example 11 to obtain 4-((2-fluorophenyl)ethynyl)-N-((4-methoxytetrahydro-2H-pyran-4-yl)methyl)benzamide (0.080 g, 74.7%) as pale yellow oil: LRMS (ES) m/z 368.20 [M+H]$^+$, calculated MW 367.42; $^1$H-NMR (400 MHz, CDCl$_3$) d 7.76 (d, J=8.0 Hz, 2H), 7.61 (d, J=7.6 Hz, 2H), 7.52 (m, 1H), 7.35~7.33 (m, 1H), 7.16~7.11 (m, 2H), 6.32 (bs, 1H), 3.73 (m, 4H), 3.57 (d, J=4.8 Hz, 2H), 3.26 (s, 3H), 1.82~1.67 (m, 4H).

Example 67: Synthesis of N-((2,2-dimethyltetrahydro-2H-pyran-4-yl)methyl)-4-((2-fluorophenyl)ethynyl)benzamide

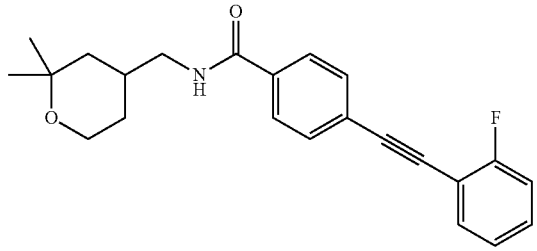 [SMILES: CC1(C)CC(CNC(=O)c2ccc(C#Cc3ccccc3F)cc2)CCO1]

Step 1: Synthesis of (2,2-dimethyltetrahydro-2H-pyran-4-yl)methanamine

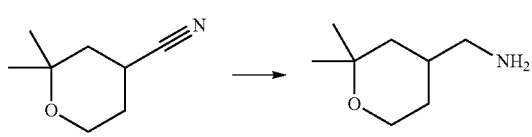

2,2-Dimethyltetrahydro-2H-pyran-4-carbonitrile (1.000 g, 7.184 mmol) as a starting material was used in a similar manner to Step 1-2 of Example 34 to obtain (2,2-dimethyltetrahydro-2H-pyran-4-yl)methanamine (0.470 g, 45.7%, yellow oil): LRMS (ES) m/z 144.07 [M+H]$^+$, calculated MW 143.23.

Step 2: Synthesis of N-((2,2-dimethyltetrahydro-2H-pyran-4-yl)methyl)-4-((2-fluorophenyl)ethynyl)benzamide

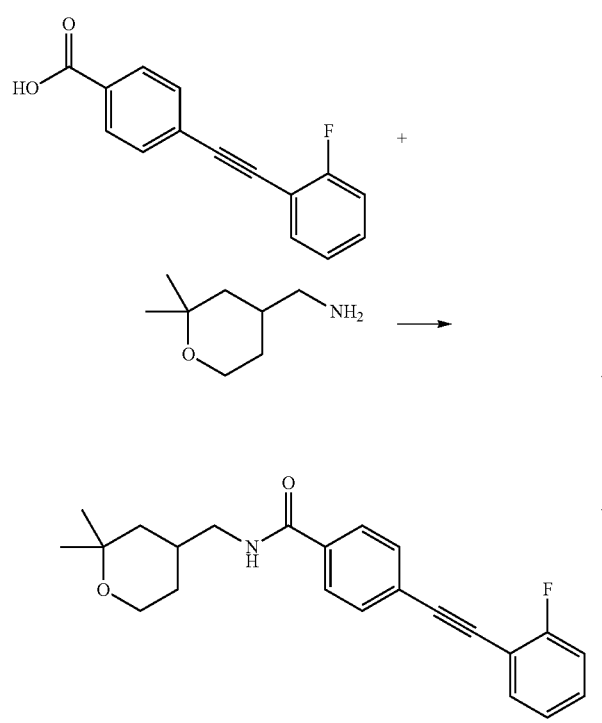

4-((2-Fluorophenyl)ethynyl)benzoic acid (0.070 g, 0.291 mmol) and (2,2-dimethyltetrahydro-2H-pyran-4-yl)methanamine (0.042 g, 0.291 mmol) as starting materials were used in a similar manner to Example 11 to obtain N-((2,2-dimethyltetrahydro-2H-pyran-4-yl)methyl)-4-((2-fluorophenyl)ethynyl)benzamide (0.035 g, 32.9%) as pale yellow oil: LRMS (ES) m/z 366.29 [M+H]$^+$, calculated MW 365.45; $^1$H-NMR (400 MHz, CDCl$_3$) d 7.76 (m, 2H), 7.62 (m, 2H), 7.54~7.50 (m, 1H), 7.35~7.30 (m, 1H), 7.18~7.11 (m, 2H), 6.23 (bs, 1H), 3.79~3.75 (m, 1H), 3.68~3.61 (m, 1H), 3.38~3.29 (m, 2H), 2.07~2.03 (m, 1H), 1.66~1.55 (m, 2H), 1.29~1.16 (m, 8H).

Example 68: Synthesis of 4-((2-fluorophenyl)ethynyl)-N-((tetrahydro-2H-pyran-4-yl)methyl-d$_2$)benzamide

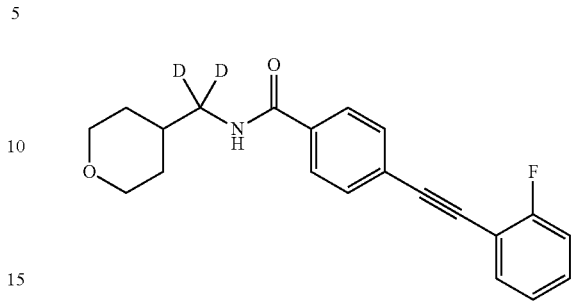

Step 1: Synthesis of tetrahydro-2H-pyran-4-yl)methane-d$_2$-amine

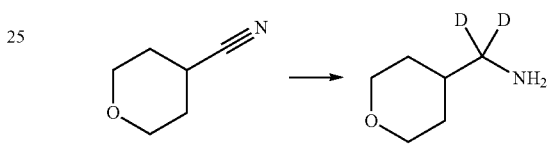

To the solution in which tetrahydro-2H-pyran-4-carbonitrile (1.000 g, 8.998 mmol) was dissolved in diethyl ether (12 mL) at 0° C., lithium aluminum deuteride (2.40 M solution, 7.498 mL, 17.995 mmol) was added and stirred at room temperature for 18 hours. Then, sodium hydroxide (NaOH, 1.00 M solution, 4.499 mL, 4.499 mmol) and water (0.973 mL, 53.986 mmol) were added to the reaction mixture at 0° C. and stirred for 30 minutes to terminate the reaction. The reaction mixture was filtered through a Celite pad to remove solids. The solvent was removed from the filtrate under reduced pressure, and the obtained product was used without further purification ((tetrahydro-2H-pyran-4-yl)methane-d$_2$-amine, 0.370 g, 35.1%, yellow oil): LRMS (ES) m/z 118.10 [M+H]$^+$, calculated MW 117.19.

Step 2: Synthesis of 4-((2-fluorophenyl)ethynyl)-N-((tetrahydro-2H-pyran-4-yl)methyl-d$_2$)benzamide

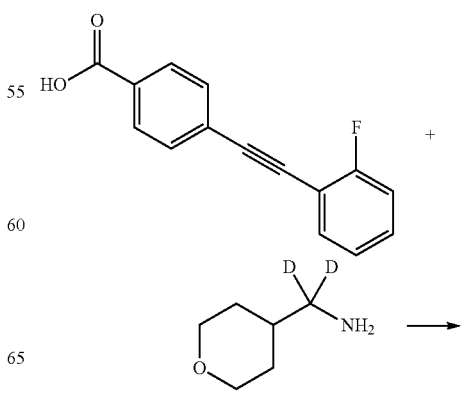

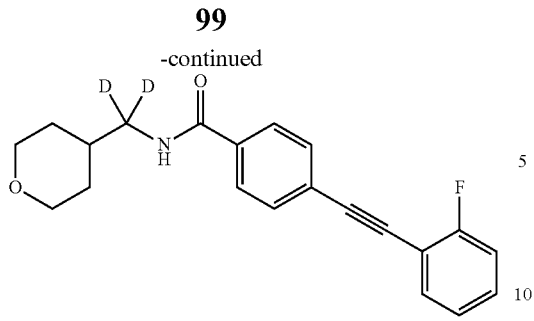

4-((2-Fluorophenyl)ethynyl)benzoic acid (0.720 g, 2.997 mmol) and (tetrahydro-2H-pyran-4-yl)methane-d$_2$-amine (0.351 g, 2.997 mmol) as starting materials were used in a similar manner to Example 11 to obtain 4-((2-fluorophenyl)ethynyl)-N-((tetrahydro-2H-pyran-4-yl)methyl-d$_2$)benzamide (0.210 g, 20.6%) as white solid: LRMS (ES) m/z 340.33 [M+H]$^+$, calculated MW 339.41; $^1$H-NMR (400 MHz, DMSO-d$_6$) d 8.57 (s, 1H), 7.86 (d, J=8.4 Hz, 2H), 7.63 (m, 3H), 7.48~7.46 (m, 1H), 7.33 (t, J=9.2 Hz, 1H), 7.25 (t, J=7.6 Hz, 1H), 3.82~3.79 (m, 2H), 3.22 (t, J=11.8 Hz, 2H), 1.80~1.74 (m, 1H), 1.57~1.54 (m, 2H), 1.20~1.10 (m, 2H).

Example 69: Synthesis of (R)-4-((2-fluorophenyl)ethynyl)-N-((tetrahydrofuran-3-yl)methyl)benzamide

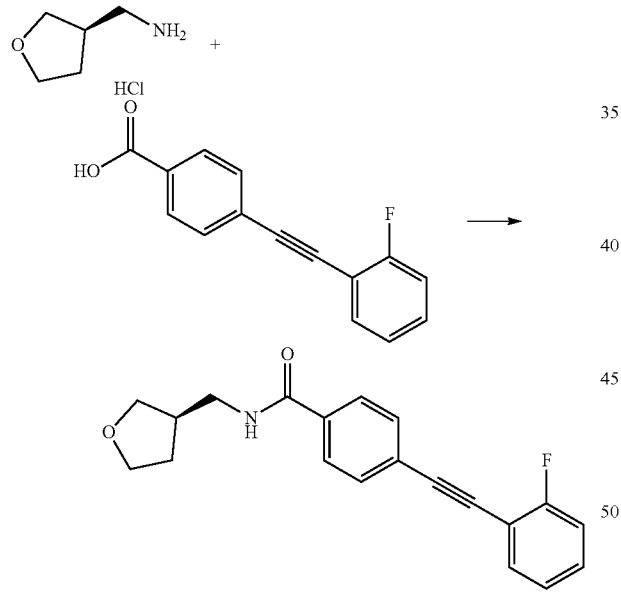

4-((2-Fluorophenyl)ethynyl)benzoic acid (0.070 g, 0.291 mmol) and (R)-(tetrahydrofuran-3-yl)methanamine hydrochloride (0.043 g, 0.321 mmol) as starting materials were used in a similar manner to Example 11 to obtain (R)-4-((2-fluorophenyl)ethynyl)-N-((tetrahydrofuran-3-yl)methyl)benzamide (0.080 g, 84.9%) as white solid: LRMS (ES) m/z 324.23 [M+H]$^+$, calculated MW 323.37; $^1$H-NMR (400 MHz, DMSO-d$_6$) d 8.67 (t, J=5.4 Hz, 1H), 7.86 (d, J=8.4 Hz, 2H), 7.64~7.62 (m, 3H), 7.50~7.45 (m, 1H), 7.33 (t, J=9.2 Hz, 1H), 7.25 (t, J=7.6 Hz, 1H), 3.71~3.55 (m, 3H), 3.45~3.42 (m, 1H), 3.27~3.19 (m, 2H), 3.13~3.12 (m, 1H), 1.95~1.86 (m, 1H), 1.60~1.52 (m, 1H).

Example 70: Synthesis of N-((5,5-dimethyltetrahydrofuran-3-yl)methyl)-4-((2-fluorophenyl)ethynyl)benzamide

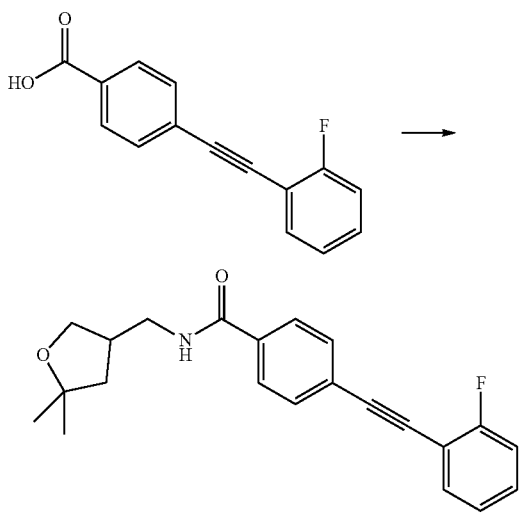

4-((2-Fluorophenyl)ethynyl)benzoic acid (0.050 g, 0.208 mmol) and (5,5-dimethyltetrahydrofuran-3-yl)methanamine (0.030 g, 0.229 mmol) as starting materials were used in a similar manner to Example 11 to obtain N-((5,5-dimethyltetrahydrofuran-3-yl)methyl)-4-((2-fluorophenyl)ethynyl)benzamide (0.036 g, 49.2%) as white solid: LRMS (ES) m/z 352.23 [M+H]$^+$, calculated MW 351.42; $^1$H-NMR (400 MHz, DMSO-d$_6$) d 8.63 (t, J=5.2 Hz, 1H), 7.86 (d, J=8.0 Hz, 2H), 7.64~7.62 (m, 3H), 7.50~7.42 (m, 1H), 7.33 (t, J=9.2 Hz, 1H), 7.25 (t, J=7.6 Hz, 1H), 3.77 (t, J=8.0 Hz, 1H), 3.46 (t, J=7.8 Hz, 1H), 3.25~3.20 (m, 2H), 2.59~2.52 (m, 1H), 1.83 (q, J=6.8 Hz, 1H), 1.38 (q, J=6.8 Hz, 1H), 1.18 (s, 3H), 1.08 (s, 3H).

Example 71: Synthesis of 4-((2-fluorophenyl)ethynyl)-N-((tetrahydrofuran-2-yl)methyl)benzamide

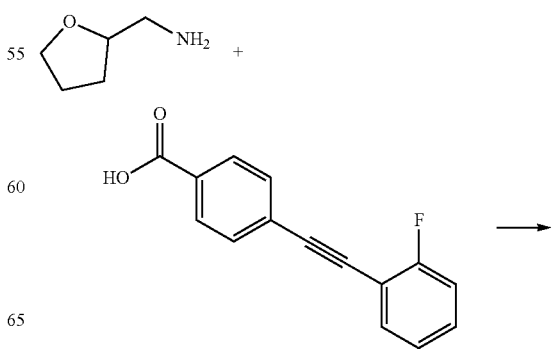

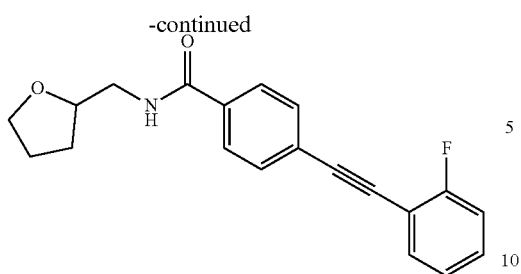

4-((2-Fluorophenyl)ethynyl)benzoic acid (0.070 g, 0.291 mmol) and (tetrahydrofuran-2-yl)methanamine (0.032 g, 0.321 mmol) as starting materials were used in a similar manner to Example 11 to obtain 4-((2-fluorophenyl)ethynyl)-N-((tetrahydrofuran-2-yl)methyl)benzamide (0.076 g, 80.7%) as white solid: LRMS (ES) m/z 324.21 [M+H]$^+$, calculated MW 323.37; $^1$H-NMR (400 MHz, DMSO-d$_6$) d 8.64 (t, J=5.6 Hz, 1H), 7.87 (d, J=7.6 Hz, 2H), 7.62 (d, J=7.6 Hz, 3H), 7.47 (q, J=6.4 Hz, 1H), 7.33 (t, J=9.2 Hz, 1H), 7.25 (t, J=7.6 Hz, 1H), 3.97~3.91 (m, 1H), 3.75~3.71 (m, 1H), 3.61~3.56 (m, 1H), 3.28~3.26 (m, 2H), 1.89~1.72 (m, 3H), 1.58~1.50 (m, 1H).

Example 72: Synthesis of N-((3-ethyloxetan-3-yl)methyl)-4-((2-fluorophenyl)ethynyl)benzamide

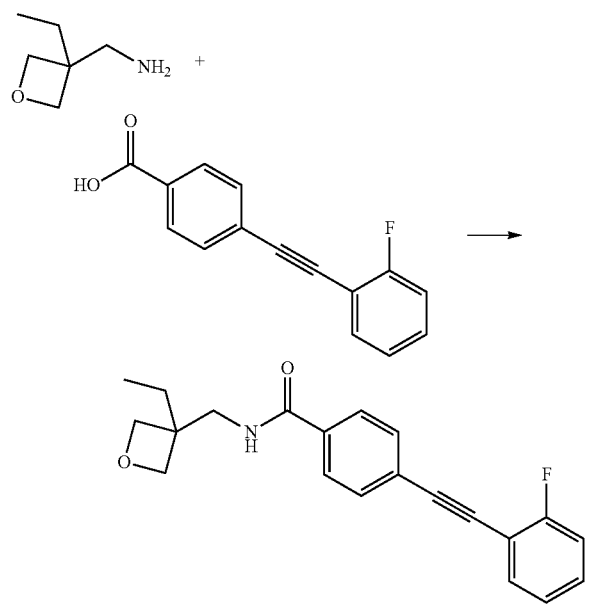

4-((2-Fluorophenyl)ethynyl)benzoic acid (0.100 g, 0.416 mmol) and (3-ethyloxetan-3-yl)methanamine (0.055 g, 0.479 mmol) as starting materials were used in a similar manner to Example 11 to obtain N-((3-ethyloxetan-3-yl)methyl)-4-((2-fluorophenyl)ethynyl)benzamide (0.091 g, 64.8%) as white solid: LRMS (ES) m/z 338.15 [M+H]$^+$, calculated MW 337.39; $^1$H-NMR (400 MHz, DMSO-d$_6$) d 8.65 (t, J=6.2 Hz, 1H), 7.88 (d, J=6.8 Hz, 2H), 7.65~7.61 (m, 3H), 7.49~7.46 (m, 1H), 7.33 (td, J=9.1, 1.1 Hz, 1H), 7.25 (td, J=7.5, 1.2 Hz, 1H), 4.40 (d, J=6.0 Hz, 2H), 4.20 (d, J=5.6 Hz, 2H), 3.47 (d, J=6.0 Hz, 2H), 1.61 (q, J=7.5 Hz, 2H), 0.86 (t, J=7.6 Hz, 3H).

Example 73: Synthesis of 4-((2,4-difluorophenyl)ethynyl)-N-((1-fluorocyclohexyl)methyl)benzamide

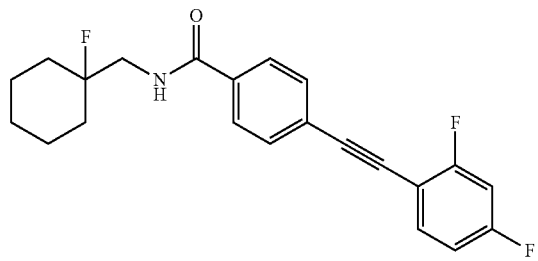 [SMILES: O=C(NCC1(F)CCCCC1)c1ccc(C#Cc2ccc(F)cc2F)cc1]

Step 1: Synthesis of (1-fluorocyclohexyl)methanamine hydrochloride

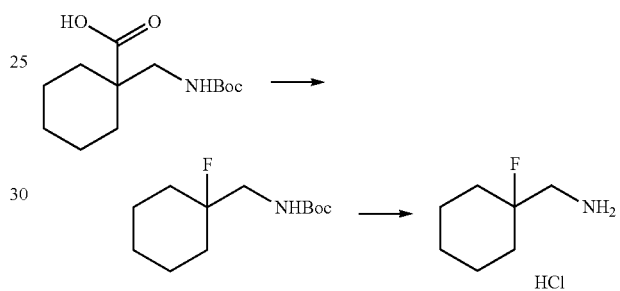

1-(((Tert-butoxycarbonyl)amino)methyl)cyclohexane-1-carboxylic acid (0.200 g, 0.777 mmol), 1-(chloromethyl)-4-fluoro-1,4-diazoniabicyclo[2.2.2]octane ditetrafluoroborate (Selectfluor®, 0.826 g, 2.332 mmol), [Ir{dF(CF$_3$)ppy}$_2$(dtbpy)]PF$_6$ (0.009 g, 0.008 mmol) and sodium hydrogen phosphate (Na$_2$HPO$_4$, 0.221 g, 1.554 mmol) were dissolved in water (3.5 mL)/acetonitrile (3.5 mL) at room temperature, and the resulting solution was stirred at the same temperature under visible light (blue LED, 60 W) for 18 hours. A saturated aqueous sodium hydrogen carbonate solution was poured into the reaction mixture, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain tert-butyl ((1-fluorocyclohexyl)methyl)carbamate (0.095 g, 52.8%) as white solid: LRMS (ES) m/z No detection [M+H]$^+$, calculated MW 231.31.

0.070 g (0.303 mmol) of the obtained product and 0.227 mL (0.908 mmol) of hydrogen chloride (4.00 M solution in 1,4-dioxane) were dissolved in dichloromethane (10 mL) at room temperature, and the resulting solution was stirred at the same temperature for 18 hours. After removing the solvent from the reaction mixture under reduced pressure, the precipitated solid was filtered, washed with diethyl ether and dried to obtain (1-fluorocyclohexyl)methanamine hydrochloride (0.057 g, 112.3%) as white solid: LRMS (ES) m/z no detection [M+H]$^+$, calculated MW 167.73; $^1$H-NMR (400 MHz, DMSO-d$_6$) d 8.03 (s, 2H), 3.01~2.96 (m, 2H), 1.87~1.76 (m, 2H), 1.50~1.41 (m, 8H).

Step 2: Synthesis of 4-((2,4-difluorophenyl)ethynyl)-N-((1-fluorocyclohexyl)methyl)benzamide

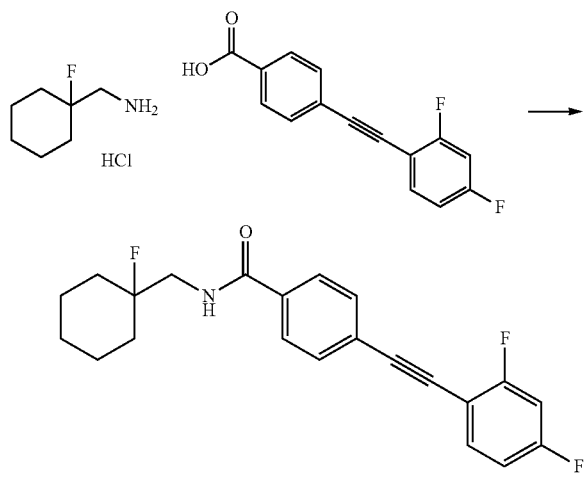

4-((2,4-Difluorophenyl)ethynyl)benzoic acid (0.035 g, 0.136 mmol) and (1-fluorocyclohexyl)methanamine hydrochloride (0.025 g, 0.149 mmol) as starting materials were used in a similar manner to Example 11 to obtain 4-((2,4-difluorophenyl)ethynyl)-N-((1-fluorocyclohexyl)methyl) benzamide (0.032 g, 63.6%) as white solid: LRMS (ES) m/z 372.23 [M+H]$^+$, calculated MW 371.4; $^1$H-NMR (400 MHz, DMSO-d$_6$) d 7.03~7.02 (m, 2H), 6.80~6.78 (m, 4H), 6.29~6.18 (m, 2H), 2.72 (d, J=3.2 Hz, 2H), 1.06~0.96 (m, 2H), 0.78 (s, 6H), 0.70~0.65 (m, 1H), 0.52~0.51 (m, 1H).

Example 74: Synthesis of methyl 2-(1-((4-((2-fluorophenyl)ethynyl)benzamido)methyl)cyclohexyl)acetate

Step 1: Synthesis of methyl 2-(1-(aminomethyl)cyclohexyl)acetate hydrochloride

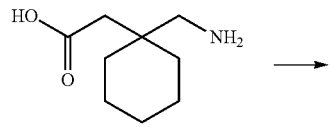

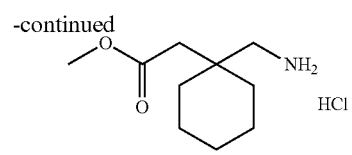

To the solution in which 2-(1-(aminomethyl)cyclohexyl) acetic acid (3.000 g, 17.519 mmol) was dissolved in methanol (50 mL) at 0° C., thionyl chloride (2.545 mL, 35.039 mmol) was added and stirred at 50° C. for 14 hours, and the temperature was lowered to room temperature to terminate the reaction. After the solvent was removed from the reaction mixture under reduced pressure, the obtained product was used without further purification (methyl 2-(1-(aminomethyl)cyclohexyl)acetate hydrochloride, 3.850 g, 99.1%, yellow solid): MOTS (ES) m/z 185.75 [M+H]$^+$, calculated MW 221.73.

Step 2: Synthesis of methyl 2-(1-((4-((2-fluorophenyl)ethynyl)benzamido)methyl)cyclohexyl)acetate

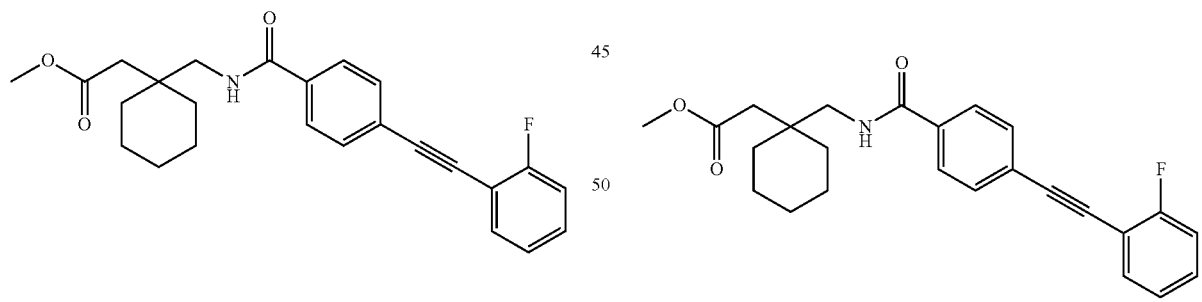

4-((2-Fluorophenyl)ethynyl)benzoic acid (0.400 g, 1.665 mmol) and methyl 2-(1-(aminomethyl)cyclohexyl)acetate hydrochloride (0.369 g, 1.665 mmol) as starting materials were used in a similar manner to Example 11 to obtain methyl 2-(1-((4-((2-fluorophenyl)ethynyl)benzamido) methyl)cyclohexyl)acetate (0.450 g, 66.3%) as yellow solid: LRMS (ES) m/z 408.29 [M+H]$^+$, calculated MW 407.49; $^1$H-NMR (400 MHz, DMSO-d$_6$) d 8.30 (t, J=6.4 Hz, 1H), 7.86 (d, J=8.8 Hz, 2H), 7.64 (m, 3H), 7.48 (m, 1H), 7.35~7.33 (m, 1H), 7.27~7.23 (m, 1H), 3.53 (s, 3H), 3.36 (m, 2H), 2.33 (s, 2H), 1.52~1.25 (m, 10H).

Example 75: Synthesis of methyl 2-(4-((4-((2-fluorophenyl)ethynyl)benzamido)methyl)tetrahydro-2H-pyran-4-yl)acetate

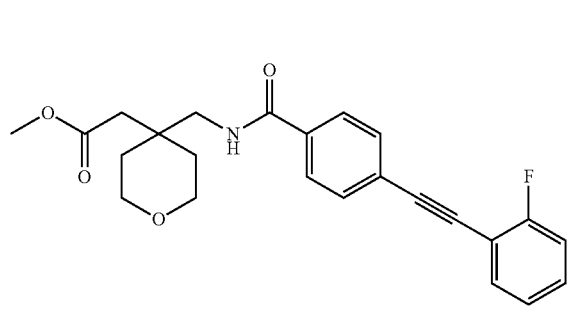 [SMILES: COC(=O)CC1(CNC(=O)c2ccc(C#Cc3ccccc3F)cc2)CCOCC1]

Step 1: Synthesis of methyl 2-(4-(aminomethyl)tetrahydro-2H-pyran-4-yl)acetate hydrochloride

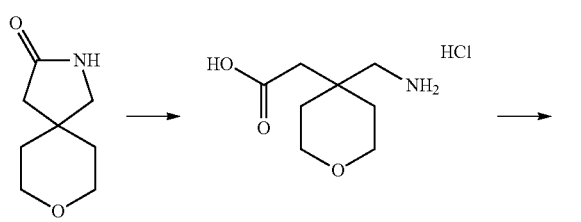

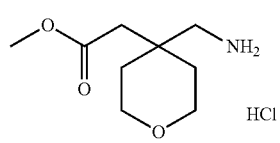

The mixture of 8-oxa-2-azaspiro[4.5]decan-3-one (0.500 g, 3.222 mmol) and hydrochloric acid (12.00 M solution, 5.369 mL, 64.433 mmol) at room temperature was heated under reflux for 8 hours, and then the temperature was lowered to room temperature. After the solvent was removed from the reaction mixture under reduced pressure, the precipitated solid was filtered, washed with dichloromethane and dried to obtain 2-(4-(aminomethyl)tetrahydro-2H-pyran-4-yl)acetic acid hydrochloride (0.620 g, 91.8%) as white solid: LRMS (ES) m/z 174.06 [M+H]$^+$, calculated MW 209.67.

To the solution in which 0.514 g (2.967 mmol) of the obtained product was dissolved in methanol (50 mL) at 0° C., thionyl chloride (0.431 mL, 5.935 mmol) was added and stirred at 50° C. for 14 hours. The temperature was lowered to room temperature to terminate the reaction. After the solvent was removed from the reaction mixture under reduced pressure, the obtained product was used without further purification (methyl 2-(4-(aminomethyl)tetrahydro-2H-pyran-4-yl)acetate, 0.660 g, 99.4%, yellow solid): LRMS (ES) m/z 188.13 [M+H]$^+$, calculated MW 223.7.

Step 2: Synthesis of methyl 2-(4-((4-((2-fluorophenyl)ethynyl)benzamido)methyl)tetrahydro-2H-pyran-4-yl)acetate

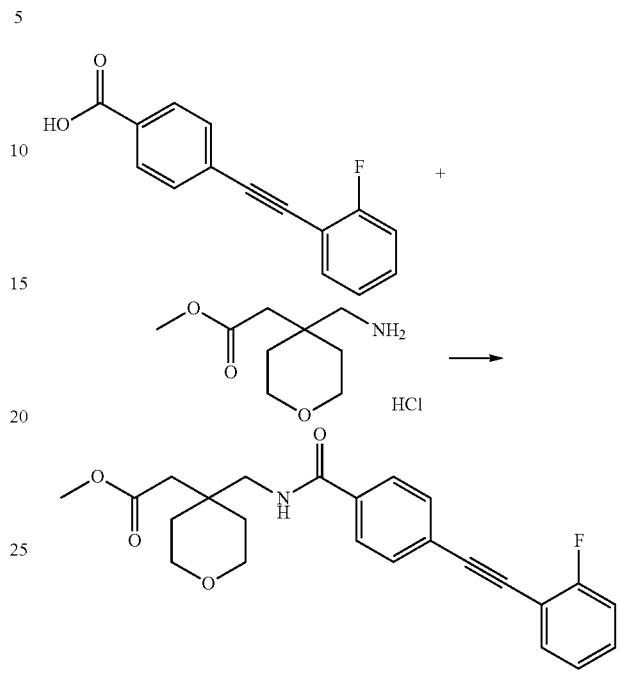

4-((2-Fluorophenyl)ethynyl)benzoic acid (0.600 g, 2.498 mmol) and methyl 2-(4-(aminomethyl)tetrahydro-2H-pyran-4-yl)acetate hydrochloride (0.559 g, 2.498 mmol) as starting materials were used in a similar manner to Example 11 to obtain methyl 2-(4-((4-((2-fluorophenyl)ethynyl)benzamido)methyl)tetrahydro-2H-pyran-4-yl)acetate (0.450 g, 44.0%) as yellow solid: LRMS (ES) m/z 410.21 [M+H]$^+$, calculated MW 409.46; $^1$H-NMR (400 MHz, DMSO-d$_6$) d 8.43 (t, J=6.2 Hz, 1H), 7.88~7.86 (m, 2H), 7.64~7.62 (m, 3H), 7.48 (m, 1H), 7.33 (m, 1H), 7.26 (t, J=3.6 Hz, 1H), 3.60 (m, 2H), 3.53 (m, 5H), 3.44 (d, J=6.4 Hz, 2H), 2.42 (s, 2H), 1.48~1.46 (m, 4H).

Example 76: Synthesis of 2-(1-((4-((2-fluorophenyl)ethynyl)benzamido)methyl)cyclohexyl)acetic acid

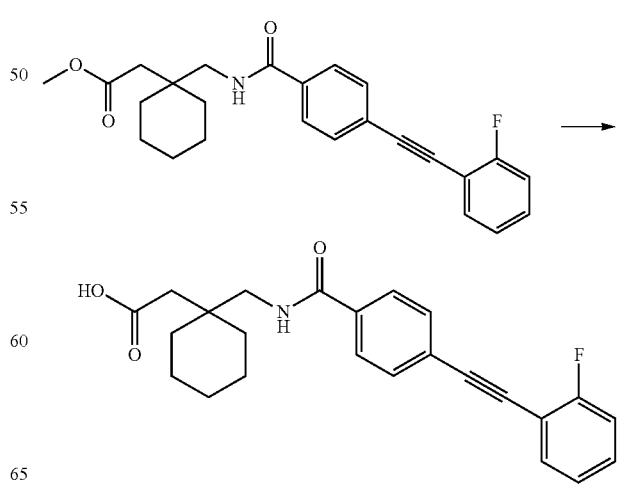

To the solution in which methyl 2-(1-((4-((2-fluorophenyl)ethynyl)benzamido)methyl)cyclohexyl)acetate (0.300 g, 0.736 mmol) obtained in Example 74 was dissolved in methanol (8 mL)/tetrahydrofuran (8 mL)/water (8 mL) at room temperature, lithium hydroxide monohydrate (0.062 g, 1.472 mmol) was added and stirred at the same temperature for 5 hours. The solvent was removed from the reaction mixture under reduced pressure, and 1N hydrochloric acid aqueous solution was added to the obtained concentrate, followed by extraction with ethyl acetate. The organic layer was washed with a saturated aqueous sodium chloride solution, dried over anhydrous sodium sulfate, filtered and concentrated under reduced pressure. The concentrate was purified by column chromatography and concentrated to obtain 2-(1-((4-((2-fluorophenyl)ethynyl)benzamido) methyl)cyclohexyl)acetic acid (0.230 g, 79.4%) as white solid: LRMS (ES) m/z 394.29 [M+H]$^+$, calculated MW 393.46; $^1$H-NMR (400 MHz, CD$_3$OD) d 7.84~7.82 (m, 2H), 7.62~7.60 (m, 2H), 7.55 (m, 1H), 7.40 (m, 1H), 7.21~7.17 (m, 2H), 3.49 (s, 2H), 2.39 (s, 2H), 1.57~1.44 (m, 10H).

Example 77: Synthesis of N-((1-(2-amino-2-oxoethyl)cyclohexyl)methyl)-4-((2-fluorophenyl)ethynyl)benzamide

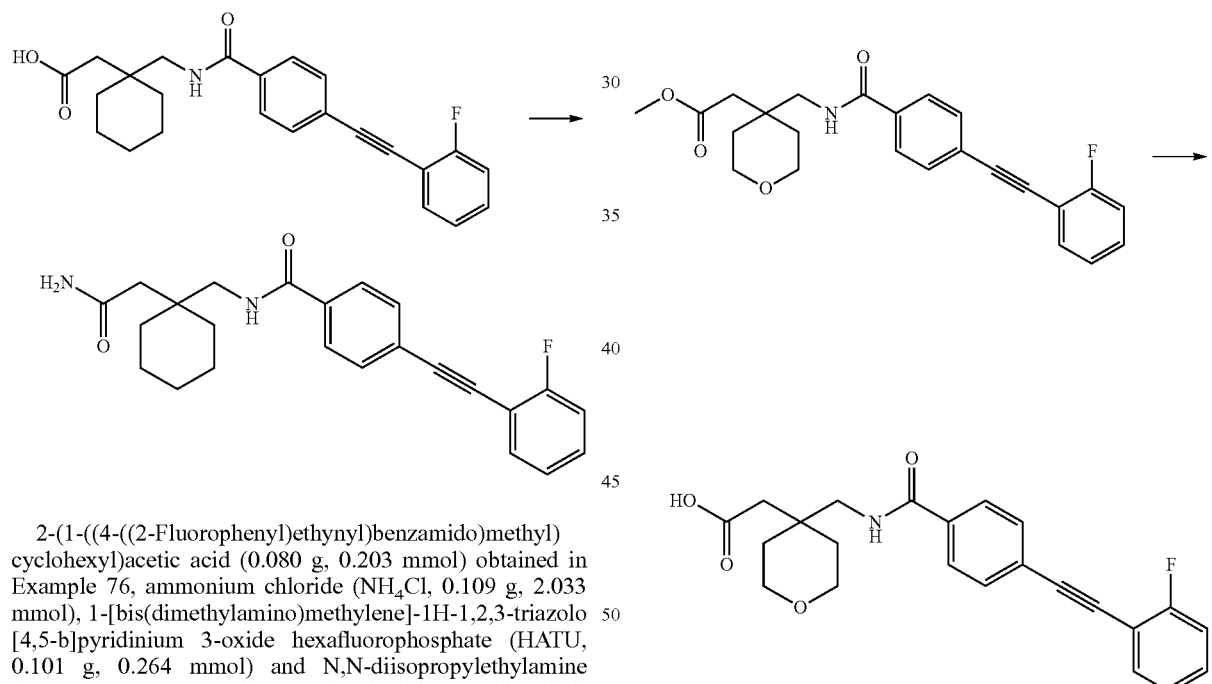

2-(1-((4-((2-Fluorophenyl)ethynyl)benzamido)methyl) cyclohexyl)acetic acid (0.080 g, 0.203 mmol) obtained in Example 76, ammonium chloride (NH$_4$Cl, 0.109 g, 2.033 mmol), 1-[bis(dimethylamino)methylene]-1H-1,2,3-triazolo[4,5-b]pyridinium 3-oxide hexafluorophosphate (HATU, 0.101 g, 0.264 mmol) and N,N-diisopropylethylamine (0.177 mL, 1.017 mmol) were dissolved in N,N-dimethylformamide (2 mL) at room temperature, and the resulting solution was stirred at 50° C. for 16 hours. Then, the temperature was lowered to room temperature to terminate the reaction. The reaction mixture was filtered through a Celite pad to remove solids. To the concentrate obtained by removing solvent from the filtrate under reduced pressure, a saturated aqueous sodium hydrogen carbonate solution was added, followed by extraction with ethyl acetate. The organic layer was washed with a saturated aqueous sodium chloride solution, dried over anhydrous magnesium sulfate, filtered and concentrated under reduced pressure to obtain N-((1-(2-amino-2-oxo ethyl)cyclohexyl)methyl)-4-((2-fluorophenyl)ethynyl)benzamide (0.055 g, 68.9%, white solid): LRMS (ES) m/z 393.30 [M+H]$^+$, calculated MW 392.47; $^1$H-NMR (400 MHz, DMSO-d$_6$) d 8.95 (t, J=5.8 Hz, 1H), 7.86 (d, J=8.8 Hz, 2H), 7.40~7.62 (m, 4H), 7.48 (m, 1H), 7.32 (m, 1H), 7.25 (m, 1H), 7.06 (bs, 1H), 3.33 (s, 2H), 2.16 (s, 2H), 1.43~1.30 (m, 10H).

Example 78: Synthesis of N-((4-(2-amino-2-oxoethyl)tetrahydro-2H-pyran-4-yl)methyl)-4-((2-fluorophenyl)ethynyl)benzamide

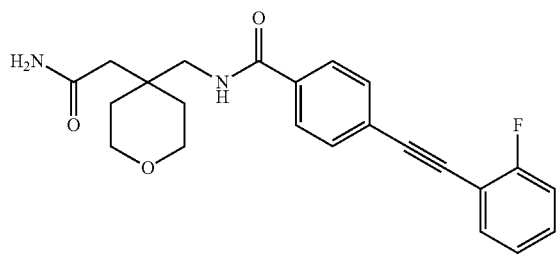 [SMILES: NC(=O)CC1(CNC(=O)c2ccc(C#Cc3ccccc3F)cc2)CCOCC1]

Step 1: Synthesis of 2-(4-((4-((2-fluorophenyl)ethynyl)benzamido)methyl)tetrahydro-2H-pyran-4-yl) acetic acid Methyl 2-(4-((4-((2-fluorophenyl)ethynyl)benzamido)methyl)tetrahydro-2H-pyran-4-yl)acetate (0.070 g, 0.171 mmol) obtained in Example 75 as a starting material was used in a similar manner to Example 76 to obtain 2-(4-((4-((2-fluorophenyl)ethynyl)benzamido)methyl)tetrahydro-2H-pyran-4-yl)acetic acid. The obtained product was used without further purification (0.055 g, 81.4%, white solid): LRMS (ES) m/z 396.27 [M+H]$^+$, calculated MW 395.43.

Step 2: Synthesis of N-((4-(2-amino-2-oxoethyl)tetrahydro-2H-pyran-4-yl)methyl)-4-((2-fluorophenyl)ethynyl)benzamide

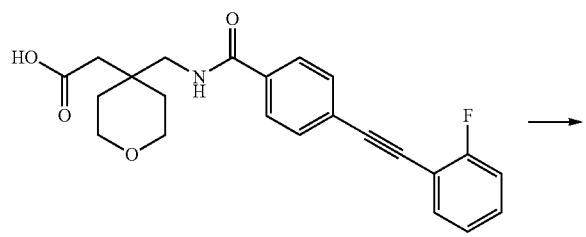

2-(4-((4-((2-Fluorophenyl)ethynyl)benzamido)methyl)tetrahydro-2H-pyran-4-yl)acetic acid (0.070 g, 0.177 mmol) as a starting material was used in a similar manner to Example 77 to obtain N-((4-(2-amino-2-oxoethyl)tetrahydro-2H-pyran-4-yl)methyl)-4-((2-fluorophenyl)ethynyl)benzamide (0.045 g, 64.4%, yellow oil): LRMS (ES) m/z 395.08 [M+H]$^+$, calculated MW 394.45; $^1$H-NMR (400 MHz, DMSO-d$_6$) d 8.84 (t, J=6.0 Hz, 1H), 7.86 (m, 2H), 7.64~7.62 (m, 4H), 7.51~7.43 (m, 1H), 7.32 (m, 1H), 7.26 (m, 1H), 7.06 (bs, 1H), 3.62~3.52 (m, 4H), 3.41 (m, 2H), 2.23 (s, 2H), 1.45~1.40 (m, 4H).

Example 79: Synthesis of 4-((2-fluorophenyl)ethynyl)-N-((1-(2-(hydroxyamino)-2-oxoethyl)cyclohexyl)methyl)benzamide

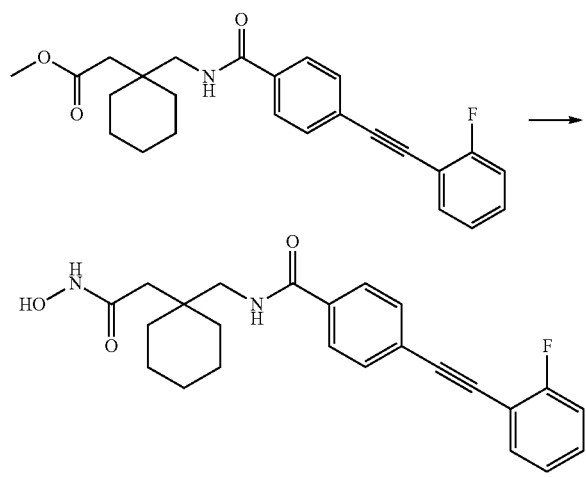

To the solution in which methyl 2-(1-((4-((2-fluorophenyl)ethynyl)benzamido)methyl)cyclohexyl)acetate (0.050 g, 0.123 mmol) obtained in Example 74 was dissolved in methanol (2 mL)/tetrahydrofuran (1 mL) at 0° C., potassium hydroxide (KOH, 0.014 g, 0.245 mmol) and hydroxylamine (50.00% solution in water, 0.081 mL, 1.227 mmol) were added and stirred at room temperature for 1 hour. After the solvent was removed from the reaction mixture under reduced pressure, a saturated aqueous sodium hydrogen carbonate solution was poured into the concentrate and stirred. The precipitated solid was filtered, washed with water and dried to obtain 4-((2-fluorophenyl)ethynyl)-N-((1-(2-(hydroxyamino)-2-oxoethyl)cyclohexyl)methyl)benzamide (0.040 g, 79.8%) as white solid: LRMS (ES) m/z 409.15 [M+H]$^+$, calculated MW 408.47; $^1$H-NMR (400 MHz, CD$_3$OD) d 7.90~7.88 (m, 2H), 7.63~7.61 (m, 2H), 7.55 (m, 1H), 7.40 (m, 1H), 7.21~7.15 (m, 2H), 3.47 (s, 2H), 2.19 (s, 2H), 1.56~1.37 (m, 10H).

Example 80: Synthesis of 4-((2-fluorophenyl)ethynyl)-N-((1-(2-(methylamino)-2-oxoethyl)cyclohexyl)methyl)benzamide

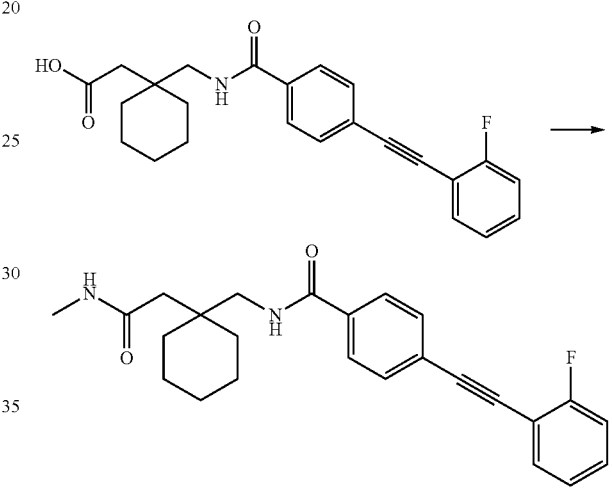

2-(1-((4-((2-Fluorophenyl)ethynyl)benzamido)methyl)cyclohexyl)acetic acid (0.050 g, 0.127 mmol) obtained in Example 76 and methanamine hydrochloride (0.017 g, 0.254 mmol) as starting materials were used in a similar manner to Example 77 to obtain 4-((2-fluorophenyl)ethynyl)-N-((1-(2-(methylamino)-2-oxo ethyl)cyclohexyl)methyl)benzamide (0.045 g, 87.1%, white solid): LRMS (ES) m/z 406.97 [M+H]$^+$, calculated MW 406.5; $^1$H-NMR (400 MHz, DMSO-d$_6$) d 8.80 (t, J=5.6 Hz, 1H), 8.06 (d, J=4.8 Hz, 1H), 7.81 (d, J=48.4 Hz, 2H), 7.65 (m, 3H), 7.48 (m, 1H), 7.32 (t, J=9.2 Hz, 1H), 7.25 (t, J=7.6 Hz, 1H), 3.31 (s, 2H), 2.57 (d, J=4.8 Hz, 3H), 2.15 (s, 2H), 1.42~1.25 (m, 10H).

Example 81: Synthesis of N-((1-(2-(dimethylamino)-2-oxoethyl)cyclohexyl)methyl)-4-((2-fluorophenyl)ethynyl)benzamide

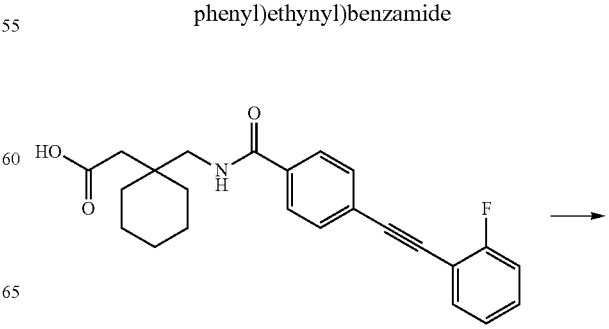

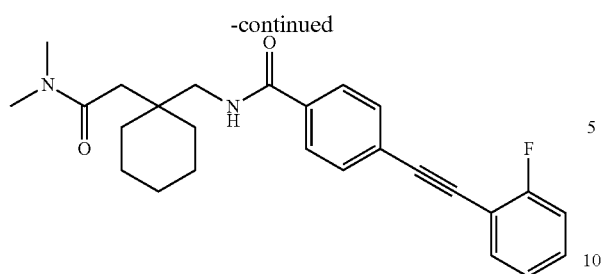

2-(1-((4-((2-Fluorophenyl)ethynyl)benzamido)methyl)cyclohexyl)acetic acid (0.050 g, 0.127 mmol) obtained in Example 76 and dimethylamine hydrochloride (0.021 g, 0.254 mmol) as starting materials were used in a similar manner to Example 77 to obtain N-((1-(2-(dimethylamino)-2-oxoethyl)cyclohexyl)methyl)-4-((2-fluorophenyl)ethynyl)benzamide, followed by purifying by column chromatography to obtain a product as white solid (0.050 g, 93.6%): LRMS (ES) m/z 421.04 [M+H]+, calculated MW 420.53; $^1$H-NMR (400 MHz, DMSO-d$_6$) d 8.69 (t, J=6.0 Hz, 1H), 7.85 (d, J=8.8 Hz, 2H), 7.65~7.62 (m, 3H), 7.48 (m, 1H), 7.33 (m, 1H), 7.26 (t, J=3.8 Hz, 1H), 3.39 (d, J=6.0 Hz, 2H), 2.99 (s, 3H), 2.81 (s, 3H), 2.35 (s, 2H), 1.45~1.28 (m, 10H).

Example 82: Synthesis of 4-((2-fluorophenyl)ethynyl)-N-((3-hydroxyoxetan-3-yl)methyl)benzamide

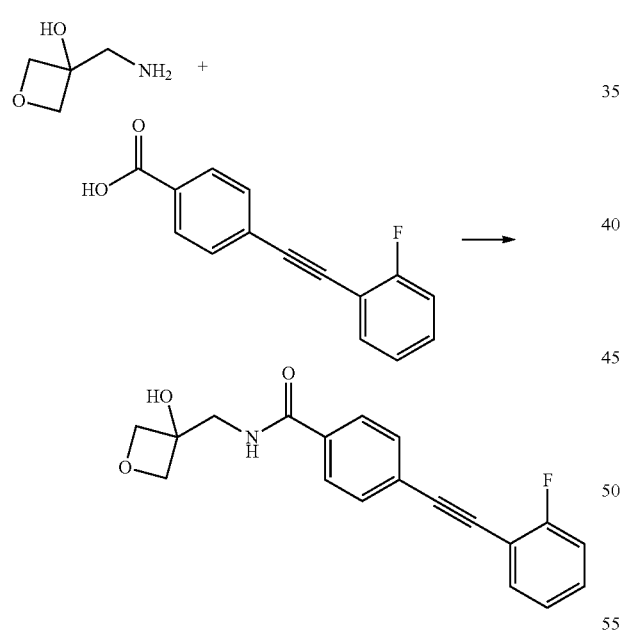

4-((2-Fluorophenyl)ethynyl)benzoic acid (0.100 g, 0.416 mmol) and 3-(aminomethyl)oxetan-3-ol (0.052 g, 0.500 mmol) as starting materials were used in a similar manner to Example 11 to obtain 4-((2-fluorophenyl)ethynyl)-N-(3-hydroxyoxetan-3-yl)methyl)benzamide (0.082 g, 60.5%) as ivory solid: LRMS (ES) m/z 326.22 [M+H]+, calculated MW 325.34; $^1$H-NMR (400 MHz, DMSO-d$_6$) d 8.71 (t, J=6.2 Hz, 1H), 7.90 (dd, J=6.8, 1.6 Hz, 2H), 7.65~7.61 (m, 3H), 7.49~7.47 (m, 1H), 7.33 (t, J=8.4 Hz, 1H), 7.25 (td, J=7.5, 0.9 Hz, 1H), 5.86 (s, 1H), 4.46 (d, J=6.8 Hz, 2H), 4.36 (d, J=6.4 Hz, 2H), 3.53 (d, J=6.0 Hz, 2H).

Example 83: Synthesis of 4-((4-fluorophenyl)ethynyl)-N-((3-methyloxetan-3-yl)methyl)benzamide

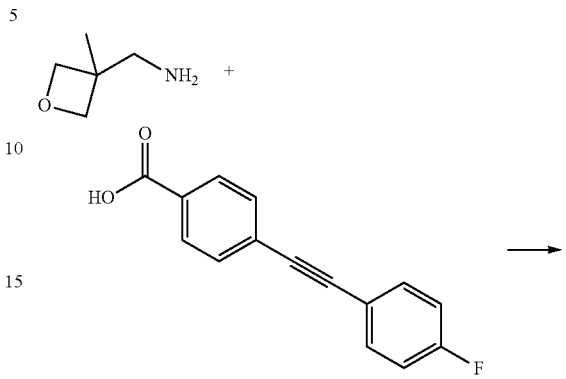

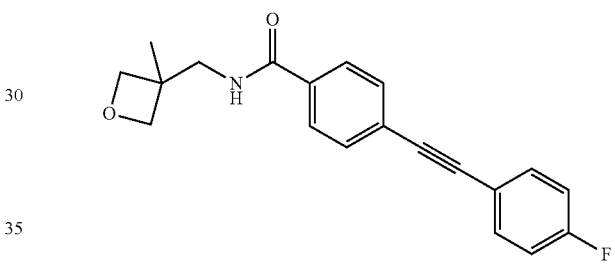

4-((4-Fluorophenyl)ethynyl)benzoic acid (0.070 g, 0.291 mmol) and (3-methyloxetan-3-yl)methanamine (0.035 g, 0.350 mmol) as starting materials were used in a similar manner to Example 11 to obtain 4-((4-fluorophenyl)ethynyl)-N-(3-methyloxetan-3-yl)methyl)benzamide (0.089 g, 94.5%) as white solid: LRMS (ES) m/z 324.11 [M+H]+, calculated MW 323.37; $^1$H-NMR (400 MHz, DMSO-d$_6$) d 8.69 (t, J=6.2 Hz, 1H), 7.87 (d, J=8.0 Hz, 2H), 7.64~7.58 (m, 4H), 7.29~7.23 (m, 2H), 4.44 (d, J=5.6 Hz, 2H), 4.17 (d, J=6.0 Hz, 2H), 3.43 (d, J=6.0 Hz, 2H), 1.22 (s, 3H).

Example 84: Synthesis of 3-fluoro-4-((2-fluorophenyl)ethynyl)-N-((3-methyloxetan-3-yl)methyl)benzamide

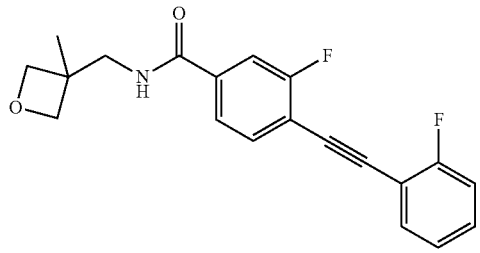 [SMILES: CC1(CNC(=O)c2ccc(C#Cc3ccccc3F)c(F)c2)COC1]

Step 1: Synthesis of 3-fluoro-4-((2-fluorophenyl)ethynyl)benzoic acid

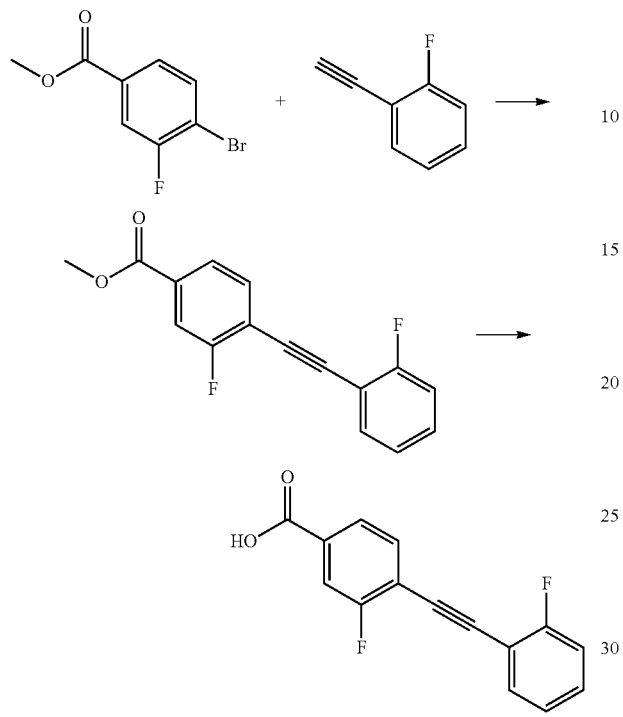

Methyl 4-bromo-3-fluorobenzoate (2.000 g, 8.582 mmol) and 1-ethynyl-2-fluorobenzene (1.031 g, 8.582 mmol) as starting materials were used in a similar manner to Step 1 of Example 3 to obtain methyl 3-fluoro-4-((2-fluorophenyl)ethynyl)benzoate (1.800 g, 77.0%, LRMS (ES) m/z 272.94 [M+H]$^+$, calculated MW 272.25) as white solid, followed by obtaining 3-fluoro-4-((2-fluorophenyl)ethynyl)benzoic acid (1.700 g, 99.6%) as white solid: LRMS (ES) m/z 257.03 [M−H]$^+$, calculated MW 258.22.

Step 2: Synthesis of 3-fluoro-4-((2-fluorophenyl)ethynyl)-N-((3-methyloxetan-3-yl)methyl)benzamide

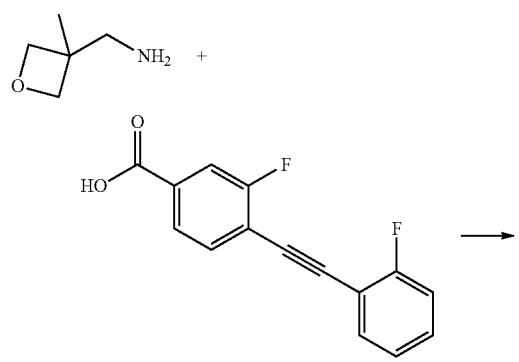

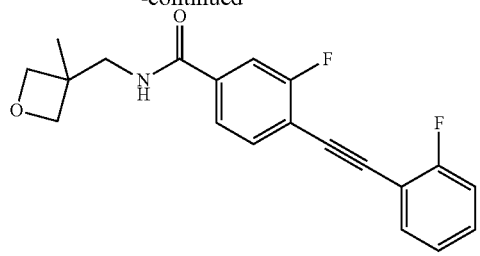

3-Fluoro-4-((2-fluorophenyl)ethynyl)benzoic acid (0.070 g, 0.271 mmol) and (3-methyloxetan-3-yl)methanamine (0.036 g, 0.352 mmol) as starting materials were used in a similar manner to Example 11 to obtain 3-fluoro-4-((2-fluorophenyl)ethynyl)-N-((3-methyloxetan-3-yl)methyl)benzamide as white solid: LRMS (ES) m/z 342.11 [M+H]$^+$, calculated MW 341.36; $^1$H-NMR (400 MHz, DMSO-d$_6$) d 8.76 (t, J=6.0 Hz, 1H), 7.78~7.71 (m, 3H), 7.64 (td, J=7.5, 1.7 Hz, 1H), 7.54~7.48 (m, 1H), 7.35 (t, J=8.6 Hz, 1H), 7.27 (td, J=7.5, 0.9 Hz, 1H), 4.43 (d, J=6.0 Hz, 2H), 4.17 (d, J=6.0 Hz, 2H), 3.45 (d, J=6.4 Hz, 2H), 1.22 (s, 3H).

Example 85: Synthesis of 4-((2-fluorophenyl)ethynyl)-N-(((1s,3s)-3-hydroxycyclobutyl)methyl)benzamide

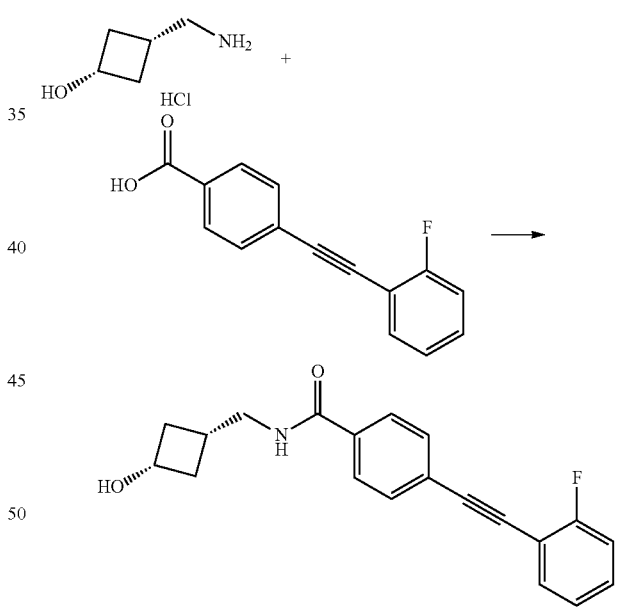

4-((2-Fluorophenyl)ethynyl)benzoic acid (0.050 g, 0.208 mmol) and (1s,3s)-3-(aminomethyl)cyclobutan-1-ol (0.025 g, 0.250 mmol) as starting materials were used in a similar manner to Example 11 to obtain 4-((2-fluorophenyl)ethynyl)-N-(((1s,3s)-3-hydroxycyclobutyl)methyl)benzamide (0.059 g, 87.7%) as ivory solid: LRMS (ES) m/z 324.24 [M+H]$^+$, calculated MW 323.37; $^1$H-NMR (400 MHz, DMSO-d$_6$) d 8.54 (t, J=5.8 Hz, 1H), 7.87~7.85 (m, 2H), 7.65~7.61 (m, 3H), 7.48~7.44 (m, 1H), 7.33 (t, J=8.8 Hz, 1H), 7.25 (td, J=7.6, 1.1 Hz, 1H), 4.91 (d, J=6.4 Hz, 1H), 3.88~3.79 (m, 1H), 3.23 (t, J=6.0 Hz, 2H), 2.21~2.17 (m, 2H), 1.92~1.82 (m, 1H), 1.53~1.46 (m, 2H).

Example 86: Synthesis of 4-((2-fluorophenyl)ethynyl)-N-(1r,3r)-3-hydroxycyclobutyl)methyl)benzamide

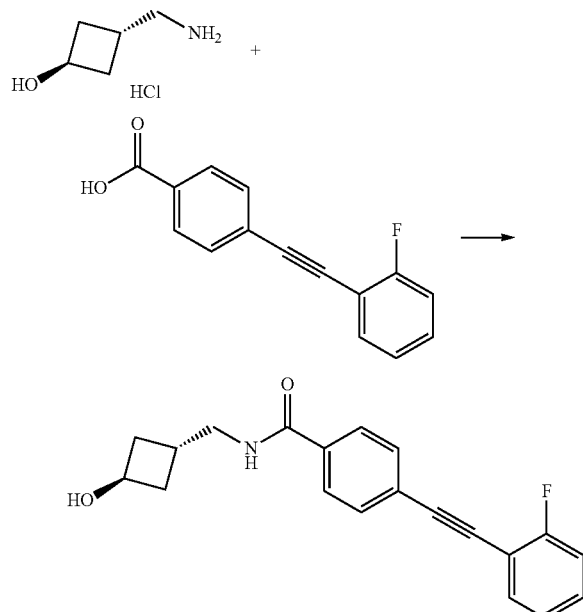

4-((2-Fluorophenyl)ethynyl)benzoic acid (0.050 g, 0.208 mmol) and (1r,3r)-3-(aminomethyl)cyclobutan-1-ol (0.025 g, 0.250 mmol) as starting materials were used in a similar manner to Example 11 to obtain 4-((2-fluorophenyl)ethynyl)-N-(((1r,3r)-3-hydroxycyclobutyl)methyl)benzamide (0.053 g, 78.7%) as ivory solid: LRMS (ES) m/z 324.14 [M+H]$^+$, calculated MW 323.37; $^1$H-NMR (400 MHz, DMSO-d$_6$) d 8.58 (t, J=5.4 Hz, 1H), 7.86 (dd, J=6.6, 1.8 Hz, 2H), 7.65~7.61 (m, 3H), 7.48~7.45 (m, 1H), 7.33 (t, J=9.2 Hz, 1H), 7.25 (td, J=7.6, 0.9 Hz, 1H), 4.92 (d, J=6.0 Hz, 1H), 4.22~4.13 (m, 1H), 3.30~3.25 (m, 2H), 2.29~2.22 (m, 1H), 2.02~1.95 (m, 2H), 1.89~1.82 (m, 2H).

Example 87: Synthesis of 4-((2-fluorophenyl)ethynyl)-N-(((1s,3s)-3-hydroxy-3-methylcyclobutyl)methyl)benzamide

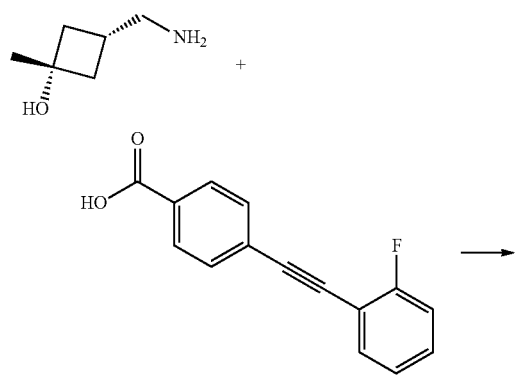

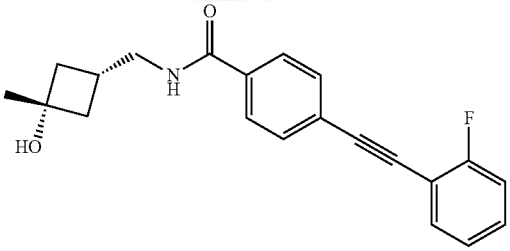

4-((2-Fluorophenyl)ethynyl)benzoic acid (0.070 g, 0.291 mmol) and (1s,3s)-3-(aminomethyl)-1-methylcyclobutan-1-ol (0.044 g, 0.379 mmol) as starting materials were used in a similar manner to Example 11 to obtain 4-((2-fluorophenyl)ethynyl)-N-(((1s,3s)-3-hydroxy-3-methylcyclobutyl)methyl)benzamide (0.097 g, 98.7%) as white solid: LRMS (ES) m/z 338.08 [M+H]$^+$, calculated MW 337.39; $^1$H-NMR (400 MHz, DMSO-d$_6$) d 8.53 (t, J=5.8 Hz, 1H), 7.86 (dd, J=6.4, 2.0 Hz, 2H), 7.65~7.61 (m, 3H), 7.53~7.44 (m, 1H), 7.33 (t, J=9.6 Hz, 1H), 7.25 (td, J=7.6, 0.9 Hz, 1H), 4.84 (s, 1H), 3.24 (t, J=6.0 Hz, 2H), 1.97~1.92 (m, 3H), 1.73~1.67 (m, 2H), 1.16 (s, 3H).

Example 88: Synthesis of N-((4,4-difluorocyclohexyl)methyl)-4-(pyridin-4-ylethynyl)benzamide

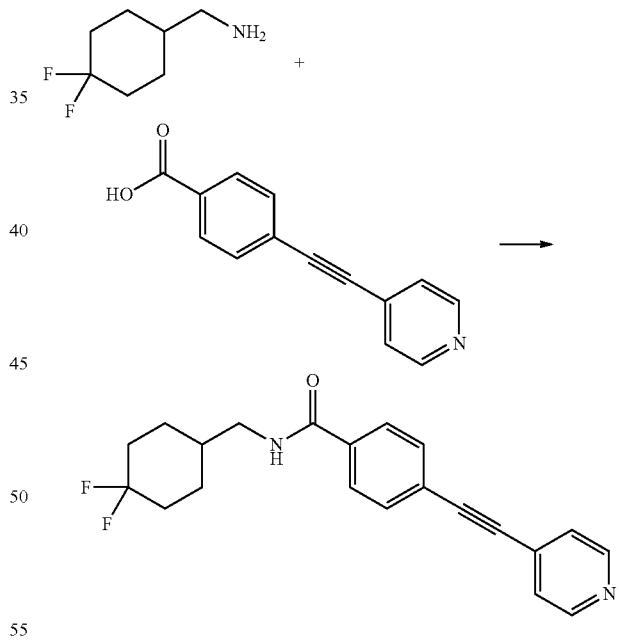

4-(Pyridin-4-ylethynyl)benzoic acid (0.200 g, 0.896 mmol) and (4,4-difluorocyclohexyl)methanamine (0.160 g, 1.075 mmol) as starting materials were used in a similar manner to Example 11 to obtain N-((4,4-difluorocyclohexyl)methyl)-4-(pyridin-4-ylethynyl)benzamide (0.210 g, 66.1%) as white solid: LRMS (ES) m/z 354.79 [M+H]$^+$, calculated MW 354.4; $^1$H-NMR (400 MHz, DMSO-d$_6$) d 8.64 (t, J=5.8 Hz, 1H), 8.62~8.60 (m, 2H), 7.88 (d, J=8.8 Hz, 2H), 7.67 (d, J=6.8 Hz, 2H), 7.52 (dd, J=4.4, 2.0 Hz, 2H), 3.14 (t, J=6.4 Hz, 2H), 1.98~1.96 (m, 2H), 1.77~1.65 (m, 5H), 1.22~1.13 (m, 2H).

Example 89: Synthesis of N-((3,3-difluorocyclobutyl)methyl)-4-(pyridin-4-ylethynyl)benzamide

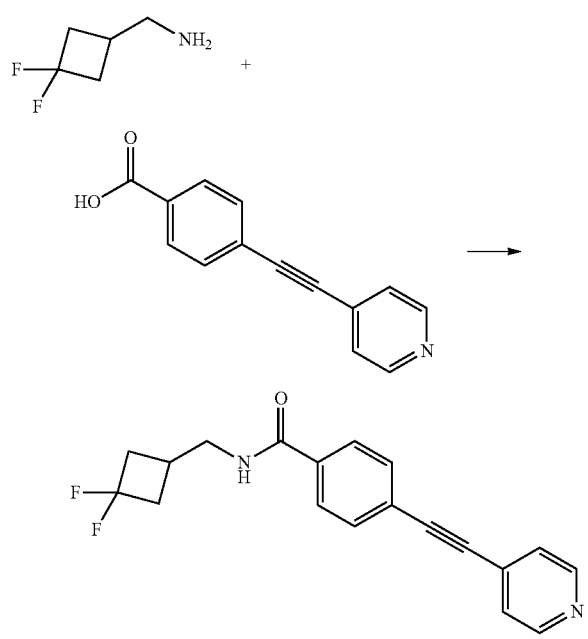

4-(Pyridin-4-ylethynyl)benzoic acid (0.100 g, 0.448 mmol) and (3,3-difluorocyclobutyl)methanamine (0.065 g, 0.538 mmol) as starting materials were used in a similar manner to Example 11 to obtain N-((3,3-difluorocyclobutyl)methyl)-4-(pyridin-4-ylethynyl)benzamide (0.089 g, 60.9%) as white solid: LRMS (ES) m/z 327.18 [M+H]$^+$, calculated MW 326.35; $^1$H-NMR (400 MHz, DMSO-d$_6$) d 8.75 (t, J=5.6 Hz, 1H), 8.65 (dd, J=4.4, 1.6 Hz, 2H), 7.91 (d, J=8.4 Hz, 2H), 7.72 (d, J=8.8 Hz, 2H), 7.56 (dd, J=4.2, 1.8 Hz, 2H), 3.40 (t, J=5.0 Hz, 2H), 2.67~2.62 (m, 2H), 2.42~2.33 (m, 3H).

Example 90: Synthesis of N-((3,3-difluorocyclobutyl)methyl)-4-(phenylethynyl)benzamide

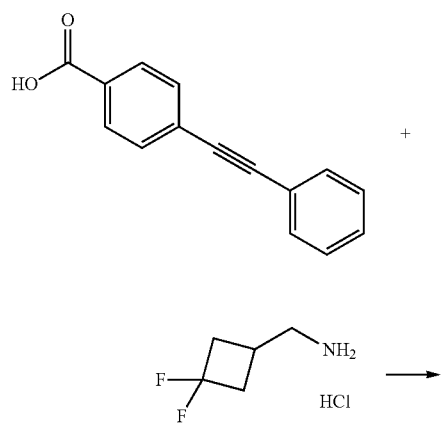

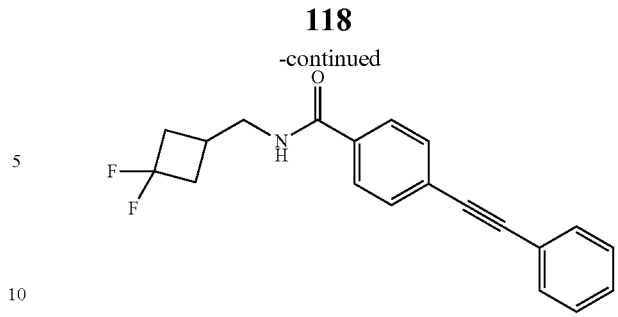

4-(Phenylethynyl)benzoic acid (0.070 g, 0.315 mmol) and (3,3-difluorocyclobutyl)methanamine hydrochloride (0.050 g, 0.315 mmol) as starting materials were used in a similar manner to Example 11 to obtain N-((3,3-difluorocyclobutyl)methyl)-4-(phenylethynyl)benzamide (0.080 g, 78.1%) as white solid: LRMS (ES) m/z 326.13 [M+H]$^+$, calculated MW 325.36; $^1$H-NMR (400 MHz, DMSO-d$_6$) d 8.70 (t, J=5.6 Hz, 1H), 7.85 (dd, J=6.4, 2.0 Hz, 2H), 7.62 (d, J=8.0 Hz, 2H), 7.54 (m, 2H), 7.42~7.40 (m, 3H), 3.35 (t, J=5.4 Hz, 2H), 2.63~2.52 (m, 2H), 2.40~2.32 (m, 3H).

Example 91: Synthesis of (S)-4-((2-fluorophenyl)ethynyl)-N-((tetrahydro-2H-pyran-3-yl)methyl)benzamide

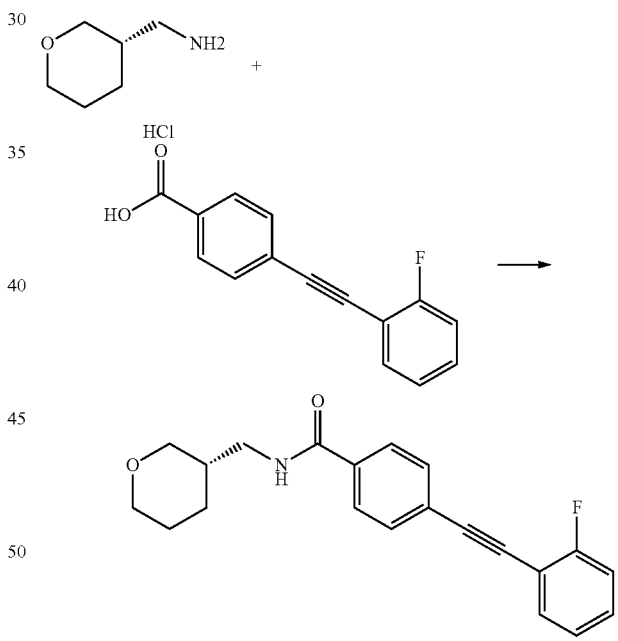

4-((2-Fluorophenyl)ethynyl)benzoic acid (0.050 g, 0.208 mmol) and (S)-(tetrahydro-2H-pyran-3-yl)methanamine hydrochloride (0.035 g, 0.229 mmol) as starting materials were used in a similar manner to Example 11 to obtain (S)-4-((2-fluorophenyl)ethynyl)-N-((tetrahydro-2H-pyran-3-yl)methyl)benzamide (0.066 g, 93.3%) as white solid: LRMS (ES) m/z 338.13 [M+H]$^+$, calculated MW 337.39; $^1$H-NMR (400 MHz, DMSO-d$_6$) d 8.58 (t, J=6.0 Hz, 1H), 7.86 (d, J=8.0 Hz, 2H), 7.65~7.56 (m, 3H), 7.50~7.44 (m, 1H), 7.33 (t, J=9.2 Hz, 1H), 7.25 (td, J=7.6, 1.1 Hz, 1H), 3.75~3.61 (m, 2H), 3.31~3.28 (m, 2H), 3.13~3.05 (m, 3H), 1.77~1.69 (m, 2H), 1.56~1.40 (m, 2H).

Example 92: Synthesis of (R)-4-((2-fluorophenyl)ethynyl)-N-((tetrahydro-2H-pyran-3-yl)methyl)benzamide

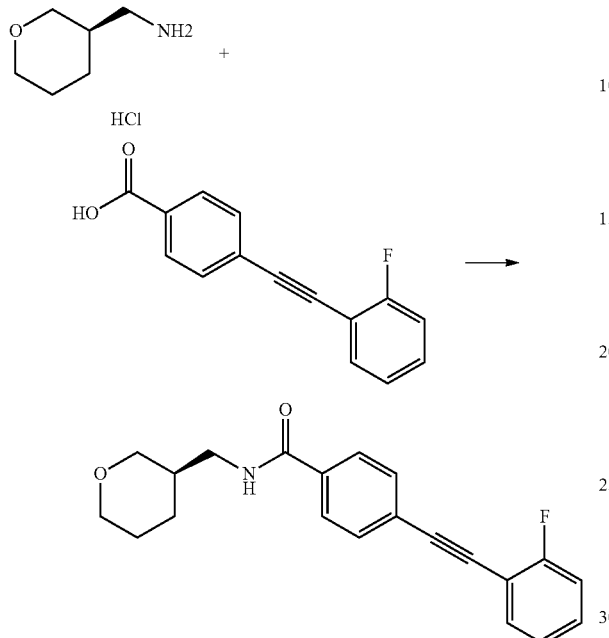

4-((2-Fluorophenyl)ethynyl)benzoic acid (0.050 g, 0.208 mmol) and (R)-(tetrahydro-2H-pyran-3-yl)methanamine hydrochloride (0.035 g, 0.229 mmol) as starting materials were used in a similar manner to Example 11 to obtain (R)-4-((2-fluorophenyl)ethynyl)-N-((tetrahydro-2H-pyran-3-yl)methyl)benzamide (0.055 g, 78.3%) as white solid: LRMS (ES) m/z 338.20 [M+H]$^+$, calculated MW 337.39; $^1$H-NMR (400 MHz, DMSO-d$_6$) d 8.58 (t, J=5.8 Hz, 1H), 7.86 (dd, J=6.6, 1.8 Hz, 2H), 7.65~7.61 (m, 3H), 7.44~7.35 (m, 1H), 7.33 (td, J=9.2, 0.8 Hz, 1H), 7.25 (td, J=7.6, 1.1 Hz, 1H), 3.75~3.72 (m, 1H), 3.69 (s, 1H), 3.30~3.25 (m, 1H), 3.15~3.05 (m, 3H), 1.79~1.72 (m, 2H), 1.57~1.52 (m, 1H), 1.49~1.35 (m, 1H), 1.26~1.21 (m, 1H).

Example 93: Synthesis of (S)-4-((2-fluorophenyl)ethynyl)-N-((tetrahydrofuran-3-yl)methyl)benzamide

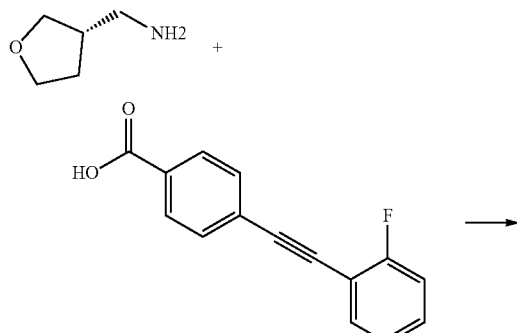

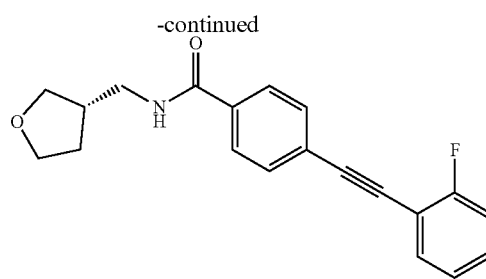

4-((2-Fluorophenyl)ethynyl)benzoic acid (0.070 g, 0.291 mmol) and (S)-(tetrahydrofuran-3-yl)methanamine (0.032 g, 0.321 mmol) as starting materials were used in a similar manner to Example 11 to obtain (S)-4-((2-fluorophenyl)ethynyl)-N-((tetrahydrofuran-3-yl)methyl)benzamide (0.089 g, 94.5%) as clear liquid: MOTS (ES) m/z 324.05 [M+H]$^+$, calculated MW 323.37; $^1$H-NMR (400 MHz, DMSO-d$_6$) d 8.68 (t, J=5.8 Hz, 1H), 7.86 (dd, J=6.8, 2.0 Hz, 2H), 7.65~7.61 (m, 3H), 7.50~7.43 (m, 1H), 7.33 (td, J=9.1, 1.1 Hz, 1H), 7.25 (td, J=7.7, 1.1 Hz, 1H), 3.75~3.69 (m, 1H), 3.68~3.62 (m, 1H), 3.60~3.55 (m, 1H), 3.45~3.40 (m, 1H), 3.33~3.19 (m, 3H), 1.95~1.87 (m, 1H), 1.61~1.51 (m, 1H).

Example 94: Synthesis of 4-((4-fluorophenyl)ethynyl)-N-((tetrahydrofuran-3-yl)methyl)benzamide

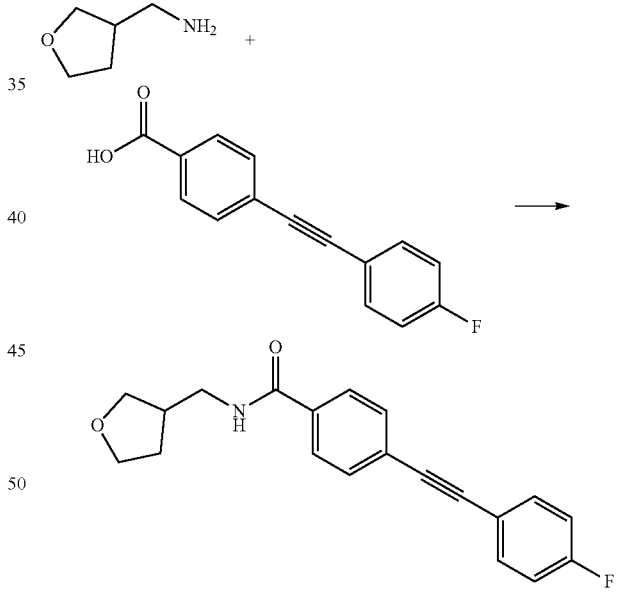

4-((4-Fluorophenyl)ethynyl)benzoic acid (0.070 g, 0.291 mmol) and (tetrahydrofuran-3-yl)methanamine (0.035 g, 0.350 mmol) as starting materials were used in a similar manner to Example 11 to obtain 4-((4-fluorophenyl)ethynyl)-N-((tetrahydrofuran-3-yl)methyl)benzamide (0.079 g, 83.8%) as ivory solid: LRMS (ES) m/z 324.14 [M+H]$^+$, calculated MW 323.37; $^1$H-NMR (400 MHz, DMSO-d$_6$) d 8.64 (t, J=5.8 Hz, 1H), 7.85 (dd, J=6.8, 2.0 Hz, 2H), 7.64~7.58 (m, 4H), 7.29~7.23 (m, 2H), 3.73~3.68 (m, 1H), 3.65~3.63 (m, 1H), 3.61~3.55 (m, 1H), 3.45~3.42 (m, 1H), 3.22~3.15 (m, 3H), 1.95~1.86 (m, 1H), 1.60~1.52 (m, 1H).

Example 95: Synthesis of 4-((2-fluorophenyl)ethynyl)-N-((3-methyloxetan-3-yl)methyl-d)benzamide

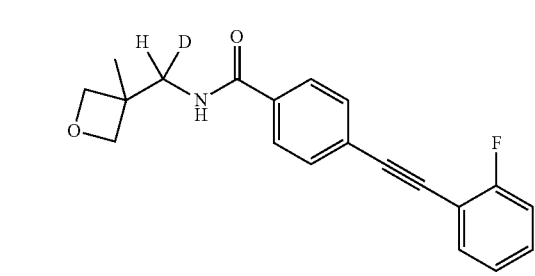 [SMILES: [2H]C(NC(=O)c1ccc(C#Cc2ccccc2F)cc1)C1(C)COC1]

Step 1: Synthesis of (3-methyloxetan-3-yl)methane-d-amine

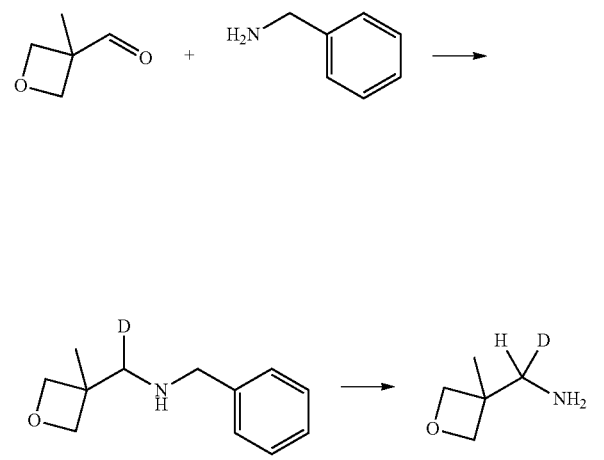

3-Methyloxetane-3-carbaldehyde (2.000 g, 19.976 mmol), phenylmethanamine (2.141 g, 19.976 mmol) and acetic acid (0.114 mL, 1.998 mmol) were dissolved in tetrahydrofuran (18 mL), and the resulting solution was stirred at room temperature for 1 hour. Sodium borodeuteride (1.254 g, 29.964 mmol) was added thereto and further stirred at the same temperature for 24 hours. A saturated aqueous sodium hydrogen carbonate solution was poured into the reaction mixture, followed by extraction with dichloromethane. The organic layer was washed with a saturated aqueous solution of ammonium chloride, dried over anhydrous magnesium sulfate, filtered and concentrated under reduced pressure to obtain N-benzyl-1-(3-methyloxetan-3-yl)methane-d-amine (3.800 g, 98.9%, light yellow oil): LRMS (ES) m/z 193.15 [M+H]$^+$, calculated MW 192.28.

The obtained product, 10% Pd/C (600 mg) and ammonium formate (4.985 g, 79.051 mmol) were dissolved in methanol (20 mL) at room temperature. The resulting solution was stirred at 65° C. for 14 hours, and then the temperature was lowered to room temperature to terminate the reaction. The reaction mixture was filtered through a Celite pad to remove the solid, and the solvent was removed from the filtrate under reduced pressure to obtain (3-methyloxetan-3-yl)methane-d-amine (1.280 g, 63.4%, yellow oil): LRMS (ES) m/z 102.97 [M+H]$^+$, calculated MW 102.16.

Step 2: Synthesis of 4-((2-fluorophenyl)ethynyl)-N-(3-methyloxetan-3-yl)methyl-d)benzamide

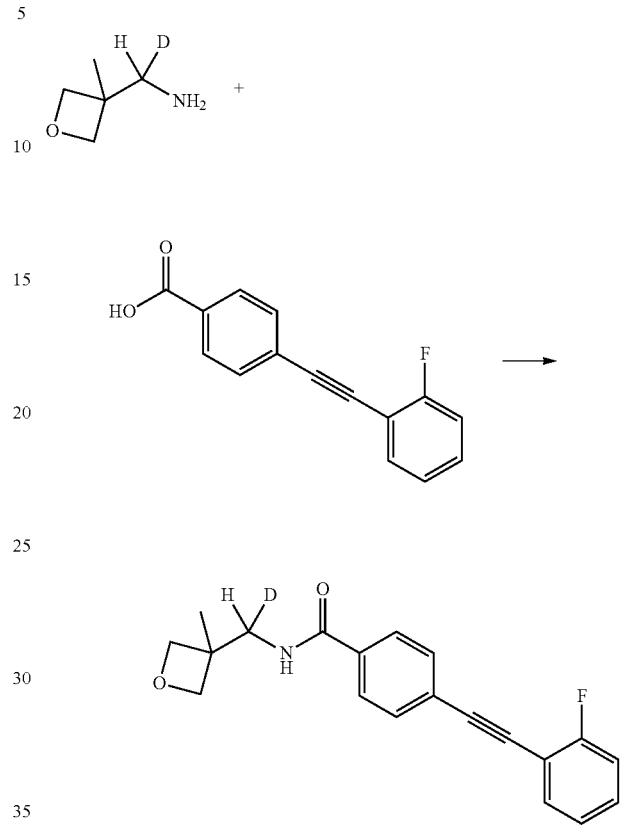

4-((2-Fluorophenyl)ethynyl)benzoic acid (3.010 g, 12.529 mmol) and (3-methyloxetan-3-yl)methane-d-amine (1.280 g, 12.529 mmol) as starting materials were used in a similar manner to Example 11 to obtain 4-((2-fluorophenyl)ethynyl)-N-(3-methyloxetan-3-yl)methyl-d)benzamide (1.750 g, 43.1%) as white solid: LRMS (ES) m/z 325.14 [M+H]$^+$, calculated MW 324.37; $^1$H-NMR (400 MHz, DMSO-d$_6$) d 8.69 (d, J=6.0 Hz, 1H), 7.88 (dd, J=7.0, 1.8 Hz, 2H), 7.65~7.63 (m, 3H), 7.51~7.45 (m, 1H), 7.33 (m, 1H), 7.25 (m, 1H), 4.44 (d, J=6.0 Hz, 2H), 4.17 (d, J=5.6 Hz, 2H), 3.41 (d, J=6.0 Hz, 1H), 1.22 (s, 3H).

Example 96: Synthesis of 4-((2-fluorophenyl)ethynyl)-N-((1-morpholinocyclobutyl)methyl)benzamide

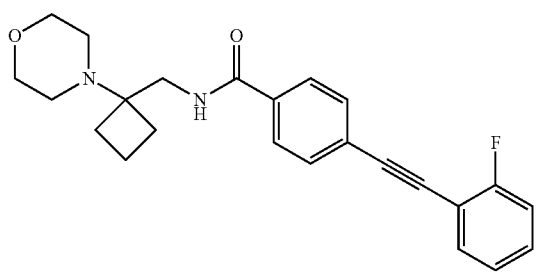 [SMILES: O=C(NCC1(N2CCOCC2)CCC1)c1ccc(C#Cc2ccccc2F)cc1]

Step 1: Synthesis of (1-morpholinocyclobutyl)methanamine

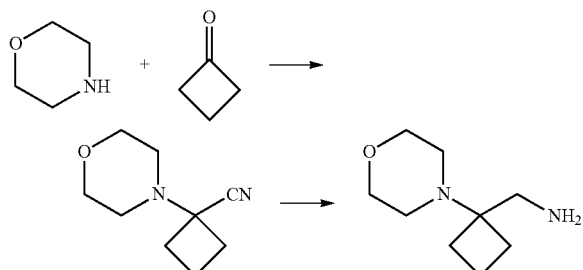

Cyclobutanone (2.000 g, 28.535 mmol) and morpholine (3.209 mL, 37.095 mmol) as starting materials were used in a similar manner to Step 2 of Example 1 to obtain 1-morpholinocyclobutane-1-carbonitrile (4.210 g, 88.8%, LRMS (ES) m/z No detection [M+H]$^+$, calculated MW 166.22) as clear liquid, followed by obtaining (1-morpholinocyclobutyl)methanamine. (2.000 g, 46.5%, clear liquid): LRMS (ES) m/z 171.02 [M+H]$^+$, calculated MW 170.26.

Step 2: Synthesis of 4-((2-fluorophenyl)ethynyl)-N-((1-morpholinocyclobutyl)methyl)benzamide

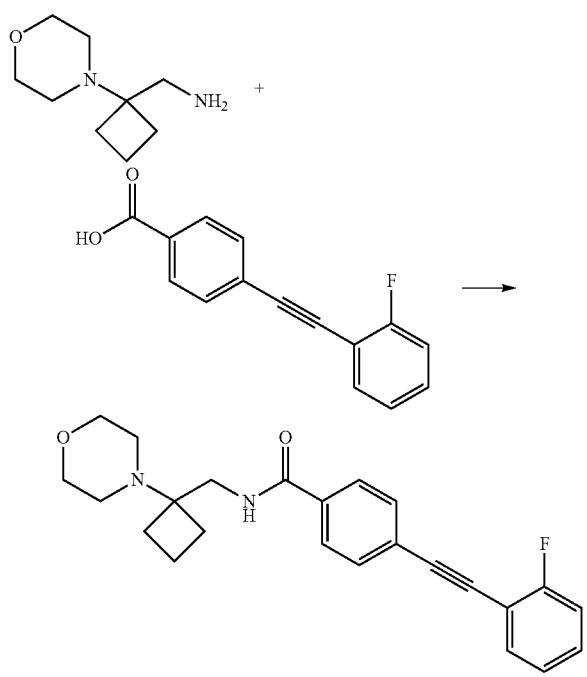

4-((2-Fluorophenyl)ethynyl)benzoic acid (0.100 g, 0.416 mmol) and (1-morpholinocyclobutyl)methanamine (0.085 g, 0.500 mmol) as starting materials were used in a similar manner to Example 11 to obtain 4-((2-fluorophenyl)ethynyl)-N-((1-morpholinocyclobutyl)methyl)benzamide (0.119 g, 72.8%) as yellow liquid: LRMS (ES) m/z 392.77 [M+H]$^+$, calculated MW 392.47; $^1$H-NMR (400 MHz, DMSO-d$_6$) d 8.41 (t, J=6.2 Hz, 1H), 7.86 (dd, J=7.0, 1.8 Hz, 2H), 7.65~7.61 (m, 3H), 7.50~7.45 (m, 1H), 7.33 (t, J=9.2 Hz, 1H), 7.25 (t, J=7.6 Hz, 1H), 4.08 (q, J=5.1 Hz, 1H), 3.50~ 3.48 (m, 5H), 3.13 (d, J=5.6 Hz, 3H), 2.49~2.47 (m, 2H), 1.93~1.83 (m, 3H), 1.69~1.61 (m, 2H).

Example 97: Synthesis of N-((3,3-difluoro-1-methylcyclobutyl)methyl)-4-((2-fluorophenyl)ethynyl)benzamide

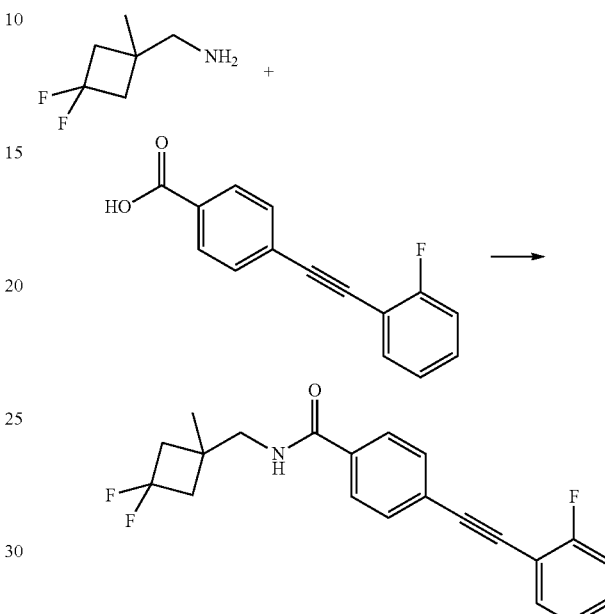

4-((2-Fluorophenyl)ethynyl)benzoic acid (0.070 g, 0.291 mmol) and (3,3-difluoro-1-methylcyclobutyl)methanamine (0.047 g, 0.350 mmol) as starting materials were used in a similar manner to Example 11 to obtain N-((3,3-difluoro-1-methyl cyclobutyl)methyl)-4-((2-fluorophenyl)ethynyl)benzamide (0.075 g, 72.0%) as white solid: LRMS (ES) m/z 358.16 [M+H]$^+$, calculated MW 357.38; $^1$H-NMR (400 MHz, DMSO-d$_6$) d 8.72 (t, J=6.2 Hz, 1H), 7.88 (d, J=6.4 Hz, 2H), 7.66~7.63 (m, 3H), 7.49~7.46 (m, 1H), 7.33 (t, J=8.8 Hz, 1H), 7.25 (td, J=7.6, 1.3 Hz, 1H), 3.34~3.33 (m, 2H), 2.67~2.57 (m, 2H), 2.29~2.16 (m, 2H), 1.17 (s, 3H).

Example 98: Synthesis of 4-((2-fluorophenyl)ethynyl)-N-((2-methyltetrahydrofuran-2-yl)methyl)benzamide

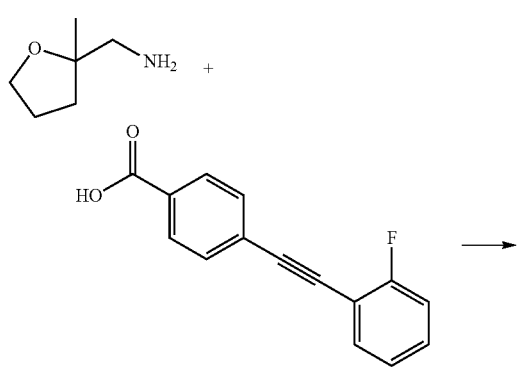

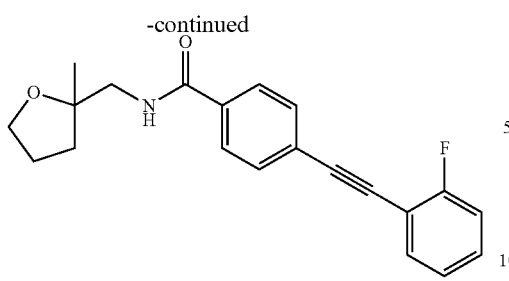

4-((2-Fluorophenyl)ethynyl)benzoic acid (0.070 g, 0.291 mmol) and (2-methyltetrahydrofuran-2-yl)methanamine (0.045 mL, 0.350 mmol) as starting materials were used in a similar manner to Example 11 to obtain 4-((2-fluorophenyl)ethynyl)-N-((2-methyltetrahydrofuran-2-yl)methyl)benzamide (0.074 g, 75.3%) as yellow solid: LRMS (ES) m/z 338.15 [M+H]+, calculated MW 337.39; $^1$H-NMR (400 MHz, DMSO-$d_6$) d 8.50 (t, J=6.2 Hz, 1H), 7.88 (dd, J=6.4, 2.0 Hz, 2H), 7.66~7.61 (m, 3H), 7.48~7.46 (m, 1H), 7.35~7.30 (m, 1H), 7.25 (td, J=7.6, 1.1 Hz, 1H), 3.73~3.69 (m, 2H), 3.29~3.27 (m, 2H), 1.87~1.79 (m, 3H), 1.57~1.46 (m, 1H), 1.11 (s, 3H).

Example 99: Synthesis of (R)-4-((4-fluorophenyl)ethynyl)-N-((tetrahydro-2H-pyran-3-yl)methyl)benzamide

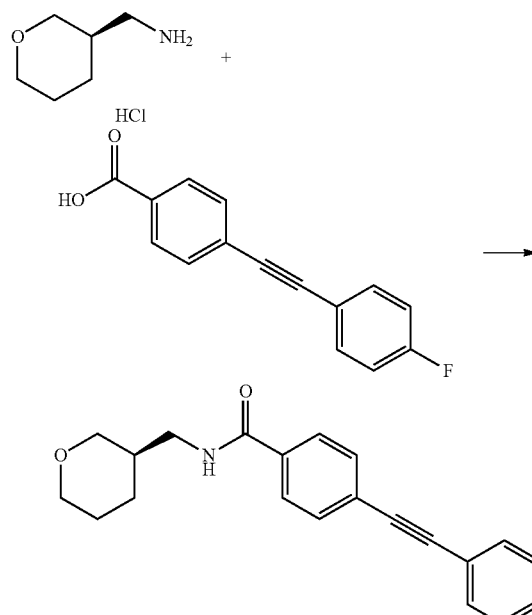

4-((4-Fluorophenyl)ethynyl)benzoic acid (0.120 g, 0.500 mmol) and (R)-(tetrahydro-2H-pyran-3-yl)methanamine hydrochloride (0.083 g, 0.549 mmol) as starting materials were used in a similar manner to Example 11 to obtain (R)-4-((4-fluorophenyl)ethynyl)-N-((tetrahydro-2H-pyran-3-yl)methyl)benzamide (0.130 g, 77.1%) as white solid: LRMS (ES) m/z 338.21 [M+H]+, calculated MW 337.39; $^1$H-NMR (400 MHz, DMSO-$d_6$) d 8.55 (t, J=6.8 Hz, 1H), 7.84 (d, J=8.0 Hz, 2H), 7.64~7.59 (m, 4H), 7.29~7.23 (m, 2H), 3.75~3.62 (m, 2H), 3.28 (s, 1H), 3.16~3.05 (m, 3H), 1.82~1.71 (m, 2H), 1.57~1.52 (m, 1H), 1.46~1.37 (m, 1H), 1.25~1.15 (m, 1H).

Example 100: Synthesis of (S)-4-((4-fluorophenyl)ethynyl)-N-((tetrahydro-2H-pyran-3-yl)methyl)benzamide

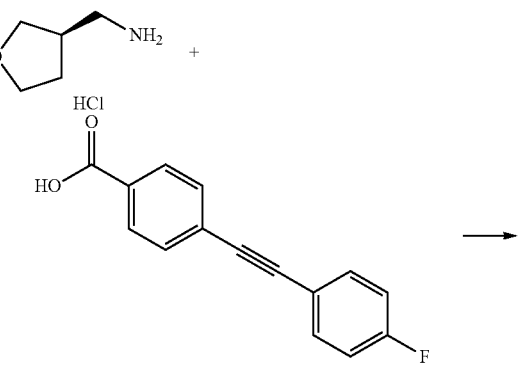

4-((4-Fluorophenyl)ethynyl)benzoic acid (0.150 g, 0.624 mmol) and (S)-(tetrahydro-2H-pyran-3-yl)methanamine hydrochloride (0.104 g, 0.687 mmol) as starting materials were used in a similar manner to Example 11 to obtain (S)-4-((4-fluorophenyl)ethynyl)-N-((tetrahydro-2H-pyran-3-yl)methyl)benzamide (0.194 g, 92.1%) as white solid: LRMS (ES) m/z 338.21 [M+H]+, calculated MW 337.39; $^1$H-NMR (400 MHz, DMSO-$d_6$) d 8.55 (t, J=5.6 Hz, 1H), 7.84 (d, J=8.0 Hz, 2H), 7.64~7.56 (m, 4H), 7.31~7.21 (m, 2H), 3.75~3.62 (m, 2H), 3.32~3.27 (m, 1H), 3.13~3.05 (m, 3H), 1.83~1.68 (m, 2H), 1.54~1.52 (m, 1H), 1.43~1.39 (m, 1H), 1.24~1.18 (m, 1H).

Example 101: Synthesis of (R)-4-((4-fluorophenyl)ethynyl)-N-((tetrahydrofuran-3-yl)methyl)benzamide -continued

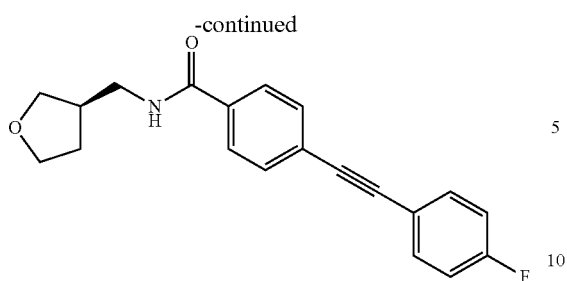

4-((4-Fluorophenyl)ethynyl)benzoic acid (0.100 g, 0.416 mmol) and (R)-(tetrahydrofuran-3-yl)methanamine hydrochloride (0.069 g, 0.500 mmol) as starting materials were used in a similar manner to Example 11 to obtain (R)-4-((4-fluorophenyl)ethynyl)-N-((tetrahydrofuran-3-yl)methyl)benzamide (0.096 g, 71.3%) as yellow solid: LRMS (ES) m/z 324.14 [M+H]$^+$, calculated MW 323.37; $^1$H-NMR (400 MHz, DMSO-d$_6$) d 8.65 (t, J=4.8 Hz, 1H), 7.85 (d, J=6.8 Hz, 2H), 7.64~7.58 (m, 4H), 7.29~7.23 (m, 2H), 3.73~3.68 (m, 1H), 3.66~3.32 (m, 1H), 3.60~3.55 (m, 1H), 3.45~3.42 (m, 1H), 3.30~3.12 (m, 3H), 1.96~1.84 (m, 1H), 1.60~1.49 (m, 1H).

Example 102: Synthesis of (S)-4-((4-fluorophenyl)ethynyl)-N-((tetrahydrofuran-3-yl)methyl)benzamide

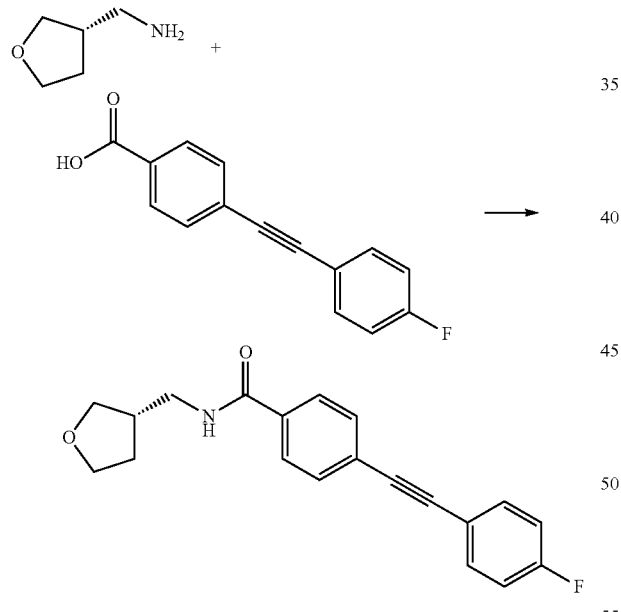

4-((4-Fluorophenyl)ethynyl)benzoic acid (0.150 g, 0.624 mmol) and (S)-(tetrahydrofuran-3-yl)methanamine (0.076 g, 0.749 mmol) as starting materials were used in a similar manner to Example 11 to obtain (S)-4-((4-fluorophenyl)ethynyl)-N-((tetrahydrofuran-3-yl)methyl)benzamide (0.152 g, 75.3%) as yellow solid: LRMS (ES) m/z 324.08 [M+H]$^+$, calculated MW 323.37; $^1$H-NMR (400 MHz, DMSO-d$_6$) d 8.66 (t, J=5.6 Hz, 1H), 7.85 (d, J=8.4 Hz, 2H), 7.63~7.60 (m, 4H), 7.29~7.24 (m, 2H), 3.73~3.68 (m, 1H), 3.66~3.62 (m, 1H), 3.60~3.55 (m, 1H), 3.45~3.42 (m, 1H), 3.29~3.12 (m, 3H), 1.94~1.86 (m, 1H), 1.60~1.52 (m, 1H).

Example 103: Synthesis of N-((3-fluorooxetan-3-yl)methyl)-4-((2-fluorophenyl)ethynyl)benzamide

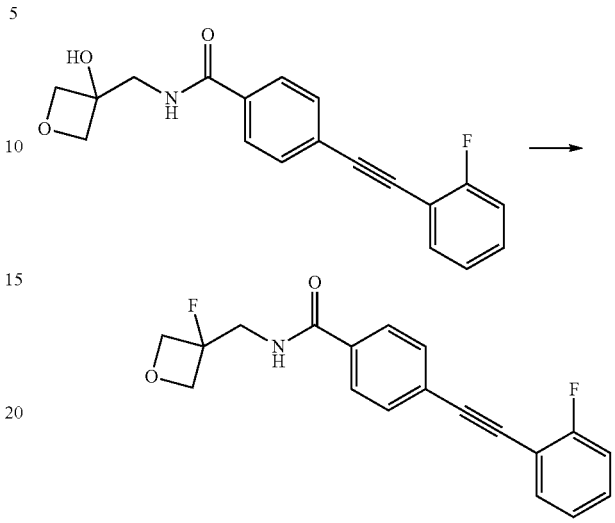

To the solution in which 4-((2-fluorophenyl)ethynyl)-N-(3-hydroxyoxetan-3-yl)methyl)benzamide (0.100 g, 0.307 mmol) obtained in Example 82 as a starting material was dissolved in dichloromethane (5 mL), diethylaminosulfur trifluoride (DAST, 0.049 mL, 0.369 mmol) was added at –78° C. and stirred at the same temperature for 1 hour. The solvent was removed from the reaction mixture under reduced pressure, and a saturated aqueous sodium hydrogen carbonate solution was poured into the obtained concentrate, followed by extraction with ethyl acetate. The organic layer was washed with a saturated aqueous sodium chloride solution, dried over anhydrous magnesium sulfate, filtered and concentrated under reduced pressure. The concentrate was purified by column chromatography and concentrated to obtain N-(3-fluorooxetan-3-yl)methyl)-4-((2-fluorophenyl)ethynyl)benzamide (0.017 g, 16.9%) as white solid: LRMS (ES) m/z 328.24 [M+H]$^+$, calculated MW 327.33; $^1$H-NMR (400 MHz, DMSO-d$_6$) d 8.88 (t, J=5.8 Hz, 1H), 7.90 (dd, J=7.0, 1.8 Hz, 2H), 7.66~7.60 (m, 3H), 7.50~7.45 (m, 1H), 7.35~7.30 (m, 1H), 7.28~7.23 (m, 1H), 4.68~4.53 (m, 4H), 3.78 (dd, J=19.8, 6.2 Hz, 2H).

Example 104: Synthesis of 4-((4-fluorophenyl)ethynyl)-N-((1-methylcyclohexyl)methyl)benzamide

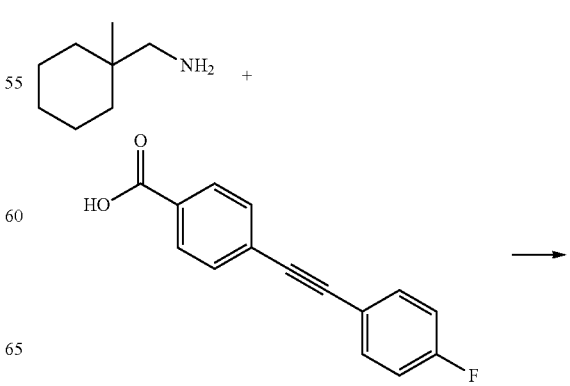

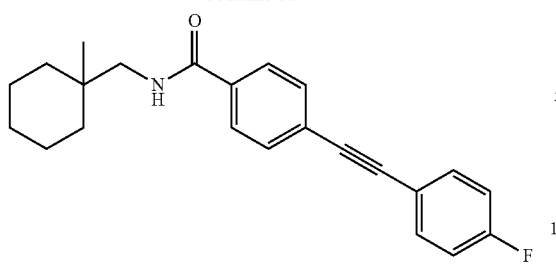

(1-Methylcyclohexyl)methanamine (0.100 g, 0.786 mmol) and 4-((4-fluorophenyl)ethynyl)benzoic acid (0.208 g, 0.865 mmol) as starting materials were used in a similar manner to Example 11 to obtain 4-((4-fluorophenyl)ethynyl)-N-((1-methylcyclohexyl)methyl)benzamide (0.056 g, 20.4%) as white solid: LRMS (ES) m/z 350.24 [M+H]$^+$, calculated MW 349.45; $^1$H-NMR (400 MHz, DMSO-$d_6$) d 8.36 (t, J=6.2 Hz, 1H), 7.85 (d, J=8.8 Hz, 2H), 7.59~7.63 (m, 4H), 7.26 (t, J=9.0 Hz, 2H), 3.12 (d, J=6.0 Hz, 2H), 1.16~1.45 (m, 10H), 0.84 (s, 3H).

Example 105: Synthesis of 4-((2-fluorophenyl)ethynyl)-N-((1-methylcyclobutyl)methyl)benzamide

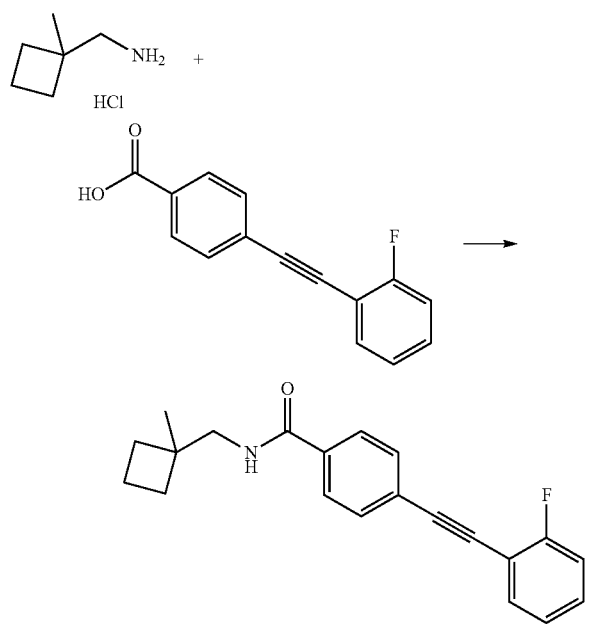

(1-Methylcyclobutyl)methanamine hydrochloride (0.050 g, 0.369 mmol) and 4-((2-fluorophenyl)ethynyl)benzoic acid (0.097 g, 0.405 mmol) as starting materials were used in a similar manner to Example 11 to obtain 4-((2-fluorophenyl)ethynyl)-N-((1-methylcyclobutyl)methyl)benzamide (0.068 g, 57.4%) as white solid: LRMS (ES) m/z 322.16 [M+H]$^+$, calculated MW 321.4; $^1$H-NMR (400 MHz, CDCl$_3$) d 7.74 (d, J=8.0 Hz, 2H), 7.59 (d, J=8.4 Hz, 2H), 7.51 (t, J=6.8 Hz, 1H), 7.32 (dd, J=13.2, 6.4 Hz, 1H), 7.11 (dd, J=18.2, 8.6 Hz, 2H), 6.22 (s, 1H), 3.44 (d, J=6.0 Hz, 2H), 1.84~1.94 (m, 4H), 1.72~1.76 (m, 2H), 1.17 (s, 3H).

Example 106: Synthesis of 4-((4-fluorophenyl)ethynyl)-N-((1-methylcyclobutyl)methyl)benzamide

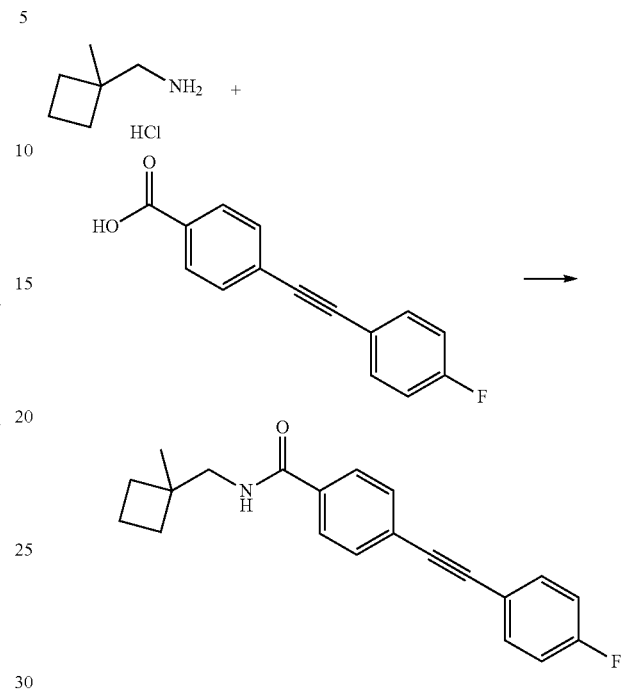

(1-Methylcyclobutyl)methanamine hydrochloride (0.050 g, 0.369 mmol) and 4-((4-fluorophenyl)ethynyl)benzoic acid (0.097 g, 0.405 mmol) as starting materials were used in a similar manner to Example 11 to obtain 4-((4-fluorophenyl)ethynyl)-N-((1-methylcyclobutyl)methyl)benzamide (0.070 g, 59.1%) as white solid: LRMS (ES) m/z 322.16 [M+H]$^+$, calculated MW 321.4; $^1$H-NMR (400 MHz, CDCl$_3$) d 7.74 (d, J=8.8 Hz, 2H), 7.57 (d, J=8.8 Hz, 2H), 7.52 (dd, J=9.0, 5.0 Hz, 2H), 7.05 (t, J=8.6 Hz, 2H), 3.46 (d, J=6.0 Hz, 2H), 1.89~1.93 (m, 4H), 1.71~1.78 (m, 2H), 1.19 (s, 3H).

Example 107: Synthesis of 4-((2,4-difluorophenyl)ethynyl)-N-((1-methylcyclobutyl)methyl)benzamide

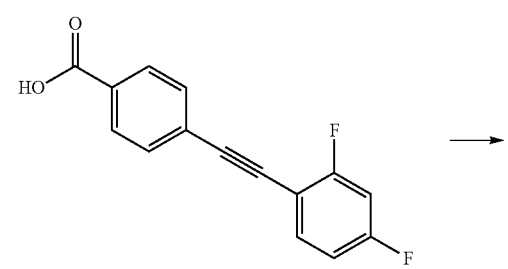

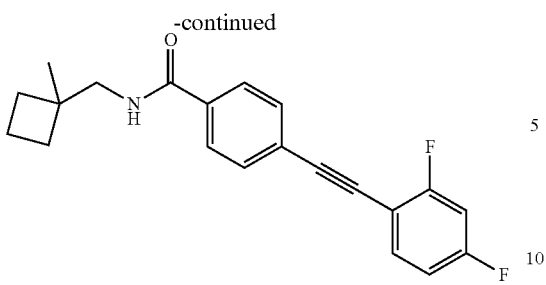

(1-Methylcyclobutyl)methanamine hydrochloride (0.050 g, 0.369 mmol) and 4-((2,4-difluorophenyl)ethynyl)benzoic acid (0.095 g, 0.369 mmol) as starting materials were used in a similar manner to Example 11 to obtain 4-((2,4-difluorophenyl)ethynyl)-N-((1-methylcyclobutyl)methyl)benzamide (0.077 g, 61.5%) as white solid: LRMS (ES) m/z 340.20 [M+H]$^+$, calculated MW 339.39; $^1$H-NMR (400 MHz, CDCl$_3$) 7.74 (d, J=8.4 Hz, 2H), 7.58 (d, J=8.8 Hz, 2H), 7.47~7.52 (m, 1H), 6.84~6.90 (m, 2H), 6.13 (bs, 1H), 3.45 (d, J=6.0 Hz, 2H), 1.90~1.92 (m, 4H), 1.73 (m, 2H), 1.16 (s, 3H).

Example 108: Synthesis of 4-((2,4-difluorophenyl)ethynyl)-N-((1-methylcyclopentyl)methyl)benzamide

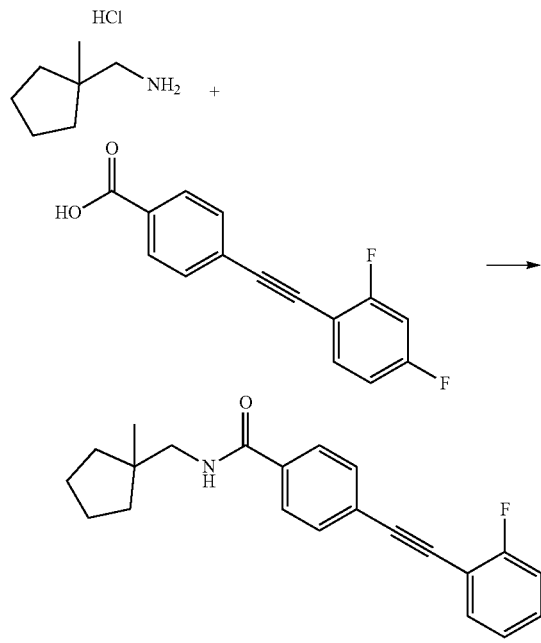

(1-Methylcyclopentyl)methanamine hydrochloride (0.050 g, 0.334 mmol) and 4-((2,4-difluorophenyl)ethynyl)benzoic acid (0.086 g, 0.334 mmol) as starting materials were used in a similar manner to Example 11 to obtain 4-((2,4-difluorophenyl)ethynyl)-N-((1-methylcyclopentyl)methyl)benzamide (0.069 g, 58.4%) as ivory solid: LRMS (ES) m/z 354.20 [M+H]$^+$, calculated MW 353.41; $^1$H-NMR (400 MHz, CDCl$_3$) d 7.74 (d, J=8.4 Hz, 2H), 7.59 (d, J=8.0 Hz, 2H), 7.47~7.53 (m, 1H), 6.85~6.91 (m, 2H), 6.14 (bs, 1H), 3.37 (d, J=6.0 Hz, 2H), 1.37~1.70 (m, 8H), 1.05 (s, 3H).

Example 109: Synthesis of (R)-4-((2,4-difluorophenyl)ethynyl)-N-((tetrahydrofuran-3-yl)methyl)benzamide

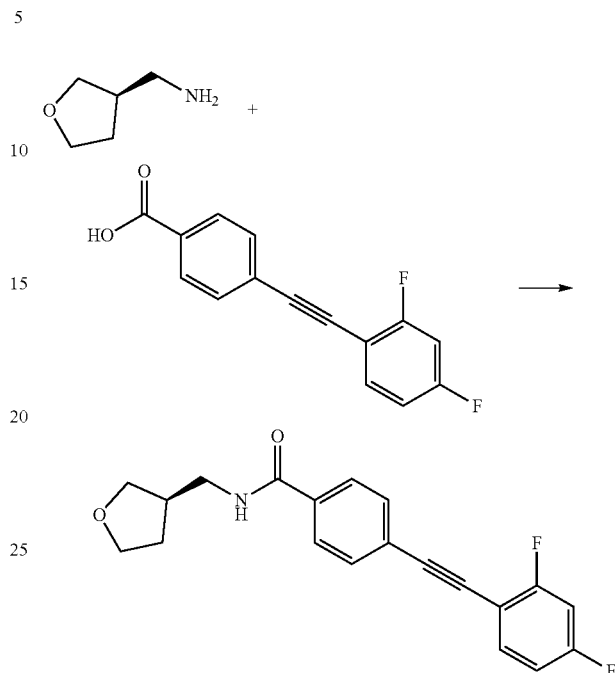

4-((2,4-Difluorophenyl)ethynyl)benzoic acid (0.200 g, 0.775 mmol) and (R)-(tetrahydrofuran-3-yl)methanamine (0.086 g, 0.852 mmol) as starting materials were used in a similar manner to Example 11 to obtain (R)-4-((2,4-difluorophenyl)ethynyl)-N-((tetrahydrofuran-3-yl)methyl)benzamide (0.230 g, 87.0%) as white solid: LRMS (ES) m/z 342.18 [M+H]$^+$, calculated MW 341.36; $^1$H-NMR (400 MHz, DMSO-d$_6$) d 8.66 (t, J=5.8 Hz, 1H), 7.86 (d, J=8.8 Hz, 2H), 7.74~7.68 (m, 1H), 7.63 (d, J=14.8 Hz, 2H), 7.47~7.38 (m, 1H), 7.19~7.15 (m, 1H), 3.73~3.69 (m, 1H), 3.67~3.63 (m, 1H), 3.61~3.55 (m, 1H), 3.45~3.42 (m, 1H), 3.26~3.17 (m, 2H), 3.13 (d, J=5.6 Hz, 1H), 1.96~1.84 (m, 1H), 1.60~1.52 (m, 1H).

Example 110: Synthesis of (R)-4-((4-fluorophenyl)ethynyl)-N-((tetrahydrofuran-2-yl)methyl)benzamide

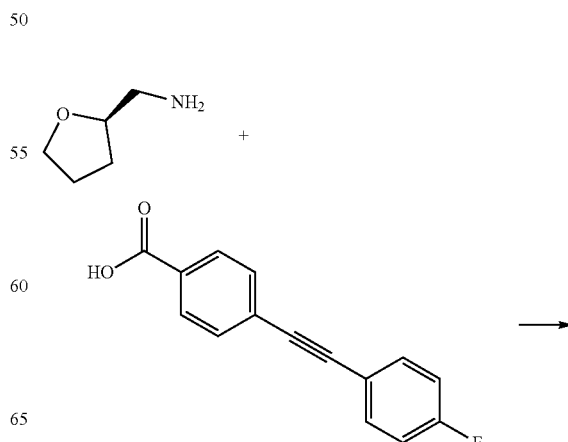

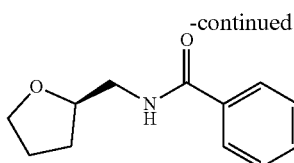

4-((4-Fluorophenyl)ethynyl)benzoic acid (0.050 g, 0.208 mmol) and (R)-(tetrahydrofuran-2-yl)methanamine (0.025 g, 0.250 mmol) as starting materials were used in a similar manner to Example 11 to obtain (R)-4-((4-fluorophenyl)ethynyl)-N-((tetrahydrofuran-2-yl)methyl)benzamide (0.032 g, 47.5%) as yellow solid: LRMS (ES) m/z 324.14 [M+H]$^+$, calculated MW 323.37; $^1$H-NMR (400 MHz, DMSO-d$_6$) d 8.65~8.63 (m, 1H), 7.86 (dd, J=6.8, 1.6 Hz, 2H), 7.37~7.56 (m, 4H), 7.30~7.24 (m, 2H), 3.97~3.90 (m, 1H), 3.75~3.73 (m, 1H), 3.61~3.56 (m, 1H), 3.29~3.26 (m, 2H), 1.91~1.85 (m, 1H), 1.81~1.70 (m, 2H), 1.58~1.50 (m, 1H).

Example 111: Synthesis of (S)-4-((4-fluorophenyl)ethynyl)-N-((tetrahydrofuran-2-yl)methyl)benzamide

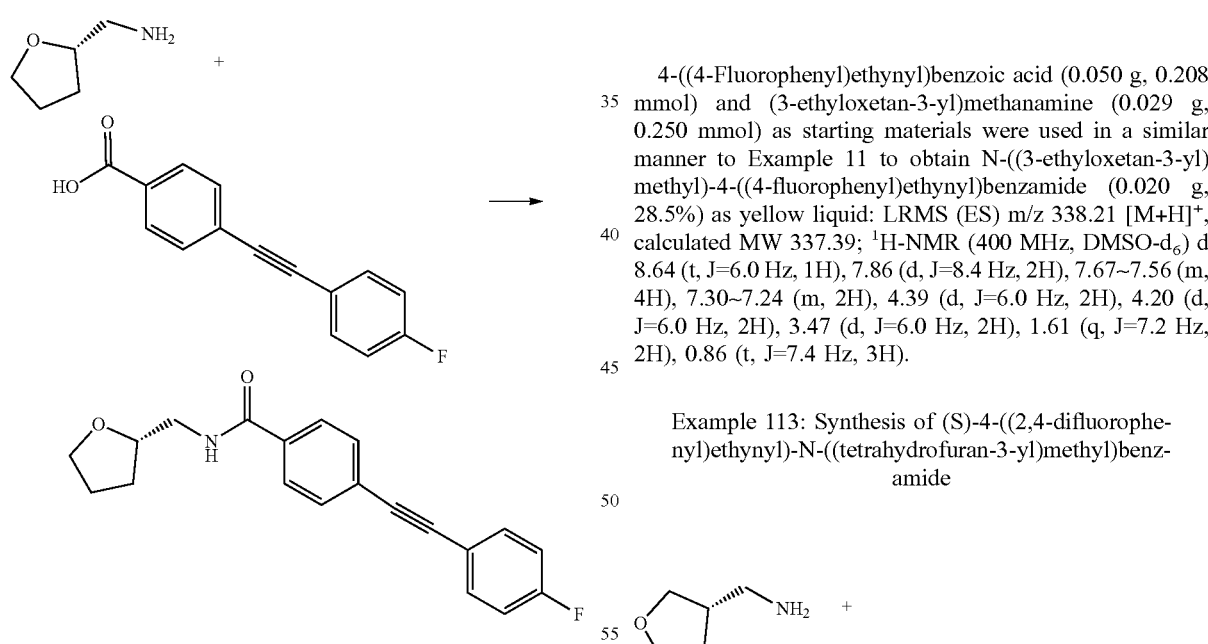

4-((4-Fluorophenyl)ethynyl)benzoic acid (0.050 g, 0.208 mmol) and (S)-(tetrahydrofuran-2-yl)methanamine (0.025 g, 0.250 mmol) as starting materials were used in a similar manner to Example 11 to obtain (S)-4-((4-fluorophenyl)ethynyl)-N-((tetrahydrofuran-2-yl)methyl)benzamide (0.052 g, 77.3%) as yellow solid: MOTS (ES) m/z 324.21 [M+H]$^+$, calculated MW 323.37; $^1$H-NMR (400 MHz, DMSO-d$_6$) d 8.63 (t, J=5.8 Hz, 1H), 7.91 (d, J=32.0 Hz, 2H), 7.63~7.60 (m, 4H), 7.29~7.23 (m, 2H), 3.97~3.91 (m, 1H), 3.75~3.72 (m, 1H), 3.61~3.56 (m, 1H), 3.29~3.26 (m, 2H), 1.91~1.85 (m, 1H), 1.80~1.70 (m, 2H), 1.58~1.50 (m, 1H).

Example 112: Synthesis of N-((3-ethyloxetan-3-yl)methyl)-4-((4-fluorophenyl)ethynyl)benzamide

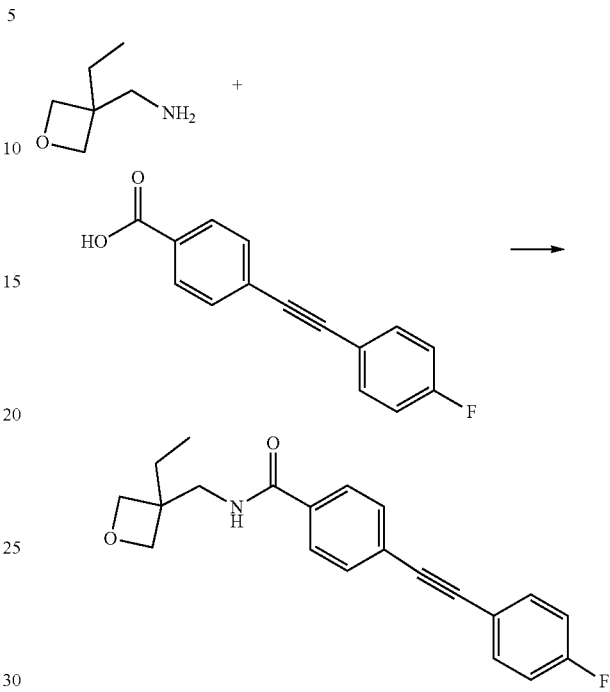

4-((4-Fluorophenyl)ethynyl)benzoic acid (0.050 g, 0.208 mmol) and (3-ethyloxetan-3-yl)methanamine (0.029 g, 0.250 mmol) as starting materials were used in a similar manner to Example 11 to obtain N-((3-ethyloxetan-3-yl)methyl)-4-((4-fluorophenyl)ethynyl)benzamide (0.020 g, 28.5%) as yellow liquid: LRMS (ES) m/z 338.21 [M+H]$^+$, calculated MW 337.39; $^1$H-NMR (400 MHz, DMSO-d$_6$) d 8.64 (t, J=6.0 Hz, 1H), 7.86 (d, J=8.4 Hz, 2H), 7.67~7.56 (m, 4H), 7.30~7.24 (m, 2H), 4.39 (d, J=6.0 Hz, 2H), 4.20 (d, J=6.0 Hz, 2H), 3.47 (d, J=6.0 Hz, 2H), 1.61 (q, J=7.2 Hz, 2H), 0.86 (t, J=7.4 Hz, 3H).

Example 113: Synthesis of (S)-4-((2,4-difluorophenyl)ethynyl)-N-((tetrahydrofuran-3-yl)methyl)benzamide

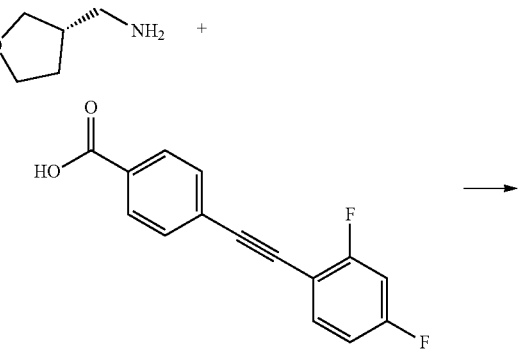

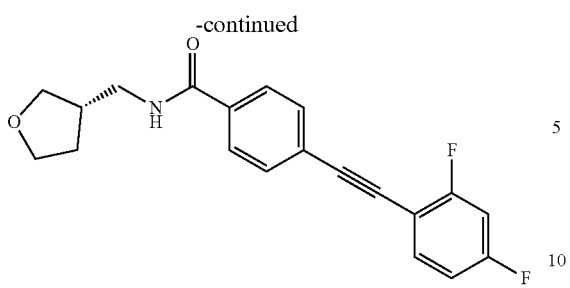

4-((2,4-Difluorophenyl)ethynyl)benzoic acid (0.060 g, 0.232 mmol) and (S)-(tetrahydrofuran-3-yl)methanamine (0.026 g, 0.256 mmol) as starting materials were used in a similar manner to Example 11 to obtain (S)-4-((2,4-difluorophenyl)ethynyl)-N-((tetrahydrofuran-3-yl)methyl)benzamide (0.073 g, 92.0%) as white solid: LRMS (ES) m/z 342.18 [M+H]$^+$, calculated MW 341.36; $^1$H-NMR (400 MHz, DMSO-d$_6$) d 8.66 (t, J=5.6 Hz, 1H), 7.86 (dd, J=6.6, 2.2 Hz, 2H), 7.71 (q, J=7.9 Hz, 1H), 7.62 (d, J=8.8 Hz, 2H), 7.43 (dt, J=16.4, 4.8 Hz, 1H), 7.18 (d, J=26.0 Hz, 1H), 3.73~3.63 (m, 2H), 3.61~3.42 (m, 2H), 3.26~3.16 (m, 3H), 1.95~1.86 (m, 1H), 1.61~1.52 (m, 1H).

Example 114: Synthesis of (R)-4-((2,4-difluorophenyl)ethynyl)-N-((tetrahydrofuran-2-yl)methyl)benzamide

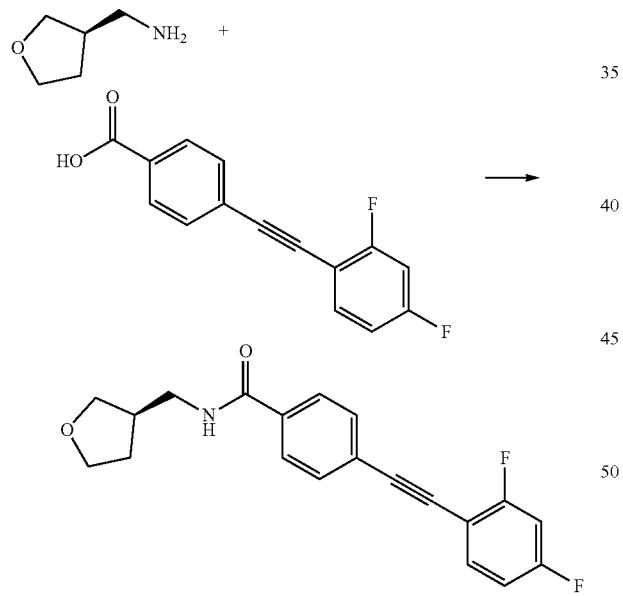

4-((2,4-Difluorophenyl)ethynyl)benzoic acid (0.060 g, 0.232 mmol) and (R)-(tetrahydrofuran-2-yl)methanamine (0.026 g, 0.256 mmol) as starting materials were used in a similar manner to Example 11 to obtain (R)-4-((2,4-difluorophenyl)ethynyl)-N-((tetrahydrofuran-2-yl)methyl)benzamide (0.075 g, 94.6%) as white solid: LRMS (ES) m/z 342.11 [M+H]$^+$, calculated MW 341.36; $^1$H-NMR (400 MHz, DMSO-d$_6$) d 8.63 (t, J=6.0 Hz, 1H), 7.87 (d, J=8.8 Hz, 2H), 7.74~7.68 (m, 1H), 7.62 (d, J=8.8 Hz, 2H), 7.45~7.40 (m, 1H), 7.21~7.14 (m, 1H), 3.96~3.91 (m, 1H), 3.75~3.56 (m, 2H), 3.28~3.26 (m, 2H), 1.92~1.50 (m, 4H).

Example 115: Synthesis of 4-((2,4-difluorophenyl)ethynyl)-N-((tetrahydro-2H-pyran-2-yl)methyl)benzamide

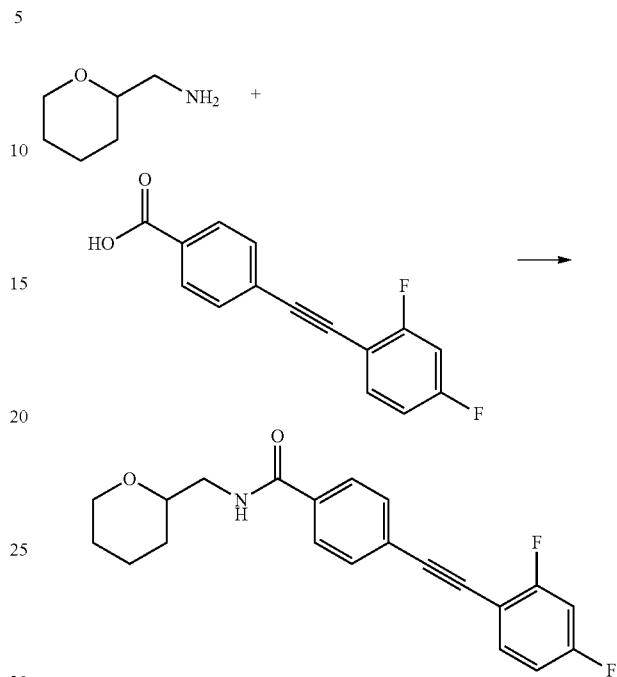

4-((2,4-Difluorophenyl)ethynyl)benzoic acid (0.060 g, 0.232 mmol) and (tetrahydro-2H-pyran-2-yl)methanamine (0.029 g, 0.256 mmol) as starting materials were used in a similar manner to Example 11 to obtain 4-((2,4-difluorophenyl)ethynyl)-N-((tetrahydro-2H-pyran-2-yl)methyl)benzamide (0.051 g, 61.8%) as white solid: LRMS (ES) m/z 356.25 [M+H]$^+$, calculated MW 355.38; $^1$H-NMR (400 MHz, DMSO-d$_6$) d 8.57 (t, J=18.8 Hz, 1H), 7.87 (dd, J=6.4, 1.6 Hz, 2H), 7.74~7.68 (m, 1H), 7.61 (dd, J=6.4, 1.6 Hz, 2H), 7.42 (td, J=9.6, 2.8 Hz, 1H), 7.21~7.14 (m, 1H), 3.83 (d, J=11.2 Hz, 1H), 3.42~3.33 (m, 1H), 3.25~3.20 (m, 3H), 1.74~1.74 (m, 1H), 1.58 (d, J=12.8 Hz, 1H), 1.42~1.34 (m, 3H), 1.17~1.08 (m, 1H).

Example 116: Synthesis of 4-((4-fluorophenyl)ethynyl)-N-((2-methyltetrahydrofuran-2-yl)methyl)benzamide

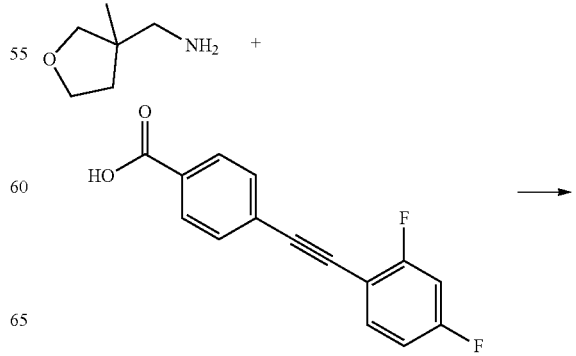

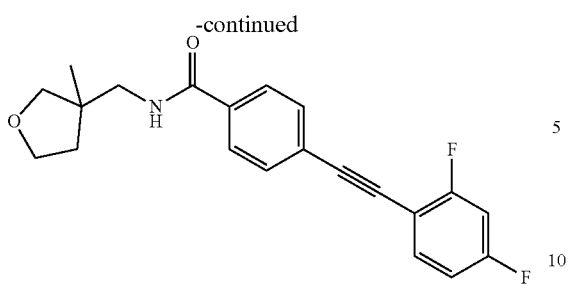

4-((4-Fluorophenyl)ethynyl)benzoic acid (0.060 g, 0.250 mmol) and (2-methyltetrahydrofuran-2-yl)methanamine (0.032 g, 0.275 mmol) as starting materials were used in a similar manner to Example 11 to obtain 4-((4-fluorophenyl)ethynyl)-N-((2-methyltetrahydrofuran-2-yl)methyl)benzamide (0.025 g, 29.7%) as yellow solid: LRMS (ES) m/z 338.21 [M+H]$^+$, calculated MW 337.39; $^1$H-NMR (400 MHz, DMSO-d$_6$) d 8.46 (t, J=6.4 Hz, 1H), 7.86 (d, J=8.8 Hz, 2H), 7.64~7.56 (m, 4H), 7.29~7.23 (m, 2H), 3.73~3.69 (m, 2H), 3.37~3.22 (m, 2H), 1.89~1.79 (m, 3H), 1.56~1.46 (m, 1H), 1.11 (s, 3H).

Example 117: Synthesis of (S)-4-((2,4-difluorophenyl)ethynyl)-N-((tetrahydrofuran-2-yl)methyl)benzamide

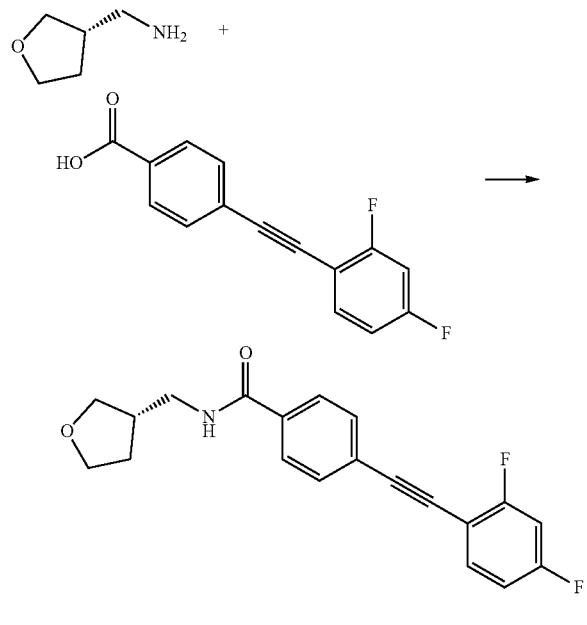

4-((2,4-Difluorophenyl)ethynyl)benzoic acid (0.060 g, 0.232 mmol) and (S)-(tetrahydrofuran-2-yl)methanamine (0.026 g, 0.256 mmol) as starting materials were used in a similar manner to Example 11 to obtain (S)-4-((2,4-difluorophenyl)ethynyl)-N-((tetrahydrofuran-2-yl)methyl)benzamide (0.073 g, 92.0%) as white solid: LRMS (ES) m/z 342.18 [M+H]$^+$, calculated MW 341.36; $^1$H-NMR (400 MHz, DMSO-d$_6$) d 8.63 (t, J=5.8 Hz, 1H), 7.87 (d, J=8.8 Hz, 2H), 7.74~7.68 (m, 1H), 7.62 (d, J=8.8 Hz, 2H), 7.45~7.40 (m, 1H), 7.21~7.14 (m, 1H), 3.96~3.91 (m, 1H), 3.75~3.56 (m, 2H), 3.27~3.21 (m, 2H), 1.92~1.50 (m, 4H).

Example 118: Synthesis of 4-((2,4-difluorophenyl)ethynyl)-N-(oxetan-2-ylmethyl)benzamide

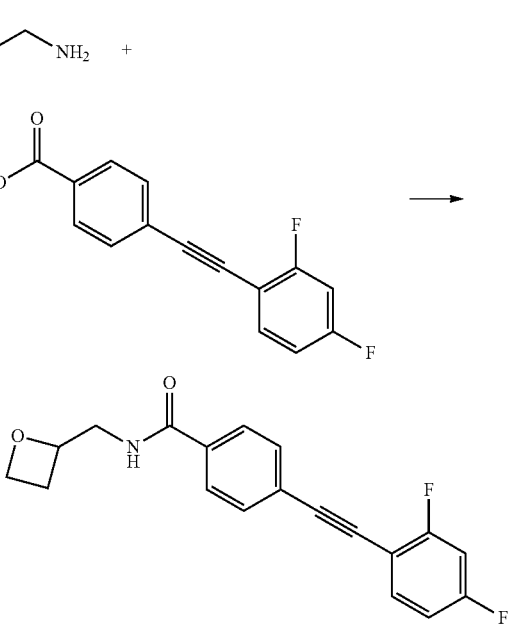

4-((2,4-Difluorophenyl)ethynyl)benzoic acid (0.060 g, 0.232 mmol) and oxetan-2-ylmethanamine (0.022 g, 0.256 mmol) as starting materials were used in a similar manner to Example 11 to obtain 4-((2,4-difluorophenyl)ethynyl)-N-(oxetan-2-ylmethyl)benzamide (0.064 g, 84.1%) as ivory solid: LRMS (ES) m/z 328.17 [M+H]$^+$, calculated MW 327.33; $^1$H-NMR (400 MHz, DMSO-d$_6$) d 8.73 (t, J=5.8 Hz, 1H), 7.89 (d, J=8.4 Hz, 2H), 7.74~7.61 (m, 1H), 7.62 (d, J=8.8 Hz, 2H), 7.45~7.40 (m, 1H), 7.21~7.15 (m, 1H), 4.82~4.76 (m, 1H), 4.48~4.38 (m, 2H), 3.55~3.42 (m, 2H), 2.61~2.57 (m, 1H), 2.41~2.34 (m, 1H).

Example 119: Synthesis of 4-((2,4-difluorophenyl)ethynyl)-N-((2-methyltetrahydrofuran-2-yl)methyl)benzamide

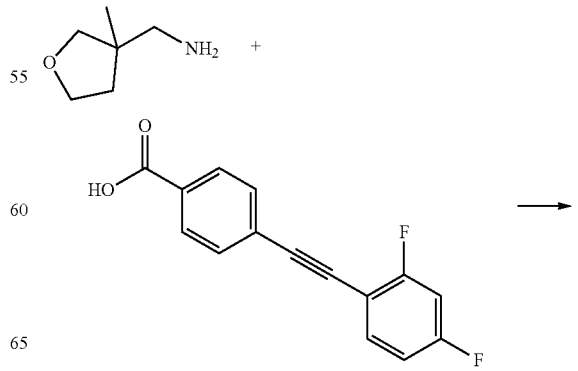

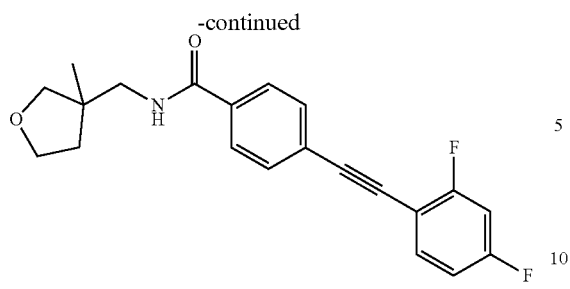

4-((2,4-Difluorophenyl)ethynyl)benzoic acid (0.060 g, 0.232 mmol) and (2-methyltetrahydrofuran-2-yl)methanamine (0.029 g, 0.256 mmol) as starting materials were used in a similar manner to Example 11 to obtain 4-((2,4-difluorophenyl)ethynyl)-N-((2-methyltetrahydrofuran-2-yl)methyl)benzamide (0.064 g, 77.5%) as white solid: LRMS (ES) m/z 356.25 [M+H]$^+$, calculated MW 355.38; $^1$H-NMR (400 MHz, DMSO-d$_6$) d 8.48 (t, J=6.4 Hz, 1H), 7.88 (dd, J=6.4, 2.0 Hz, 2H), 7.72~7.68 (m, 1H), 7.61 (d, J=8.4 Hz, 2H), 7.42 (td, J=9.6, 2.4 Hz, 1H), 7.21~7.13 (m, 1H), 3.75~3.67 (m, 2H), 3.33~3.24 (m, 2H), 1.87~1.79 (m, 3H), 1.54~1.49 (m, 1H), 1.11 (s, 3H).

Example 120: Synthesis of N-((3,3-difluorocyclobutyl)methyl)-4-((2,4-difluorophenyl)ethynyl)benzamide

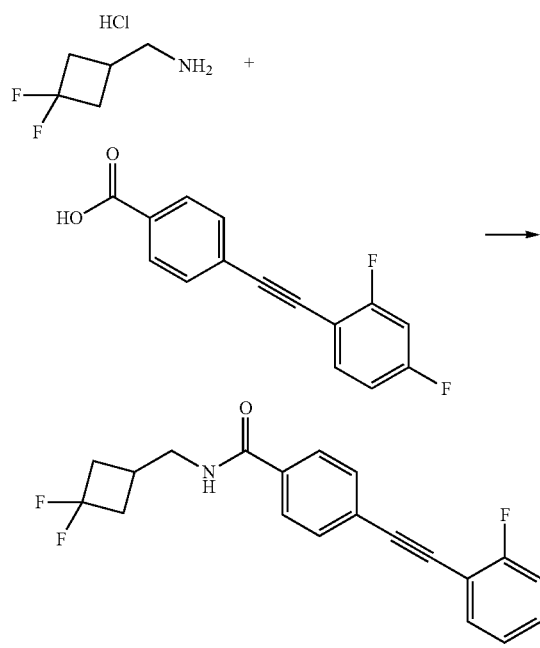

(3,3-Difluorocyclobutyl)methanamine hydrochloride (0.050 g, 0.317 mmol) and 4-((2,4-difluorophenyl)ethynyl)benzoic acid (0.098 g, 0.381 mmol) as starting materials were used in a similar manner to Example 11 to obtain N-((3,3-difluorocyclobutyl)methyl)-4-((2,4-difluorophenyl)ethynyl)benzamide (0.049 g, 42.7%) as white solid: LRMS (ES) m/z 362.19 [M+H]$^+$, calculated MW 361.34; $^1$H-NMR (400 MHz, CD$_3$OD) d 7.75~7.81 (m, 2H), 7.54~7.59 (m, 3H), 7.02 (m, 2H), 3.48 (d, J=6.0 Hz, 2H), 3.28~3.29 (m, 1H), 2.62 (m, 2H), 2.32 (m, 2H).

Example 121: Synthesis of N-((4,4-difluorocyclohexyl)methyl)-4-((2,4-difluorophenyl)ethynyl)benzamide

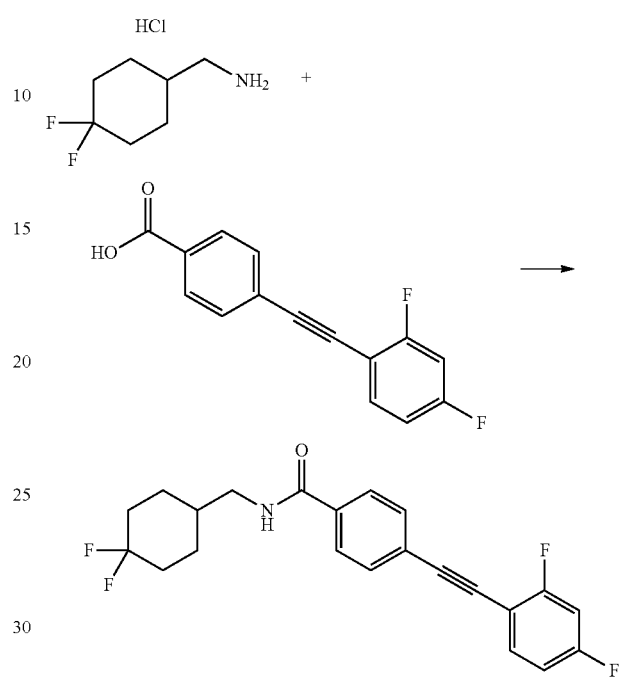

(4,4-Difluorocyclohexyl)methanamine hydrochloride (0.050 g, 0.269 mmol) and 4-((2,4-difluorophenyl)ethynyl)benzoic acid (0.083 g, 0.323 mmol) as starting materials were used in a similar manner to Example 11 to obtain N-((4,4-difluorocyclohexyl)methyl)-4-((2,4-difluorophenyl)ethynyl)benzamide (0.048 g, 63.7%) as white solid: LRMS (ES) m/z 390.26 [M+H]$^+$, calculated MW 389.39; $^1$H-NMR (400 MHz, CD$_3$OD) d 8.58 (t, J=5.2 Hz, 1H), 7.81 (d, J=8.4 Hz, 2H), 7.55~7.65 (m, 3H), 6.97~7.08 (m, 2H), 3.28~3.29 (m, 3H), 2.01~2.05 (m, 2H), 1.69~1.85 (m, 4H), 1.25~1.33 (m, 2H).

Example 122: Synthesis of 4-((2,4-difluorophenyl)ethynyl)-N-((3-ethyloxetan-3-yl)methyl)benzamide

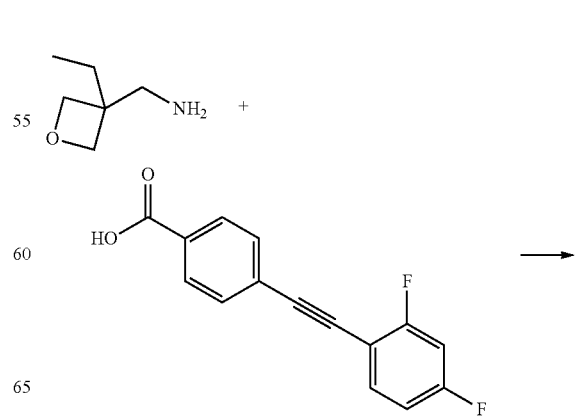

-continued

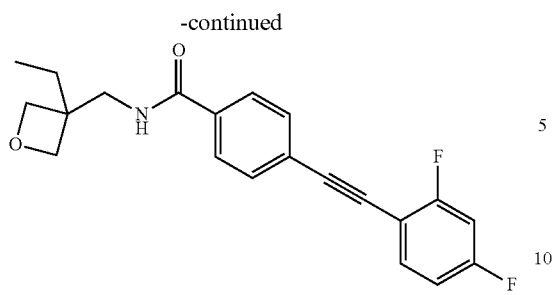

(3-Ethyloxetan-3-yl)methanamine (0.050 g, 0.434 mmol) and 4-((2,4-difluorophenyl)ethynyl)benzoic acid (0.135 g, 0.521 mmol) as starting materials were used in a similar manner to Example 11 to obtain 4-((2,4-difluorophenyl)ethynyl)-N-(3-ethyloxetan-3-yl)methyl)benzamide (0.070 g, 45.4%) as white solid: LRMS (ES) m/z 356.18 [M+H]$^+$, calculated MW 355.38; $^1$H-NMR (400 MHz, CD$_3$OD) d 7.82 (d, J=8.4 Hz, 2H), 7.58 (d, J=8.4 Hz, 2H), 7.54~7.60 (m, 1H), 6.96~7.07 (m, 2H), 4.56 (d, J=6.4 Hz, 2H), 4.39 (d, J=6.0 Hz, 2H), 3.59 (s, 2H), 1.74 (q, J=7.5 Hz, 2H), 0.97 (t, J=7.4 Hz, 3H).

Example 123: Synthesis of 4-((2,4-difluorophenyl)ethynyl)-N-((3-fluorooxetan-3-yl)methyl)benzamide

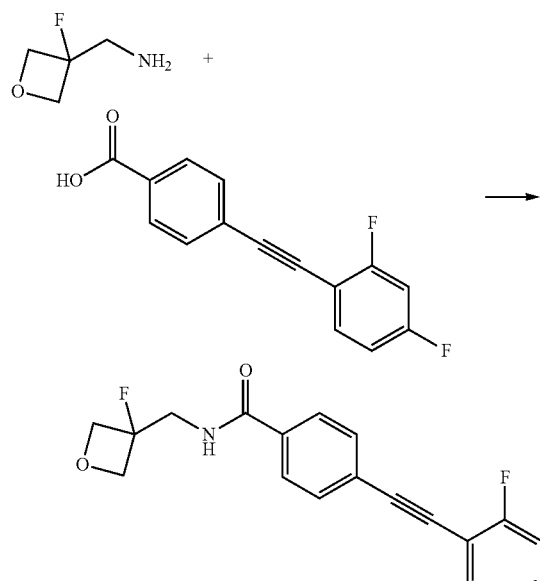

(3-Fluorooxetan-3-yl)methanamine (0.050 g, 0.476 mmol) and 4-((2,4-difluorophenyl)ethanyl)benzoic acid (0.147 g, 0.571 mmol) as starting materials were used in a similar manner to Example 11 to obtain 4-((2,4-difluorophenyl)ethynyl)-N-(3-fluorooxetan-3-yl)methyl)benzamide (0.090 g, 54.8%) as white solid: LRMS (ES) m/z 346.21 [M+H]$^+$, calculated MW 345.32; $^1$H-NMR (400 MHz, CD$_3$OD) d 7.83 (d, J=8.0 Hz, 2H), 7.58 (d, J=8.4 Hz, 2H), 7.54~7.60 (m, 1H), 7.04 (td, J=9.4, 2.4 Hz, 1H), 6.99 (td, J=8.6, 2.0 Hz, 1H), 4.74 (s, 2H), 4.69 (s, 2H), 3.90 (d, J=20.0 Hz, 2H).

Example 124: Synthesis of (S)-4-((2,4-difluorophenyl)ethynyl)-N-((tetrahydro-2H-pyran-3-yl)methyl)benzamide

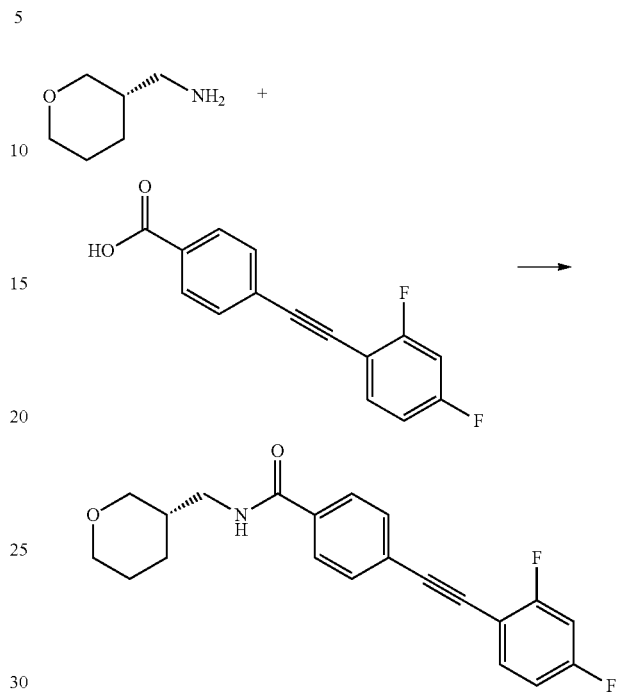

(S)-(tetrahydro-2H-pyran-3-yl)methanamine hydrochloride (0.050 g, 0.330 mmol) and 4-((2,4-difluorophenyl)ethynyl)benzoic acid (0.102 g, 0.396 mmol) as starting materials were used in a similar manner to Example 11 to obtain (S)-4-((2,4-difluorophenyl)ethynyl)-N-((tetrahydro-2H-pyran-3-yl)methyl)benzamide (0.050 g, 42.7%) as white solid: LRMS (ES) m/z 356.18 [M+H]$^+$, calculated MW 355.38; $^1$H-NMR (400 MHz, CD$_3$OD) d 8.54 (bs, 1H), 7.81 (d, J=6.4 Hz, 2H), 7.58 (d, J=7.2 Hz, 3H), 6.98~7.05 (m, 2H), 3.79~3.88 (m, 2H), 3.42 (m, 1H), 3.25 (m, 2H), 1.89 (m, 2H), 1.56~1.64 (m, 2H), 1.30~1.32 (m, 2H).

Example 125: Synthesis of 4-((2,4-difluorophenyl)ethynyl)-N-((4-methyltetrahydro-2H-pyran-4-yl)methyl)benzamide

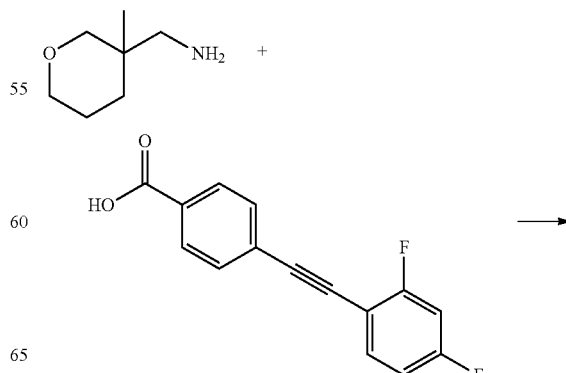

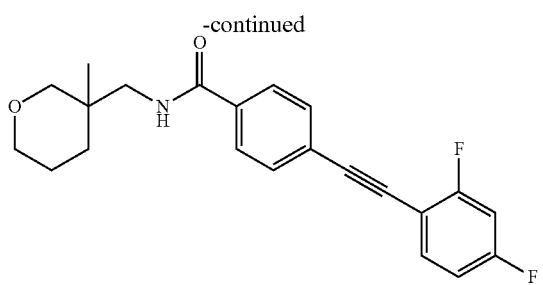

(4-Methyltetrahydro-2H-pyran-4-yl)methanamine (0.050 g, 0.387 mmol) and 4-((2,4-difluorophenyl)ethynyl)benzoic acid (0.120 g, 0.464 mmol) as starting materials were used in a similar manner to Example 11 to obtain 4-((2,4-difluorophenyl)ethynyl)-N-((4-methyltetrahydro-2H-pyran-4-yl)methyl)benzamide (0.042 g, 29.4%) as white solid: LRMS (ES) m/z 370.25 [M+H]$^+$, calculated MW 369.41; $^1$H-NMR (400 MHz, CD$_3$OD) d 7.82 (d, J=8.0 Hz, 2H), 7.59 (d, J=8.8 Hz, 2H), 7.55~7.61 (m, 1H), 6.97~7.09 (m, 2H), 3.58~3.76 (m, 4H), 3.26~3.35 (m, 2H), 1.52~1.57 (m, 2H), 1.34 (m, 2H), 1.02 (s, 3H).

Experimental Example 1: Confirmation of Synergistic Analgesic Effect Via Dual Action The confirmation of the synergistic analgesic effect via the dual action of mGluR5 and 5-HT2AR was carried out by the use of representative mGluR5 antagonist MPEP (2-methyl-6-(phenylethynyl)pyridine) and 5-HT2AR antagonist MDL11,939 in a "spinal nerve ligation model" which is a neuropathic pain model.

In order to measure the analgesic effect of MPEP and MDL11,939, when administered alone or simultaneously together, the reversibility rate of pain relieving parameter (% reversal) was calculated according to the method of Experimental Example 4 and the results are represented in FIG. 1. As shown in FIG. 1, either MPEP or MDL11,939 alone did not show a significant analgesic effect by sub-effective doses (a sub-effective dose: a dose under the efficacy doses which induced significant pain relieving effects). However, a significant analgesic effect was evident when they were administered simultaneously. The result clearly demonstrated that MPEP and MDL11,939 acted to relieve pain synergistically.

Experimental Example 2: Fluorescence-Based Ca$^{2+}$ Mobilization Assay

In order to measure the activity on the mGluR5, an experiment was carried out to check the change in the intracellular Ca$^{2+}$ level using the HEK293 cell line permanently overexpressing the mGluR5. The cells in the cell culture medium were aliquoted into a 384-well plate coated with poly-D-lysine and cultured in a 37° C. incubator supplied with 5% CO$_2$. The next day, the medium was removed and a dye loading buffer—in which a reagent capable of measuring Ca$^{2+}$ was dissolved—was added, and then incubated at 37° C. for 60 minutes. The test compounds were dissolved in 100% DMSO at a final concentration of 10 mM to make a stock solution. The starting concentration of 10 μM was prepared from the stock solution, followed by serial dilutions to prepare working solutions (test compound working solutions). The test compound working solutions were added to the cells that were incubated in the dye loading buffer, which were maintained for 30 minutes at room temperature in a light-shielding state before measurement. The Ca$^{2+}$ level change induced by L-glutamate at EC$_{80}$ concentration was measured for 2 minutes using FLIPR Tetra (MDS Analytical Technologies). The fluorescent Ca$^{2+}$ signal values in the presence of the test compounds were normalized to the fluorescent signal elicited by EC$_{80}$ concentration of L-glutamate as 100% and that elicited by vehicle as 0% to estimate % inhibition of the test compounds. The efficacy of the test compounds was calculated as IC$_{50}$ values and represented in Table 1. (+: 1,000-2,000 nM, ++: 500-1,000 nM, +++: 100-500 nM, ++++: less than 100 nM).

Experimental Example 3: HTRF-Based IP1 Accumulation Assay

The 5-HT2AR antagonistic effect of the test compounds was confirmed by measuring the production amount of IP1 using the HEK293 cell line permanently overexpressing the human 5-HT2AR. The test compounds were dissolved in 100% DMSO to a final concentration of 10 mM. The starting concentration of 10 μM was prepared from the stock solution, followed by serial dilutions to prepare working solutions in a buffer containing lithium chloride (LiCl). The cells and compounds prepared in the test buffer were placed in a 96-well plate and incubated at room temperature for 10 minutes. Serotonin of EC$_{80}$ concentration was added, followed by incubation at 37° C. for 30 minutes in a light-shielding state. To measure IP1 accumulation in cells, IP1-d$_2$ acceptor and IP1-Cryptate donor—which are HTRF-based substances for fluorescence signals—were added and incubated for 1 hour at room temperature in a light-shielded state. The fluorescent emission signals of acceptor and donor were detected, and HTRF ratio values were subtracted by mean value of serotonin control. The percentage of activation was calculated by normalization of the serotonin control (0%) and IP1 control (100%). The IC$_{50}$ values of the test compounds are represented in Table 1. (+: 1,000-2,000 nM, ++: 500-1,000 nM, +++: 100-500 nM, ++++: less than 100 nM).

TABLE 1

| Example | Human 5-HT2AR (IC$_{50}$, nM) | Human mGluR5 (IC$_{50}$, nM) | Example | Human 5-HT2AR (IC$_{50}$, nM) | Human mGluR5 (IC$_{50}$, nM) |
|---|---|---|---|---|---|
| 1 | +++ | + | 64 | ++ | ++++ |
| 2 | ++++ | ++ | 65 | ++ | ++++ |
| 3 | +++ | ++ | 66 | ++ | ++++ |
| 4 | +++ | + | 67 | ++ | +++ |
| 5 | +++ | +++ | 68 | ++ | +++ |
| 6 | ++++ | ++ | 69 | ++ | +++ |
| 7 | +++ | + | 70 | ++ | +++ |
| 8 | + | ++ | 71 | ++ | ++++ |
| 9 | ++++ | +++ | 72 | +++ | ++++ |
| 10 | +++ | +++ | 73 | + | ++++ |
| 11 | ++++ | +++ | 74 | ++ | +++ |
| 12 | +++ | +++ | 75 | ++ | +++ |
| 13 | ++++ | ++ | 76 | +++ | ++ |
| 14 | ++++ | +++ | 77 | + | ++++ |
| 15 | +++ | ++ | 78 | + | +++ |
| 16 | +++ | ++ | 79 | + | +++ |
| 17 | +++ | + | 80 | +++ | +++ |
| 18 | ++ | + | 81 | +++ | ++ |
| 19 | ++++ | + | 82 | ++ | ++ |
| 20 | ++++ | ++ | 83 | +++ | ++++ |
| 21 | ++ | + | 84 | + | + |
| 22 | ++++ | +++ | 85 | ++ | +++ |
| 23 | +++ | ++ | 86 | + | +++ |
| 24 | +++ | ++ | 87 | +++ | ++++ |
| 25 | ++++ | +++ | 88 | ++ | ++++ |
| 26 | ++++ | + | 89 | +++ | ++++ |

TABLE 1-continued

| Example | Human 5-HT2AR (IC$_{50}$, nM) | Human mGluR5 (IC$_{50}$, nM) | Example | Human 5-HT2AR (IC$_{50}$, nM) | Human mGluR5 (IC$_{50}$, nM) |
|---|---|---|---|---|---|
| 27 | +++ | ++++ | 90 | +++ | ++++ |
| 28 | +++ | + | 91 | + | ++++ |
| 29 | +++ | +++ | 92 | +++ | ++++ |
| 30 | ++++ | ++ | 93 | +++ | +++ |
| 31 | + | + | 94 | +++ | +++ |
| 32 | ++ | ++++ | 95 | ++ | ++++ |
| 33 | + | +++ | 96 | ++ | + |
| 34 | + | ++ | 97 | + | ++++ |
| 35 | + | ++++ | 98 | ++ | ++++ |
| 36 | ++ | ++++ | 99 | +++ | ++++ |
| 37 | +++ | ++++ | 100 | ++ | +++ |
| 38 | ++ | +++ | 101 | +++ | ++++ |
| 39 | ++++ | ++++ | 102 | ++++ | +++ |
| 40 | +++ | ++++ | 103 | + | + |
| 41 | ++ | +++ | 104 | + | ++++ |
| 42 | +++ | ++++ | 105 | ++ | ++++ |
| 43 | +++ | ++++ | 106 | +++ | ++++ |
| 44 | ++++ | ++ | 107 | ++++ | ++++ |
| 45 | +++ | ++++ | 108 | +++ | ++++ |
| 46 | +++ | +++ | 109 | +++ | ++ |
| 47 | +++ | ++++ | 110 | +++ | ++++ |
| 48 | ++ | ++++ | 111 | +++ | +++ |
| 49 | +++ | ++++ | 112 | +++ | +++ |
| 50 | ++ | ++++ | 113 | ++++ | ++ |
| 51 | +++ | ++++ | 114 | ++++ | ++++ |
| 52 | +++ | ++++ | 115 | ++++ | +++ |
| 53 | + | ++ | 116 | ++++ | ++++ |
| 54 | +++ | ++++ | 117 | ++++ | ++ |
| 55 | ++++ | + | 118 | ++++ | + |
| 56 | +++ | ++++ | 119 | ++++ | ++++ |
| 57 | ++ | ++++ | 120 | ++++ | +++ |
| 58 | +++ | +++ | 121 | ++ | ++++ |
| 59 | ++ | +++ | 122 | ++++ | +++ |
| 60 | ++ | ++ | 123 | ++++ | ++ |
| 61 | ++ | + | 124 | +++ | +++ |
| 62 | + | +++ | 125 | +++ | ++++ |
| 63 | +++ | ++++ | | | |

Experimental Example 4: Analgesic Efficacy Experiment Using Animal Model (Chung Model)

The Chung model (spinal nerve ligation model) is a representative animal model to study neuropathic pain and is widely accepted as a gold standard for an animal pain model by global pharmaceutical companies around the world.

In this experiment, male Sprague-Dawley rats (100-120 g) purchased from Koatech (Pyeongtaek-si, Gyeonggi-do) were used. Rats were kept in a room maintained at constant temperature and humidity with a 12 hour light-dark cycle. Rats were allowed to eat and drink freely during the experiment.

For the Chung surgery, rats were anesthetized by isoflurane inhalation and the left lumbar nerves L5 and L6 were tightly tied with a suture thread (6-0 silk thread) at the end of the dorsal ganglion and at a front of an entrance to the sciatic nerve according to the article (Kim and Chung (1992), Pain 50(3):355-63). After suturing the incision, the rats were recovered for 2 weeks in the controlled maintenance room to induce physical allodynia in the left hind paw of the rat. To measure physical (tactile) allodynia, the rats were placed in a cage with a wire mesh on the bottom. Stimuli of increasing intensity (using the von Frey filaments in a range of 0.41 to 15.8 g) were placed on the plantar surface on the side of the nerve injury. The stimulus intensity at which the pain response (abrupt lifting, licking or sucking of the foot) was induced was recorded while applying gradual increment of stimuli. As described in the study of Chaplan et al. (1994) (Chaplan et al. (1994) J. Neurosci. Methods 53(1):55-63), the paw withdrawal threshold (PWT) was determined by increasing or decreasing continuous stimulus intensity, and the result was analyzed by applying Dixon's up-down method. Only rats showing no behavior dysfunction (e.g., feet dragging or dropping) were selected and included in the study, and the PWT of the rats used was 3.16 g or less.

After measuring the degree of basic reaction before drug injection, each compound and solvent were injected by oral administration (12.5-100 mg/kg), and the measurement was repeated at regular time intervals (60 and 120 minutes) after the drug was injected.

The experimenter conducted the PWT measurement in a blind condition not knowing which rat was administered with which drug. The control group was administered with gabapentin (65 mg/kg, intraperitoneal administration), and was randomly mixed during the measurement. Statistical analysis was performed on the measured pain response threshold by calculating the reversal rate (% reversal) from pain in Equation 1 below. A high reversal rate means that allodynia is greatly reduced after drug administration.

$$\text{Pain reversal rate (\% reversal)} = \frac{(PWT \text{ after drug administration}) - (PWT \text{ before drug administration})}{(15\,g,\ \text{Estimated } PWT \text{ in normal animals}) - (PWT \text{ before drug administration})} * 100 \quad \text{[Equation 1]}$$

The PWT used in this time is a value obtained by multiplying the gram, the unit of "force" measure, by 10,000, and taking the logarithm, which is a method generally used in academia. The results are represented in Table 2.

Each experiment consisted of the compound group, the solvent group of the compound and the gabapentin (GBP) group as positive control group. As solvent of the compound, 0.5% HPMC (hydroxypropylmethyl cellulose) was used.

TABLE 2

| Example | % reversal (1 h/2 h) | Example | % reversal (1 h/2 h) | Example | % reversal (1 h/2 h) |
|---|---|---|---|---|---|
| 1 | 60.51/85.69 (100 mpk) | 2 | 3.91/28.07 (12.5 mpk) | 3 | 59.03/87.87 (50 mpk) |
| 5 | 43.11/34.44 (50 mpk) | 9 | 63.98/59.56 (100 mpk) | 10 | 44.93/36.12 (50 mpk) |
| 11 | 58.73/57.37 (100 mpk) | 12 | 53.82/74.80 (100 mpk) | 16 | 60.96/95.76 (50 mpk) |
| 20 | 34.97/66.98 (100 mpk) | 22 | 19.33/77.46 (50 mpk) | 25 | 36.49/36.56 (25 mpk) |

TABLE 2-continued

| Example | % reversal (1 h/2 h) | Example | % reversal (1 h/2 h) | Example | % reversal (1 h/2 h) |
|---|---|---|---|---|---|
| 27 | 70.26/66.31 (50 mpk) | 37 | 37.07/18.80 (100 mpk) | 39 | 25.37/33.47 (100 mpk) |
| 40 | 102.89/110.69 (50 mpk) | 42 | 82.88/88.12 (100 mpk) | 43 | 72.87/90.75 (50 mpk) |
| 44 | 3.45/9.13 (50 mpk) | 45 | 77.70/50.62 (50 mpk) | 46 | 73.02/99.82 (100 mpk) |
| 49 | 28.46/22.03 (25 mpk) | 51 | 5.97/14.48 (50 mpk) | 52 | 90.81/100.78 (100 mpk) |
| 55 | 68.88/80.24 (100 mpk) | 56 | 47.44/43.65 (50 mpk) | 58 | 61.48/28.29 (25 mpk) |
| 63 | 70.93/42.06 (50 mpk) | 64 | 10.41/45.16 (50 mpk) | 65 | 33.97/80.77 (50 mpk) |
| 66 | 64.09/43.19 (25 mpk) | 69 | 110.32/110.32 (50 mpk) | 72 | 41.87/71.78 (50 mpk) |
| 82 | 70.29/89.13 (50 mpk) | 83 | 55.01/67.85 (25 mpk) | 87 | 93.67/104.29 (50 mpk) |
| 88 | 97.78/110.43 (50 mpk) | 89 | 110.84/102.57 (50 mpk) | 92 | 39.77/48.69 (25 mpk) |
| 94 | 74.19/97.73 (50 mpk) | | | | |

As can be seen from Table 2, it was confirmed that the compound according to one embodiment of the present invention has excellent analgesic effect.

The invention claimed is:

1. A compound of the following Formula 1 or a pharmaceutically acceptable salt thereof:

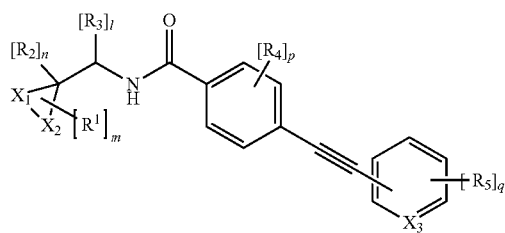

[Formula 1]

wherein
$X_1$ and $X_2$ together with carbon atom to which they are attached form 4- to 7-membered aliphatic ring selected from the group consisting of cyclobutane, cyclopentane, and cycloheptane; or a 4- to 6-membered heteroaliphatic ring selected from the group consisting of oxetane, tetrahydrofuran, tetrahydropyran, dioxane, and piperidine;
$X_3$ is CH or N;
$R_1$ is hydroxy, halo, alkyl, heterocycloalkyl or heterocycloalkyl-alkyl;
R2 is hydroxy, halo, alkyl, alkoxy, heterocycloalkyl, hydroxyalkyl, haloalkyl, amino, alkylamino, dialkylamino, cycloalkyl-alkyl, cycloalkylamino, haloalkylamino, aminocarbonyl, alkylaminocarbonyl, alkoxycarbonylalkyl, carboxyalkyl, aminocarbonylalkyl, hydroxyaminocarbonylalkyl, alkylaminocarbonylalkyl, dialkylaminocarbonylalkyl, or 5- or 6-membered heteroaryl;
$R_3$ is deuterium, halo or alkyl;
$R_4$ is halo or alkyl;
$R_5$ is fluoro;
m is an integer of 0 to 3;
n is 0 or 1; and
l and p are each independently an integer of 0 to 2;
q is 1 or 2;
wherein the heterocycloalkyl or heteroaryl has one or more heteroatoms selected from the group consisting of N, O and S.

2. The compound or pharmaceutically acceptable salt thereof according to claim 1, wherein
$X_1$ and $X_2$ together with carbon atom to which they are attached form $C_4$-$C_7$ cycloalkyl selected from the group consisting of cyclobutane, cyclopentane, and cycloheptane; or 4- to 6-membered heterocycloalkyl selected from the group consisting of oxetane, tetrahydrofuran, tetrahydropyran, dioxane, and piperidine;
$X_3$ is CH or N;
$R_1$ is hydroxy, halo or $C_1$-$C_5$ alkyl;
$R_2$ is hydroxy, halo, $C_1$-$C_5$ alkyl, $C_1$-$C_5$ alkoxy, 4- to 6-membered heterocycloalkyl, hydroxy-$C_1$-$C_5$ alkyl, halo-$C_1$-$C_5$ alkyl, $C_1$-$C_5$ alkylamino, $C_3$-$C_6$ cycloalkyl-$C_1$-$C_5$ alkyl, $C_3$-$C_6$ cycloalkylamino, halo-$C_1$-$C_5$ alkylamino, $C_1$-$C_5$ alkylaminocarbonyl, $C_1$-$C_5$ alkoxycarbonyl-$C_1$-$C_5$ alkyl, carboxy-$C_1$-$C_5$ alkyl, aminocarbonyl-$C_1$-$C_5$ alkyl, hydroxyaminocarbonyl-$C_1$-$C_5$ alkyl, $C_1$-$C_5$ alkylaminocarbonyl-$C_1$-$C_5$ alkyl, di($C_1$-$C_5$ alkyl)aminocarbonyl-$C_1$-$C_5$ alkyl or pyridyl;
$R_3$ is deuterium, fluoro or $C_1$-$C_5$ alkyl;
$R_4$ is halo or $C_1$-$C_5$ alkyl;
$R_5$ is fluoro;
m is an integer of 0 to 2;
n is 0 or 1; and
l and p are each independently an integer of 0 to 2;
q is 1 or 2;
wherein the heterocycloalkyl has 1 to 3 heteroatoms selected from the group consisting of N and O.

3. The compound or pharmaceutically acceptable salt thereof according to claim 1, wherein $X_1$ and $X_2$ together with carbon atom to which they are attached form oxetane, tetrahydrofuran, tetrahydropyran, cyclobutane, or cyclopentane.

4. The compound or pharmaceutically acceptable salt thereof according to claim 1, wherein p is 0.

5. The compound or pharmaceutically acceptable salt thereof according to claim 1, wherein $X_3$ is CH.

6. The compound or pharmaceutically acceptable salt thereof according to claim 5, wherein n is not 0.

7. The compound or pharmaceutically acceptable salt thereof according to claim 1, wherein $R_5$ is at ortho and/or para position of phenyl.

8. A compound selected from the group consisting of:
N-((1-(cyclopropylamino)cyclopentyl)methyl)-4-((5-fluoropyridin-2-yl)ethynyl)benzamide;
N-((1-(cyclopropylamino)cyclobutyl)methyl)-4-((5-fluoropyridin-2-yl)ethynyl)benzamide;
N-((1-(cyclopropylamino)cyclobutyl)methyl)-4-((4-fluorophenyl)ethynyl)benzamide;
N-((1-(cyclopropylamino)cyclobutyl)methyl)-4-((2-fluorophenyl)ethynyl)benzamide;
N-((1-(cyclopropylamino)cyclopentyl)methyl)-4-((2-fluorophenyl)ethynyl)benzamide;
N-((1-(cyclopropylamino)cycloheptyl)methyl)-4-((2-fluorophenyl)ethynyl)benzamide;
N-((1-(cyclopropylamino)cyclopentyl)methyl)-4-((4-fluorophenyl)ethynyl)benzamide;
N-((1-(cyclopropylamino)cycloheptyl)methyl)-4-((4-fluorophenyl)ethynyl)benzamide;
N-((1-(cyclopropylamino)cycloheptyl)methyl)-4-((5-fluoropyridin-2-yl)ethynyl)benzamide;
N-((1-(cyclopropylamino)cycloheptyl)methyl)-4-((3-fluoropyridin-4-yl)ethynyl)benzamide;
N-((1-(cyclopropylamino)cyclopentyl)methyl)-4-((3,4-difluorophenyl)ethynyl)benzamide;
N-((1-(cyclopropylamino)cycloheptyl)methyl)-4-((3,4-difluorophenyl)ethynyl)benzamide;
N-((4-(cyclopropylamino)tetrahydro-2H-pyran-4-yl)methyl)-4-((2-fluorophenyl)ethynyl)benzamide;
4-((2-fluorophenyl)ethynyl)-N-((1-morpholinocyclopentyl)methyl)benzamide;
4-((2-fluorophenyl)ethynyl)-N-((4-(isopropylamino)tetrahydro-2H-pyran-4-yl)methyl)benzamide;
4-((2-fluorophenyl)ethynyl)-N-((tetrahydro-2H-pyran-4-yl)methyl)benzamide;
N-((4-(cyclopropylmethyl)tetrahydro-2H-pyran-4-yl)methyl)-4-((2-fluorophenyl)ethynyl)benzamide;
4-((2-fluorophenyl)ethynyl)-N-((1-(isopropylamino)cyclopentyl)methyl)benzamide;
4-((4-fluorophenyl)ethynyl)-N-((tetrahydro-2H-pyran-4-yl)methyl)benzamide;
4-((2-fluorophenyl)ethynyl)-N-((1-(pyridin-3-yl)cyclopentyl)methyl)benzamide;
2-fluoro-4-((2-fluorophenyl)ethynyl)-N-((tetrahydro-2H-pyran-4-yl)methyl)benzamide;
4-((2-fluorophenyl)ethynyl)-N-((4-methyltetrahydro-2H-pyran-4-yl)methyl)benzamide;
4-((2-fluorophenyl)ethynyl)-N-((4-(hydroxymethyl)tetrahydro-2H-pyran-4-yl)methyl)benzamide;
4-((2-fluorophenyl)ethynyl)-N-((tetrahydro-2H-pyran-3-yl)methyl)benzamide;
4-((2-fluorophenyl)ethynyl)-N-((4-hydroxytetrahydro-2H-pyran-4-yl)methyl)benzamide;
4-((2-fluorophenyl)ethynyl)-N-(1-(tetrahydro-2H-pyran-4-yl)ethyl)benzamide;
4-((2-fluorophenyl)ethynyl)-N-((tetrahydrofuran-3-yl)methyl)benzamide;
4-((2,4-difluorophenyl)ethynyl)-N-((tetrahydro-2H-pyran-4-yl)methyl)benzamide;
(R)-4-((2-fluorophenyl)ethynyl)-N-((tetrahydrofuran-2-yl)methyl)benzamide;
(S)-4-((2-fluorophenyl)ethynyl)-N-((tetrahydrofuran-2-yl)methyl)benzamide;
(R)-4-((2-fluorophenyl)ethynyl)-N-(1-(tetrahydro-2H-pyran-4-yl)ethyl)benzamide;
4-((2-fluorophenyl)ethynyl)-N-((4-fluorotetrahydro-2H-pyran-4-yl)methyl)benzamide;
N-((4-(fluoromethyl)tetrahydro-2H-pyran-4-yl)methyl)-4-((2-fluorophenyl)ethynyl)benzamide;
N-((1,4-dioxan-2-yl)methyl)-4-((2-fluorophenyl)ethynyl)benzamide;
4-((2-fluorophenyl)ethynyl)-N-((3-methyloxetan-3-yl)methyl)benzamide;
4-((4-((2-fluorophenyl)ethynyl)benzamido)methyl)-N-methyltetrahydro-2H-pyran-4-carboxamide;
4-((2-fluorophenyl)ethynyl)-N-((tetrahydro-2H-pyran-2-yl)methyl)benzamide;
N-((3,3-difluorocyclobutyl)methyl)-4-((2-fluorophenyl)ethynyl)benzamide;
4-((2-fluorophenyl)ethynyl)-N-((1-hydroxycyclobutyl)methyl)benzamide;
4-((2-fluorophenyl)ethynyl)-N-(oxetan-2-ylmethyl)benzamide;
3-(4-((4-((2-fluorophenyl)ethynyl)benzamido)methyl)tetrahydro-2H-pyran-4-yl)propanoic acid;
4-((2-fluorophenyl)ethynyl)-N-((4-methoxytetrahydro-2H-pyran-4-yl)methyl)benzamide;
N-((2,2-dimethyltetrahydro-2H-pyran-4-yl)methyl)-4-((2-fluorophenyl)ethynyl)benzamide;
4-((2-fluorophenyl)ethynyl)-N-((tetrahydro-2H-pyran-4-yl)methyl-$d_2$)benzamide;
(R)-4-((2-fluorophenyl)ethynyl)-N-((tetrahydrofuran-3-yl)methyl)benzamide;
N-((5,5-dimethyltetrahydrofuran-3-yl)methyl)-4-((2-fluorophenyl)ethynyl)benzamide;
4-((2-fluorophenyl)ethynyl)-N-((tetrahydrofuran-2-yl)methyl)benzamide;
N-((3-ethyloxetan-3-yl)methyl)-4-((2-fluorophenyl)ethynyl)benzamide;
methyl 2-(4-((4-((2-fluorophenyl)ethynyl)benzamido)methyl)tetrahydro-2H-pyran-4-yl)acetate;
N-((1-(2-amino-2-oxoethyl)cyclohexyl)methyl)-4-((2-fluorophenyl)ethynyl)benzamide;
N-((4-(2-amino-2-oxoethyl)tetrahydro-2H-pyran-4-yl)methyl)-4-((2-fluorophenyl)ethynyl)benzamide;
4-((2-fluorophenyl)ethynyl)-N-((3-hydroxyoxetan-3-yl)methyl)benzamide;
4-((4-fluorophenyl)ethynyl)-N-((3-methyloxetan-3-yl)methyl)benzamide;
3-fluoro-4-((2-fluorophenyl)ethynyl)-N-((3-methyloxetan-3-yl)methyl)benzamide;
4-((2-fluorophenyl)ethynyl)-N-(((1s,3s)-3-hydroxycyclobutyl)methyl)benzamide;
4-((2-fluorophenyl)ethynyl)-N-(((1r,3r)-3-hydroxycyclobutyl)methyl)benzamide;
4-((2-fluorophenyl)ethynyl)-N-(((1s,3s)-3-hydroxy-3-methylcyclobutyl)methyl)benzamide;
(S)-4-((2-fluorophenyl)ethynyl)-N-((tetrahydro-2H-pyran-3-yl)methyl)benzamide;
(R)-4-((2-fluorophenyl)ethynyl)-N-((tetrahydro-2H-pyran-3-yl)methyl)benzamide;
(S)-4-((2-fluorophenyl)ethynyl)-N-((tetrahydrofuran-3-yl)methyl)benzamide;
4-((4-fluorophenyl)ethynyl)-N-((tetrahydrofuran-3-yl)methyl)benzamide;
4-((2-fluorophenyl)ethynyl)-N-((3-ethyloxetan-3-yl)methyl-d)benzamide;
4-((2-fluorophenyl)ethynyl)-N-((1-morpholinocyclobutyl)methyl)benzamide;
N-((3,3-difluoro-1-methylcyclobutyl)methyl)-4-((2-fluorophenyl)ethynyl)benzamide;

4-((2-fluorophenyl)ethynyl)-N-((2-methyltetrahydrofuran-2-yl)methyl)benzamide;
(R)-4-((4-fluorophenyl)ethynyl)-N-((tetrahydro-2H-pyran-3-yl)methyl)benzamide;
(S)-4-((4-fluorophenyl)ethynyl)-N-((tetrahydro-2H-pyran-3-yl)methyl)benzamide;
(R)-4-((4-fluorophenyl)ethynyl)-N-((tetrahydrofuran-3-yl)methyl)benzamide;
(S)-4-((4-fluorophenyl)ethynyl)-N-((tetrahydrofuran-3-yl)methyl)benzamide;
N-((3-fluorooxetan-3-yl)methyl)-4-((2-fluorophenyl)ethynyl)benzamide;
4-((4-fluorophenyl)ethynyl)-N-((1-methylcyclohexyl)methyl)benzamide;
4-((2-fluorophenyl)ethynyl)-N-((1-methylcyclobutyl)methyl)benzamide;
4-((4-fluorophenyl)ethynyl)-N-((1-methylcyclobutyl)methyl)benzamide;
4-((2,4-difluorophenyl)ethynyl)-N-((1-methylcyclobutyl)methyl)benzamide;
4-((2,4-difluorophenyl)ethynyl)-N-((1-methylcyclopentyl)methyl)benzamide;
(R)-4-((2,4-difluorophenyl)ethynyl)-N-((tetrahydrofuran-3-yl)methyl)benzamide;
(R)-4-((4-fluorophenyl)ethynyl)-N-((tetrahydrofuran-2-yl)methyl)benzamide;
(S)-4-((4-fluorophenyl)ethynyl)-N-((tetrahydrofuran-2-yl)methyl)benzamide;
N-((3-ethyloxetan-3-yl)methyl)-4-((4-fluorophenyl)ethynyl)benzamide;
(S)-4-((2,4-difluorophenyl)ethynyl)-N-((tetrahydrofuran-3-yl)methyl)benzamide;
(R)-4-((2,4-difluorophenyl)ethynyl)-N-((tetrahydrofuran-2-yl)methyl)benzamide;
4-((2,4-difluorophenyl)ethynyl)-N-((tetrahydro-2H-pyran-2-yl)methyl)benzamide;
4-((4-fluorophenyl)ethynyl)-N-((2-methyltetrahydrofuran-2-yl)methyl)benzamide;
(S)-4-((2,4-difluorophenyl)ethynyl)-N-((tetrahydrofuran-2-yl)methyl)benzamide;
4-((2,4-difluorophenyl)ethynyl)-N-(oxetan-2-ylmethyl)benzamide;
4-((2,4-difluorophenyl)ethynyl)-N-((2-methyltetrahydrofuran-2-yl)methyl)benzamide;
N-((3,3-difluorocyclobutyl)methyl)-4-((2,4-difluorophenyl)ethynyl)benzamide;
N-((4,4-difluorocyclohexyl)methyl)-4-((2,4-difluorophenyl)ethynyl)benzamide;
4-((2,4-difluorophenyl)ethynyl)-N-((3-ethyloxetan-3-yl)methyl)benzamide;
4-((2,4-difluorophenyl)ethynyl)-N-((3-fluorooxetan-3-yl)methyl)benzamide;
(S)-4-((2,4-difluorophenyl)ethynyl)-N-((tetrahydro-2H-pyran-3-yl)methyl)benzamide; and
4-((2,4-difluorophenyl)ethynyl)-N-((4-methyltetrahydro-2H-pyran-4-yl)methyl)benzamide;
or a pharmaceutically acceptable salt thereof.

9. The compound or pharmaceutically acceptable salt thereof according to claim 8, wherein the compound is selected from the group consisting of:
N-((1-(cyclopropylamino)cyclobutyl)methyl)-4-((2-fluorophenyl)ethynyl)benzamide;
N-((1-(cyclopropylamino)cyclopentyl)methyl)-4-((2-fluorophenyl)ethynyl)benzamide;
4-((2-fluorophenyl)ethynyl)-N-((tetrahydro-2H-pyran-4-yl)methyl)benzamide;
4-((2-fluorophenyl)ethynyl)-N-((tetrahydro-2H-pyran-3-yl)methyl)benzamide;
4-((2-fluorophenyl)ethynyl)-N-((tetrahydrofuran-3-yl)methyl)benzamide;
4-((2-fluorophenyl)ethynyl)-N-((3-methyloxetan-3-yl)methyl)benzamide;
(R)-4-((2-fluorophenyl)ethynyl)-N-((tetrahydrofuran-3-yl)methyl)benzamide;
4-((2-fluorophenyl)ethynyl)-N-((3-hydroxyoxetan-3-yl)methyl)benzamide;
4-((4-fluorophenyl)ethynyl)-N-((3-methyloxetan-3-yl)methyl)benzamide;
4-((2-fluorophenyl)ethynyl)-N-(((1s,3s)-3-hydroxy-3-methylcyclobutyl)methyl)benzamide;
4-((4-fluorophenyl)ethynyl)-N-((tetrahydrofuran-3-yl)methyl)benzamide;
(S)-4-((4-fluorophenyl)ethynyl)-N-((tetrahydrofuran-3-yl)methyl)benzamide;
(R)-4-((2,4-difluorophenyl)ethynyl)-N-((tetrahydrofuran-3-yl)methyl)benzamide;
4-((4-fluorophenyl)ethynyl)-N-((2-methyltetrahydrofuran-2-yl)methyl)benzamide;
4-((2,4-difluorophenyl)ethynyl)-N-((2-methyltetrahydrofuran-2-yl)methyl)benzamide; and
(S)-4-((2,4-difluorophenyl)ethynyl)-N-((tetrahydro-2H-pyran-3-yl)methyl)benzamide.

10. A pharmaceutical composition for the prevention or treatment of pain comprising a therapeutically effective amount of the compound or pharmaceutically acceptable salt thereof as defined in claim 1 as active ingredient, together with a pharmaceutically acceptable carrier or excipient.

11. The pharmaceutical composition according to claim 10, wherein the pain is neuropathic pain.

\* \* \* \* \*